(12) United States Patent
Hogrefe et al.

(10) Patent No.: US 9,085,762 B2
(45) Date of Patent: Jul. 21, 2015

(54) COMPOSITIONS AND METHODS USING SPLIT POLYMERASES

(75) Inventors: Holly Hogrefe, San Diego, CA (US); Lydia Wu, San Diego, CA (US); Jeffrey D. Fox, Escondido, CA (US); Connie Jo Hansen, San Diego, CA (US)

(73) Assignee: Agilent Technologies, Inc., Santa Clara, CA (US)

( * ) Notice: Subject to any disclaimer, the term of this patent is extended or adjusted under 35 U.S.C. 154(b) by 1210 days.

(21) Appl. No.: 11/968,152

(22) Filed: Dec. 31, 2007

(65) Prior Publication Data
US 2008/0227159 A1    Sep. 18, 2008

Related U.S. Application Data

(60) Provisional application No. 60/878,020, filed on Dec. 29, 2006, provisional application No. 60/881,694, filed on Jan. 19, 2007.

(51) Int. Cl.
*C12N 9/12*    (2006.01)

(52) U.S. Cl.
CPC .................................. *C12N 9/1252* (2013.01)

(58) Field of Classification Search
None
See application file for complete search history.

(56) References Cited

U.S. PATENT DOCUMENTS 6,946,273 B1    9/2005    Sorge

FOREIGN PATENT DOCUMENTS

WO    2005/118866    12/2005

OTHER PUBLICATIONS

Ngo et al. in The Protein Folding Problem and Tertiary Structure Prediction, 1994, Merz et al. (ed.), Birkhauser, Boston, MA, pp. 433 and 492-495.*
Arezi, B., et al., Efficient and High Fidelity Incorporation of Dye-Terminators by a Novel Archaeal DNA Polymerase Mutant, 2002, Journal of Molecular Biology, vol. 322(4), pp. 719-729.
Cambon-Bonavita, M.A., et al., Cloning, Expression, and Characterization of DNA Polymerase I from the Hyperthermophilic Archaea *Thermococcus fumicolans*, 2000, Extremophiles: Life Under Extreme Conditions, vol. 4(4), pp. 215-225.
Supplementary European Search Report received in EP2097523, dated Jan. 5, 2010, pp. 1-8.
Petrov et al. (2006) J Mol Biol. 361:46-68.
Kelman et al. (1999) JBC 274:28751-61.
Choi et al. (2006) J Mol Biol. 356:1093-1106.
Savino et al. (2004) Structure. 12:2001-2008.
Kelman,Z. et al., "Isolation and Characterization of a Split B-type DNA Polymerase from the Archaeon *Methanobacterium thermautotrophicum* H", The Journal of Biological Chemistry, 1999, vol. 274, No. 40, pp. 28751-28761.
Savino,C. et al., "Insight into DNA Replication: The Crystal Structure of DNA Polymerase B1 from the Archaeon *Sulfolobus solfataricus*' Structure", Nov. 2004, vol. 12, pp. 2001-2008.
Hopfner,K. et al., "Crystal Structure of a Thermostable Type B DNA Polymerase from *Thermococcus gorgonarius* " Proc.Natl.Acad.Sci. USA, Mar. 1999, vol. 96, pp. 3600-3605.
PCT International Search Report and Written Opinion received in Application No. PCT/US2007/089242, mailed Jul. 30, 2008, pp. 1-12.

* cited by examiner

*Primary Examiner* — Richard Hutson

(57) ABSTRACT

The invention relates to compositions and methods utilizing split polymerase enzymes composed of at least two discrete polypeptides that stably associate to form a single polymerase. The invention further relates to nucleic acid constructs for expressing the split polymerases of the invention, and methods for using the split polymerases of the invention. The enzymes of the invention are useful in many applications calling for the detectable labeling of nucleic acids and are particularly useful in quantitative PCR (QPCR) and DNA sequencing applications.

17 Claims, 59 Drawing Sheets

Figure 1

| | | SEQ ID NO: |
|---|---|---|
| Glycinemax | -GILPEILEELLTARKRAKADLKEA-KDPLEKAVLDGRQLALKISANSVYGF- 50 | 106 |
| athaliana | -GILPEILEELLTARKRAKADLKEA-KDPLEKAVLDGRQLALKISANSVYGF- 50 | 107 |
| Homosapiens | -GLLPQILENLLSARKRAKAELAKE-TDPLRRQVLDGRQLALKVSANSVYGF- 50 | 108 |
| Homosapiensdelta | -GLLPQILENLLSARKRAKAELAKE-TDPLRRQVLDGRQLGLKVSANSVYGF- 50 | 109 |
| Mus | -GLLPQILENLLSARKRAKAELAQE-TDPLRRQVLDGRQLALKVSANSVYGF- 50 | 110 |
| Danio | -GLLPEILENLLSARKRAKAELKKE-TDPFKQVLDGRQLALKISANSVYGF- 50 | 111 |
| Dicty | -GLLPRILEELLSARKKADELKNE-KDPFKRAVLDGRQLALKISANSVYGF- 50 | 112 |
| T_castaneum | -GLLPHILQHLLAARKKTKAELKEA-TDPVVRAVLDGRQLAYKISANSVYGF- 50 | 113 |
| Mth | -GFVPSVIGEILSERVRIKEEMKGS-DDPMERKILNVQQEALKRLANTMYGVY 51 | 114 |
| Methanosphaera | -GFIPSIIGYILDERQRIKKLMYEE-TVPEQKKAYDFEQQGLKRLANSMFGAY 51 | 115 |
| DeepVent | -GFIPSLLKRLLDERQEIKRKMKAS-KDPIEKKMLDYRQRAIKILANS----- 46 | 116 |
| Pgly | -GFIPSLLKRLLDERQEIKRKMKAS-KDPIEKKMLDYRQRAIKILANS----- 46 | 117 |
| Pgly2 | -GFIPSLLKRLLDERQEIKRRMKAS-KDPIEKKMLDYRQRAIKILANS----- 46 | 118 |
| PspGI-J | ---------QEIKRKMKAS-KDPIEKKKLDYRQRAIKILANSYYGYY 37 | 119 |
| Pfu | -GFIPSLLGHLLEERQKIKTKMKET-QDPIEKILLDYRQKAIKLLANSFYGYY 51 | 120 |
| vent2 | -GFIPSLLGHLLEERQKIKTKMKEQ-QDPIEKILLDYRQKAIKILANS----- 46 | 121 |
| Tsp_NA1 | -GFIPSLLGNLLEERQKIKRKMKAT-IDPLEKKLLDYRQRAIKILANS----- 46 | 122 |
| Tsp_GE8 | -GFIPSLLGDLLEERQKIKRKMRAT-IDPVEKKLLDYRQRAIKILANS----- 46 | 123 |
| 9degN | -GFIPSLLGDLLEERQKIKRKMKAT-VDPLEKKLLDYRQRAIKILANSFYGYY 51 | 124 |
| Tzil | -GFIPSLLGDLLEERQKVKKKMKAT-VDPIERKLLDYRQRAIKILANS----- 46 | 125 |
| dtok | -GFIPSLLGDLLEERQKVKKKMKAT-VDPIERKLLDYRQRAIKILANS----- 46 | 126 |
| Tful | -GFIPSLLGDLLDERQKVKKHMKAT-VDPIEKKLLDYRQRAIKILANSFYGYY 51 | 127 |
| Tgo | -G-IPSLLGDLLEERQKVKKKMKAT-IDPIEKKLLDYRQRAIKILANSFYGYY 50 | 128 |
| Tkod | -GFIPSLLGDLLEERQKIKRKMKAT-IDPIERKLLDYRQRAIKILANS----- 46 | 129 |
| Pho | -GFIPSLLGQLLEERQKIKKRMKES-KDPVEKKLLDYRQRAIKILANS----- 46 | 130 |
| Pab | -GFIPSLLGNLLEERQKIKKRMKES-KDPVEKKLLDYRQRAIKILANS----- 46 | 131 |
| PspST700 | -GFIPSLLGDLLEERQKIKKRMKES-KDPIEKKLLDYRQRAIKILANSFYGYY 51 | 132 |
| Tsp_GT | -GFIPSLLGALLDERQKIKKRMKAS-IDPLEKKLLDYRQKAIKILANSL---- 47 | 133 |
| Thy | -GFIPSLLGALLDERQKIKKRMKAS-IDPLEKKLLDYRQKAIKILANSL---- 47 | 134 |
| Taggr | -GFIPSILGELITMRQEIKKKMKAT-IDPIEKKMLDYRQRAVKLLANS----- 46 | 135 |
| Macetivorans | -GIVPSILEDLLNKRGDTKKRMKRT-SDENEHRVLDATQLAIKILLNSFYGY- 50 | 136 |
| Methanoburtonii | -GIVPSVLESLLDKRIETKKLLMKQA-SDEGEYQVLDATQLALKILLNSFYGY- 50 | 137 |
| Sulfotokodaii | -GLYKNVLEKLIQERKEVKKLMEKT-MDEYDKRVLDARQRALKVMANAFYGY- 50 | 138 |
| Sul_ohwakuensis | -GLYKNVLEKLIQERKEVKKLMEKT-IDEYDKRVLDARQRALKVMANAFYGY- 50 | 139 |
| Apernix | -GFFKKILERFLSWRRQIRSEMKHPPDSPEYKLLDERQKAIKLLANASYGY- 51 | 140 |
| Pocultum | -GFFKTVLENLLKLRRQVKEKMKEFPPDSPEYRLYDERQKALKVLANASYGY- 51 | 141 |
| Pyrobaculum | -GFIPLVLRQLIELRKRVREELKKYPPDSPEYRVLDERQRALKIMANAMYGY- 51 | 142 |
| Tvolcanium | -GLIPRILQELMADRDDVKKRMKEA-KSEDERLFYDGIQNAIKVLMNTFYG-- 49 | 143 |
| ScePolIpprimase | -GVLPRLLANLVDRRREVKKVMKTE-TDPHKRVQCDIRQQALKLTANSMYG-- 49 | 144 |
| Cruscytomegalovirus | PSILAELLTRWLAQRKAVRESMKRC-EDPMRRLLLDKEQALKVTCNSFYGF- 51 | 145 |
| Humanherpesvirus5 | ---LSELLNKWVSQRRAVRECMREC-QDPVRRMLLDKEQMALKVTCNAFYGF- 48 | 146 |
| | :      *  .      *      ..  *   .* | |

| | | |
|---|---|---|
| Deep | EIAKETQAKVLEAILKHGNVEEAVKIVKEVTEKLSKYEIPPEKLVIYEQITRPLHEYKAI | 677 |
| Pho | EIAKETQARVLEAILKHGNVEEAVKIVKDVTEKLTNYEVPPEKLVIYEQITRPINBYKAI | 1137 |
| Pfu | EIAKETQARVLETILKHGDVEEAVRIVKEVIQKLANYEIPPEKLAIYEQITRPLHEYKAI | 675 |
| Tgo | EIAKETQARVLEAILKHGDVBEAVRIVKEVTEKLSKYEVPPEKLVIYEQITRDLKDYKAT | 676 |
| Archaeal | EIAKETQARVLEALLKDGDVEEAVRIVKEVTEKLSKYEVPPEKLVIHEQITRDLKDYKAT | 676 |
| Jdf3 | EIAKETQARVLEAILRHGDVEEAVRIVKEVTEKLSKYEVPPEKLVIHEQITRELKDYKAT | 676 |
| 9oN | EIAKETQARVLEAILKHGDVEEAVRIVKEVTEKLSKYEVPPEKLVIHEQITRDLRDYKAT | 676 |
| Vent | EIAKETQAKVLEAILKEGSVEKAVEVVRDVVEKIAKYRVPLEKLVIHEQITRDLKDYKAI | 679 |
| | *****:*:.*.****..*:*.:**.*:* :******* | |
| Deep | GPHVAVAKRLAARGKVRPGMVIGYIVLRGDGPISKRAILAESFDLRKHKYDAEYYIENQ | 737 |
| Pho | GPHVAVAKRLMARGIKVKPGMVIGYIVLRGDGPISKRAISIEEFDPRKHKYDAEYYIENQ | 1197 |
| Pfu | GPHVAVAKKLAAKGVKIKPGMVIGYIVLRGDGPISNRAILAEEYDPKKHKYDAEYYIENQ | 735 |
| Tgo | GPHVAVAKRLAARGIKIRPGTVISYIVLKGSGRIGDRAIPFDEFDPAKHKYDAEYYIENQ | 736 |
| Archaeal | GPHVAVAKRLAARGVKIRPGTVISYIVLKGSGRIGDRAIPFDEFDPTKHKYDAEYYIENQ | 736 |
| Jdf3 | GPHVAIAKRLAARGVKIRPGTVISYIVLKGSGRIGDRAIPFDEFDPTKHKYDADYYIENQ | 736 |
| 9oN | GPHVAVAKRLAARGVKIRPGTVISYIVLKGSGRIGDRAIPADEFDPTKHRYDAEYYIENQ | 736 |
| Vent | GPHVAIAKRLAARGIKVKPGTIISYIVLKGSGKISDRVILLTEYDPRKHKYDPDYYIENQ | 739 |
| | **** *:*:* : ****:.:: ** :*.****;*.* *..*.* | |
| Deep | VLPAVLRILEAFGYRKEDLRWQKTKQTGLTAWLNIKKK-- | 775 | (SEQ ID NO:7) |
| Pho | VLPAVERILKAFGYRKEDLRWQKTKQVGLGAWIKVKKS-- | 1235 | (SEQ ID NO:8) |
| Pfu | VLPAVLRILEGFGYRKEDLRYQKTRQVGLTSWLNIKKS-- | 773 | (SEQ ID NO:3) |
| Tgo | VLPAVERILRAFGYRKEDLRYQKTRQVGLGAWLKPKT--- | 773 | (SEQ ID NO:9) |
| Archaeal | VLPAVERILRAFGYRKEDLRYQKTRQVGLSAWLKPKGT-- | 774 | (SEQ ID NO:10) |
| Jdf3 | VLPAVERILKAFGYRKEDLRYQKTRQVGLGAWLKPKGKKK | 776 | (SEQ ID NO:11) |
| 9oN | VLPAVERILKAFGYRKEDLRYQKTKQVGLGAWLRVKGKK- | 775 | (SEQ ID NO:12) |
| Vent | VLPAVLRILEAFGYRKEDLRYQSSKQTGLDAWLKR----- | 774 | (SEQ ID NO:13) |
| | *** *..*::**:*..:*.** :*:: | | |

Figure 2A-7

```
Deep        FIPSLLKRLLDERQEIKRKMKASKDPIEKKMLDYRQRAIKILAN   492  (from SEQ ID NO:7)
Pho         FIPSLLGQLLEERQKIKRKMKESKDPVEKKLLDYRQRAIKILAN   492  (from SEQ ID NO:8)
Pfu         FIPSLLGHLLEERQKIKTKMKETQDPIEKILLDYRQKAIKILAN   492  (from SEQ ID NO:3)
Tgo         FIPSLLGDLLEERQKVKKKMKATIDPIEKKLLDYRQKAIKILAN   491  (from SEQ ID NO:9)
Archaeal    FIPSLLGDLLEERQKIKKKMKATIDPIERKLLDYRQRAIKILAN   491  (from SEQ ID NO:10)
Jdf3        FIPSLLGNLLEERQKIKRKMKATLDPLEKNLLDYRQRAIKILAN   491  (from SEQ ID NO:11)
9oN         FIPSLLGDLLEERQKIKRKMKATVDPLEKKLLDYRQRAIKILAN   491  (from SEQ ID NO:12)
Vent        FIPSILGDLIAMRQDIKKKMKSTIDPIEKKMLDYRQRAIKLLAN   494  (from SEQ ID NO:13)
            ****:*  *:  **..:*  .:**  :  **:*: .:*******:****:***

Consensus   FIPSXLXXLXXXRQXXKXXMKXXXDPXEKXXLDYRQXAIKXLAN        (SEQ ID NO:5)
            FIPSBLXXLBXXRXXBKXZMKXJXDPBEKXBLDYRQZAIKBLAN        (SEQ ID NO:6)

B- M, V, L, I
J- S, T
U- F, Y
Z- Q, K, R

X- any amino acid
```

MILDVDYITENGKPVIRVFKKENGEFRIEYDREFEPYFYALLRDDSAIEE
IKKITAERHGRVVKVKRAEKVKKKFLGRSVEVWVLYFTHPQDVPAIRDKI
RKHPAVIDIYEYDIPFAKRYLIDKGLIPMEGEELKLMSFAIATLYHEGE
EFGTGPILMISYADESEARVITWKKIDLPYEVVSTEKEMIKRFLRVVKE
KDPDVLITYNGDNFDFAYLKKRCEKLGVSFTLGRDGSEPKIQRMGDRFAV
EVKGRVHFDLYPVIRRTINLPTYTLEAVYEAVFGKPKEKVYAEEIATAWE
TGEGLERVARYSMEDARVTYELGREFFPMEAQLSRLIGQGLWDVSRSSTG
NLVEWFLLRKAYERNELAPNKPDERELARRRGGYAGGYVKEPERGLWDNI
VYLDFRSHYPSIIITHNVSPDTLNREGCRSYDVAPEVGHKFCKDFPGFIP
SLLGNLLEERQKIARKMKAEDSKEDEGRR   (SEQ ID NO:97)

B

DNA:  GGCAGAAGATAGCAAGGAAGATGAAGGCAACTCTCGACCCGCTGGAGAAGA
+3:     Q   K   I   A   R   K   M   K   A   T   L   D   P   L   E   K   N
+1:   G   R   R   *   Q   G   R   *   R   R   Q   L   S   T   R   W   R   R (SEQ ID NOS:158-160)

C

MKATLDPLEKNLLDYRQR
AIKILANSYYGYYGYARARWYCRECAESVTAWGREYIEMVIRELEEKFGF
KVLYADTDGLHATIPGADAETVKKKAMEFLNYINPKLPGLLELEYEGFYV
RGFFVTKKKYAVIDEEGKITTRGLEIVRRDWSEIAKETQARVLEAILRHG
DVEEAVRIVREVTEKLSKYEVPPEKLVIHEQITRELKDYKATGPHVAIAK
RLAARGVKIRPGTVISYIVLKGSGXIGDRAIPFDEFDPTKHKYDADYYIE
NQVLPAVERILRAFGYRKEDLRYQKTRQVLGAWLKPKGKKK   (SEQ ID NO:98)

Figure 6

```
VENT      .........MILDTDYTTKDGKPVIRIFKKEN-GEFKIELDPHPQPYIYALLKDDSAIEEIKAI 54
TLI       .........MILDTDYTTKDGKPVIRIFKKEN-GEFKIELDPHPQPYIYALLKDDSAIEEIKAI 54
TFU       .........MILDTDYTTKDGKPITRIFKKEN-GEFKIELDPHPQPYIYALLKDDSAIDEIKAI 54
PAB       .........MILDADYITEDGKPITRIFKKEK-GEFKVEYDRTFNPYIYALLKDDSAIDEVEKI 54
PSP       .........MILDADYITEDGKPITRIFKKEK-GEFKVEYDRTFRPYIYALLKDDSAIDEVEKI 54
PHO       .........MILDADYITEDGKPITRIFKKEN-GEFKVEYDRNFNPYIYALLKDDSAIDEIEKI 54
ST700     .........MILDADYITENGKPITRLSKKEN-GKFKVSYDRSFRPYIYALLSKDDSAIDDVEMI 54
DEENVENT  .........MILDADYITEDGKPIIRIFSKEN-QEFKVEYDRNFKPYIYALLKDDSQIDSVRKI 54
PGL       .........MILDADYITEDGKPIIRIFNKEN-GEFKVEYDRNFKPYIYALLKDDSQIDEVKMI 54
PFU       .........MILDVDYITEEGKPVIRLFKKEN-GEFKIENDRTFNPYIYALLRDDSEIENVKMI 54
PWO-?     .........MILTDYITENGKPVIRVFKKEN-GEFKIEYDRTIFRPYFYALLKDDSAIEDVKSV 54
TSPGEB    .........MILTDYITEDGKPVIRVFRKEN-GEPKIEYDRNFSPYPYALLKDDSAIEBVRKI 54
TGO       .........MILTDYITEDGKPVIRIFKKEN-GEFKIDYDRNFEPTYALLKDDSAIEDVEKI 54
TZI       .........MILGADYITRDAGKPVIRVFKKEK-GEPKIDYDROPEPYTYALLKDDSAIEDIKKI 54
TSPNA1    .........MILDVDYITEDGKPVIRVFKKEK-GEFKIDYDROFEFYIYALLKDDSAIEBVRKI 54
TSPROD    .........MILTDYITEDGKPVIRIFKKEN-GEFKIBYDRTFRPYFYALLKDDSAIEBVEKI 54
TNY       .........MILTDYITEDGKPVIRIFKKEN-GEFKIBYDRTFSPYFYALLKDDSAIEBVEKI 54
SULSOLFO  MIDNFFILDFSYDVVSNKPVIYIWAIDKEGKNRYVLLEKKPEFYYALVDDNYNIDEIRKE 60
TOK       .........XFPVTTQQSSQ------------QTQPPQMKGITSPYSLAAPKETDCL 37
```

Figure 6, cont.

| | | |
|---|---|---|
| VENT | MGERHGKTVRVLDAVKVRKKFLGREVEVWKLIFSSPQDYPAMRGKIREHPAVVDIYEYDI | 113 |
| TLI | MGIERHGKTVRVLDAVKVRKKFLGREVEVWKLIPEHPQDYPAMRGKIREHPAVVDIYEYDI | 114 |
| TFU | MGERHGKIVRVVDAVKVNKKFLSGRDVEVWKLIPENPQDYPALRGKIREHPAVIDIYEYDI | 114 |
| PAB | TAERHGSIVRITEVEKVQKMFLGRPIEVWKLYEHPQDYPAIREKIREHPAVVDIFEYDI | 114 |
| PSP | TAERHGKIVRITEVEKVQMMFLGRPIEVWKLYLEHPQDYPAIREKIREHPAVVDIFSYDI | 114 |
| PHO | TAQRHGKIVRIVEVETSKIQKMFLGRMFLGRPIEVWKLYLEHPQDYPAIREKIREHPAVVDIFSYDI | 114 |
| SW700 | TSERHGKVVRVIDVEKVSKKFLGRPIEVWKLYFEHPQDYPAIRDKIREHPAVIDIFSYDI | 114 |
| DEEPVENT | TAERHGKIVRIIDASKVRKKFLGRPIEVWKLYFERPQDYPAIRDKIREHSAVIDIFSYDI | 114 |
| PGL | TAERHGKIVRIVDVEKVRKKFLGRPIEVWKLYFEHPQDYPAIRDKIREHPAVVDIFSYDI | 114 |
| PWO | TNERHGKIVRIVDVEKVEKMFLGKPITVWKLYFNHPQDYPFTIREKVREHPAVVDIFSYDI | 114 |
| 9ON-7 | TAERHGTVVKVRRAEKVQKMFLGRPIEVWKLYFNHPQDYPAIRDKIREHPAVIDIYSYDI | 114 |
| TSPGB8 | TAERHGTVVRVKRAEKVKKMFLGRPIEVWKLYFTHPQDYPAIRDKIRAHFAVVDIYSYDI | 114 |
| TGO | TAERHGTTVRSVRAEKVVKKMFLGRPIEVWKLYFTHPQDYPAIRDKIMEHPAVVDIYSYDI | 114 |
| TZI | TAERHGTTVRVTVRSVTRASRVRKKFLGRPVEVRKLYFTHPQDYPAIRDKIREHPAVVDIYEYDI | 114 |
| TSPNA1 | TAERHGKVVKVRAEKVNKKFLGRPVEVRKLYFERPQDYPAIRDKIRAHPGVIDIYEYDI | 114 |
| TSPKOD | TAERHGTVVTVKVRAEKVQKKFLGRPVEVRKLYFTHPQDYPAIRDKIREHQAVIDIYEYDI | 114 |
| THY | TAERHGTVVTVKVRSRVQKMFLGRPVEVRKLYFTHPQDYPAIRDKIREHPAVIDIYSYDI | 114 |
| SULFOSO | ILKLSKFYSPITSINVEEKMYFGSPVKVLKIETVIPAYVRVVRDKVAKINGVESVLEADI | 120 |
| TOK | LTQKLVETLRPPGVFEEEELQRRILLGMLNNLVREMINEISESKNLPQSVIENVGGMI | 97 |

Figure 6, cont.

| | | |
|---|---|---|
| VENT | PFAKRYLIDKGLIPMEGDE | ELKLLAFDIE 143 |
| TLI | PFAKRYLIDKGLIPMEGDE | ELKLLAFDIE 143 |
| TFU | PFAKRYLIDKGLIPMEGDE | ELKLMAFDIE 143 |
| RAS | PFAKRYLIDKGLIPMEGNE | RITFLAVDIE 143 |
| PSF | PFAKRYLIDKGLITPMEGNE | ELTFLAVDIE 143 |
| PWO | PFAKRYLIDKGLTPMEGNE | KLTFLAVDIE 143 |
| ST700 | PFAKRYLIDKGLIPMEGNE | ELSFLAVDIE 143 |
| DEEPVENT | PFAKRYLIDKGLIPMEGDE | ELKLLAFDIE 143 |
| PGL | PFAKRYLIDKGLIPMEGDE | ELKLLAFDIE 143 |
| PFU | PFAKRYLIDKGLIPMEGES | ELKLLAFDIE 143 |
| 9ON-7 | PFAKRYLIDKGLIPMEGDS | ELTMLAFAIA 143 |
| TSEGE8 | PFAKRYLIDKGLIPMEGDS | ELKMLAFDIE 143 |
| TGO | PFAKRYLIDKGLIPMEGDS | ELKMLAFDIE 143 |
| THI | PFAKRYLIDKGLIPMEGDS | ELRMLAFDIE 143 |
| TSPMA1 | PFAKRYLIDKGLVPMEGDS | ELKMLAFDIE 143 |
| TSFMOD | PFAKRYLIDKGLVPMEGDS | ELKMLAFDIQ 143 |
| TNY | PFAKRYLIDKGLVPMEGDS | ELKMLAFDIE 143 |
| SULFOTO | RFYMRYSTDNNLMPYWISARVESSKSNFRVKMVYELKIKINKLYEDKIFELKVLAFDIE 180 |
| TOK | FTIFGSYFLG | VNTNGADIG 115 |

Figure 6, cont.

```
VENT        TFYHEGD-EFGKGEIIMISYADEEEARVITWKNIDLPYVDVVSNEREMIKRFVQVVKEKD 202
TLI         TFYHEGD-EFGKGEIIMISYADEEEARVITWKNIDLPYVDVVSNEREMIKRFVQVVKEKD 202
TFU         TFYHEGD-EFGKGEIIMISYADEEEARVITWKNIDLPYVDVVSNEREMIKRFVQIVREKD 202
PAB         TLYHEGE-EFGKGPIIMISYADEEGAKVITWKSIDLPYVEVVSSEREMIKRLVKVIREKD 202
PSP         TLYHEGE-EFGKGPIIMISYADEEGAKVITWKSIDLPYVEVVSSEREMIKRLVKVIREKD 202
PHO         TLYHEGE-EFGKGPVIMISYADEEGAKVITWKKIDLPYVEVVSSEREMIKRLIRVIKEKD 202
ST700       TLYHEGE-EFGKGPIIMISYADEEGAKVITWKKIDLPYVEVVANEREMIKRLVRIIREKD 202
DEEPVENT    TLYHEGE-EFAKGPIIMISYADEEEAKVITWKKIDLPYVEVVSSEREMIKRFLKVIREKD 202
PGL         TLYHEGE-EFAKGPIIMISYADEEGAKVITWKKVDLPYVEVVSSEREMIKRFLKVIREKD 202
PFU         TLYHEGE-EFGKGPIIMISYADENEAKVITWKNIDLPYVEVVSSEREMIKRFLRIIREKD 202
9ON-7       TLYHEGE-EFGTGPILMISYADGSEARVITWKKIDLPYVDVVSTEKEMIKRFLRVVREKD 202
TSPGE8      TLYHEGE-EFAEGPILMISYADEEGARVITWKKVDLPYVDVVSTEKEMIKRFLRVVKEKD 202
TGO         TLYHEGE-EFAEGPILMISYADEEGARVITWKNIDLPYVDVVSTEKEMIKRFLKVVKEKD 202
TZI         TLYHEGE-EFGEGPILMISYADEEGARVITWKNIDLPYVESVSTEKEMIKRFLKVIQEKD 202
TSPNA1      TLYHEGE-EFGTGPILMISYADENEARVITWKKIDLPYVDVVSTEKEMIKRFLRVVKEKD 202
TSPKOD      TLYHEGE-EFAEGPILMISYADEEGARVITWKNVDLPYVDVVSTEREMIKRFLRVVKEKD 202
THY         TLYEEGE-EFAEGPILMISYADEEGARVITWKNVDLPYVDVVSTEREMIKRFLRVVKEKD 202
SULFOTO     VYNKYGSPNPREDPVIIIGVWTKEGGKQFLADKYD---------DLRAIEEFINPVQTYD 231
TOK         ALCVAPK--HVDRSDFFTSFYDKLKLQ-------------------ESVKDLRAVEEAFV 154
            .              :: .       :                   . :: :  . .
```

| | |
|---|---|
| VENT | |
| TLI | |
| TFU | IDGWQRVKKVWKYHYEGSLININGLKCTFMHKVPVVTKNEPQTRLRDSLAKSFLSGKVKG 498 |
| PAB | |
| PSF | |
| PHO | |
| ST700 | |
| DEEPVENT | |
| POL | |
| PFU | |
| 9ON-7 | |
| TSPGE8 | |
| TGO | |
| TZI | |
| TSPNA1 | |
| TSPKOD | IDGWQRVKRVWEYDYKGRLWNINGLKCTFMHKLPVVTKNEPQTRLRDSLAKSFLTKKVKG 495 |
| THY | |
| SULFOTO | |
| TOK | |

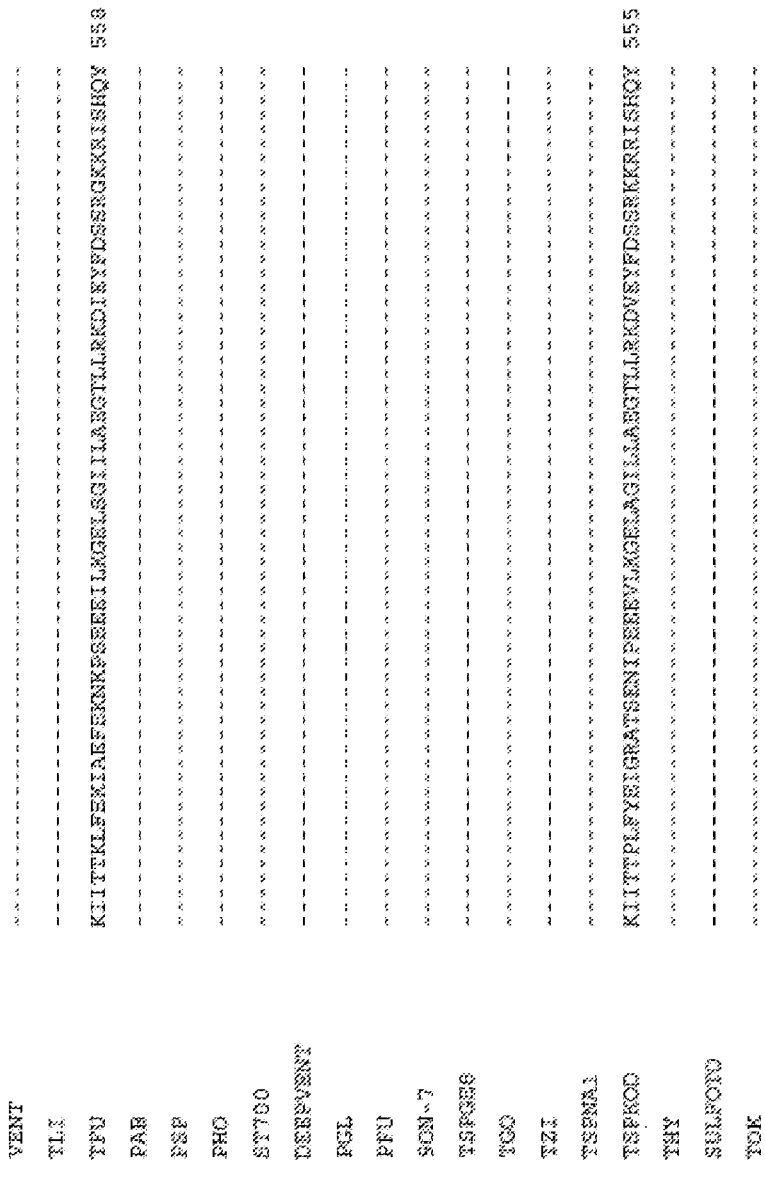
Figure 6, cont.

Figure 6, cont.

| | |
|---|---|
| VENT | |
| TLI | |
| TFU | RVEITIGHMERKELERILYIPCKLFGIRPSVKRKSDTNALKITTAKKAVYLQIEELLKNI 618 |
| PAB | |
| PSP | |
| PHO | |
| ST700 | |
| DEEPVENT | |
| PGL | |
| PFU | |
| 9ON-7 | |
| TSPGE8 | |
| TGO | |
| TZI | |
| TSPNA1 | |
| TSPKOD | RVEITIGKDEEFRDRITYIPEELFGITPSISRRKSTNAVTLKVAXKNVYLKVKSIMDNI 615 |
| THY | |
| SULFOTO | |
| TOK | |

```
VENT    ------------------------------------------------------
TLI     ------------------------------------------------------
TVO     ENGKELTKHILEITGRDGLILFQTLVGPISSEKNEALEKAIEVKEMNRLKKNSFYNLSTF 738
PAB     ------------------------------------------------------
9SP     ------------------------------------------------------
PHO     ------------------------------------------------------
ST700   ------------------------------------------------------
DEEPVENT------------------------------------------------------
PGL     ------------------------------------------------------
PFU     ------------------------------------------------------
9ON-7   ------------------------------------------------------
TSPGE8  ------------------------------------------------------
TGO     ------------------------------------------------------
TZI     ------------------------------------------------------
TSPWA1  ------------------------------------------------------
TSPKOD  ENGKKDRSKYILEITSEDGLILFQTLIGPISERKNALLKKAISQRENNMILENNGFYRLSEF 735
THY     ------------------------------------------------------
SULFOTO ------------------------------------------------------
TOK     ------------------------------------------------------
```

```
VENT       IVGYRFCKDFPGFIPSILGDLIANRQITKRQMXSTIDFIEKKMLDYRQRAIKLLANSILP  498
TLI        IVGYRFCKDFPGFIPSILGDLIAMRQDIIAMRQDIKRNMSTIDFIEKKMLDYRQRAIKLLAN-----  494
TFU        IVGYRFCKDFPGFIPSILGDLITNRQHIKKRQNATIDFIEKKMLDYRQRAVKLLANSILP  858
PAB        QVGHRFCKDFPGFIPSILLGNLLEERQKIKRMESSKDFVEKKLLDYRQRAIKILAN-----  492
95P        QVGHRFCKDFPGFIPSILLGNLLEERQKIKRMNESSKDFVEKKLLDYRQRAIKILAN-----  492
SHO        KVGHRFCKDFPGFIPSILLGQLLEERQKIKRMNESSKDFVEKKLLDYRQRAIKILANSILP  496
ST700      EWGHRFCKDFPGFIPSILLGDLLEERQKIKKRMXESRDFIEKKLLDYRQRAIKILAN-----  492
DEEPVENT   EVGHRFCKDFPGFIPSILLKRLLDERQKIKRNMASKDFIERKMLDYRQRAIKILANSILP  495
PGL        SVGHRFCKDFPGFIPSILLKRLLDERQKTKRNMASKDFIEKILLDYRQRAIKILAN-----  492
PFU        QVGHRFCKDIPGFIPSLLGNLLEERQKITPQMSTQDFIEKILLDYRQRAIKLLAN-----  492
9QN-7      EVGHRFCKDFPGFIPSILLGDLLEERQKIKRNMXATVDFLEKKLLDYRQRAIKILAN-----  492
TSPGE8     QVGHRFCKDFPGFIPSILLGDLLEERQKIKRQMXATIDFVEKKLLDYRQRAIKILANSILP  495
TGO        QVGHRFCKDFPGFIPSILLGDLLEERQKVKKRNMASVDFIEKKLLDYRQRAIKILAN-----  492
TZI        QVGHRFCKDFPGFIPSILLGDLLEERQNVKKRNKATVDFIERNLLDYRQRAIKILANSILP  495
TSPNA1     QVGHRFCKDFPGFIPSILLGNLLEERQKIKRRNMATIDFLEKKLLDYRQRAIKILANSILP  495
TSPKOD     QVGHRFCKDFPGFIPSILLGDLLEERQKIKRQMXATIDFIERNLLDYRQRAIKILANSILP  855
TNY        QVGHRFCKDFPGFIPSILLGDLLEERQKIKRQMXATIDFIERSLLDYRQRAIKILAN-----  492
SULFOTO    -AGHKFRKDPPGLYKNVLEKLIQERKEVNKCMSKTNDETDKRVLDARQRALKVMAN-----  515
TOK        ILTPAYFQQNSTINVSVSTKXVX------VRRSRKQGLATTDEILLS------  384
```

| | | |
|---|---|---|
| VENT | TFNRYLFHLEKLGLIKLLPRGYEVTDNSRLKKYKQLYEKLAGSSVKYNGNKRSYLVNFNES | 738 |
| TLI | | |
| TYU | TFNRYLFHLEELGFVKLLPRGYEVTDWEGLKRYRQLYEMLVKRLRYNGNMREYLYKFNDI | 1098 |
| SAB | | |
| PSP | | |
| PHO | TAGRYLKHLERLGYVRLKRRQCEVLSWEGLKFYRKLYETLIRQLLKTNGNSRAVMYEFNSL | 735 |
| ST700 | | |
| DEEPVENT | TASRYLRHLENLGYIRLRMLGYDLIDKEGLEKYRTLVEKLVDVVRYNGNMKREYLVEFNAV | 735 |
| PGL | | |
| FFU | | |
| 9°N-7 | | |
| TSPGE8 | TARRYLEHLQRLGYVRLMKRAYEIVNKEALRMYRKLYEVLAERVEYNGNMREYLVEFNDL | 732 |
| TGO | | |
| TZI | TARRYLEHLQRLGYVRLQKIGYEIVNEEALRDYRGLYETLIGKVKYNGNVKREYLVHFNDI | 732 |
| TSPNA1 | TARRYLEHLQRLGYVRLMKIGYEVLSEKALRKYEALYEVLAEKVEYNGNNKREYLVAFNDL | 732 |
| TSPKOD | TARRYLRHLERLGYVRLMKIGYEVLSWDSLKMYRRLYEALVENVRYNGNMKREYLVSFNGI | 1094 |
| THY | | |
| SULFOTO | | |
| TOK | | |

Figure 6, cont.

| | | |
|---|---|---|
| VENT | KDFISYFPQKELSEWKIQTLNGFRTNCIAVDEDPGKLLGYYVSEGYAGAQRNWTGGISY | 798 |
| TLI | | |
| TFU | KDSVSCTFRKELEEWKIQTAKGFRKKCIAVDEDFGKFLGYYVSEGYAGAQRNWTGGMSY | 1158 |
| PAB | | |
| PSP | | |
| PHO | RDVVSLMFIBELKEWIIGEPRGWKLGTFIDVEDSPAKLLGYYISSQDVEKDR- | 787 |
| ST770 | | |
| DEEPVENT | RDVISLMFEBELKEWRIGTRNGFRMGTFVDIEDFAKLLGYYVSEGSARWKNQTGGMSY | 795 |
| PGL | | |
| PFU | | |
| 9ON-7 | | |
| TSPGE8 | RMEIKPMPDELLEWKVGTLNGFRMEPFIENGEDPAKLLGYYVSEGYARMQRNQKNGNSY | 793 |
| TGO | | |
| TZI | RDIIRLMPEKELFEWKVGTLNGFRMETSIEVKEDFAKLLGYYVSEGYAGEQRSQKHGNNY | 792 |
| TSPMA3 | RDMIEPMPEESLREWKIGTLNGFRMEPFIEVNRDLAKLLGYYVSEGYAGMQRNQRNGNSY | 792 |
| TSPKOD | RDAYGIMPLKELKEWKIQTLNGFRNRKLIEVSBSLAKLLGYYVSEGYARMQRNSKNGNSY | 1164 |
| THY | | |
| SULFOTO | | |
| TOK | | |

Figure 6, cont.

| | | |
|---|---|---|
| VENT | SVKLVNSDFNVLSSMKNVAEKFFGRVEVDRNCVSISKKMAYLVMKCLCGALAENKRIPSV | 858 |
| TLI | | |
| TFU | SVELVNEMFNVLEDMKNIARKFFGKVEVGKNCVDIPKKMAYLLAKSLCGVTAENKRIPSI | 1218 |
| PAB | | |
| PSP | | |
| PHO | -VSPHSKDQNVLEDIAKLABRLFGKVERGKGYIEVSGKISHAIFRVLABGKRIPEPIFTS | 846 |
| ST700 | | |
| DSRPVENT | TVRLVNSMDENLDDMSNLAKFFGKVKRGSNYVEIPKKMAYIIPSSLCGTLAENKRVFEV | 855 |
| PGL | | |
| PFU | | |
| 9CM-7 | | |
| TSPGE8 | SVELYNNDQNVLDNMERLASKFFGKVVRGKNYVEISKKMAYYLFRSLCGTLAENKRVPEV | 852 |
| TGO | | |
| TZI | SVELYNNDQNVLDNMETLASKFFGKVVRGKRNYVEIPRKMAYVLFRSLCGTLAENKRVPSI | 852 |
| TSPNA1 | SVELYNNDQKVLDNERLASKFFGKVVRGRRNYVEMPKKMAYVLFRSLCGTLAENKRVPSV | 852 |
| TSPWOD | SVELYNNEDPEVLDDMERLASPFGKVVRGRNYVEIPKKIGYLLFENMCGVLAENKRIPSP | 1214 |
| TNY | | |
| SULSOTO | | |
| TOK | | |

Figure 6, cont.

| | | |
|---|---|---|
| VENT | ILNSSEPVRWSFLEAYFTQIKSDIHFSKRFRLSTKSELLANQEVFLLMSLQISSVKIGFDS | 918 |
| TLI | | |
| TFU | IFDSSEPVRWAFLRAYFVGIKGDIHFSKRLRLSTKSELLANQLVFLLMSLQVSSIRIGFDS | 1278 |
| PAB | | |
| PSP | | |
| PHO | SMDIKVAFL~~~~~~~~~~KGLMGNAEELTFSTKSELLVNQLILLLNSIGVSDIKIEHEM | 895 |
| SY700 | | |
| DEEPVENT | IFTSSKGVRWAFLEGYFIGDGDVNFSKRVRLSTKSELLVNGLVLLMSLGVSAIKLGYDS | 915 |
| PGL | | |
| PFU | | |
| 9ON-7 | | |
| TSINGER | IFTSPESVRWAFFEGYFIQDGDLNFGKSVRLSTKSEELVNGLVLLMSLGISAIKIRFDS | 913 |
| TGO | | |
| TZI | IFTSPESVRWAFLEGCFIQDGDLNFGKSVRLSTKSEELVNGLVILLNSLGVSALRINFDS | 913 |
| TSPNAL | IFTSPENVRWAFLEGYFIQDGDNRFSKSVRLSTKSETLVNGLIILLNSLGISAVKIRFBS | 913 |
| TSPKOD | VFTSPKGVRLAFLEGYSSANATSTRQSYQRLMEK~EALANQLVLLNSVGVSAVKLGNDS | 1273 |
| THY | | |
| SULSOLO | | |
| TOK | | |

```
VENT       REKAKLLEFFLNGSIVLDRVKSVKEKDYEGYVYDLSVEDMENFLNGFPSLLYAHNSYYGYM  1036
TLI        ----------------------------------------------------SYYGYM  500
TFU        KRKVRLLDPLLNGDIVLDRVKNVERKREYEGYVYDLSVEDMENFLNGFGLLYAHNSYYGYM  1198
PAB        ----------------------------------------------------SYYGYY  498
PSP        ----------------------------------------------------SYYGYY  498
PHO        -------SNGGDIVLDSVESIEVEKYESYVYDLSVEDMENFLNGFGLLYAHNSYYGYY  958
ST700      ----------------------------------------------------SFYGYY  498
DEEPVENT   REKAKRIEWLLNGDIVLDRVEISREYYDGYVYDLSVEDDENFLAGFGFLYAHNSYYGYY  1035
PGB        ----------------------------------------------------SYYGYY  498
PFU        ----------------------------------------------------SFYGYY  497
9GN-7      ----------------------------------------------------SFYGYY  497
TSP-GEB    AQWAKRRIAWLLRGDYVLDRVERKVTYEGYVEGYVYDLSVEEMENFLAGFGMEYAHNSYYGYY  1032
TGO        ----------------------------------------------------SFYGYY  497
TZI        AEKYKRVWLLRGDYVLDRVESVAVDDYEGYVYDLSVEEMENFLAGFGMEYAHNSYYGYY  1029
TSPMA1     QEKAKRISWLLEGDIVLDRVEEVEVEDYSGYVYDLSVEEMENFLAGFGMIYAHNSYYGYY  1032
TSPKOD     PEKAQRLSWLIRGFYVLDRVESVGVEDYSGYVYDLSVEDMENFLVGFGLYAHNSYYGYY  1393
TNY        ----------------------------------------------------SYYGYY  497
SULFOTO    ----------------------------------------------------AFYGYM  521
TOK        ------------------------------------------------------------
```

Figure 6, cont.

| | | |
|---|---|---|
| VENT | GYPKARWYSKECAESVTAWGRHYITEMYIREIEEMFGFKVLYADSVSGESEIITEQNGKIR | 1096 |
| TLI | GYPKARWYSKECAESVTAWGRHYIEMYIREIEERFGFKVLYAD--------------- | 543 |
| TFU | GYPKARWYSKECAESVTAWGRHYIEMYIKEIEERFGFKVLYADSVTGDTRIIVRPNGKIE | 1458 |
| PAB | GYAKARWYCKECAESVTAWGRQYIDLVRRELSSR-GFKVLYID--------------- | 540 |
| PSF | GYAKARWYCKECAESVTAWGRQYIDLVRRELSAR--GFKVLYID--------------- | 540 |
| PNO | GYAKARWYCKECAESVTAWGRQYIDLVRRELSAR--GFKVLYID--------------- | 1000 |
| ST700 | GYAKARWYCKECAESVTAWGRQYIELVRRELSFR-GFKVLYID--------------- | 540 |
| DEEPVENT | GYAKARWYCKECAESVTAWGREYIEFVRKELSERKGFKVLYID--------------- | 1078 |
| PGL | GYAKARWYCKECAESVTAWGREYIEFVRKELSERKGFKVLYID--------------- | 541 |
| PFU | GYAKARWYCKECAESVTAWGRKYIELVWKELAREKFGFKVLYID--------------- | 541 |
| 9CN-7 | GYAKARWYCKECAESVTAWGRSYIETYIREIEERFGFKVLYAD--------------- | 540 |
| TSFGE8 | GYAKARWYCRECAESVTAWGRQYIETYIREIEERFGFKVLYADSVAGNTEVLIRENGKYS | 1092 |
| TGO | GYAKARWYCKECAESVTAWGRQYIETYIREIEERFGFKVLYAD--------------- | 540 |
| TZI | GYANARWYCRECAESVTAWGRQYIETYMREIEERFGFKVLYADSVTGDTEVIIRENGRIE | 1089 |
| TSPNA1 | GYPKARWYCKECAESVTAWGREYIEMYIRRIEERKYGFKVLYAD--------------- | 1075 |
| TSPROD | GYAKARWYCKECAESVTAWGREYINMYIKEIEEKYGFKVLYSD--------------- | 1436 |
| THY | GYRKARWYCKECAESVTAWGREYINMYIMTIREIERKYGFKVLYSD--------------- | 540 |
| SULFOTO | GWLGARWYSKEGAEAVTAWGRQTISRSAKIANEK-GFTVIYGD--------------- | 543 |
| TOK | ----KAEWSKLFEAPNFFQKYKHYIVLLASASTEK--------------- | 385 |

Figure 6, cont.

| | | |
|---|---|---|
| VENT | FVPKIKDLFSRVDYSIGEKEYCILEGVEALTLDDGKKLVKKPVPVVNRRPANKEMFRIWLT | 1158 |
| TLI | | |
| TFU | FVPIEKLFERVDYRIGREEYCILEGVEALTLGNRRGKLIWKKVPFYVMNRAKKKVYRIWIT | 1518 |
| PAB | | |
| PSP | | |
| PWO | | |
| ST700 | | |
| DEEPVENT | | |
| RGL | | |
| PFU | | |
| 9CM-7 | | |
| TSPGEO | FVPIEKLFQRVDYRIGEKEYCALEGVEALTLDNRGRLVNKRVPFYMRHSNKKIYRVMFT | 1152 |
| TGO | | |
| TZI | FVPIERLFERVDYRVGEKEYCVLSGVEALTLDNRGRLVNKKVPFYMRHTSGKKIYRVWVT | 1149 |
| TSPWA1 | | |
| TSPKOD | | |
| THY | | |
| SULFOTO | | |
| TOK | | |

Figure 6, cont.

| | | |
|---|---|---|
| VENT | NSWYIDVTEDMSSLIGYLMTSKTXTAKKIGERLKSVKPSSLGKAVRSLIGFMARPKDRNTK | 1218 |
| TLI | | |
| TFU | NSWYISVTEDMSLIVAEDG | 1537 |
| PAB | | |
| PSP | | |
| PHO | | |
| ST700 | | |
| DEEPVENT | | |
| PGL | | |
| FFU | | |
| 9ON-7 | | |
| TSPGE8 | NSWYLSVTEDMSLIGYLMTSKVKSEKFLKERLVEVKPRELGERVKSLITLNRAIA-ESIK | 1211 |
| TGO | | |
| TZI | NSWYLRVTEDMSLIGYLDGMYLEISPADIPMDSDIKLITLASPGLGBVALKT--------- | 1301 |
| TSFNA1 | | |
| TSPKOD | | |
| THY | | |
| SULFOTO | | |
| TOK | | |

Figure 6, cont.
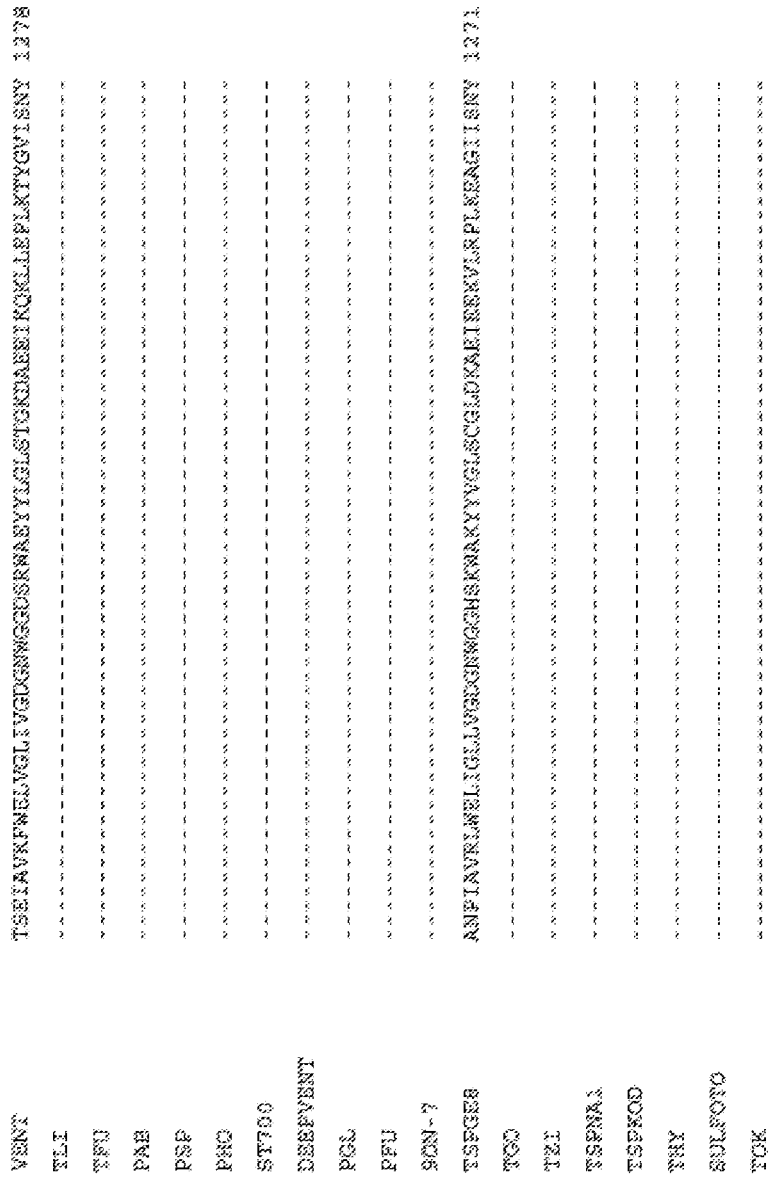

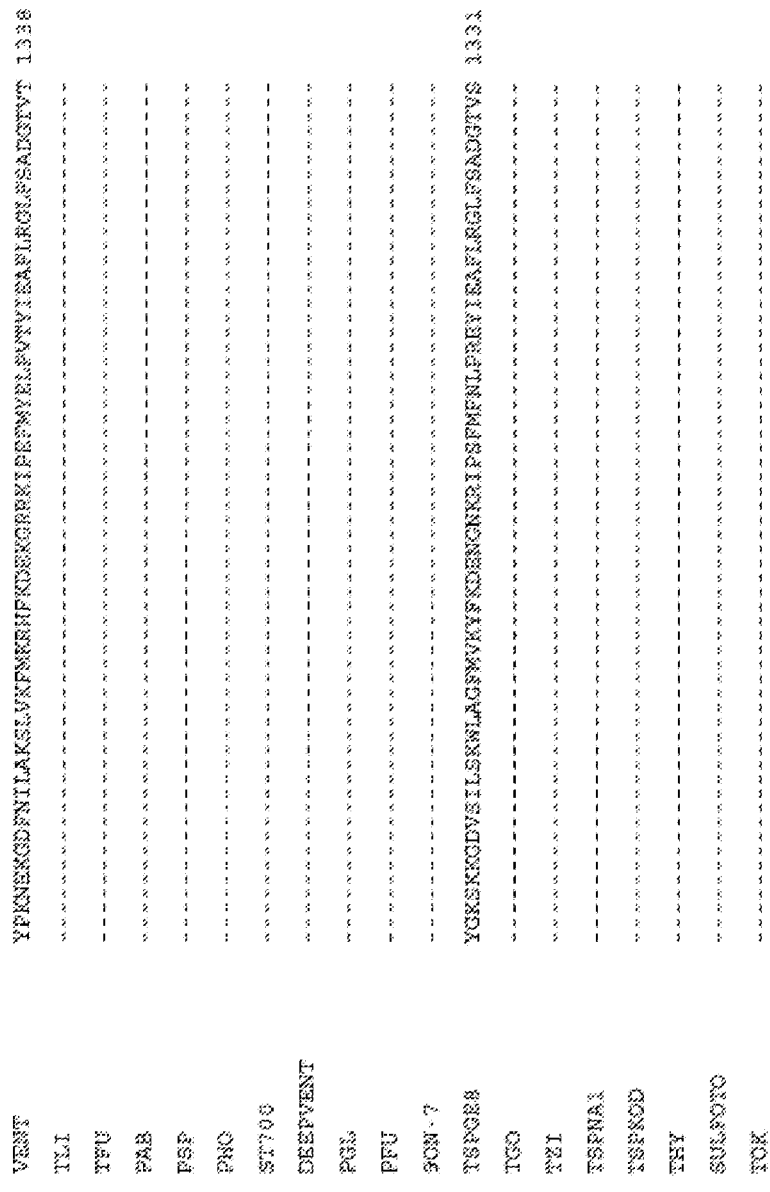
Figure 6, cont.

Figure 6, cont.

| | |
|---|---|
| VENT | LRKGVPEIRLINIDADFLREVEKLLWIVGISNSIFAETTPNRINGVSTSTYSKHLRIKNK 1398 |
| TLI | |
| TFU | |
| PAB | |
| PSP | |
| PHO | |
| ST700 | |
| DEEPVENT | |
| PGL | |
| PFU | |
| 9ON-7 | |
| TSPGE8 | LRKGIPEIRLTSVNRELSNEVEKLLWLNGVSNSMFTETTPNKYLRNESGTRSIHVEIKNK 1391 |
| TGO | |
| KZI | |
| TSPMA1 | |
| TSPKOD | |
| THY | |
| SULFOTO | |
| TOK | |

Figure 6, cont.

| | | |
|---|---|---|
| VENT | RRFAKRIGFLIERNQKRLLERLKGARVKRNTIDFGFDLNVYKKVEEIFYEGYVVDIEVES | 1458 |
| TLI | ------------------------------------------------------------ | |
| TFU | ------------LNEARWSIEGKSLIATKDDLSQVEYIKFEAIREISYNGYVYDIEVES | 1585 |
| RAB | ------------------------------------------------------------ | |
| PSP | ------------------------------------------------------------ | |
| PHO | ------------------------------------------------------------ | |
| ST700 | ------------------------------------------------------------ | |
| DEEPVENT | ------------------------------------------------------------ | |
| PGL | ------------------------------------------------------------ | |
| PFU | ------------------------------------------------------------ | |
| 9ON-7 | ------------------------------------------------------------ | |
| TSPGB3 | RRFAKRIGFLLGTRKATKLSDNLREHTNKKMAYRYDFNLYFKRIESNTDRYVTDIEVRG | 1491 |
| TGO | ------------------------------------------------------------ | |
| TZI | ------------------------------PSRLEETYEGYVVDIEVRG | 1221 |
| TSPNA1 | ------------------------------------------------------------ | |
| TSFKOD | ------------------------------------------------------------ | |
| THY | ------------------------------------------------------------ | |
| SULFOTO | ------------------------------------------------------------ | |
| TCK | ------------------------------------------------------------ | |

| | | |
|---|---|---|
| VENT | FFVT-KKRYAVIDEEGKITTRGLEVVRRDWSEIAKETQARVLEAILKEGSVEKAVEVVRD | 1576 |
| TLI | KKRYAVIDEEGRITTRGLEVVRRDWSEIAKETQARVLEAILKEGSVEKAVEVVRD | 648 |
| TFU | FFVA-KKRYAVIDEEGRITTRGLEVVRRDWSEIAKETQAKVLEAILKEDSVEKAYEIVKD | 1703 |
| PAB | FFVT-KKKYALIDEEGKIVTRGLEIVRRDWSEIAKETQAKVLEAILKHGNVDEAVKIVKE | 645 |
| PSP | FFVT-KKKYALIDEEGKIVTRGLEIVRRDWSEIAKETQAKVLEAILKNGNVDEAVKIVKE | 645 |
| PHO | FFPT-KKKYALIDEEGKIVTRGLEIVRRDWSEIAKETQAKVLEAILKHGNVEEAVKIVKE | 1106 |
| ST700 | FFVT-KKKYALIDEEGKIITRGLEIVRRDWSEIAKETQAKVLEAILKNGNVEEAVKIVKE | 646 |
| DEEPVENT | FFVT-KKKYALIDEEGKIITRGLEIVRRDWSEIAKETQAKVLEAILKHGNVEEAVKIVKE | 1183 |
| PGL | FFVT-KKKYAVIDEEGKITRGLEIVRRDWSEIAKETQAKVLEAILKNGNVEAVKIVKE | 646 |
| DFU | FFVT-KKRYAVIDEEGKIVTRGLEIVRRDWSEIAKETQARVLETILKHGDVEEAVRIVKE | 646 |
| 9CM-7 | FFVT-KKKYAVIDEEGKITTRGLEIVRRDWSEIAKETQARVLEAILKHGDVEEAVRIVKE | 645 |
| TSPGE8 | FFVT-KKKYAVIDEEGKITTRGLEIVRRDWSEIAKETQARVLEAILKNGDVEBAVRIVKE | 1569 |
| TGO | FFVT-KKKYAVIDEEGKITTRGLEIVRRDWSEIAKETQARVLEAILKHGDVEEAVRIVKE | 645 |
| TZI | FFVT-KKKYAVIDEEGKITTRGLEIVRRDWSEIAKETQARVLEAILKHGDVEEAVRIVKE | 1339 |
| TSPKA1 | FFVT-KKKYAVIDEEGKIVTRGLEIVRRDWSDIAKETQARVLEALLEDGNVEKAVKIVKE | 1180 |
| TSPKOD | FFVT-KKKYAVIDEEGKITTRGLEIVRRDWSEIAKETQARVLEAILKDGDVEKAVRIVKE | 1541 |
| TNY | FFVT-KKKYAVIDEEGKITTRGLEIVRRDWSEIAKETQARVLEALKDGSVEKAVRIVKE | 645 |
| SULSOLO | FFTRNKKRYAGLTEDGKIDIVGFEAVRGDWCDLAKQVQFNVIELILKSGKVEDAIKYVKT | 659 |
| TOK | AKVN-PQSFVAPKENF--------DKEEFRTXFVIGLVFKKTENSENLSVD | 455 |

Figure 6, cont.

```
VENT     VTEKIAKYEVPLEKLVIHEQITEDLKDYKAIGPHVAIAKELAAKGIKVKFGTIISYIVLK 1635
TLI      VTEKIAKYEVPLEKLVIHEQITRDLKDYKAIGPHVAIAKRLAAKGIKVKPGTIISYIVLK  706
TFU      VTEKIAKYQVPLEKLVINEQITEDLGEYKAIGPHVAIAKELAAKGIKVREGTIISYIVLR 1763
PAB      VTEKLSKYEIPPEKLVIYEQITRPLSEYKAIGPHVAIAKELAAKGVEYKPGMYIGYIVLR  705
PSP      VTEKLSKYEIPPEKLVIYEQITRPLSEYKAIGPHVAVAKRLAAKGVKYKPGMVIGYIVLR  705
PHO      VTEKLINYEVPPEKLVIYEQITRPINEYKAIGPHVAVAKRLMARGIKVKEGMVIGYIVLR 1166
ST700    VTEKLSNVEIPVEKLVIYEQITEQITNPLMEYKAIGPHVAVAKRLAAKGIKIKFGMVIGYVLLR  706
DEEPVENT VTEKLSKYEIPPEKLVIYEQITRPLHEYKAIGPHVAIGPHVAVAKRLAARGVEVKFGMVIGYIVLR 1243
PGL      VTEKLSKYEIPPEKLVIYEQITRPLHEYKAIGPHVAVAKRLAAKGVEVKPGMVIGYIVLR  706
PFU      VIQKLANYEIPPEKLAIYEQITRPLHEYKAIGPHVAVAKRLAAKGVIKPGTVIGYIVLR  706
9ON-7    VTEKLSKYEVPPEKLVIHEQITRDLRDYKAIGPHVAVAKRLAARGVIKINEGTVIEGTVISYIVLK  705
TSPGB8   VTEKLSKYEVPPEKLVIYEQITRDLKDYKAIGPHVAVAKRLAAKGIKIKFGTVIEPGTVIKFGTVISYIVLR 1829
TGO      VTEKLSKYEVPPEKLVIYEQITRDLRDYKAIGPHVAVAKRLAAKGIKIKFGTVISYIVLK  705
TZI      VTEKLSNYEVPPEKLVIYEQITRCLRDYKAIGPHVAVAKRLAAKGIKIKFGTVISYIVLK 1399
TSPNA1   ITEKLSKYEIPPEKLVIHEQITRELKDYKAIGPHVAIARKLAAKGIKVKFGTVISYIVLK 1240
TSPKOD   VTEKLSKYEVPPEKLVIHEQITRDLKDYKAIGPHVAVAKRLAAKGIKVKFGTVISYIVLK 1801
THY      VTEKLSKYEVPPEKLVINEQITEDLKDYKAIGPHVAIGPHVAVAKRLAAKGVKIKFGTVISYIVLK  705
SULFOTO  VIRLRFYMFRIEDLIINKTIGKNLDRYDVTAPKVVRAKRKAAAKAGYIVSKGVRLIGYIVKR  719
TOK      LCVDIDIQSFTDTVYRQAIMEKX--------FEVDKKLAAKHVRSKQ---------   492
```

| | | |
|---|---|---|
| VENT | DAWLKR---- 1702 | (SEQ ID NO: 57) |
| TLI | DAWLKR----- 774 | (SEQ ID NO: 58) |
| TFU | DAWLKK----- 1849 | (SEQ ID NO: 59) |
| PAB | GAWLKF----- 771 | (SEQ ID NO: 60) |
| PSP | GAWLKF----- 771 | (SEQ ID NO: 61) |
| PHO | GAWLKVKKS-- 1235 | (SEQ ID NO: 62) |
| ST700 | ---------- | (SEQ ID NO: 63) |
| DEEPVENT | TAWLNIKKK-- 1312 | (SEQ ID NO: 64) |
| PGL | TAWLNVKKK-- 775 | (SEQ ID NO: 65) |
| PFU | TSWLNIKRS-- 775 | (SEQ ID NO: 66) |
| MON-? | GAWLKVKGKK 775 | (SEQ ID NO: 67) |
| TSPGE8 | GAWLKVKGKK 1699 | (SEQ ID NO: 68) |
| TGO | GAWLPKT--773 | (SEQ ID NO: 69) |
| TZI | GAWLPKT-1467 | (SEQ ID NO: 70) |
| TSPNA1 | GAWLPKK-1308 | (SEQ ID NO: 71) |
| TSPROD | SAWLMPKGT- 1670 | (SEQ ID NO: 72) |
| THI | SAWLPKGT-- 774 | (SEQ ID NO: 73) |
| SULFOTO | LSFVKK----- 781 | (SEQ ID NO: 74) |
| TOK | ---------- | (SEQ ID NO: 75) |

Figure 7

| Species | Sequence | SEQ ID NO |
|---|---|---|
| JDF-3 | GFIPSLLGNLLEERQKIKRKMKATLDPI | 33 |
| PHO | GFIPSLLGQLLEERQKIKKRMKESKDPV | 34 |
| PAB | GFIPSLLGNLLEERQKIKKRMKESKDPV | 35 |
| PSP | GFIPSLLGNLLEERQKIKKRMKESKDPV | 36 |
| VENT | GFIPSLILGDLIAMRQDIKKKMKSTIDPI | 37 |
| DEEPVENT | GFIPSLLGDLLEERQKIKRKMKATVDPL | 38 |
| 9ON-7 | GFIPSLLGDLLEERQKIKRKMKATIDPI | 39 |
| TGO | GFIPSLLGDLLDEROKVKKHMKATIDPI | 40 |
| TFU | GFIPSLLGDLLEERQKVKKHMKATVDPI | 41 |
| ST700 | GFIPSLLGDLLEERQKIKRMKESKDPI | 42 |
| PFU | GFIPSLLGHLLEERQKIKTKMKETQDPI | 43 |
| TSPGE8 | GFIPSLLGDLLEERQKIKRKMNRATHDPV | 44 |
| TLI | GFIPSLLGDLIAMRQDIKKKMKSTIDPI | 45 |
| TSPNA1 | GFIPSLLGNLLEERQKIKRKMKATIDPI | 46 |
| TSPKOD | GFIPSLLGDLLEERQKIKKKMKATIDPI | 47 |
| TZI | GFIPSLLGDLLEERQKVKKKMKATVDPI | 48 |
| THY | GFIPSLGALDEROKIKKRMKASIDPI | 49 |
| PGL | GFIPSLKRLDEROKIKRKMKMKASKDPI | 50 |
| SULFOTO | GLYKNVLEKLIQEKKEVKKLMEKTMDEY | 51 |
| TOK | GFIPSLLGDLLEERQKIKRKMKATVDPL | 52 |
| consensus II | GXXXXXXIXXIXXXXXXXXXXXMXXXXDXX | 53 |
|  | GXXXXXBLXXIBXXXXBXXXXMXXXJXDXX | 54 |
| consensus III | GFIPSXXIXXIXXXXXRQXXKXXXXMZXXXDPX | 55 |
|  | GFIPSBLXXIBXXXBXXXBXXXMZXJXDPB | 56 |
| B- M,V,L,I |  |  |
| J- S,T |  |  |
| O- D,E |  |  |
| U- F,Y |  |  |
| Z- Q,K,R |  |  |
| X- any amino acid |  |  |

Figure 7, cont.

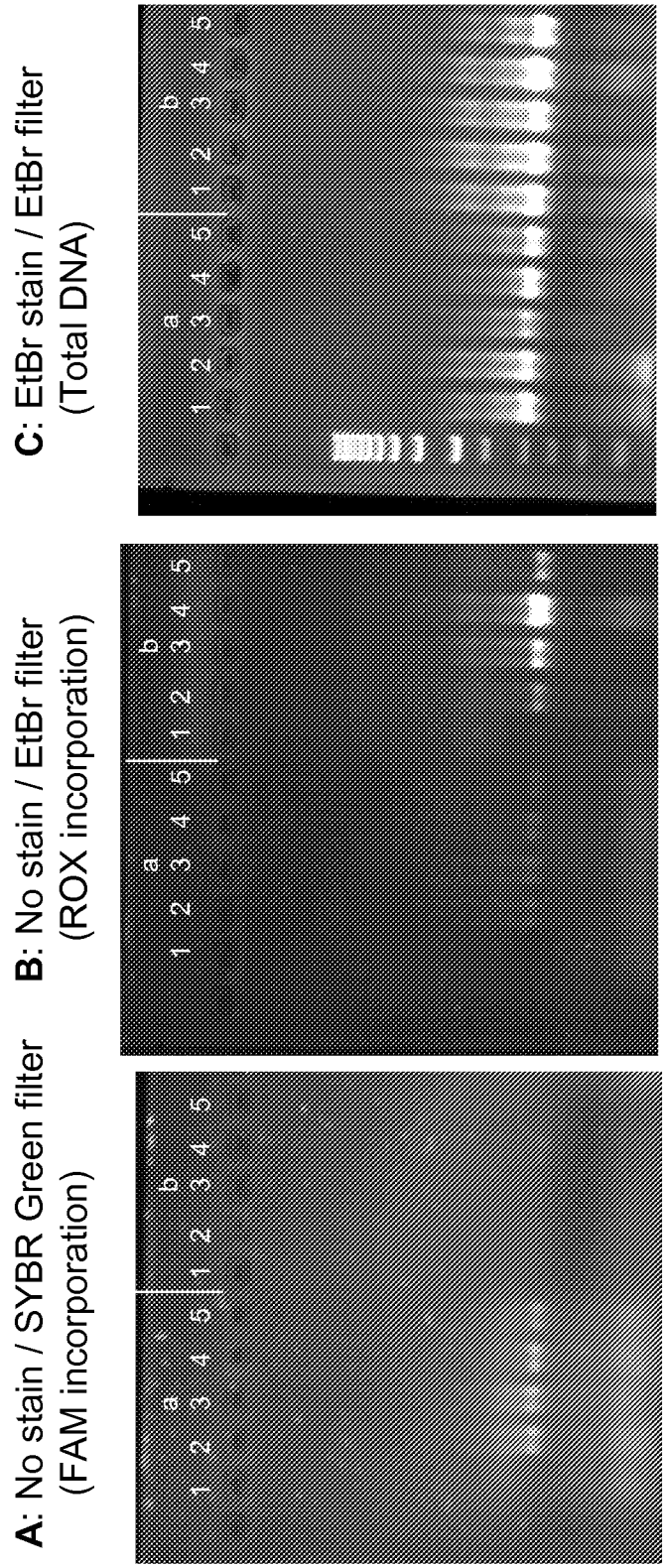

```
Amino Fragment

1 MILDVDYITE EGKPVIRLFK KENGKFKIEH DRTFRPYIYA LLRDDSKIEE
 51 VKKITGERHG KIVRIVDVEK VEKKFLGKPI TVWKLYLEHP QDVPTIREKV
101 REHPAVVDIF EYDIPFAKRY LIDKGLIPME GEEELKILAFAIATLYHEGE
                                              141 143
151 EFGKGPIIMI SYADENEAKV ITWKNIDLPY VEVVSSEREM IKRFLRIIRE
201 KDPDIIVTYN GDSFDFPYLA KRAEKLGIKL TIGRDGSEPK MQRIGDMTAV
251 EVKGRIHFDL YHVITRTINL PTYTLEAVYE AIFGKPKEKV YADEIAKAWE
301 SGENLERVAK YSMEDAKATY ELGKEFLEME IQLSRLVGQP LWDVSRSSTG
351 NLVEWFLLRK AYERNEVAPN KPSEEEYQRR LRESYTGGFV KEPEKGLWEN
401 IVYLDFRALY PSIIITHNVS PDTLNLEGCK NYDIAPQVGH KFCKDIPGFI
451 PSLLGHLLEE RQKIKTK  (SEQ ID NO:161)
```

B

```
Carboxyl Fragment

1 MKETQDPIEK ILLDYRQKAI KLLANSFYGY YGYAKARWYC KECAESVTAW
           17               if numbering is reinitiated
          484               if wildtype numbering is maintained
 51 GRKYIELVWK ELEEKFGFKV LYIDTDGLYA TIPGGESEEI KKKALEFVKY
101 INSKLPGLLE LEYEGFYKRG FFVTKKRYAV IDEEGKVITR GLEIVRRDWS
151 EIAKETQARV LETILKHGDV EEAVRIVKEV IQKLANYEIP PEKLAIYEQI
201 TRPLHEYKAI GPHVAVAKKL AAKGVKIKPG MVIGYIVLRG DGPISNRAIL
251 AEEYDPKKHK YDAEYYIENQ VLPAVLRILE GFGYRKEDLR YQKTRQVGLT
301 SWLNIKKS  (SEQ ID NO:162)
```

MILDVDYITEEGKPVIRLFKKENGKFKIEHDRTFRPYIYALLRDDSKIEE
VKKITGERHGKIVRIVDVEKVEKKFLGKPITVWKLYLEHPQDVPTIREKV
REHPAVVDIFEYDIPFAKRYLIDKGLIPMEGEEELKILAFAIATLYHEGE
EFGKGPIIMISYADENEAKVITWKNIDLPYVEVVSSEREMIKRFLRIRE
KDPDIIVTYNGDSFDFPYLAKRAEKLGIKLTIGRDGSEPKMQRIGDMTAV
EVKGRIHFDLYHVITRTINLPTYTLEAVYEAIFGKPKEKVYADEIAKAWE
SGENLERVAKYSMEDAKATYELGKEFLPMEIQLSRLVGQPLWDVSRSSTG
NLVEWFLLRKAYERNEVAPNKPSEEEYQRRLRESYTGGFVKEPEKGLWEN
IVYLDFRALYPSIIITHNVSPDTLNLEGCKNYDIAPQVGHKFCKDIPGFI
PSLLGHLLEERQKIKTK (SEQ ID NO:94)                                 Fragment I

B

DNA: GAAAGACAAAAGATTAAGACAAAATGAAGGAAACTCAAGATCCTATAGAAA
+3:  K  T  K  D  *  D  K  M  K  E  T  Q  D  P  I  E  K
+1:  E  R  Q  K  I  K  T  K  *  R  K  L  K  I  L  *  K (SEQ ID NOS:163-167)

C

MKETQDPIEKILLDYRRKAIKLLANSFYGYYGYA
KARWYCKECAESVTAWGRKYIELVWKELEEKFGFKVLYIDTDGLYATIPG
GESEEIKKKALEFVKYINSKLPGLLELEYEGFYKRGFFVTKKRYAVIDEE
GKVITRGLEIVRRDWSEIAKETQARVLETILKHGDVEEAVRIVKEVIQKL
ANYEIPPEKLAIYEQITRPLHEYKAIGPHVAVAKKLAAKGVKIKPGMVIG
YIVLRGDGPISNRAILAEEYDPKKHKYDAEYYIENQVLPAVLRILEGFGY
RKEDLRYQKTRQVGLTSWLNIKKS*(SEQ ID NO:95)                          Fragment II

```
                          SEQUENCE LISTING

<160> NUMBER OF SEQ ID NOS: 167

<210> SEQ ID NO 1
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(4)
<223> OTHER INFORMATION: Any amino acid
<220> FEATURE:
<221> NAME/KEY: MOD_RES
<222> LOCATION: (7)..(7)
<223> OTHER INFORMATION: Any amino acid

<400> SEQUENCE: 1

Lys Xaa Xaa Xaa Asn Ser Xaa Tyr Gly
1               5

<210> SEQ ID NO 2
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(4)
<223> OTHER INFORMATION: Any amino acid
<220> FEATURE:
<221> NAME/KEY: MOD_RES
<222> LOCATION: (5)..(5)
<223> OTHER INFORMATION: Phe or Tyr
<220> FEATURE:
<221> NAME/KEY: MOD_RES
<222> LOCATION: (7)..(8)
<223> OTHER INFORMATION: Any amino acid

<400> SEQUENCE: 2

Lys Xaa Xaa Xaa Xaa Gly Xaa Xaa Tyr Gly
1               5                   10

<210> SEQ ID NO 3
<211> LENGTH: 775
<212> TYPE: PRT
<213> ORGANISM: Pyrococcus furiosus

<400> SEQUENCE: 3
```

-continued

```
Met Ile Leu Asp Val Asp Tyr Ile Thr Glu Glu Gly Lys Pro Val Ile
1               5                   10                  15

Arg Leu Phe Lys Lys Glu Asn Gly Lys Phe Lys Ile Glu His Asp Arg
            20                  25                  30

Thr Phe Arg Pro Tyr Ile Tyr Ala Leu Leu Arg Asp Asp Ser Lys Ile
        35                  40                  45

Glu Glu Val Lys Lys Ile Thr Gly Glu Arg His Gly Lys Ile Val Arg
    50                  55                  60

Ile Val Asp Val Glu Lys Val Glu Lys Lys Phe Leu Gly Lys Pro Ile
65                  70                  75                  80

Thr Val Trp Lys Leu Tyr Leu Glu His Pro Gln Asp Val Pro Thr Ile
            85                  90                  95

Arg Glu Lys Val Arg Glu His Pro Ala Val Val Asp Ile Phe Glu Tyr
            100                 105                 110

Asp Ile Pro Phe Ala Lys Arg Tyr Leu Ile Asp Lys Gly Leu Ile Pro
            115                 120                 125

Met Glu Gly Glu Glu Leu Lys Ile Leu Ala Phe Asp Ile Glu Thr
        130                 135                 140

Leu Tyr His Glu Gly Glu Glu Phe Gly Lys Gly Pro Ile Ile Met Ile
145                 150                 155                 160

Ser Tyr Ala Asp Glu Asn Glu Ala Lys Val Ile Thr Trp Lys Asn Ile
            165                 170                 175

Asp Leu Pro Tyr Val Glu Val Val Ser Ser Glu Arg Glu Met Ile Lys
            180                 185                 190

Arg Phe Leu Arg Ile Ile Arg Glu Lys Asp Pro Asp Ile Ile Val Thr
            195                 200                 205

Tyr Asn Gly Asp Ser Phe Asp Phe Pro Tyr Leu Ala Lys Arg Ala Glu
            210                 215                 220

Lys Leu Gly Ile Lys Leu Thr Ile Gly Arg Asp Gly Ser Glu Pro Lys
225                 230                 235                 240

Met Gln Arg Ile Gly Asp Met Thr Ala Val Glu Val Lys Gly Arg Ile
            245                 250                 255

His Phe Asp Leu Tyr His Val Ile Thr Arg Thr Ile Asn Leu Pro Thr
            260                 265                 270

Tyr Thr Leu Glu Ala Val Tyr Glu Ala Ile Phe Gly Lys Pro Lys Glu
            275                 280                 285

Lys Val Tyr Ala Asp Glu Ile Ala Lys Ala Trp Glu Ser Gly Glu Asn
            290                 295                 300

Leu Glu Arg Val Ala Lys Tyr Ser Met Glu Asp Ala Lys Ala Thr Tyr
305                 310                 315                 320

Glu Leu Gly Lys Glu Phe Leu Pro Met Glu Ile Gln Leu Ser Arg Leu
            325                 330                 335

Val Gly Gln Pro Leu Trp Asp Val Ser Arg Ser Ser Thr Gly Asn Leu
            340                 345                 350

Val Glu Trp Phe Leu Leu Arg Lys Ala Tyr Arg Asn Glu Val Ala
            355                 360                 365

Pro Asn Lys Pro Ser Glu Glu Glu Tyr Gln Arg Arg Leu Arg Glu Ser
            370                 375                 380

Tyr Thr Gly Gly Phe Val Lys Glu Pro Glu Lys Gly Leu Trp Glu Asn
385                 390                 395                 400

Ile Val Tyr Leu Asp Phe Arg Ala Leu Tyr Pro Ser Ile Ile Ile Thr
            405                 410                 415

His Asn Val Ser Pro Asp Thr Leu Asn Leu Glu Gly Cys Lys Asn Tyr
```

```
                420                 425                 430
Asp Ile Ala Pro Gln Val Gly His Lys Phe Cys Lys Asp Ile Pro Gly
            435                 440                 445
Phe Ile Pro Ser Leu Leu Gly His Leu Leu Glu Glu Arg Gln Lys Ile
        450                 455                 460
Lys Thr Lys Met Lys Glu Thr Gln Asp Pro Ile Glu Lys Ile Leu Leu
465                 470                 475                 480
Asp Tyr Arg Gln Lys Ala Ile Lys Leu Leu Ala Asn Ser Phe Tyr Gly
                485                 490                 495
Tyr Tyr Gly Tyr Ala Lys Ala Arg Trp Tyr Cys Lys Glu Cys Ala Glu
            500                 505                 510
Ser Val Thr Ala Trp Gly Arg Lys Tyr Ile Glu Leu Val Trp Lys Glu
        515                 520                 525
Leu Glu Glu Lys Phe Gly Phe Lys Val Leu Tyr Ile Asp Thr Asp Gly
        530                 535                 540
Leu Tyr Ala Thr Ile Pro Gly Gly Glu Ser Glu Glu Ile Lys Lys Lys
545                 550                 555                 560
Ala Leu Glu Phe Val Lys Tyr Ile Asn Ser Lys Leu Pro Gly Leu Leu
                565                 570                 575
Glu Leu Glu Tyr Glu Gly Phe Tyr Lys Arg Gly Phe Phe Val Thr Lys
            580                 585                 590
Lys Arg Tyr Ala Val Ile Asp Glu Glu Gly Lys Val Ile Thr Arg Gly
        595                 600                 605
Leu Glu Ile Val Arg Arg Asp Trp Ser Glu Ile Ala Lys Glu Thr Gln
        610                 615                 620
Ala Arg Val Leu Glu Thr Ile Leu Lys His Gly Asp Val Glu Glu Ala
625                 630                 635                 640
Val Arg Ile Val Lys Glu Val Ile Gln Lys Leu Ala Asn Tyr Glu Ile
                645                 650                 655
Pro Pro Glu Lys Leu Ala Ile Tyr Glu Gln Ile Thr Arg Pro Leu His
            660                 665                 670
Glu Tyr Lys Ala Ile Gly Pro His Val Ala Val Ala Lys Lys Leu Ala
        675                 680                 685
Ala Lys Gly Val Lys Ile Lys Pro Gly Met Val Ile Gly Tyr Ile Val
        690                 695                 700
Leu Arg Gly Asp Gly Pro Ile Ser Asn Arg Ala Ile Leu Ala Glu Glu
705                 710                 715                 720
Tyr Asp Pro Lys Lys His Lys Tyr Asp Ala Glu Tyr Tyr Ile Glu Asn
                725                 730                 735
Gln Val Leu Pro Ala Val Leu Arg Ile Leu Glu Gly Phe Gly Tyr Arg
            740                 745                 750
Lys Glu Asp Leu Arg Tyr Gln Lys Thr Arg Gln Val Gly Leu Thr Ser
        755                 760                 765
Trp Leu Asn Ile Lys Lys Ser
    770                 775

<210> SEQ ID NO 4
<211> LENGTH: 98
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(4)
```

```
<223> OTHER INFORMATION: Any amino acid
<220> FEATURE:
<221> NAME/KEY: MOD_RES
<222> LOCATION: (6)..(85)
<223> OTHER INFORMATION: Any amino acid and this region may encompass 15
      to 80 residues
<220> FEATURE:
<221> NAME/KEY: MOD_RES
<222> LOCATION: (87)..(89)
<223> OTHER INFORMATION: Any amino acid
<220> FEATURE:
<221> NAME/KEY: MOD_RES
<222> LOCATION: (91)..(93)
<223> OTHER INFORMATION: Any amino acid
<220> FEATURE:
<221> NAME/KEY: MOD_RES
<222> LOCATION: (96)..(96)
<223> OTHER INFORMATION: Any amino acid
<220> FEATURE:
<221> NAME/KEY: MOD_RES
<222> LOCATION: (98)..(98)
<223> OTHER INFORMATION: Any amino acid

<400> SEQUENCE: 4

Arg Xaa Xaa Xaa Lys Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa
    50                  55                  60

Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa Gln Xaa Xaa Xaa Lys Xaa Xaa Xaa Asn Ser Xaa
                85                  90                  95

Gly Xaa

<210> SEQ ID NO 5
<211> LENGTH: 44
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Any amino acid
<220> FEATURE:
<221> NAME/KEY: MOD_RES
<222> LOCATION: (7)..(8)
<223> OTHER INFORMATION: Any amino acid
<220> FEATURE:
<221> NAME/KEY: MOD_RES
<222> LOCATION: (10)..(12)
<223> OTHER INFORMATION: Any amino acid
<220> FEATURE:
<221> NAME/KEY: MOD_RES
<222> LOCATION: (15)..(16)
<223> OTHER INFORMATION: Any amino acid
<220> FEATURE:
<221> NAME/KEY: MOD_RES
<222> LOCATION: (18)..(19)
<223> OTHER INFORMATION: Any amino acid
<220> FEATURE:
<221> NAME/KEY: MOD_RES
<222> LOCATION: (22)..(24)
<223> OTHER INFORMATION: Any amino acid
<220> FEATURE:
<221> NAME/KEY: MOD_RES
```

```
<222> LOCATION: (27)..(27)
<223> OTHER INFORMATION: Any amino acid
<220> FEATURE:
<221> NAME/KEY: MOD_RES
<222> LOCATION: (30)..(

```
<221> NAME/KEY: MOD_RES
<222> LOCATION: (27)..(27)
<223> OTHER INFORMATION: Met, Val, Leu or Ile
<220> FEATURE:
<221> NAME/KEY: MOD_RES
<222> LOCATION: (30)..(30)
<223> OTHER INFORMATION: Any amino acid
<220> FEATURE:
<221> NAME/KEY: MOD_RES
<222> LOCATION: (31)..(31)
<223> OTHER INFORMATION: Met, Val, Leu or Ile
<220> FEATURE:
<221> NAME/KEY: MOD_RES
<222> LOCATION: (37)..(37)
<223> OTHER INFORMATION: Gln, Lys or Arg
<220> FEATURE:
<221> NAME/KEY: MOD_RES
<222> LOCATION: (41)..(41)
<223> OTHER INFORMATION: Met, Val, Leu or Ile

<400> SEQUENCE: 6

Phe Ile Pro Ser Xaa Leu Xaa Xaa Leu Xaa Xaa Xaa Arg Xaa Xaa Xaa
1               5                   10                  15

Lys Xaa Xaa Met Lys Xaa Xaa Xaa Asp Pro Xaa Glu Lys Xaa Xaa Leu
            20                  25                  30

Asp Tyr Arg Gln Xaa Ala Ile Lys Xaa Leu Ala Asn
        35                  40

<210> SEQ ID NO 7
<211> LENGTH: 775
<212> TYPE: PRT
<213> ORGANISM: Pyrococcus sp.

<400> SEQUENCE: 7

Met Ile Leu Asp Ala Asp Tyr Ile Thr Glu Asp Gly Lys Pro Ile Ile
1               5                   10                  15

Arg Ile Phe Lys Lys Glu Asn Gly Glu Phe Lys Val Glu Tyr Asp Arg
            20                  25                  30

Asn Phe Arg Pro Tyr Ile Tyr Ala Leu Leu Lys Asp Asp Ser Gln Ile
        35                  40                  45

Asp Glu Val Arg Lys Ile Thr Ala Glu Arg His Gly Lys Ile Val Arg
    50                  55                  60

Ile Ile Asp Ala Glu Lys Val Arg Lys Phe Leu Gly Arg Pro Ile
65                  70                  75                  80

Glu Val Trp Arg Leu Tyr Phe Glu His Pro Gln Asp Val Pro Ala Ile
                85                  90                  95

Arg Asp Lys Ile Arg Glu His Ser Ala Val Ile Asp Ile Phe Glu Tyr
            100                 105                 110

Asp Ile Pro Phe Ala Lys Arg Tyr Leu Ile Asp Lys Gly Leu Ile Pro
        115                 120                 125

Met Glu Gly Asp Glu Glu Leu Lys Leu Leu Ala Phe Asp Ile Glu Thr
    130                 135                 140

Leu Tyr His Glu Gly Glu Glu Phe Ala Lys Gly Pro Ile Ile Met Ile
145                 150                 155                 160

Ser Tyr Ala Asp Glu Glu Glu Ala Lys Val Ile Thr Trp Lys Lys Ile
                165                 170                 175

Asp Leu Pro Tyr Val Glu Val Val Ser Ser Glu Arg Glu Met Ile Lys
            180                 185                 190

Arg Phe Leu Lys Val Ile Arg Glu Lys Asp Pro Asp Val Ile Ile Thr
        195                 200                 205

Tyr Asn Gly Asp Ser Phe Asp Leu Pro Tyr Leu Val Lys Arg Ala Glu
```

```
                210                 215                 220
Lys Leu Gly Ile Lys Leu Pro Leu Gly Arg Asp Gly Ser Glu Pro Lys
225                 230                 235                 240

Met Gln Arg Leu Gly Asp Met Thr Ala Val Glu Ile Lys Gly Arg Ile
                245                 250                 255

His Phe Asp Leu Tyr His Val Ile Arg Arg Thr Ile Asn Leu Pro Thr
                260                 265                 270

Tyr Thr Leu Glu Ala Val Tyr Glu Ala Ile Phe Gly Lys Pro Lys Glu
                275                 280                 285

Lys Val Tyr Ala His Glu Ile Ala Glu Ala Trp Glu Thr Gly Lys Gly
                290                 295                 300

Leu Glu Arg Val Ala Lys Tyr Ser Met Glu Asp Ala Lys Val Thr Tyr
305                 310                 315                 320

Glu Leu Gly Arg Glu Phe Phe Pro Met Glu Ala Gln Leu Ser Arg Leu
                325                 330                 335

Val Gly Gln Pro Leu Trp Asp Val Ser Arg Ser Ser Thr Gly Asn Leu
                340                 345                 350

Val Glu Trp Tyr Leu Leu Arg Lys Ala Tyr Glu Arg Asn Glu Leu Ala
                355                 360                 365

Pro Asn Lys Pro Asp Glu Arg Glu Tyr Glu Arg Arg Leu Arg Glu Ser
370                 375                 380

Tyr Ala Gly Gly Tyr Val Lys Glu Pro Glu Lys Gly Leu Trp Glu Gly
385                 390                 395                 400

Leu Val Ser Leu Asp Phe Arg Ser Leu Tyr Pro Ser Ile Ile Ile Thr
                405                 410                 415

His Asn Val Ser Pro Asp Thr Leu Asn Arg Glu Gly Cys Arg Glu Tyr
                420                 425                 430

Asp Val Ala Pro Glu Val Gly His Lys Phe Cys Lys Asp Phe Pro Gly
                435                 440                 445

Phe Ile Pro Ser Leu Leu Lys Arg Leu Leu Asp Glu Arg Gln Glu Ile
                450                 455                 460

Lys Arg Lys Met Lys Ala Ser Lys Asp Pro Ile Glu Lys Lys Met Leu
465                 470                 475                 480

Asp Tyr Arg Gln Arg Ala Ile Lys Ile Leu Ala Asn Ser Tyr Tyr Gly
                485                 490                 495

Tyr Tyr Gly Tyr Ala Lys Ala Arg Trp Tyr Cys Lys Glu Cys Ala Glu
                500                 505                 510

Ser Val Thr Ala Trp Gly Arg Glu Tyr Ile Glu Phe Val Arg Lys Glu
                515                 520                 525

Leu Glu Glu Lys Phe Gly Phe Lys Val Leu Tyr Ile Asp Thr Asp Gly
                530                 535                 540

Leu Tyr Ala Thr Ile Pro Gly Ala Lys Pro Glu Ile Lys Lys Lys
545                 550                 555                 560

Ala Leu Glu Phe Val Asp Tyr Ile Asn Ala Lys Leu Pro Gly Leu Leu
                565                 570                 575

Glu Leu Glu Tyr Glu Gly Phe Tyr Val Arg Gly Phe Phe Val Thr Lys
                580                 585                 590

Lys Lys Tyr Ala Leu Ile Asp Glu Glu Gly Lys Ile Ile Thr Arg Gly
                595                 600                 605

Leu Glu Ile Val Arg Arg Asp Trp Ser Glu Ile Ala Lys Glu Thr Gln
                610                 615                 620

Ala Lys Val Leu Glu Ala Ile Leu Lys His Gly Asn Val Glu Glu Ala
625                 630                 635                 640
```

```
Val Lys Ile Val Lys Glu Val Thr Glu Lys Leu Ser Lys Tyr Glu Ile
                645                 650                 655

Pro Pro Glu Lys Leu Val Ile Tyr Glu Gln Ile Thr Arg Pro Leu His
            660                 665                 670

Glu Tyr Lys Ala Ile Gly Pro His Val Ala Val Ala Lys Arg Leu Ala
            675                 680                 685

Ala Arg Gly Val Lys Val Arg Pro Gly Met Val Ile Gly Tyr Ile Val
    690                 695                 700

Leu Arg Gly Asp Gly Pro Ile Ser Lys Arg Ala Ile Leu Ala Glu Glu
705                 710                 715                 720

Phe Asp Leu Arg Lys His Lys Tyr Asp Ala Gly Tyr Tyr Ile Glu Asn
                725                 730                 735

Gln Val Leu Pro Ala Val Leu Arg Ile Leu Glu Ala Phe Gly Tyr Arg
            740                 745                 750

Lys Glu Asp Leu Arg Trp Gln Lys Thr Lys Gln Thr Gly Leu Thr Ala
            755                 760                 765

Trp Leu Asn Ile Lys Lys Lys
    770                 775

<210> SEQ ID NO 8
<211> LENGTH: 1235
<212> TYPE: PRT
<213> ORGANISM: Pyrococcus horikoshii

<400> SEQUENCE: 8

Met Ile Leu Asp Ala Asp Tyr Ile Thr Glu Asp Gly Lys Pro Ile Ile
1               5                   10                  15

Arg Ile Phe Lys Lys Glu Asn Gly Glu Phe Lys Val Glu Tyr Asp Arg
            20                  25                  30

Asn Phe Arg Pro Tyr Ile Tyr Ala Leu Leu Arg Asp Asp Ser Ala Ile
        35                  40                  45

Asp Glu Ile Lys Lys Ile Thr Ala Gln Arg His Gly Lys Val Val Arg
    50                  55                  60

Ile Val Glu Thr Glu Lys Ile Gln Arg Lys Phe Leu Gly Arg Pro Ile
65                  70                  75                  80

Glu Val Trp Lys Leu Tyr Leu Glu His Pro Gln Asp Val Pro Ala Ile
                85                  90                  95

Arg Asp Lys Ile Arg Glu His Pro Ala Val Val Asp Ile Phe Glu Tyr
            100                 105                 110

Asp Ile Pro Phe Ala Lys Arg Tyr Leu Ile Asp Lys Gly Leu Thr Pro
        115                 120                 125

Met Glu Gly Asn Glu Lys Leu Thr Phe Leu Ala Val Asp Ile Glu Thr
    130                 135                 140

Leu Tyr His Glu Gly Glu Glu Phe Gly Lys Gly Pro Val Ile Met Ile
145                 150                 155                 160

Ser Tyr Ala Asp Glu Glu Gly Ala Lys Val Ile Thr Trp Lys Lys Ile
                165                 170                 175

Asp Leu Pro Tyr Val Glu Val Val Ser Ser Glu Arg Glu Met Ile Lys
            180                 185                 190

Arg Leu Ile Arg Val Ile Lys Glu Lys Asp Pro Asp Val Ile Ile Thr
        195                 200                 205

Tyr Asn Gly Asp Asn Phe Asp Phe Pro Tyr Leu Leu Lys Arg Ala Glu
    210                 215                 220

Lys Leu Gly Ile Lys Leu Leu Leu Gly Arg Asp Asn Ser Glu Pro Lys
```

-continued

```
            225                 230                 235                 240
        Met Gln Lys Met Gly Asp Ser Leu Ala Val Glu Ile Lys Gly Arg Ile
                        245                 250                 255

His Phe Asp Leu Phe Pro Val Ile Arg Arg Thr Ile Asn Leu Pro Thr
                        260                 265                 270

Tyr Thr Leu Glu Ala Val Tyr Glu Ala Ile Phe Gly Lys Pro Lys Glu
                        275                 280                 285

Lys Val Tyr Ala Asp Glu Ile Ala Lys Ala Trp Glu Thr Gly Glu Gly
                        290                 295                 300

Leu Glu Arg Val Ala Lys Tyr Ser Met Glu Asp Ala Lys Val Thr Tyr
        305                 310                 315                 320

Glu Leu Gly Arg Glu Phe Pro Met Glu Ala Gln Leu Ala Arg Leu
                        325                 330                 335

Val Gly Gln Pro Val Trp Asp Val Ser Arg Ser Thr Gly Asn Leu
                        340                 345                 350

Val Glu Trp Phe Leu Leu Arg Lys Ala Tyr Glu Arg Asn Glu Leu Ala
                        355                 360                 365

Pro Asn Lys Pro Asp Glu Lys Glu Tyr Glu Arg Arg Leu Arg Glu Ser
                        370                 375                 380

Tyr Glu Gly Gly Tyr Val Lys Glu Pro Glu Lys Gly Leu Trp Glu Gly
        385                 390                 395                 400

Ile Val Ser Leu Asp Phe Arg Ser Leu Tyr Pro Ser Ile Ile Ile Thr
                        405                 410                 415

His Asn Val Ser Pro Asp Thr Leu Asn Arg Glu Gly Cys Glu Glu Tyr
                        420                 425                 430

Asp Val Ala Pro Lys Val Gly His Arg Phe Cys Lys Asp Phe Pro Gly
                        435                 440                 445

Phe Ile Pro Ser Leu Leu Gly Gln Leu Leu Glu Glu Arg Gln Lys Ile
                        450                 455                 460

Lys Lys Arg Met Lys Glu Ser Lys Asp Pro Val Glu Lys Lys Leu Leu
        465                 470                 475                 480

Asp Tyr Arg Gln Arg Ala Ile Lys Ile Leu Ala Asn Ser Ile Leu Pro
                        485                 490                 495

Asp Glu Trp Leu Pro Ile Val Glu Asn Glu Lys Val Arg Phe Val Lys
                        500                 505                 510

Ile Gly Asp Phe Ile Asp Arg Glu Ile Glu Glu Asn Ala Glu Arg Val
                        515                 520                 525

Lys Arg Asp Gly Glu Thr Glu Ile Leu Glu Val Lys Asp Leu Lys Ala
        530                 535                 540

Leu Ser Phe Asn Arg Glu Thr Lys Lys Ser Glu Leu Lys Lys Val Lys
        545                 550                 555                 560

Ala Leu Ile Arg His Arg Tyr Ser Gly Lys Val Tyr Ser Ile Lys Leu
                        565                 570                 575

Lys Ser Gly Arg Arg Ile Lys Ile Thr Ser Gly His Ser Leu Phe Ser
                        580                 585                 590

Val Lys Asn Gly Lys Leu Val Lys Val Arg Gly Asp Glu Leu Lys Pro
                        595                 600                 605

Gly Asp Leu Val Val Val Pro Gly Arg Leu Lys Leu Pro Glu Ser Lys
                        610                 615                 620

Gln Val Leu Asn Leu Val Glu Leu Leu Leu Lys Leu Pro Glu Glu Glu
        625                 630                 635                 640

Thr Ser Asn Ile Val Met Met Ile Pro Val Lys Gly Arg Lys Asn Phe
                        645                 650                 655
```

-continued

Phe Lys Gly Met Leu Lys Thr Leu Tyr Trp Ile Phe Gly Glu Gly Glu
            660                 665                 670

Arg Pro Arg Thr Ala Gly Arg Tyr Leu Lys His Leu Glu Arg Leu Gly
            675                 680                 685

Tyr Val Lys Leu Lys Arg Arg Gly Cys Glu Val Leu Asp Trp Glu Ser
            690                 695                 700

Leu Lys Arg Tyr Arg Lys Leu Tyr Glu Thr Leu Ile Lys Asn Leu Lys
705                 710                 715                 720

Tyr Asn Gly Asn Ser Arg Ala Tyr Met Val Glu Phe Asn Ser Leu Arg
                725                 730                 735

Asp Val Val Ser Leu Met Pro Ile Glu Glu Leu Lys Glu Trp Ile Ile
            740                 745                 750

Gly Glu Pro Arg Gly Pro Lys Ile Gly Thr Phe Ile Asp Val Asp Asp
            755                 760                 765

Ser Phe Ala Lys Leu Leu Gly Tyr Tyr Ile Ser Ser Gly Asp Val Glu
            770                 775                 780

Lys Asp Arg Val Lys Phe His Ser Lys Asp Gln Asn Val Leu Glu Asp
785                 790                 795                 800

Ile Ala Lys Leu Ala Glu Lys Leu Phe Gly Lys Val Arg Arg Gly Arg
                805                 810                 815

Gly Tyr Ile Glu Val Ser Gly Lys Ile Ser His Ala Ile Phe Arg Val
            820                 825                 830

Leu Ala Glu Gly Lys Arg Ile Pro Glu Phe Ile Phe Thr Ser Pro Met
            835                 840                 845

Asp Ile Lys Val Ala Phe Leu Lys Gly Leu Asn Gly Asn Ala Glu Glu
            850                 855                 860

Leu Thr Phe Ser Thr Lys Ser Glu Leu Leu Val Asn Gln Leu Ile Leu
865                 870                 875                 880

Leu Leu Asn Ser Ile Gly Val Ser Asp Ile Lys Ile Glu His Glu Lys
                885                 890                 895

Gly Val Tyr Arg Val Tyr Ile Asn Lys Lys Glu Ser Ser Asn Gly Asp
            900                 905                 910

Ile Val Leu Asp Ser Val Glu Ser Ile Glu Val Glu Lys Tyr Glu Gly
            915                 920                 925

Tyr Val Tyr Asp Leu Ser Val Glu Asp Asn Glu Asn Phe Leu Val Gly
            930                 935                 940

Phe Gly Leu Leu Tyr Ala His Asn Ser Tyr Tyr Gly Tyr Tyr Gly Tyr
945                 950                 955                 960

Ala Lys Ala Arg Trp Tyr Cys Lys Glu Cys Ala Glu Ser Val Thr Ala
                965                 970                 975

Trp Gly Arg Gln Tyr Ile Asp Leu Val Arg Arg Glu Leu Glu Ala Arg
            980                 985                 990

Gly Phe Lys Val Leu Tyr Ile Asp Thr Asp Gly Leu Tyr Ala Thr Ile
            995                 1000                1005

Pro Gly Val Lys Asp Trp Glu Val Lys Arg Arg Ala Leu Glu
            1010                1015                1020

Phe Val Asp Tyr Ile Asn Ser Lys Leu Pro Gly Val Leu Glu Leu
            1025                1030                1035

Glu Tyr Glu Gly Phe Tyr Ala Arg Gly Phe Phe Val Thr Lys Lys
            1040                1045                1050

Lys Tyr Ala Leu Ile Asp Glu Glu Gly Lys Ile Val Thr Arg Gly
            1055                1060                1065

```
Leu Glu Ile Val Arg Arg Asp Trp Ser Glu Ile Ala Lys Glu Thr
    1070                1075                1080

Gln Ala Arg Val Leu Glu Ala Ile Leu Lys His Gly Asn Val Glu
    1085                1090                1095

Glu Ala Val Lys Ile Val Lys Asp Val Thr Glu Lys Leu Thr Asn
    1100                1105                1110

Tyr Glu Val Pro Pro Glu Lys Leu Val Ile Tyr Glu Gln Ile Thr
    1115                1120                1125

Arg Pro Ile Asn Glu Tyr Lys Ala Ile Gly Pro His Val Ala Val
    1130                1135                1140

Ala Lys Arg Leu Met Ala Arg Gly Ile Lys Val Lys Pro Gly Met
    1145                1150                1155

Val Ile Gly Tyr Ile Val Leu Arg Gly Asp Gly Pro Ile Ser Lys
    1160                1165                1170

Arg Ala Ile Ser Ile Glu Glu Phe Asp Pro Arg Lys His Lys Tyr
    1175                1180                1185

Asp Ala Glu Tyr Tyr Ile Glu Asn Gln Val Leu Pro Ala Val Glu
    1190                1195                1200

Arg Ile Leu Lys Ala Phe Gly Tyr Lys Arg Glu Asp Leu Arg Trp
    1205                1210                1215

Gln Lys Thr Lys Gln Val Gly Leu Gly Ala Trp Ile Lys Val Lys
    1220                1225                1230

Lys Ser
    1235

<210> SEQ ID NO 9
<211> LENGTH: 773
<212> TYPE: PRT
<213> ORGANISM: Thermococcus gorgonarius

<400> SEQUENCE: 9

Met Ile Leu Asp Thr Asp Tyr Ile Thr Glu Asp Gly Lys Pro Val Ile
1               5                   10                  15

Arg Ile Phe Lys Lys Glu Asn Gly Glu Phe Lys Ile Asp Tyr Asp Arg
                20                  25                  30

Asn Phe Glu Pro Tyr Ile Tyr Ala Leu Leu Lys Asp Asp Ser Ala Ile
            35                  40                  45

Glu Asp Val Lys Lys Ile Thr Ala Glu Arg His Gly Thr Thr Val Arg
        50                  55                  60

Val Val Arg Ala Glu Lys Val Lys Lys Phe Leu Gly Arg Pro Ile
65                  70                  75                  80

Glu Val Trp Lys Leu Tyr Phe Thr His Pro Gln Asp Val Pro Ala Ile
                85                  90                  95

Arg Asp Lys Ile Lys Glu His Pro Ala Val Val Asp Ile Tyr Glu Tyr
            100                 105                 110

Asp Ile Pro Phe Ala Lys Arg Tyr Leu Ile Asp Lys Gly Leu Ile Pro
        115                 120                 125

Met Glu Gly Asp Glu Glu Leu Lys Met Leu Ala Phe Asp Ile Glu Thr
130                 135                 140

Leu Tyr His Glu Gly Glu Glu Phe Ala Glu Gly Pro Ile Leu Met Ile
145                 150                 155                 160

Ser Tyr Ala Asp Glu Glu Gly Ala Arg Val Ile Thr Trp Lys Asn Ile
                165                 170                 175

Asp Leu Pro Tyr Val Asp Val Val Ser Thr Glu Lys Glu Met Ile Lys
            180                 185                 190
```

```
Arg Phe Leu Lys Val Val Lys Glu Lys Asp Pro Asp Val Leu Ile Thr
            195                 200                 205

Tyr Asn Gly Asp Asn Phe Asp Phe Ala Tyr Leu Lys Lys Arg Ser Glu
        210                 215                 220

Lys Leu Gly Val Lys Phe Ile Leu Gly Arg Glu Gly Ser Glu Pro Lys
225                 230                 235                 240

Ile Gln Arg Met Gly Asp Arg Phe Ala Val Glu Val Lys Gly Arg Ile
                245                 250                 255

His Phe Asp Leu Tyr Pro Val Ile Arg Arg Thr Ile Asn Leu Pro Thr
                260                 265                 270

Tyr Thr Leu Glu Ala Val Tyr Glu Ala Ile Phe Gly Gln Pro Lys Glu
            275                 280                 285

Lys Val Tyr Ala Glu Glu Ile Ala Gln Ala Trp Glu Thr Gly Glu Gly
        290                 295                 300

Leu Glu Arg Val Ala Arg Tyr Ser Met Glu Asp Ala Lys Val Thr Tyr
305                 310                 315                 320

Glu Leu Gly Lys Glu Phe Phe Pro Met Glu Ala Gln Leu Ser Arg Leu
                325                 330                 335

Val Gly Gln Ser Leu Trp Asp Val Ser Arg Ser Ser Thr Gly Asn Leu
            340                 345                 350

Val Glu Trp Phe Leu Leu Arg Lys Ala Tyr Glu Arg Asn Glu Leu Ala
        355                 360                 365

Pro Asn Lys Pro Asp Glu Arg Glu Leu Ala Arg Arg Arg Glu Ser Tyr
        370                 375                 380

Ala Gly Gly Tyr Val Lys Glu Pro Glu Arg Gly Leu Trp Glu Asn Ile
385                 390                 395                 400

Val Tyr Leu Asp Phe Arg Ser Leu Tyr Pro Ser Ile Ile Thr His
                405                 410                 415

Asn Val Ser Pro Asp Thr Leu Asn Arg Glu Gly Cys Glu Glu Tyr Asp
                420                 425                 430

Val Ala Pro Gln Val Gly His Lys Phe Cys Lys Asp Phe Pro Gly Phe
            435                 440                 445

Ile Pro Ser Leu Leu Gly Asp Leu Leu Glu Glu Arg Gln Lys Val Lys
        450                 455                 460

Lys Lys Met Lys Ala Thr Ile Asp Pro Ile Glu Lys Lys Leu Leu Asp
465                 470                 475                 480

Tyr Arg Gln Arg Ala Ile Lys Ile Leu Ala Asn Ser Phe Tyr Gly Tyr
                485                 490                 495

Tyr Gly Tyr Ala Lys Ala Arg Trp Tyr Cys Lys Glu Cys Ala Glu Ser
            500                 505                 510

Val Thr Ala Trp Gly Arg Gln Tyr Ile Glu Thr Thr Ile Arg Glu Ile
        515                 520                 525

Glu Glu Lys Phe Gly Phe Lys Val Leu Tyr Ala Asp Thr Asp Gly Phe
        530                 535                 540

Phe Ala Thr Ile Pro Gly Ala Asp Ala Glu Thr Val Lys Lys Lys Ala
545                 550                 555                 560

Lys Glu Phe Leu Asp Tyr Ile Asn Ala Lys Leu Pro Gly Leu Leu Glu
                565                 570                 575

Leu Glu Tyr Glu Gly Phe Tyr Lys Arg Gly Phe Phe Val Thr Lys Lys
            580                 585                 590

Lys Tyr Ala Val Ile Asp Glu Glu Asp Lys Ile Thr Thr Arg Gly Leu
        595                 600                 605
```

-continued

```
Glu Ile Val Arg Arg Asp Trp Ser Glu Ile Ala Lys Glu Thr Gln Ala
        610                 615                 620

Arg Val Leu Glu Ala Ile Leu Lys His Gly Asp Val Glu Glu Ala Val
625                 630                 635                 640

Arg Ile Val Lys Glu Val Thr Glu Lys Leu Ser Lys Tyr Glu Val Pro
                645                 650                 655

Pro Glu Lys Leu Val Ile Tyr Glu Gln Ile Thr Arg Asp Leu Lys Asp
                660                 665                 670

Tyr Lys Ala Thr Gly Pro His Val Ala Val Ala Lys Arg Leu Ala Ala
                675                 680                 685

Arg Gly Ile Lys Ile Arg Pro Gly Thr Val Ile Ser Tyr Ile Val Leu
690                 695                 700

Lys Gly Ser Gly Arg Ile Gly Asp Arg Ala Ile Pro Phe Asp Glu Phe
705                 710                 715                 720

Asp Pro Ala Lys His Lys Tyr Asp Ala Glu Tyr Tyr Ile Glu Asn Gln
                725                 730                 735

Val Leu Pro Ala Val Glu Arg Ile Leu Arg Ala Phe Gly Tyr Arg Lys
                740                 745                 750

Glu Asp Leu Arg Tyr Gln Lys Thr Arg Gln Val Gly Leu Gly Ala Trp
                755                 760                 765

Leu Lys Pro Lys Thr
                770

<210> SEQ ID NO 10
<211> LENGTH: 774
<212> TYPE: PRT
<213> ORGANISM: Thermococcus kodakarensis

<400> SEQUENCE: 10

Met Ile Leu Asp Thr Asp Tyr Ile Thr Glu Asp Gly Lys Pro Val Ile
1               5                   10                  15

Arg Ile Phe Lys Lys Glu Asn Gly Glu Phe Lys Ile Glu Tyr Asp Arg
                20                  25                  30

Thr Phe Glu Pro Tyr Phe Tyr Ala Leu Leu Lys Asp Asp Ser Ala Ile
            35                  40                  45

Glu Glu Val Lys Lys Ile Thr Ala Glu Arg His Gly Thr Val Val Thr
50                  55                  60

Val Lys Arg Val Glu Lys Val Gln Lys Lys Phe Leu Gly Arg Pro Val
65                  70                  75                  80

Glu Val Trp Lys Leu Tyr Phe Thr His Pro Gln Asp Val Pro Ala Ile
                85                  90                  95

Arg Asp Lys Ile Arg Glu His Pro Ala Val Ile Asp Ile Tyr Glu Tyr
                100                 105                 110

Asp Ile Pro Phe Ala Lys Arg Tyr Leu Ile Asp Lys Gly Leu Val Pro
            115                 120                 125

Met Glu Gly Asp Glu Glu Leu Lys Met Leu Ala Phe Asp Ile Glu Thr
130                 135                 140

Leu Tyr His Glu Gly Glu Glu Phe Ala Glu Gly Pro Ile Leu Met Ile
145                 150                 155                 160

Ser Tyr Ala Asp Glu Glu Gly Ala Arg Val Ile Thr Trp Lys Asn Val
                165                 170                 175

Asp Leu Pro Tyr Val Asp Val Val Ser Thr Glu Arg Glu Met Ile Lys
            180                 185                 190

Arg Phe Leu Arg Val Val Lys Glu Lys Asp Pro Asp Val Leu Ile Thr
        195                 200                 205
```

```
Tyr Asn Gly Asp Asn Phe Asp Phe Ala Tyr Leu Lys Lys Arg Cys Glu
    210                 215                 220
Lys Leu Gly Ile Asn Phe Ala Leu Gly Arg Asp Gly Ser Glu Pro Lys
225                 230                 235                 240
Ile Gln Arg Met Gly Asp Arg Phe Ala Val Glu Val Lys Gly Arg Ile
                245                 250                 255
His Phe Asp Leu Tyr Pro Val Ile Arg Arg Thr Ile Asn Leu Pro Thr
            260                 265                 270
Tyr Thr Leu Glu Ala Val Tyr Glu Ala Val Phe Gly Gln Pro Lys Glu
        275                 280                 285
Lys Val Tyr Ala Glu Glu Ile Thr Thr Ala Trp Glu Thr Gly Glu Asn
290                 295                 300
Leu Glu Arg Val Ala Arg Tyr Ser Met Glu Asp Ala Lys Val Thr Tyr
305                 310                 315                 320
Glu Leu Gly Lys Glu Phe Leu Pro Met Glu Ala Gln Leu Ser Arg Leu
                325                 330                 335
Ile Gly Gln Ser Leu Trp Asp Val Ser Arg Ser Ser Thr Gly Asn Leu
            340                 345                 350
Val Glu Trp Phe Leu Leu Arg Lys Ala Tyr Glu Arg Asn Glu Leu Ala
        355                 360                 365
Pro Asn Lys Pro Asp Glu Lys Glu Leu Ala Arg Arg Gln Ser Tyr
370                 375                 380
Glu Gly Gly Tyr Val Lys Glu Pro Glu Arg Gly Leu Trp Glu Asn Ile
385                 390                 395                 400
Val Tyr Leu Asp Phe Arg Ser Leu Tyr Pro Ser Ile Ile Ile Thr His
                405                 410                 415
Asn Val Ser Pro Asp Thr Leu Asn Arg Glu Gly Cys Lys Glu Tyr Asp
            420                 425                 430
Val Ala Pro Gln Val Gly His Arg Phe Cys Lys Asp Phe Pro Gly Phe
        435                 440                 445
Ile Pro Ser Leu Leu Gly Asp Leu Leu Glu Glu Arg Gln Lys Ile Lys
450                 455                 460
Lys Lys Met Lys Ala Thr Ile Asp Pro Ile Glu Arg Lys Leu Leu Asp
465                 470                 475                 480
Tyr Arg Gln Arg Ala Ile Lys Ile Leu Ala Asn Ser Tyr Tyr Gly Tyr
                485                 490                 495
Tyr Gly Tyr Ala Arg Ala Arg Trp Tyr Cys Lys Glu Cys Ala Glu Ser
            500                 505                 510
Val Thr Ala Trp Gly Arg Glu Tyr Ile Thr Met Thr Ile Lys Glu Ile
        515                 520                 525
Glu Glu Lys Tyr Gly Phe Lys Val Ile Tyr Ser Asp Thr Asp Gly Phe
530                 535                 540
Phe Ala Thr Ile Pro Gly Ala Asp Ala Glu Thr Val Lys Lys Lys Ala
545                 550                 555                 560
Met Glu Phe Leu Lys Tyr Ile Asn Ala Lys Leu Pro Gly Ala Leu Glu
                565                 570                 575
Leu Glu Tyr Glu Gly Phe Tyr Lys Arg Gly Phe Phe Val Thr Lys Lys
            580                 585                 590
Lys Tyr Ala Val Ile Asp Glu Glu Gly Lys Ile Thr Thr Arg Gly Leu
        595                 600                 605
Glu Ile Val Arg Arg Asp Trp Ser Glu Ile Ala Lys Glu Thr Gln Ala
610                 615                 620
```

```
Arg Val Leu Glu Ala Leu Leu Lys Asp Gly Asp Val Glu Lys Ala Val
625                 630                 635                 640

Arg Ile Val Lys Glu Val Thr Glu Lys Leu Ser Lys Tyr Glu Val Pro
            645                 650                 655

Pro Glu Lys Leu Val Ile His Glu Gln Ile Thr Arg Asp Leu Lys Asp
        660                 665                 670

Tyr Lys Ala Thr Gly Pro His Val Ala Val Lys Arg Leu Ala Ala
    675                 680                 685

Arg Gly Val Lys Ile Arg Pro Gly Thr Val Ile Ser Tyr Ile Val Leu
690                 695                 700

Lys Gly Ser Gly Arg Ile Gly Asp Arg Ala Ile Pro Phe Asp Glu Phe
705                 710                 715                 720

Asp Pro Thr Lys His Lys Tyr Asp Ala Glu Tyr Tyr Ile Glu Asn Gln
            725                 730                 735

Val Leu Pro Ala Val Glu Arg Ile Leu Arg Ala Phe Gly Tyr Arg Lys
        740                 745                 750

Glu Asp Leu Arg Tyr Gln Lys Thr Arg Gln Val Gly Leu Ser Ala Trp
    755                 760                 765

Leu Lys Pro Lys Gly Thr
    770

<210> SEQ ID NO 11
<211> LENGTH: 776
<212> TYPE: PRT
<213> ORGANISM: Thermococcus sp.

<400> SEQUENCE: 11

Met Ile Leu Asp Val Asp Tyr Ile Thr Glu Asn Gly Lys Pro Val Ile
1               5                   10                  15

Arg Val Phe Lys Lys Glu Asn Gly Glu Phe Arg Ile Glu Tyr Asp Arg
            20                  25                  30

Glu Phe Glu Pro Tyr Phe Tyr Ala Leu Leu Arg Asp Asp Ser Ala Ile
        35                  40                  45

Glu Glu Ile Lys Lys Ile Thr Ala Glu Arg His Gly Arg Val Val Lys
    50                  55                  60

Val Lys Arg Ala Glu Lys Val Lys Lys Phe Leu Gly Arg Ser Val
65                  70                  75                  80

Glu Val Trp Val Leu Tyr Phe Thr His Pro Gln Asp Val Pro Ala Ile
                85                  90                  95

Arg Asp Lys Ile Arg Lys His Pro Ala Val Ile Asp Ile Tyr Glu Tyr
            100                 105                 110

Asp Ile Pro Phe Ala Lys Arg Tyr Leu Ile Asp Lys Gly Leu Ile Pro
        115                 120                 125

Met Glu Gly Glu Glu Glu Leu Lys Leu Met Ser Phe Asp Ile Glu Thr
130                 135                 140

Leu Tyr His Glu Gly Glu Glu Phe Gly Thr Gly Pro Ile Leu Met Ile
145                 150                 155                 160

Ser Tyr Ala Asp Glu Ser Glu Ala Arg Val Ile Thr Trp Lys Lys Ile
                165                 170                 175

Asp Leu Pro Tyr Val Glu Val Val Ser Thr Glu Lys Glu Met Ile Lys
            180                 185                 190

Arg Phe Leu Arg Val Val Lys Glu Lys Asp Pro Asp Val Leu Ile Thr
        195                 200                 205

Tyr Asn Gly Asp Asn Phe Asp Phe Ala Tyr Leu Lys Lys Arg Cys Glu
    210                 215                 220
```

-continued

```
Lys Leu Gly Val Ser Phe Thr Leu Gly Arg Asp Gly Ser Glu Pro Lys
225                 230                 235                 240

Ile Gln Arg Met Gly Asp Arg Phe Ala Val Glu Val Lys Gly Arg Val
            245                 250                 255

His Phe Asp Leu Tyr Pro Val Ile Arg Arg Thr Ile Asn Leu Pro Thr
        260                 265                 270

Tyr Thr Leu Glu Ala Val Tyr Glu Ala Val Phe Gly Lys Pro Lys Glu
    275                 280                 285

Lys Val Tyr Ala Glu Glu Ile Ala Thr Ala Trp Glu Thr Gly Glu Gly
290                 295                 300

Leu Glu Arg Val Ala Arg Tyr Ser Met Glu Asp Ala Arg Val Thr Tyr
305                 310                 315                 320

Glu Leu Gly Arg Glu Phe Phe Pro Met Glu Ala Gln Leu Ser Arg Leu
            325                 330                 335

Ile Gly Gln Gly Leu Trp Asp Val Ser Arg Ser Thr Gly Asn Leu
        340                 345                 350

Val Glu Trp Phe Leu Leu Arg Lys Ala Tyr Glu Arg Asn Glu Leu Ala
    355                 360                 365

Pro Asn Lys Pro Asp Glu Arg Glu Leu Ala Arg Arg Gly Gly Tyr
370                 375                 380

Ala Gly Gly Tyr Val Lys Glu Pro Glu Arg Gly Leu Trp Asp Asn Ile
385                 390                 395                 400

Val Tyr Leu Asp Phe Arg Ser Leu Tyr Pro Ser Ile Ile Thr His
            405                 410                 415

Asn Val Ser Pro Asp Thr Leu Asn Arg Glu Gly Cys Arg Ser Tyr Asp
        420                 425                 430

Val Ala Pro Glu Val Gly His Lys Phe Cys Lys Asp Phe Pro Gly Phe
    435                 440                 445

Ile Pro Ser Leu Leu Gly Asn Leu Leu Glu Glu Arg Gln Lys Ile Lys
450                 455                 460

Arg Lys Met Lys Ala Thr Leu Asp Pro Leu Glu Lys Asn Leu Leu Asp
465                 470                 475                 480

Tyr Arg Gln Arg Ala Ile Lys Ile Leu Ala Asn Ser Tyr Tyr Gly Tyr
            485                 490                 495

Tyr Gly Tyr Ala Arg Ala Arg Trp Tyr Cys Arg Glu Cys Ala Glu Ser
        500                 505                 510

Val Thr Ala Trp Gly Arg Glu Tyr Ile Glu Met Val Ile Arg Glu Leu
    515                 520                 525

Glu Glu Lys Phe Gly Phe Lys Val Leu Tyr Ala Asp Thr Asp Gly Leu
530                 535                 540

His Ala Thr Ile Pro Gly Ala Asp Ala Glu Thr Val Lys Lys Lys Ala
545                 550                 555                 560

Met Glu Phe Leu Asn Tyr Ile Asn Pro Lys Leu Pro Gly Leu Leu Glu
            565                 570                 575

Leu Glu Tyr Glu Gly Phe Tyr Val Arg Gly Phe Phe Val Thr Lys Lys
        580                 585                 590

Lys Tyr Ala Val Ile Asp Glu Glu Gly Lys Ile Thr Thr Arg Gly Leu
    595                 600                 605

Glu Ile Val Arg Arg Asp Trp Ser Glu Ile Ala Lys Glu Thr Gln Ala
610                 615                 620

Arg Val Leu Glu Ala Ile Leu Arg His Gly Asp Val Glu Glu Ala Val
625                 630                 635                 640
```

```
Arg Ile Val Arg Glu Val Thr Glu Lys Leu Ser Lys Tyr Glu Val Pro
                645                 650                 655

Pro Glu Lys Leu Val Ile His Glu Gln Ile Thr Arg Glu Leu Lys Asp
            660                 665                 670

Tyr Lys Ala Thr Gly Pro His Val Ala Ile Ala Lys Arg Leu Ala Ala
        675                 680                 685

Arg Gly Val Lys Ile Arg Pro Gly Thr Val Ile Ser Tyr Ile Val Leu
    690                 695                 700

Lys Gly Ser Gly Arg Ile Gly Asp Arg Ala Ile Pro Phe Asp Glu Phe
705                 710                 715                 720

Asp Pro Thr Lys His Lys Tyr Asp Ala Asp Tyr Tyr Ile Glu Asn Gln
                725                 730                 735

Val Leu Pro Ala Val Glu Arg Ile Leu Arg Ala Phe Gly Tyr Arg Lys
            740                 745                 750

Glu Asp Leu Arg Tyr Gln Lys Thr Arg Gln Val Gly Leu Gly Ala Trp
        755                 760                 765

Leu Lys Pro Lys Gly Lys Lys
    770                 775

<210> SEQ ID NO 12
<211> LENGTH: 775
<212> TYPE: PRT
<213> ORGANISM: Thermococcus sp.

<400> SEQUENCE: 12

Met Ile Leu Asp Thr Asp Tyr Ile Thr Glu Asn Gly Lys Pro Val Ile
1               5                   10                  15

Arg Val Phe Lys Lys Glu Asn Gly Glu Phe Lys Ile Glu Tyr Asp Arg
            20                  25                  30

Thr Phe Glu Pro Tyr Phe Tyr Ala Leu Leu Lys Asp Asp Ser Ala Ile
        35                  40                  45

Glu Asp Val Lys Lys Val Thr Ala Lys Arg His Gly Thr Val Val Lys
    50                  55                  60

Val Lys Arg Ala Glu Lys Val Gln Lys Phe Leu Gly Arg Pro Ile
65                  70                  75                  80

Glu Val Trp Lys Leu Tyr Phe Asn His Pro Gln Asp Val Pro Ala Ile
                85                  90                  95

Arg Asp Arg Ile Arg Ala His Pro Ala Val Val Asp Ile Tyr Glu Tyr
            100                 105                 110

Asp Ile Pro Phe Ala Lys Arg Tyr Leu Ile Asp Lys Gly Leu Ile Pro
        115                 120                 125

Met Glu Gly Asp Glu Glu Leu Thr Met Leu Ala Phe Asp Ile Glu Thr
    130                 135                 140

Leu Tyr His Glu Gly Glu Phe Gly Thr Gly Pro Ile Leu Met Ile
145                 150                 155                 160

Ser Tyr Ala Asp Gly Ser Glu Ala Arg Val Ile Thr Trp Lys Lys Ile
                165                 170                 175

Asp Leu Pro Tyr Val Asp Val Val Ser Thr Glu Lys Glu Met Ile Lys
            180                 185                 190

Arg Phe Leu Arg Val Val Arg Glu Lys Asp Pro Asp Val Leu Ile Thr
        195                 200                 205

Tyr Asn Gly Asp Asn Phe Asp Phe Ala Tyr Leu Lys Lys Arg Cys Glu
    210                 215                 220

Glu Leu Gly Ile Lys Phe Thr Leu Gly Arg Asp Gly Ser Glu Pro Lys
225                 230                 235                 240
```

-continued

Ile Gln Arg Met Gly Asp Arg Phe Ala Val Glu Val Lys Gly Arg Ile
            245                 250                 255

His Phe Asp Leu Tyr Pro Val Ile Arg Arg Thr Ile Asn Leu Pro Thr
        260                 265                 270

Tyr Thr Leu Glu Ala Val Tyr Glu Ala Val Phe Gly Lys Pro Lys Glu
    275                 280                 285

Lys Val Tyr Ala Glu Glu Ile Ala Gln Ala Trp Glu Ser Gly Glu Gly
290                 295                 300

Leu Glu Arg Val Ala Arg Tyr Ser Met Glu Asp Ala Lys Val Thr Tyr
305                 310                 315                 320

Glu Leu Gly Arg Glu Phe Phe Pro Met Glu Ala Gln Leu Ser Arg Leu
                325                 330                 335

Ile Gly Gln Ser Leu Trp Asp Val Ser Arg Ser Ser Thr Gly Asn Leu
            340                 345                 350

Val Glu Trp Phe Leu Leu Arg Lys Ala Tyr Lys Arg Asn Glu Leu Ala
        355                 360                 365

Pro Asn Lys Pro Asp Glu Arg Glu Leu Ala Arg Arg Gly Gly Tyr
    370                 375                 380

Ala Gly Gly Tyr Val Lys Glu Pro Glu Arg Gly Leu Trp Asp Asn Ile
385                 390                 395                 400

Val Tyr Leu Asp Phe Arg Ser Leu Tyr Pro Ser Ile Ile Thr His
                405                 410                 415

Asn Val Ser Pro Asp Thr Leu Asn Arg Glu Gly Cys Lys Glu Tyr Asp
            420                 425                 430

Val Ala Pro Glu Val Gly His Lys Phe Cys Lys Asp Phe Pro Gly Phe
        435                 440                 445

Ile Pro Ser Leu Leu Gly Asp Leu Leu Glu Glu Arg Gln Lys Ile Lys
    450                 455                 460

Arg Lys Met Lys Ala Thr Val Asp Pro Leu Glu Lys Lys Leu Leu Asp
465                 470                 475                 480

Tyr Arg Gln Arg Ala Ile Lys Ile Leu Ala Asn Ser Phe Tyr Gly Tyr
                485                 490                 495

Tyr Gly Tyr Ala Lys Ala Arg Trp Tyr Cys Lys Glu Cys Ala Glu Ser
            500                 505                 510

Val Thr Ala Trp Gly Arg Glu Tyr Ile Glu Met Val Ile Arg Glu Leu
        515                 520                 525

Glu Glu Lys Phe Gly Phe Lys Val Leu Tyr Ala Asp Thr Asp Gly Leu
    530                 535                 540

His Ala Thr Ile Pro Gly Ala Asp Ala Glu Thr Val Lys Lys Lys Ala
545                 550                 555                 560

Lys Glu Phe Leu Lys Tyr Ile Asn Pro Lys Leu Pro Gly Leu Leu Glu
                565                 570                 575

Leu Glu Tyr Glu Gly Phe Tyr Val Arg Gly Phe Phe Val Thr Lys Lys
            580                 585                 590

Lys Tyr Ala Val Ile Asp Glu Glu Gly Lys Ile Thr Thr Arg Gly Leu
        595                 600                 605

Glu Ile Val Arg Arg Asp Trp Ser Glu Ile Ala Lys Glu Thr Gln Ala
    610                 615                 620

Arg Val Leu Glu Ala Ile Leu Lys His Gly Asp Val Glu Glu Ala Val
625                 630                 635                 640

Arg Ile Val Lys Glu Val Thr Glu Lys Leu Ser Lys Tyr Glu Val Pro
                645                 650                 655

```
Pro Glu Lys Leu Val Ile His Glu Gln Ile Thr Arg Asp Leu Arg Asp
            660                 665                 670

Tyr Lys Ala Thr Gly Pro His Val Ala Val Ala Lys Arg Leu Ala Ala
        675                 680                 685

Arg Gly Val Lys Ile Arg Pro Gly Thr Val Ile Ser Tyr Ile Val Leu
    690                 695                 700

Lys Gly Ser Gly Arg Ile Gly Asp Arg Ala Ile Pro Ala Asp Glu Phe
705                 710                 715                 720

Asp Pro Thr Lys His Arg Tyr Asp Ala Glu Tyr Ile Glu Asn Gln
            725                 730                 735

Val Leu Pro Ala Val Glu Arg Ile Leu Lys Ala Phe Gly Tyr Arg Lys
        740                 745                 750

Glu Asp Leu Arg Tyr Gln Lys Thr Lys Gln Val Gly Leu Gly Ala Trp
        755                 760                 765

Leu Lys Val Lys Gly Lys Lys
        770                 775

<210> SEQ ID NO 13
<211> LENGTH: 774
<212> TYPE: PRT
<213> ORGANISM: Thermococcus litoralis

<400> SEQUENCE: 13

Met Ile Leu Asp Thr Asp Tyr Ile Thr Lys Asp Gly Lys Pro Ile Ile
1               5                   10                  15

Arg Ile Phe Lys Lys Glu Asn Gly Glu Phe Lys Ile Glu Leu Asp Pro
            20                  25                  30

His Phe Gln Pro Tyr Ile Tyr Ala Leu Leu Lys Asp Asp Ser Ala Ile
        35                  40                  45

Glu Glu Ile Lys Ala Ile Lys Gly Glu Arg His Gly Lys Thr Val Arg
    50                  55                  60

Val Leu Asp Ala Val Lys Val Arg Lys Lys Phe Leu Gly Arg Glu Val
65                  70                  75                  80

Glu Val Trp Lys Leu Ile Phe Glu His Pro Gln Asp Val Pro Ala Met
            85                  90                  95

Arg Gly Lys Ile Arg Glu His Pro Ala Val Val Asp Ile Tyr Glu Tyr
            100                 105                 110

Asp Ile Pro Phe Ala Lys Arg Tyr Leu Ile Asp Lys Gly Leu Ile Pro
        115                 120                 125

Met Glu Gly Asp Glu Glu Leu Lys Leu Leu Ala Phe Asp Ile Glu Thr
    130                 135                 140

Phe Tyr His Glu Gly Asp Glu Phe Gly Lys Gly Glu Ile Ile Met Ile
145                 150                 155                 160

Ser Tyr Ala Asp Glu Glu Ala Arg Val Ile Thr Trp Lys Asn Ile
            165                 170                 175

Asp Leu Pro Tyr Val Asp Val Ser Asn Glu Arg Glu Met Ile Lys
        180                 185                 190

Arg Phe Val Gln Val Val Lys Glu Lys Asp Pro Asp Val Ile Ile Thr
        195                 200                 205

Tyr Asn Gly Asp Asn Phe Asp Leu Pro Tyr Leu Ile Lys Arg Ala Glu
    210                 215                 220

Lys Leu Gly Val Arg Leu Val Leu Gly Arg Asp Lys Glu His Pro Glu
225                 230                 235                 240

Pro Lys Ile Gln Arg Met Gly Asp Ser Phe Ala Val Glu Ile Lys Gly
            245                 250                 255
```

-continued

```
Arg Ile His Phe Asp Leu Phe Pro Val Val Arg Thr Ile Asn Leu
            260                 265                 270

Pro Thr Tyr Thr Leu Glu Ala Val Tyr Glu Ala Val Leu Gly Lys Thr
            275                 280                 285

Lys Ser Lys Leu Gly Ala Glu Glu Ile Ala Ala Ile Trp Glu Thr Glu
            290                 295                 300

Glu Ser Met Lys Lys Leu Ala Gln Tyr Ser Met Glu Asp Ala Arg Ala
305                 310                 315                 320

Thr Tyr Glu Leu Gly Lys Glu Phe Phe Pro Met Glu Ala Glu Leu Ala
                    325                 330                 335

Lys Leu Ile Gly Gln Ser Val Trp Asp Val Ser Arg Ser Ser Thr Gly
            340                 345                 350

Asn Leu Val Glu Trp Tyr Leu Leu Arg Val Ala Tyr Ala Arg Asn Glu
            355                 360                 365

Leu Ala Pro Asn Lys Pro Asp Glu Glu Tyr Lys Arg Arg Leu Arg
370                 375                 380

Thr Thr Tyr Leu Gly Gly Tyr Val Lys Glu Pro Glu Lys Gly Leu Trp
385                 390                 395                 400

Glu Asn Ile Ile Tyr Leu Asp Phe Arg Ser Leu Tyr Pro Ser Ile Ile
                    405                 410                 415

Val Thr His Asn Val Ser Pro Asp Thr Leu Glu Lys Glu Gly Cys Lys
            420                 425                 430

Asn Tyr Asp Val Ala Pro Ile Val Gly Tyr Arg Phe Cys Lys Asp Phe
            435                 440                 445

Pro Gly Phe Ile Pro Ser Ile Leu Gly Asp Leu Ile Ala Met Arg Gln
450                 455                 460

Asp Ile Lys Lys Met Lys Ser Thr Ile Asp Pro Ile Glu Lys Lys
465                 470                 475                 480

Met Leu Asp Tyr Arg Gln Arg Ala Ile Lys Leu Leu Ala Asn Ser Tyr
                    485                 490                 495

Tyr Gly Tyr Met Gly Tyr Pro Lys Ala Arg Trp Tyr Ser Lys Glu Cys
            500                 505                 510

Ala Glu Ser Val Thr Ala Trp Gly Arg His Tyr Ile Glu Met Thr Ile
            515                 520                 525

Arg Glu Ile Glu Glu Lys Phe Gly Phe Lys Val Leu Tyr Ala Asp Thr
            530                 535                 540

Asp Gly Phe Tyr Ala Thr Ile Pro Gly Glu Lys Pro Glu Leu Ile Lys
545                 550                 555                 560

Lys Lys Ala Lys Glu Phe Leu Asn Tyr Ile Asn Ser Lys Leu Pro Gly
                    565                 570                 575

Leu Leu Glu Leu Glu Tyr Glu Gly Phe Tyr Leu Arg Gly Phe Phe Val
            580                 585                 590

Thr Lys Lys Arg Tyr Ala Val Ile Asp Glu Glu Gly Arg Ile Thr Thr
            595                 600                 605

Arg Gly Leu Glu Val Val Arg Arg Asp Trp Ser Glu Ile Ala Lys Glu
            610                 615                 620

Thr Gln Ala Lys Val Leu Glu Ala Ile Leu Lys Glu Gly Ser Val Glu
625                 630                 635                 640

Lys Ala Val Glu Val Val Arg Asp Val Val Glu Lys Ile Ala Lys Tyr
                    645                 650                 655

Arg Val Pro Leu Glu Lys Leu Val Ile His Glu Gln Ile Thr Arg Asp
            660                 665                 670
```

Leu Lys Asp Tyr Lys Ala Ile Gly Pro His Val Ala Ile Ala Lys Arg
            675                 680                 685

Leu Ala Ala Arg Gly Ile Lys Val Lys Pro Gly Thr Ile Ile Ser Tyr
        690                 695                 700

Ile Val Leu Lys Gly Ser Gly Lys Ile Ser Asp Arg Val Ile Leu Leu
705                 710                 715                 720

Thr Glu Tyr Asp Pro Arg Lys His Lys Tyr Asp Pro Asp Tyr Tyr Ile
                725                 730                 735

Glu Asn Gln Val Leu Pro Ala Val Leu Arg Ile Leu Glu Ala Phe Gly
            740                 745                 750

Tyr Arg Lys Glu Asp Leu Arg Tyr Gln Ser Ser Lys Gln Thr Gly Leu
        755                 760                 765

Asp Ala Trp Leu Lys Arg
    770

<210> SEQ ID NO 14
<211> LENGTH: 58
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
gttagaggaa agacaaaaga ttaagacatg aaaatgaagg aaactcaaga tcctatag        58

<210> SEQ ID NO 15
<211> LENGTH: 58
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
gttagaggaa agacaaaaga ttaagacatg aaaaagaagg aaactcaaga tcctatag        58

<210> SEQ ID NO 16
<211> LENGTH: 74
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
cctctacatt gacactgatg gtctctattg aggaggcaca caaatggcaa ctatcccagg        60
aggagaaagt gagg                                                         74

<210> SEQ ID NO 17
<211> LENGTH: 52
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
ctgatggtct ctatgcaact atcccaggat aatggaaagt gaggaaataa ag              52

<210> SEQ ID NO 18
<211> LENGTH: 52
<212> TYPE: DNA

```
<213> ORGANISM: Artificial Sequence
<220> FEATURE:
<223> OTHER INFORMATION: Description of Artificial Sequence: Synthetic
      primer

<400> SEQUENCE: 18
ctttatttcc tcactttcca ttatcctggg atagttgcat agagaccatc ag            52

<210> SEQ ID NO 19
<211> LENGTH: 49
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
caaaagatta atacaaaaat gaaggaatga atgcctatag aaaaaatac                49

<210> SEQ ID NO 20
<211> LENGTH: 49
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
gtattttttc ttataggcat tcattccttc attttttgtct tatcttttg               49

<210> SEQ ID NO 21
<211> LENGTH: 52
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
gattaagaca aaaatgaagg aatgatagaa aaaatactcc ttgactatag ac            52

<210> SEQ ID NO 22
<211> LENGTH: 52
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
gtctatagtc aaggagtatt ttttctatca ttccttcatt tttgtcttaa tc            52

<210> SEQ ID NO 23
<211> LENGTH: 57
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
caaaagatta agacaaaaat gaagtaaatg gaaactcaag atcctataga aaaaata       57

<210> SEQ ID NO 24
<211> LENGTH: 55
<212> TYPE: DNA
<213> ORGANISM: Artificial Sequence
```

<220> FEATURE:
<223> OTHER INFORMATION: Description of Artificial Sequence: Synthetic
      primer

<400> SEQUENCE: 24
gtattttttc tataggatct tgcattcatt ccttcatttt tgtcttaatc ttttg    55

<210> SEQ ID NO 25
<211> LENGTH: 57
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
caaaagatta agacaaaaat gaagtaaatg gaaactcaag atcctataga aaaaata    57

<210> SEQ ID NO 26
<211> LENGTH: 56
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
tattttttct atagatcttg agtttccatt tacttcattt tgtcttaat cttttg    56

<210> SEQ ID NO 27
<211> LENGTH: 51
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
catccctggt tttataccaa gtctctgaat gggacatttg ttagaggaaa g    51

<210> SEQ ID NO 28
<211> LENGTH: 50
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
ctttcctcta acaaatgtcc cattcagaac ttggtataaa accagggatg    50

<210> SEQ ID NO 29
<211> LENGTH: 55
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
gtaggccaca agttctgcaa ggactgatgc cctggtttta taccaagtct cttgg    55

<210> SEQ ID NO 30
<211> LENGTH: 54
<212> TYPE: DNA
<213> ORGANISM: Artificial Sequence
<220> FEATURE:

-continued

<223> OTHER INFORMATION: Description of Artificial Sequence: Synthetic
      primer

<400> SEQUENCE: 30
ccaagagact tcctataaaa ccaggcatca gtccttgcag aacttgtggc ctac                54

<210> SEQ ID NO 31
<211> LENGTH: 55
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
gctatgcaaa agcaagatgg tactgatgaa ggagtgtgct gagagcgtta ctgcc             55

<210> SEQ ID NO 32
<211> LENGTH: 55
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
ggcagtaacg ctctcagcac actccttcat cagtaccatc ttgcttttgc atagc             55

<210> SEQ ID NO 33
<211> LENGTH: 53
<212> TYPE: PRT
<213> ORGANISM: Thermococcus sp.

<400> SEQUENCE: 33

Gly Phe Ile Pro Ser Leu Leu Gly Asn Leu Leu Glu Glu Arg Gln Lys
1               5                   10                  15

Ile Lys Arg Lys Met Lys Ala Thr Leu Asp Pro Leu Glu Lys Asn Leu
            20                  25                  30

Leu Asp Tyr Arg Gln Arg Ala Ile Lys Ile Leu Ala Asn Ser Tyr Tyr
        35                  40                  45

Gly Tyr Tyr Gly Tyr
    50

<210> SEQ ID NO 34
<211> LENGTH: 53
<212> TYPE: PRT
<213> ORGANISM: Pyrococcus horikoshii

<400> SEQUENCE: 34

Gly Phe Ile Pro Ser Leu Leu Gly Gln Leu Leu Glu Glu Arg Gln Lys
1               5                   10                  15

Ile Lys Lys Arg Met Lys Glu Ser Lys Asp Pro Val Glu Lys Lys Leu
            20                  25                  30

Leu Asp Tyr Arg Gln Arg Ala Ile Lys Ile Leu Ala Asn Ser Tyr Tyr
        35                  40                  45

Gly Tyr Tyr Gly Tyr
    50

<210> SEQ ID NO 35
<211> LENGTH: 53
<212> TYPE: PRT
<213> ORGANISM: Pyrococcus abyssi -continued

<400> SEQUENCE: 35

Gly Phe Ile Pro Ser Leu Leu Gly Asn Leu Leu Glu Glu Arg Gln Lys
1               5                   10                  15

Ile Lys Lys Arg Met Lys Glu Ser Lys Asp Pro Val Glu Lys Lys Leu
            20                  25                  30

Leu Asp Tyr Arg Gln Arg Ala Ile Lys Ile Leu Ala Asn Ser Tyr Tyr
        35                  40                  45

Gly Tyr Tyr Gly Tyr
    50

<210> SEQ ID NO 36
<211> LENGTH: 53
<212> TYPE: PRT
<213> ORGANISM: Pyrococcus sp.

<400> SEQUENCE: 36

Gly Phe Ile Pro Ser Leu Leu Gly Asn Leu Leu Glu Glu Arg Gln Lys
1               5                   10                  15

Ile Lys Lys Arg Met Lys Glu Ser Lys Asp Pro Val Glu Lys Lys Leu
            20                  25                  30

Leu Asp Tyr Arg Gln Arg Ala Ile Lys Ile Leu Ala Asn Ser Tyr Tyr
        35                  40                  45

Gly Tyr Tyr Gly Tyr
    50

<210> SEQ ID NO 37
<211> LENGTH: 53
<212> TYPE: PRT
<213> ORGANISM: Thermococcus litoralis

<400> SEQUENCE: 37

Gly Phe Ile Pro Ser Ile Leu Gly Asp Leu Ile Ala Met Arg Gln Asp
1               5                   10                  15

Ile Lys Lys Lys Met Lys Ser Thr Ile Asp Pro Ile Glu Lys Lys Met
            20                  25                  30

Leu Asp Tyr Arg Gln Arg Ala Ile Lys Leu Leu Ala Asn Ser Tyr Tyr
        35                  40                  45

Gly Tyr Met Gly Tyr
    50

<210> SEQ ID NO 38
<211> LENGTH: 53
<212> TYPE: PRT
<213> ORGANISM: Pyrococcus sp.

<400> SEQUENCE: 38

Gly Phe Ile Pro Ser Leu Leu Gly Asp Leu Leu Glu Glu Arg Gln Lys
1               5                   10                  15

Ile Lys Arg Lys Met Lys Ala Thr Val Asp Pro Leu Glu Lys Lys Leu
            20                  25                  30

Leu Asp Tyr Arg Gln Arg Ala Ile Lys Ile Leu Ala Asn Ser Tyr Tyr
        35                  40                  45

Gly Tyr Tyr Gly Tyr
    50

<210> SEQ ID NO 39
<211> LENGTH: 53
<212> TYPE: PRT
<213> ORGANISM: Thermococcus sp.

<400> SEQUENCE: 39

Gly Phe Ile Pro Ser Leu Leu Gly Asp Leu Leu Glu Glu Arg Gln Lys
1               5                   10                  15

Ile Lys Arg Lys Met Lys Ala Thr Val Asp Pro Leu Glu Lys Lys Leu
            20                  25                  30

Leu Asp Tyr Arg Gln Arg Ala Ile Lys Ile Leu Ala Asn Ser Phe Tyr
        35                  40                  45

Gly Tyr Tyr Gly Tyr
    50

<210> SEQ ID NO 40
<211> LENGTH: 53
<212> TYPE: PRT
<213> ORGANISM: Thermococcus gorgonarius

<400> SEQUENCE: 40

Gly Phe Ile Pro Ser Leu Leu Gly Asp Leu Leu Glu Glu Arg Gln Lys
1               5                   10                  15

Val Lys Lys Lys Met Lys Ala Thr Ile Asp Pro Ile Glu Lys Lys Leu
            20                  25                  30

Leu Asp Tyr Arg Gln Arg Ala Ile Lys Ile Leu Ala Asn Ser Phe Tyr
        35                  40                  45

Gly Tyr Tyr Gly Tyr
    50

<210> SEQ ID NO 41
<211> LENGTH: 53
<212> TYPE: PRT
<213> ORGANISM: Thermococcus aggregans

<400> SEQUENCE: 41

Gly Phe Ile Pro Ser Leu Leu Gly Asp Leu Leu Asp Glu Arg Gln Lys
1               5                   10                  15

Val Lys Lys His Met Lys Ala Thr Val Asp Pro Ile Glu Lys Lys Leu
            20                  25                  30

Leu Asp Tyr Arg Gln Arg Ala Ile Lys Ile Leu Ala Asn Ser Phe Tyr
        35                  40                  45

Gly Tyr Tyr Gly Tyr
    50

<210> SEQ ID NO 42
<211> LENGTH: 53
<212> TYPE: PRT
<213> ORGANISM: Pyrococcus sp.

<400> SEQUENCE: 42

Gly Phe Ile Pro Ser Leu Leu Gly Asp Leu Leu Glu Glu Arg Gln Lys
1               5                   10                  15

Ile Lys Lys Arg Met Lys Glu Ser Lys Asp Pro Ile Glu Lys Lys Leu
            20                  25                  30

Leu Asp Tyr Arg Gln Arg Ala Ile Lys Ile Leu Ala Asn Ser Phe Tyr
        35                  40                  45

Gly Tyr Tyr Gly Tyr
    50

<210> SEQ ID NO 43
<211> LENGTH: 53
<212> TYPE: PRT

<213> ORGANISM: Pyrococcus furiosus

<400> SEQUENCE: 43

Gly Phe Ile Pro Ser Leu Leu Gly His Leu Glu Glu Arg Gln Lys
1               5                   10                  15

Ile Lys Thr Lys Met Lys Glu Thr Gln Asp Pro Ile Gly Lys Ile Leu
            20                  25                  30

Leu Asp Tyr Arg Gln Lys Ala Ile Lys Leu Leu Ala Asn Ser Phe Tyr
        35                  40                  45

Gly Tyr Tyr Gly Tyr
        50

<210> SEQ ID NO 44
<211> LENGTH: 53
<212> TYPE: PRT
<213> ORGANISM: Thermococcus sp.

<400> SEQUENCE: 44

Gly Phe Ile Pro Ser Leu Leu Gly Asp Leu Leu Glu Glu Arg Gln Lys
1               5                   10                  15

Ile Lys Arg Lys Met Arg Ala Thr Ile Asp Pro Val Glu Lys Lys Leu
            20                  25                  30

Leu Asp Tyr Arg Gln Arg Ala Ile Lys Ile Leu Ala Asn Ser Tyr Tyr
        35                  40                  45

Gly Tyr Tyr Gly Tyr
        50

<210> SEQ ID NO 45
<211> LENGTH: 53
<212> TYPE: PRT
<213> ORGANISM: Thermococcus litoralis

<400> SEQUENCE: 45

Gly Phe Ile Pro Ser Ile Leu Gly Asp Leu Ile Ala Met Arg Gln Asp
1               5                   10                  15

Ile Lys Lys Lys Met Lys Ser Thr Ile Asp Pro Ile Glu Lys Lys Met
            20                  25                  30

Leu Asp Tyr Arg Gln Arg Ala Ile Lys Leu Leu Ala Asn Ser Tyr Tyr
        35                  40                  45

Gly Tyr Met Gly Tyr
        50

<210> SEQ ID NO 46
<211> LENGTH: 53
<212> TYPE: PRT
<213> ORGANISM: Thermococcus sp.

<400> SEQUENCE: 46

Gly Phe Ile Pro Ser Leu Leu Gly Asn Leu Leu Glu Glu Arg Gln Lys
1               5                   10                  15

Ile Lys Arg Lys Met Lys Ala Thr Ile Asp Pro Leu Glu Lys Lys Leu
            20                  25                  30

Leu Asp Tyr Arg Gln Arg Ala Ile Lys Ile Leu Ala Asn Ser Tyr Tyr
        35                  40                  45

Gly Tyr Tyr Gly Tyr
        50

<210> SEQ ID NO 47
<211> LENGTH: 53

```
<212> TYPE: PRT
<213> ORGANISM: Pyrococcus sp.

<400> SEQUENCE: 47

Gly Phe Ile Pro Ser Leu Leu Gly Asp Leu Leu Glu Glu Arg Gln Lys
1               5                   10                  15

Ile Lys Lys Lys Met Lys Ala Thr Ile Asp Pro Ile Glu Arg Lys Leu
            20                  25                  30

Leu Asp Tyr Arg Gln Arg Ala Ile Lys Ile Leu Ala Asn Ser Tyr Tyr
        35                  40                  45

Gly Tyr Tyr Gly Tyr
    50

<210> SEQ ID NO 48
<211> LENGTH: 53
<212> TYPE: PRT
<213> ORGANISM: Thermococcus zilligii

<400> SEQUENCE: 48

Gly Phe Ile Pro Ser Leu Leu Gly Asp Leu Leu Glu Glu Arg Gln Lys
1               5                   10                  15

Val Lys Lys Lys Met Lys Ala Thr Val Asp Pro Ile Glu Arg Lys Leu
            20                  25                  30

Leu Asp Tyr Arg Gln Arg Ala Ile Lys Ile Leu Ala Asn Ser Tyr Tyr
        35                  40                  45

Gly Tyr Tyr Gly Tyr
    50

<210> SEQ ID NO 49
<211> LENGTH: 53
<212> TYPE: PRT
<213> ORGANISM: Thermococcus kodakarensis

<400> SEQUENCE: 49

Gly Phe Ile Pro Ser Leu Leu Gly Ala Leu Leu Asp Glu Arg Gln Lys
1               5                   10                  15

Ile Lys Lys Arg Met Lys Ala Ser Ile Asp Pro Leu Glu Lys Lys Leu
            20                  25                  30

Leu Asp Tyr Arg Gln Lys Ala Ile Lys Ile Leu Ala Asn Ser Tyr Tyr
        35                  40                  45

Gly Tyr Tyr Gly Tyr
    50

<210> SEQ ID NO 50
<211> LENGTH: 53
<212> TYPE: PRT
<213> ORGANISM: Pyrococcus glycovorans

<400> SEQUENCE: 50

Gly Phe Ile Pro Ser Leu Leu Lys Arg Leu Leu Asp Glu Arg Gln Glu
1               5                   10                  15

Ile Lys Arg Lys Met Lys Ala Ser Lys Asp Pro Ile Glu Lys Lys Met
            20                  25                  30

Leu Asp Tyr Arg Gln Arg Ala Ile Lys Ile Leu Ala Asn Ser Tyr Tyr
        35                  40                  45

Gly Tyr Tyr Gly Tyr
    50

<210> SEQ ID NO 51
```

```
<211> LENGTH: 53
<212> TYPE: PRT
<213> ORGANISM: Sulfolobus tokodaz

<400> SEQUENCE: 51

Gly Leu Tyr Lys Asn Val Leu Glu Lys Leu Ile Gln Glu Arg Lys Glu
1               5                   10                  15

Val Lys Lys Leu Met Glu Lys Thr Met Asp Glu Tyr Asp Lys Arg Val
            20                  25                  30

Leu Asp Ala Arg Gln Arg Ala Leu Lys Val Met Ala Asn Ala Phe Tyr
        35                  40                  45

Gly Tyr Met Gly Trp
    50

<210> SEQ ID NO 52
<211> LENGTH: 53
<212> TYPE: PRT
<213> ORGANISM: Desulfurococcus sp.

<400> SEQUENCE: 52

Gly Phe Ile Pro Ser Leu Leu Gly Asp Leu Leu Glu Glu Arg Gln Lys
1               5                   10                  15

Ile Lys Arg Lys Met Lys Ala Thr Val Asp Pro Leu Glu Lys Lys Leu
            20                  25                  30

Leu Asp Tyr Arg Gln Arg Ala Ile Lys Ile Leu Ala Asn Ser Tyr Tyr
        35                  40                  45

Gly Tyr Tyr Ala Tyr
    50

<210> SEQ ID NO 53
<211> LENGTH: 53
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(6)
<223> OTHER INFORMATION: Any amino acid
<220> FEATURE:
<221> NAME/KEY: MOD_RES
<222> LOCATION: (8)..(9)
<223> OTHER INFORMATION: Any amino acid
<220> FEATURE:
<221> NAME/KEY: MOD_RES
<222> LOCATION: (11)..(13)
<223> OTHER INFORMATION: Any amino acid
<220> FEATURE:
<221> NAME/KEY: MOD_RES
<222> LOCATION: (15)..(17)
<223> OTHER INFORMATION: Any amino acid
<220> FEATURE:
<221> NAME/KEY: MOD_RES
<222> LOCATION: (19)..(20)
<223> OTHER INFORMATION: Any amino acid
<220> FEATURE:
<221> NAME/KEY: MOD_RES
<222> LOCATION: (22)..(25)
<223> OTHER INFORMATION: Any amino acid
<220> FEATURE:
<221> NAME/KEY: MOD_RES
<222> LOCATION: (27)..(32)
<223> OTHER INFORMATION: Any amino acid
<220> FEATURE:
<221> NAME/KEY: MOD_RES
<222> LOCATION: (35)..(35)
<223> OTHER INFORMATION: Any amino acid
<220> FEATURE:
```

```
<221> NAME/KEY: MOD_RES
<222> LOCATION: (38)..(38)
<223> OTHER INFORMATION: Any amino acid
<220> FEATURE:
<221> NAME/KEY: MOD_RES
<222> LOCATION: (40)..(40)
<223> OTHER INFORMATION: Any amino acid
<220> FEATURE:
<221> NAME/KEY: MOD_RES
<222> LOCATION: (42)..(43)
<223> OTHER INFORMATION: Any amino acid
<220> FEATURE:
<221> NAME/KEY: MOD_RES
<222> LOCATION: (46)..(47)
<223> OTHER INFORMATION: Any amino acid
<220> FEATURE:
<221> NAME/KEY: MOD_RES
<222> LOCATION: (51)..(53)
<223> OTHER INFORMATION: Any amino acid

<400> SEQUENCE: 53

Gly Xaa Xaa Xaa Xaa Leu Xaa Xaa Leu Xaa Xaa Xaa Arg Xaa Xaa
1               5                   10                  15

Xaa Lys Xaa Xaa Met Xaa Xaa Xaa Xaa Asp Xaa Xaa Xaa Xaa Xaa
                20                  25                  30

Leu Asp Xaa Arg Gln Xaa Ala Xaa Lys Xaa Xaa Ala Asn Xaa Xaa Tyr
        35                  40                  45

Gly Tyr Xaa Xaa Xaa
        50

<210> SEQ ID NO 54
<211> LENGTH: 53
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(5)
<223> OTHER INFORMATION: Any amino acid
<220> FEATURE:
<221> NAME/KEY: MOD_RES
<222> LOCATION: (6)..(6)
<223> OTHER INFORMATION: Met, Val, Leu or Ile
<220> FEATURE:
<221> NAME/KEY: MOD_RES
<222> LOCATION: (8)..(9)
<223> OTHER INFORMATION: Any amino acid
<220> FEATURE:
<221> NAME/KEY: MOD_RES
<222> LOCATION: (11)..(11)
<223> OTHER INFORMATION: Met, Val, Leu or Ile
<220> FEATURE:
<221> NAME/KEY: MOD_RES
<222> LOCATION: (12)..(13)
<223> OTHER INFORMATION: Any amino acid
<220> FEATURE:
<221> NAME/KEY: MOD_RES
<222> LOCATION: (15)..(16)
<223> OTHER INFORMATION: Any amino acid
<220> FEATURE:
<221> NAME/KEY: MOD_RES
<222> LOCATION: (17)..(17)
<223> OTHER INFORMATION: Met, Val, Leu or Ile
<220> FEATURE:
<221> NAME/KEY: MOD_RES
<222> LOCATION: (19)..(20)
<223> OTHER INFORMATION: Any amino acid
<220> FEATURE:
<221> NAME/KEY: MOD_RES
<222> LOCATION: (22)..(23)
<223> OTHER INFORMATION: Any amino acid
<220> FEATURE:
```

```
<221> NAME/KEY: MOD_RES
<222> LOCATION: (24)..(24)
<223> OTHER INFORMATION: Ser or Thr
<220> FEATURE:
<221> NAME/KEY: MOD_RES
<222> LOCATION: (25)..(25)
<223> OTHER INFORMATION: Any amino acid
<220> FEATURE:
<221> NAME/KEY: MOD_RES
<222> LOCATION: (27)..(28)
<223> OTHER INFORMATION: Any amino acid
<220> FEATURE:
<221> NAME/KEY: MOD_RES
<222> LOCATION: (29)..(29)
<223> OTHER INFORMATION: Asp or Glu
<220> FEATURE:
<221> NAME/KEY: MOD_RES
<222> LOCATION: (30)..(30)
<223> OTHER INFORMATION: Gln, Lys or Arg
<220> FEATURE:
<221> NAME/KEY: MOD_RES
<222> LOCATION: (31)..(31)
<223> OTHER INFORMATION: Any amino acid
<220> FEATURE:
<221> NAME/KEY: MOD_RES
<222> LOCATION: (32)..(32)
<223> OTHER INFORMATION: Met, Val, Leu or Ile
<220> FEATURE:
<221> NAME/KEY: MOD_RES
<222> LOCATION: (35)..(35)
<223> OTHER INFORMATION: Any amino acid
<220> FEATURE:
<221> NAME/KEY: MOD_RES
<222> LOCATION: (38)..(38)
<223> OTHER INFORMATION: Gln, Lys or Arg
<220> FEATURE:
<221> NAME/KEY: MOD_RES
<222> LOCATION: (40)..(40)
<223> OTHER INFORMATION: Met, Val, Leu or Ile
<220> FEATURE:
<221> NAME/KEY: MOD_RES
<222> LOCATION: (42)..(43)
<223> OTHER INFORMATION: Met, Val, Leu or Ile
<220> FEATURE:
<221> NAME/KEY: MOD_RES
<222> LOCATION: (46)..(46)
<223> OTHER INFORMATION: Any amino acid
<220> FEATURE:
<221> NAME/KEY: MOD_RES
<222> LOCATION: (47)..(47)
<223> OTHER INFORMATION: Phe or Tyr
<220> FEATURE:
<221> NAME/KEY: MOD_RES
<222> LOCATION: (51)..(53)
<223> OTHER INFORMATION: Any amino acid

<400> SEQUENCE: 54

Gly Xaa Xaa Xaa Xaa Xaa Leu Xaa Xaa Leu Xaa Xaa Xaa Arg Xaa Xaa
1               5                   10                  15

Xaa Lys Xaa Xaa Met Xaa Xaa Xaa Xaa Asp Xaa Xaa Xaa Xaa Xaa Xaa
                20                  25                  30

Leu Asp Xaa Arg Gln Xaa Ala Xaa Lys Xaa Xaa Ala Asn Xaa Xaa Tyr
            35                  40                  45

Gly Tyr Xaa Xaa Xaa
        50

<210> SEQ ID NO 55
<211> LENGTH: 53
<212> TYPE: PRT
<213> ORGANISM: Artificial Sequence
<220> FEATURE:
<223> OTHER INFORMATION: Description of Artificial Sequence: Synthetic
      peptide
<220> FEATURE:
```

```
<221> NAME/KEY: MOD_RES
<222> LOCATION: (6)..(6)
<223> OTHER INFORMATION: Any amino acid
<220> FEATURE:
<221> NAME/KEY: MOD_RES
<222> LOCATION: (8)..(9)
<223> OTHER INFORMATION: Any amino acid
<220> FEATURE:
<221> NAME/KEY: MOD_RES
<222> LOCATION: (11)..(13)
<223> OTHER INFORMATION: Any amino acid
<220> FEATURE:
<221> NAME/KEY: MOD_RES
<222> LOCATION: (16)..(17)
<223> OTHER INFORMATION: Any amino acid
<220> FEATURE:
<221> NAME/KEY: MOD_RES
<222> LOCATION: (19)..(20)
<223> OTHER INFORMATION: Any amino acid
<220> FEATURE:
<221> NAME/KEY: MOD_RES
<222> LOCATION: (22)..(22)
<223> OTHER INFORMATION: Gln, Lys or Arg
<220> FEATURE:
<221> NAME/KEY: MOD_RES
<222> LOCATION: (23)..(25)
<223> OTHER INFORMATION: Any amino acid
<220> FEATURE:
<221> NAME/KEY: MOD_RES
<222> LOCATION: (28)..(32)
<223> OTHER INFORMATION: Any amino acid
<220> FEATURE:
<221> NAME/KEY: MOD_RES
<222> LOCATION: (38)..(38)
<223> OTHER INFORMATION: Any amino acid
<220> FEATURE:
<221> NAME/KEY: MOD_RES
<222> LOCATION: (42)..(42)
<223> OTHER INFORMATION: Any amino acid
<220> FEATURE:
<221> NAME/KEY: MOD_RES
<222> LOCATION: (47)..(47)
<223> OTHER INFORMATION: Phe or Tyr
<220> FEATURE:
<221> NAME/KEY: MOD_RES
<222> LOCATION: (51)..(52)
<223> OTHER INFORMATION: Any amino acid

<400> SEQUENCE: 55

Gly Phe Ile Pro Ser Xaa Leu Xaa Xaa Leu Xaa Xaa Xaa Arg Gln Xaa
1               5                   10                  15

Xaa Lys Xaa Xaa Met Xaa Xaa Xaa Xaa Asp Pro Xaa Xaa Xaa Xaa Xaa
            20                  25                  30

Leu Asp Tyr Arg Gln Xaa Ala Ile Lys Xaa Leu Ala Asn Ser Xaa Tyr
        35                  40                  45

Gly Tyr Xaa Xaa Tyr
    50

<210> SEQ ID NO 56
<211> LENGTH: 53
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Met, Val, Leu or Ile
<220> FEATURE:
<221> NAME/KEY: MOD_RES
<222> LOCATION: (8)..(9)
<223> OTHER INFORMATION: Any amino acid
<220> FEATURE:
```

```
<221> NAME/KEY: MOD_RES
<222> LOCATION: (11)..(11)
<223> OTHER INFORMATION: Met, Val, Leu or Ile
<220> FEATURE:
<221> NAME/KEY: MOD_RES
<222> LOCATION: (12)..(13)
<223> OTHER INFORMATION: Any amino acid
<220> FEATURE:
<221> NAME/KEY: MOD_RES
<222> LOCATION: (15)..(16)
<223> OTHER INFORMATION: Any amino acid
<220> FEATURE:
<221> NAME/KEY: MOD_RES
<222> LOCATION: (17)..(17)
<223> OTHER INFORMATION: Met, Val, Leu or Ile
<220> FEATURE:
<221> NAME/KEY: MOD_RES
<222> LOCATION: (19)..(20)
<223> OTHER INFORMATION: Any amino acid
<220> FEATURE:
<221> NAME/KEY: MOD_RES
<222> LOCATION: (22)..(22)
<223> OTHER INFORMATION: Gln, Lys or Arg
<220> FEATURE:
<221> NAME/KEY: MOD_RES
<222> LOCATION: (23)..(23)
<223> OTHER INFORMATION: Any amino acid
<220> FEATURE:
<221> NAME/KEY: MOD_RES
<222> LOCATION: (24)..(24)
<223> OTHER INFORMATION: Ser or Thr
<220> FEATURE:
<221> NAME/KEY: MOD_RES
<222> LOCATION: (25)..(25)
<223> OTHER INFORMATION: Any amino acid
<220> FEATURE:
<221> NAME/KEY: MOD_RES
<222> LOCATION: (28)..(28)
<223> OTHER INFORMATION: Met, Val, Leu or Ile
<220> FEATURE:
<221> NAME/KEY: MOD_RES
<222> LOCATION: (30)..(30)
<223> OTHER INFORMATION: Gln, Lys or Arg
<220> FEATURE:
<221> NAME/KEY: MOD_RES
<222> LOCATION: (31)..(32)
<223> OTHER INFORMATION: Met, Val, Leu or Ile
<220> FEATURE:
<221> NAME/KEY: MOD_RES
<222> LOCATION: (38)..(38)
<223> OTHER INFORMATION: Gln, Lys or Arg
<220> FEATURE:
<221> NAME/KEY: MOD_RES
<222> LOCATION: (42)..(42)
<223> OTHER INFORMATION: Met, Val, Leu or Ile
<220> FEATURE:
<221> NAME/KEY: MOD_RES
<222> LOCATION: (47)..(47)
<223> OTHER INFORMATION: Phe or Tyr
<220> FEATURE:
<221> NAME/KEY: MOD_RES
<222> LOCATION: (51)..(52)
<223> OTHER INFORMATION: Any amino acid

<400> SEQUENCE: 56

Gly Phe Ile Pro Ser Xaa Leu Xaa Xaa Leu Xaa Xaa Xaa Arg Xaa Xaa
1               5                   10                  15

Xaa Lys Xaa Xaa Met Xaa Xaa Xaa Xaa Asp Pro Xaa Glu Xaa Xaa Xaa
            20                  25                  30

Leu Asp Tyr Arg Gln Xaa Ala Ile Lys Xaa Leu Ala Asn Ser Xaa Tyr
        35                  40                  45

Gly Tyr Xaa Xaa Tyr
    50
```

<210> SEQ ID NO 57
<211> LENGTH: 774
<212> TYPE: PRT
<213> ORGANISM: Thermococcus litoralis

<400> SEQUENCE: 57

```
Met Ile Leu Asp Thr Asp Tyr Ile Thr Lys Asp Gly Lys Pro Ile Ile
1               5                   10                  15

Arg Ile Phe Lys Lys Glu Asn Gly Glu Phe Lys Ile Glu Leu Asp Pro
            20                  25                  30

His Phe Gln Pro Tyr Ile Tyr Ala Leu Leu Lys Asp Asp Ser Ala Ile
        35                  40                  45

Glu Glu Ile Lys Ala Ile Lys Gly Glu Arg His Gly Lys Thr Val Arg
    50                  55                  60

Val Leu Asp Ala Val Lys Val Arg Lys Lys Phe Leu Gly Arg Glu Val
65                  70                  75                  80

Glu Val Trp Lys Leu Ile Phe Glu His Pro Gln Asp Val Pro Ala Met
                85                  90                  95

Arg Gly Lys Ile Arg Glu His Pro Ala Val Val Asp Ile Tyr Glu Tyr
            100                 105                 110

Asp Ile Pro Phe Ala Lys Arg Tyr Leu Ile Asp Lys Gly Leu Ile Pro
        115                 120                 125

Met Glu Gly Asp Glu Glu Leu Lys Leu Leu Ala Phe Asp Ile Glu Thr
    130                 135                 140

Phe Tyr His Glu Gly Asp Glu Phe Gly Lys Gly Glu Ile Ile Met Ile
145                 150                 155                 160

Ser Tyr Ala Asp Glu Glu Ala Arg Val Ile Thr Trp Lys Asn Ile
                165                 170                 175

Asp Leu Pro Tyr Val Asp Val Val Ser Asn Glu Arg Glu Met Ile Lys
            180                 185                 190

Arg Phe Val Gln Val Val Lys Glu Lys Asp Pro Asp Val Ile Ile Thr
        195                 200                 205

Tyr Asn Gly Asp Asn Phe Asp Leu Pro Tyr Leu Ile Lys Arg Ala Glu
    210                 215                 220

Lys Leu Gly Val Arg Leu Val Leu Gly Arg Asp Lys Glu His Pro Glu
225                 230                 235                 240

Pro Lys Ile Gln Arg Met Gly Asp Ser Phe Ala Val Glu Ile Lys Gly
                245                 250                 255

Arg Ile His Phe Asp Leu Phe Pro Val Val Arg Arg Thr Ile Asn Leu
            260                 265                 270

Pro Thr Tyr Thr Leu Glu Ala Val Tyr Glu Ala Val Leu Gly Lys Thr
        275                 280                 285

Lys Ser Lys Leu Gly Ala Glu Glu Ile Ala Ala Ile Trp Glu Thr Glu
    290                 295                 300

Glu Ser Met Lys Lys Leu Ala Gln Tyr Ser Met Glu Asp Ala Arg Ala
305                 310                 315                 320

Thr Tyr Glu Leu Gly Lys Glu Phe Phe Pro Met Glu Ala Glu Leu Ala
                325                 330                 335

Lys Leu Ile Gly Gln Ser Val Trp Asp Val Ser Arg Ser Ser Thr Gly
            340                 345                 350

Asn Leu Val Glu Trp Tyr Leu Leu Arg Val Ala Tyr Ala Arg Asn Glu
        355                 360                 365

Leu Ala Pro Asn Lys Pro Asp Glu Glu Glu Tyr Lys Arg Arg Leu Arg
    370                 375                 380
```

```
Thr Thr Tyr Leu Gly Gly Tyr Val Lys Glu Pro Glu Lys Gly Leu Trp
385                 390                 395                 400

Glu Asn Ile Ile Tyr Leu Asp Phe Arg Ser Leu Tyr Pro Ser Ile Ile
                405                 410                 415

Val Thr His Asn Val Ser Pro Asp Thr Leu Glu Lys Glu Gly Cys Lys
            420                 425                 430

Asn Tyr Asp Val Ala Pro Ile Val Gly Tyr Arg Phe Cys Lys Asp Phe
        435                 440                 445

Pro Gly Phe Ile Pro Ser Ile Leu Gly Asp Leu Ile Ala Met Arg Gln
    450                 455                 460

Asp Ile Lys Lys Met Lys Ser Thr Ile Asp Pro Ile Glu Lys Lys
465                 470                 475                 480

Met Leu Asp Tyr Arg Gln Arg Ala Ile Lys Leu Leu Ala Asn Ser Tyr
                485                 490                 495

Tyr Gly Tyr Met Gly Tyr Pro Lys Ala Arg Trp Tyr Ser Lys Glu Cys
            500                 505                 510

Ala Glu Ser Val Thr Ala Trp Gly Arg His Tyr Ile Glu Met Thr Ile
        515                 520                 525

Arg Glu Ile Glu Glu Lys Phe Gly Phe Lys Val Leu Tyr Ala Asp Thr
    530                 535                 540

Asp Gly Phe Tyr Ala Thr Ile Pro Gly Glu Lys Pro Glu Leu Ile Lys
545                 550                 555                 560

Lys Lys Ala Lys Glu Phe Leu Asn Tyr Ile Asn Ser Lys Leu Pro Gly
                565                 570                 575

Leu Leu Glu Leu Glu Tyr Glu Gly Phe Tyr Leu Arg Gly Phe Phe Val
            580                 585                 590

Thr Lys Lys Arg Tyr Ala Val Ile Asp Glu Glu Gly Arg Ile Thr Thr
        595                 600                 605

Arg Gly Leu Glu Val Val Arg Arg Asp Trp Ser Glu Ile Ala Lys Glu
    610                 615                 620

Thr Gln Ala Lys Val Leu Glu Ala Ile Leu Lys Glu Gly Ser Val Glu
625                 630                 635                 640

Lys Ala Val Glu Val Val Arg Asp Val Val Glu Lys Ile Ala Lys Tyr
                645                 650                 655

Arg Val Pro Leu Glu Lys Leu Val Ile His Glu Gln Ile Thr Arg Asp
            660                 665                 670

Leu Lys Asp Tyr Lys Ala Ile Gly Pro His Val Ala Ile Ala Lys Arg
        675                 680                 685

Leu Ala Ala Arg Gly Ile Lys Val Lys Pro Gly Thr Ile Ile Ser Tyr
    690                 695                 700

Ile Val Leu Lys Gly Ser Gly Lys Ile Ser Asp Arg Val Ile Leu Leu
705                 710                 715                 720

Thr Glu Tyr Asp Pro Arg Lys His Lys Tyr Asp Pro Asp Tyr Tyr Ile
                725                 730                 735

Glu Asn Gln Val Leu Pro Ala Val Leu Arg Ile Leu Glu Ala Phe Gly
            740                 745                 750

Tyr Arg Lys Glu Asp Leu Arg Tyr Gln Ser Ser Lys Gln Thr Gly Leu
        755                 760                 765

Asp Ala Trp Leu Lys Arg
    770

<210> SEQ ID NO 58
<211> LENGTH: 1702
<212> TYPE: PRT
```

<213> ORGANISM: Thermococcus litoralis

<400> SEQUENCE: 58

```
Met Ile Leu Asp Thr Asp Tyr Ile Thr Lys Asp Gly Lys Pro Ile Ile
1               5                   10                  15

Arg Ile Phe Lys Lys Glu Asn Gly Glu Phe Lys Ile Glu Leu Asp Pro
            20                  25                  30

His Phe Gln Pro Tyr Ile Tyr Ala Leu Leu Lys Asp Asp Ser Ala Ile
        35                  40                  45

Glu Glu Ile Lys Ala Ile Lys Gly Glu Arg His Gly Lys Thr Val Arg
    50                  55                  60

Val Leu Asp Ala Val Lys Val Arg Lys Lys Phe Leu Gly Arg Glu Val
65                  70                  75                  80

Glu Val Trp Lys Leu Ile Phe Glu His Pro Gln Asp Val Pro Ala Met
                85                  90                  95

Arg Gly Lys Ile Arg Glu His Pro Ala Val Val Asp Ile Tyr Glu Tyr
            100                 105                 110

Asp Ile Pro Phe Ala Lys Arg Tyr Leu Ile Asp Lys Gly Leu Ile Pro
        115                 120                 125

Met Glu Gly Asp Glu Glu Leu Lys Leu Leu Ala Phe Asp Ile Glu Thr
    130                 135                 140

Phe Tyr His Glu Gly Asp Glu Phe Gly Lys Gly Glu Ile Ile Met Ile
145                 150                 155                 160

Ser Tyr Ala Asp Glu Glu Ala Arg Val Ile Thr Trp Lys Asn Ile
                165                 170                 175

Asp Leu Pro Tyr Val Asp Val Val Ser Asn Glu Arg Glu Met Ile Lys
            180                 185                 190

Arg Phe Val Gln Val Val Lys Glu Lys Asp Pro Asp Val Ile Ile Thr
        195                 200                 205

Tyr Asn Gly Asp Asn Phe Asp Leu Pro Tyr Leu Ile Lys Arg Ala Glu
    210                 215                 220

Lys Leu Gly Val Arg Leu Val Leu Gly Arg Asp Lys Glu His Pro Glu
225                 230                 235                 240

Pro Lys Ile Gln Arg Met Gly Asp Ser Phe Ala Val Glu Ile Lys Gly
                245                 250                 255

Arg Ile His Phe Asp Leu Phe Pro Val Val Arg Arg Thr Ile Asn Leu
            260                 265                 270

Pro Thr Tyr Thr Leu Glu Ala Val Tyr Glu Ala Val Leu Gly Lys Thr
        275                 280                 285

Lys Ser Lys Leu Gly Ala Glu Glu Ile Ala Ala Ile Trp Glu Thr Glu
    290                 295                 300

Glu Ser Met Lys Lys Leu Ala Gln Tyr Ser Met Glu Asp Ala Arg Ala
305                 310                 315                 320

Thr Tyr Glu Leu Gly Lys Glu Phe Phe Pro Met Glu Ala Glu Leu Ala
                325                 330                 335

Lys Leu Ile Gly Gln Ser Val Trp Asp Val Ser Arg Ser Ser Thr Gly
            340                 345                 350

Asn Leu Val Glu Trp Tyr Leu Leu Arg Val Ala Tyr Ala Arg Asn Glu
        355                 360                 365

Leu Ala Pro Asn Lys Pro Asp Glu Glu Tyr Lys Arg Arg Leu Arg
    370                 375                 380

Thr Thr Tyr Leu Gly Gly Tyr Val Lys Glu Pro Glu Lys Gly Leu Trp
385                 390                 395                 400
```

```
Glu Asn Ile Ile Tyr Leu Asp Phe Arg Ser Leu Tyr Pro Ser Ile Ile
                405                 410                 415

Val Thr His Asn Val Ser Pro Asp Thr Leu Glu Lys Glu Gly Cys Lys
            420                 425                 430

Asn Tyr Asp Val Ala Pro Ile Val Gly Tyr Arg Phe Cys Lys Asp Phe
        435                 440                 445

Pro Gly Phe Ile Pro Ser Ile Leu Gly Asp Leu Ile Ala Met Arg Gln
450                 455                 460

Asp Ile Lys Lys Lys Met Lys Ser Thr Ile Asp Pro Ile Glu Lys Lys
465                 470                 475                 480

Met Leu Asp Tyr Arg Gln Arg Ala Ile Lys Leu Leu Ala Asn Ser Ile
                485                 490                 495

Leu Pro Asn Glu Trp Leu Pro Ile Ile Glu Asn Gly Glu Ile Lys Phe
            500                 505                 510

Val Lys Ile Gly Glu Phe Ile Asn Ser Tyr Met Glu Lys Gln Lys Glu
        515                 520                 525

Asn Val Lys Thr Val Glu Asn Thr Glu Val Leu Glu Val Asn Asn Leu
530                 535                 540

Phe Ala Phe Ser Phe Asn Lys Lys Ile Lys Glu Ser Glu Val Lys Lys
545                 550                 555                 560

Val Lys Ala Leu Ile Arg His Lys Tyr Lys Gly Lys Ala Tyr Glu Ile
                565                 570                 575

Gln Leu Ser Ser Gly Arg Lys Ile Asn Ile Thr Ala Gly His Ser Leu
            580                 585                 590

Phe Thr Val Arg Asn Gly Glu Ile Lys Glu Val Ser Gly Asp Gly Ile
        595                 600                 605

Lys Glu Gly Asp Leu Ile Val Ala Pro Lys Lys Ile Lys Leu Asn Glu
610                 615                 620

Lys Gly Val Ser Ile Asn Ile Pro Glu Leu Ile Ser Asp Leu Ser Glu
625                 630                 635                 640

Glu Glu Thr Ala Asp Ile Val Met Thr Ile Ser Ala Lys Gly Arg Lys
                645                 650                 655

Asn Phe Phe Lys Gly Met Leu Arg Thr Leu Arg Trp Met Phe Gly Glu
            660                 665                 670

Glu Asn Arg Arg Ile Arg Thr Phe Asn Arg Tyr Leu Phe His Leu Glu
        675                 680                 685

Lys Leu Gly Leu Ile Lys Leu Leu Pro Arg Gly Tyr Glu Val Thr Asp
690                 695                 700

Trp Glu Arg Leu Lys Lys Tyr Lys Gln Leu Tyr Glu Lys Leu Ala Gly
705                 710                 715                 720

Ser Val Lys Tyr Asn Gly Asn Lys Arg Glu Tyr Leu Val Met Phe Asn
                725                 730                 735

Glu Ile Lys Asp Phe Ile Ser Tyr Phe Pro Gln Lys Glu Leu Glu Glu
            740                 745                 750

Trp Lys Ile Gly Thr Leu Asn Gly Phe Arg Thr Asn Cys Ile Leu Lys
        755                 760                 765

Val Asp Glu Asp Phe Gly Lys Leu Leu Gly Tyr Tyr Val Ser Glu Gly
770                 775                 780

Tyr Ala Gly Ala Gln Lys Asn Lys Thr Gly Ile Ser Tyr Ser Val
785                 790                 795                 800

Lys Leu Tyr Asn Glu Asp Pro Asn Val Leu Glu Ser Met Lys Asn Val
                805                 810                 815

Ala Glu Lys Phe Phe Gly Lys Val Arg Val Asp Arg Asn Cys Val Ser
```

-continued

```
                820                 825                 830
Ile Ser Lys Lys Met Ala Tyr Leu Val Met Lys Cys Leu Cys Gly Ala
                835                 840                 845
Leu Ala Glu Asn Lys Arg Ile Pro Ser Val Ile Leu Thr Ser Pro Glu
850                 855                 860
Pro Val Arg Trp Ser Phe Leu Glu Ala Tyr Phe Thr Gly Asp Gly Asp
865                 870                 875                 880
Ile His Pro Ser Lys Arg Phe Arg Leu Ser Thr Lys Ser Glu Leu Leu
                885                 890                 895
Ala Asn Gln Leu Val Phe Leu Leu Asn Ser Leu Gly Ile Ser Ser Val
                900                 905                 910
Lys Ile Gly Phe Asp Ser Gly Val Tyr Arg Val Tyr Ile Asn Glu Asp
                915                 920                 925
Leu Gln Phe Pro Gln Thr Ser Arg Glu Lys Asn Thr Tyr Tyr Ser Asn
                930                 935                 940
Leu Ile Pro Lys Glu Ile Leu Arg Asp Val Phe Gly Lys Glu Phe Gln
945                 950                 955                 960
Lys Asn Met Thr Phe Lys Lys Phe Lys Glu Leu Val Asp Ser Gly Lys
                965                 970                 975
Leu Asn Arg Glu Lys Ala Lys Leu Leu Glu Phe Phe Ile Asn Gly Asp
                980                 985                 990
Ile Val Leu Asp Arg Val Lys Ser Val Lys Glu Lys Asp Tyr Glu Gly
                995                 1000                1005
Tyr Val Tyr Asp Leu Ser Val Glu Asp Asn Glu Asn Phe Leu Val
                1010                1015                1020
Gly Phe Gly Leu Leu Tyr Ala His Asn Ser Tyr Tyr Gly Tyr Met
                1025                1030                1035
Gly Tyr Pro Lys Ala Arg Trp Tyr Ser Leu Glu Cys Ala Glu Ser
                1040                1045                1050
Val Thr Ala Trp Gly Arg His Tyr Ile Glu Met Thr Ile Arg Glu
                1055                1060                1065
Ile Glu Glu Lys Phe Gly Phe Lys Val Leu Tyr Ala Asp Ser Val
                1070                1075                1080
Ser Gly Glu Ser Glu Ile Ile Ile Arg Gln Asn Gly Lys Ile Arg
                1085                1090                1095
Phe Val Lys Ile Lys Asp Leu Phe Ser Lys Val Asp Tyr Ser Ile
                1100                1105                1110
Gly Glu Lys Glu Tyr Cys Ile Leu Glu Gly Val Glu Ala Leu Thr
                1115                1120                1125
Leu Asp Asp Asp Gly Lys Leu Val Trp Lys Pro Val Pro Tyr Val
                1130                1135                1140
Met Arg His Arg Ala Asn Lys Arg Met Phe Arg Ile Trp Leu Thr
                1145                1150                1155
Asn Ser Trp Tyr Ile Asp Val Thr Glu Asp His Ser Leu Ile Gly
                1160                1165                1170
Tyr Leu Asn Thr Ser Lys Thr Lys Thr Ala Lys Lys Ile Gly Glu
                1175                1180                1185
Arg Leu Lys Glu Val Lys Pro Phe Glu Leu Gly Lys Ala Val Lys
                1190                1195                1200
Ser Leu Ile Cys Pro Asn Ala Pro Leu Lys Asp Glu Asn Thr Lys
                1205                1210                1215
Thr Ser Glu Ile Ala Val Lys Phe Trp Glu Leu Val Gly Leu Ile
                1220                1225                1230
```

```
Val Gly Asp Gly Asn Trp Gly Asp Ser Arg Trp Ala Glu Tyr
    1235            1240            1245

Tyr Leu Gly Leu Ser Thr Gly Lys Asp Ala Glu Glu Ile Lys Gln
    1250            1255            1260

Lys Leu Leu Glu Pro Leu Lys Thr Tyr Gly Val Ile Ser Asn Tyr
    1265            1270            1275

Tyr Pro Lys Asn Glu Lys Gly Asp Phe Asn Ile Leu Ala Lys Ser
    1280            1285            1290

Leu Val Lys Phe Met Lys Arg His Phe Lys Asp Glu Lys Gly Arg
    1295            1300            1305

Arg Lys Ile Pro Glu Phe Met Tyr Glu Leu Pro Val Thr Tyr Ile
    1310            1315            1320

Glu Ala Phe Leu Arg Gly Leu Phe Ser Ala Asp Gly Thr Val Thr
    1325            1330            1335

Ile Arg Lys Gly Val Pro Glu Ile Arg Leu Thr Asn Ile Asp Ala
    1340            1345            1350

Asp Phe Leu Arg Glu Val Arg Lys Leu Leu Trp Ile Val Gly Ile
    1355            1360            1365

Ser Asn Ser Ile Phe Ala Glu Thr Thr Pro Asn Arg Tyr Asn Gly
    1370            1375            1380

Val Ser Thr Gly Thr Tyr Ser Lys His Leu Arg Ile Lys Asn Lys
    1385            1390            1395

Trp Arg Phe Ala Glu Arg Ile Gly Phe Leu Ile Glu Arg Lys Gln
    1400            1405            1410

Lys Arg Leu Leu Glu His Leu Lys Ser Ala Arg Val Lys Arg Asn
    1415            1420            1425

Thr Ile Asp Phe Gly Phe Asp Leu Val His Val Lys Lys Val Glu
    1430            1435            1440

Glu Ile Pro Tyr Glu Gly Tyr Val Tyr Asp Ile Glu Val Glu Glu
    1445            1450            1455

Thr His Arg Phe Phe Ala Asn Asn Ile Leu Val His Asn Thr Asp
    1460            1465            1470

Gly Phe Tyr Ala Thr Ile Pro Gly Glu Lys Pro Glu Leu Ile Lys
    1475            1480            1485

Lys Lys Ala Lys Glu Phe Leu Asn Tyr Ile Asn Ser Lys Leu Pro
    1490            1495            1500

Gly Leu Leu Glu Leu Glu Tyr Glu Gly Phe Tyr Leu Arg Gly Phe
    1505            1510            1515

Phe Val Thr Lys Lys Arg Tyr Ala Val Ile Asp Glu Glu Gly Arg
    1520            1525            1530

Ile Thr Thr Arg Gly Leu Glu Val Val Arg Arg Asp Trp Ser Glu
    1535            1540            1545

Ile Ala Lys Glu Thr Gln Ala Lys Val Leu Glu Ala Ile Leu Lys
    1550            1555            1560

Glu Gly Ser Val Glu Lys Ala Val Glu Val Val Arg Asp Val Val
    1565            1570            1575

Glu Lys Ile Ala Lys Tyr Arg Val Pro Leu Glu Lys Leu Val Ile
    1580            1585            1590

His Glu Gln Ile Thr Arg Asp Leu Lys Asp Tyr Lys Ala Ile Gly
    1595            1600            1605

Pro His Val Ala Ile Ala Lys Arg Leu Ala Ala Arg Gly Ile Lys
    1610            1615            1620
```

-continued

```
Val Lys Pro Gly Thr Ile Ile Ser Tyr Ile Val Leu Lys Gly Ser
    1625                1630                1635

Gly Lys Ile Ser Asp Arg Val Ile Leu Leu Thr Glu Tyr Asp Pro
    1640                1645                1650

Arg Lys His Lys Tyr Asp Pro Asp Tyr Tyr Ile Glu Asn Gln Val
    1655                1660                1665

Leu Pro Ala Val Leu Arg Ile Leu Glu Ala Phe Gly Tyr Arg Lys
    1670                1675                1680

Glu Asp Leu Arg Tyr Gln Ser Ser Lys Gln Thr Gly Leu Asp Ala
    1685                1690                1695

Trp Leu Lys Arg
    1700

<210> SEQ ID NO 59
<211> LENGTH: 1829
<212> TYPE: PRT
<213> ORGANISM: Thermococcus aggregans
<220> FEATURE:
<221> NAME/KEY: MOD_RES
<222> LOCATION: (1118)..(1118)
<223> OTHER INFORMATION: Any amino acid
<220> FEATURE:
<221> NAME/KEY: MOD_RES
<222> LOCATION: (1123)..(1123)
<223> OTHER INFORMATION: Any amino acid

<400> SEQUENCE: 59

Met Ile Leu Asp Thr Asp Tyr Ile Thr Lys Asp Gly Lys Pro Ile Ile
1               5                   10                  15

Arg Ile Phe Lys Lys Glu Asn Gly Glu Phe Lys Ile Glu Leu Asp Pro
            20                  25                  30

His Phe Gln Pro Tyr Ile Tyr Ala Leu Leu Lys Asp Asp Ser Ala Ile
        35                  40                  45

Asp Glu Ile Lys Ala Ile Lys Gly Glu Arg His Gly Lys Ile Val Arg
    50                  55                  60

Val Val Asp Ala Val Lys Val Lys Lys Lys Phe Leu Gly Arg Asp Val
65                  70                  75                  80

Glu Val Trp Lys Leu Ile Phe Glu His Pro Gln Asp Val Pro Ala Leu
                85                  90                  95

Arg Gly Lys Ile Arg Glu His Pro Ala Val Ile Asp Ile Tyr Glu Tyr
            100                 105                 110

Asp Ile Pro Phe Ala Lys Arg Tyr Leu Ile Asp Lys Gly Leu Ile Pro
        115                 120                 125

Met Glu Gly Asp Glu Glu Leu Lys Leu Met Ala Phe Asp Ile Glu Thr
    130                 135                 140

Phe Tyr His Glu Gly Asp Glu Phe Gly Lys Gly Glu Ile Ile Met Ile
145                 150                 155                 160

Ser Tyr Ala Asp Glu Glu Glu Ala Arg Val Ile Thr Trp Lys Asn Ile
                165                 170                 175

Asp Leu Pro Tyr Val Asp Val Val Ser Asn Glu Arg Glu Met Ile Lys
            180                 185                 190

Arg Phe Val Gln Ile Val Arg Glu Lys Asp Pro Asp Val Leu Ile Thr
        195                 200                 205

Tyr Asn Gly Asp Asn Phe Asp Leu Pro Tyr Leu Ile Lys Arg Ala Glu
    210                 215                 220

Lys Leu Gly Val Thr Leu Leu Leu Gly Arg Asp Lys Glu His Pro Glu
225                 230                 235                 240
```

```
Pro Lys Ile His Arg Met Gly Asp Ser Phe Ala Val Glu Ile Lys Gly
            245                 250                 255

Arg Ile His Phe Asp Leu Phe Pro Val Val Arg Arg Thr Ile Asn Leu
            260                 265                 270

Pro Thr Tyr Thr Leu Glu Ala Val Tyr Glu Ala Val Leu Gly Lys Thr
            275                 280                 285

Lys Ser Lys Leu Gly Ala Glu Ile Ala Ala Ile Trp Glu Thr Glu
        290                 295                 300

Glu Ser Met Lys Lys Leu Ala Gln Tyr Ser Met Glu Asp Ala Arg Ala
305                 310                 315                 320

Thr Tyr Glu Leu Gly Lys Glu Phe Phe Pro Met Glu Ala Glu Leu Ala
                325                 330                 335

Lys Leu Ile Gly Gln Ser Val Trp Asp Val Ser Arg Ser Ser Thr Gly
            340                 345                 350

Asn Leu Val Glu Trp Tyr Leu Leu Arg Val Ala Tyr Glu Arg Asn Glu
            355                 360                 365

Leu Ala Pro Asn Lys Pro Asp Glu Glu Tyr Arg Arg Arg Leu Arg
        370                 375                 380

Thr Thr Tyr Leu Gly Gly Tyr Val Lys Glu Pro Glu Arg Gly Leu Trp
385                 390                 395                 400

Glu Asn Ile Ala Tyr Leu Asp Phe Arg Cys His Pro Ala Asp Thr Lys
                405                 410                 415

Val Ile Val Lys Gly Lys Gly Ile Val Asn Ile Ser Asp Val Lys Glu
            420                 425                 430

Gly Asp Tyr Ile Leu Gly Ile Asp Gly Trp Gln Arg Val Lys Lys Val
            435                 440                 445

Trp Lys Tyr His Tyr Glu Gly Lys Leu Ile Asn Ile Asn Gly Leu Lys
        450                 455                 460

Cys Thr Pro Asn His Lys Val Pro Val Val Thr Glu Asn Asp Arg Gln
465                 470                 475                 480

Thr Arg Ile Arg Asp Ser Leu Ala Lys Ser Phe Leu Ser Gly Lys Val
                485                 490                 495

Lys Gly Lys Ile Ile Thr Thr Lys Leu Phe Glu Lys Ile Ala Glu Phe
            500                 505                 510

Glu Lys Asn Lys Pro Ser Glu Glu Ile Leu Lys Gly Glu Leu Ser
        515                 520                 525

Gly Ile Ile Leu Ala Glu Gly Thr Leu Leu Arg Lys Asp Ile Glu Tyr
            530                 535                 540

Phe Asp Ser Ser Arg Gly Lys Lys Arg Ile Ser His Gln Tyr Arg Val
545                 550                 555                 560

Glu Ile Thr Ile Gly Glu Asn Glu Lys Glu Leu Leu Glu Arg Ile Leu
                565                 570                 575

Tyr Ile Phe Asp Lys Leu Phe Gly Ile Arg Pro Ser Val Lys Lys Lys
            580                 585                 590

Gly Asp Thr Asn Ala Leu Lys Ile Thr Thr Ala Lys Lys Ala Val Tyr
            595                 600                 605

Leu Gln Ile Glu Glu Leu Leu Lys Asn Ile Glu Ser Leu Tyr Ala Pro
        610                 615                 620

Ala Val Leu Arg Gly Phe Phe Glu Arg Asp Ala Thr Val Asn Lys Ile
625                 630                 635                 640

Arg Ser Thr Ile Val Val Thr Gln Gly Thr Asn Asn Lys Trp Lys Ile
                645                 650                 655

Asp Ile Val Ala Lys Leu Leu Asp Ser Leu Gly Ile Pro Tyr Ser Arg
```

-continued

```
                660                 665                 670
Tyr Glu Tyr Lys Tyr Ile Glu Asn Gly Lys Glu Leu Thr Lys His Ile
            675                 680                 685

Leu Glu Ile Thr Gly Arg Asp Gly Leu Ile Leu Phe Gln Thr Leu Val
        690                 695                 700

Gly Phe Ile Ser Ser Glu Lys Asn Glu Ala Leu Glu Lys Ala Ile Glu
705                 710                 715                 720

Val Arg Glu Met Asn Arg Leu Lys Asn Ser Phe Tyr Asn Leu Ser
                725                 730                 735

Thr Phe Glu Val Ser Ser Glu Tyr Tyr Lys Gly Glu Val Tyr Asp Leu
                740                 745                 750

Thr Leu Glu Gly Asn Pro Tyr Tyr Phe Ala Asn Gly Ile Leu Thr His
            755                 760                 765

Asn Ser Leu Tyr Pro Ser Ile Ile Val Thr His Asn Val Ser Pro Asp
        770                 775                 780

Thr Leu Glu Arg Glu Gly Cys Lys Asn Tyr Asp Val Ala Pro Ile Val
785                 790                 795                 800

Gly Tyr Lys Phe Cys Lys Asp Phe Pro Gly Phe Ile Pro Ser Ile Leu
                805                 810                 815

Gly Glu Leu Ile Thr Met Arg Gln Glu Ile Lys Lys Met Lys Ala
                820                 825                 830

Thr Ile Asp Pro Ile Glu Lys Lys Met Leu Asp Tyr Arg Gln Arg Ala
            835                 840                 845

Val Lys Leu Leu Ala Asn Ser Ile Leu Pro Asn Glu Trp Leu Pro Ile
        850                 855                 860

Ile Glu Asn Gly Glu Val Lys Phe Val Lys Ile Gly Glu Phe Ile Asp
865                 870                 875                 880

Arg Tyr Met Glu Glu Gln Lys Asp Lys Val Arg Thr Val Asp Asn Thr
                885                 890                 895

Glu Val Leu Glu Val Asp Asn Ile Phe Ala Phe Ser Leu Asn Lys Glu
                900                 905                 910

Ser Lys Lys Ser Glu Ile Lys Lys Val Lys Ala Leu Ile Arg His Lys
            915                 920                 925

Tyr Lys Gly Glu Ala Tyr Glu Val Glu Leu Asn Ser Gly Arg Lys Ile
        930                 935                 940

His Ile Thr Arg Gly His Ser Leu Phe Thr Ile Arg Asn Gly Lys Ile
945                 950                 955                 960

Lys Glu Ile Trp Gly Glu Glu Val Lys Val Gly Asp Leu Ile Ile Val
                965                 970                 975

Pro Lys Lys Val Lys Leu Asn Glu Lys Glu Ala Val Ile Asn Ile Pro
            980                 985                 990

Glu Leu Ile Ser Lys Leu Pro Asp Glu Asp Thr Ala Asp Val Val Met
        995                 1000                1005

Thr Thr Pro Val Lys Gly Arg Lys Asn Phe Phe Lys Gly Met Leu
        1010                1015                1020

Arg Thr Leu Lys Trp Ile Phe Gly Glu Glu Ser Lys Arg Ile Arg
        1025                1030                1035

Thr Phe Asn Arg Tyr Leu Phe His Leu Glu Glu Leu Gly Phe Val
        1040                1045                1050

Lys Leu Leu Pro Arg Gly Tyr Glu Val Thr Asp Trp Glu Gly Leu
        1055                1060                1065

Lys Arg Tyr Arg Gln Leu Tyr Glu Lys Leu Val Lys Asn Leu Arg
        1070                1075                1080
```

```
Tyr Asn Gly Asn Lys Arg Glu Tyr Leu Val Arg Phe Asn Asp Ile
    1085                1090                1095
Lys Asp Ser Val Ser Cys Phe Pro Arg Lys Glu Leu Glu Glu Trp
    1100                1105                1110
Lys Ile Gly Thr Xaa Lys Gly Phe Arg Xaa Lys Cys Ile Leu Lys
    1115                1120                1125
Val Asp Glu Asp Phe Gly Lys Phe Leu Gly Tyr Tyr Val Ser Glu
    1130                1135                1140
Gly Tyr Ala Gly Ala Gln Lys Asn Lys Thr Gly Gly Met Ser Tyr
    1145                1150                1155
Ser Val Lys Leu Tyr Asn Glu Asn Pro Asn Val Leu Lys Asp Met
    1160                1165                1170
Lys Asn Ile Ala Glu Lys Phe Phe Gly Lys Val Arg Val Gly Lys
    1175                1180                1185
Asn Cys Val Asp Ile Pro Lys Lys Met Ala Tyr Leu Leu Ala Lys
    1190                1195                1200
Ser Leu Cys Gly Val Thr Ala Glu Asn Lys Arg Ile Pro Ser Ile
    1205                1210                1215
Ile Phe Asp Ser Ser Glu Pro Val Arg Trp Ala Phe Leu Arg Ala
    1220                1225                1230
Tyr Phe Val Gly Asp Gly Asp Ile His Pro Ser Lys Arg Leu Arg
    1235                1240                1245
Leu Ser Thr Lys Ser Glu Leu Leu Ala Asn Gln Leu Val Phe Leu
    1250                1255                1260
Leu Asn Ser Leu Gly Val Ser Ser Ile Lys Ile Gly Phe Asp Ser
    1265                1270                1275
Gly Val Tyr Arg Val Tyr Ile Asn Glu Asp Leu Pro Phe Leu Gln
    1280                1285                1290
Thr Ser Arg Gln Lys Asn Thr Tyr Tyr Pro Asn Leu Ile Pro Lys
    1295                1300                1305
Glu Val Leu Glu Glu Ile Phe Gly Arg Lys Phe Gln Lys Asn Ile
    1310                1315                1320
Thr Phe Glu Lys Phe Lys Glu Leu Ala Asp Ser Gly Lys Leu Asp
    1325                1330                1335
Lys Arg Lys Val Lys Leu Leu Asp Phe Leu Leu Asn Gly Asp Ile
    1340                1345                1350
Val Leu Asp Arg Val Lys Asn Val Glu Lys Arg Glu Tyr Glu Gly
    1355                1360                1365
Tyr Val Tyr Asp Leu Ser Val Glu Asp Asn Glu Asn Phe Leu Val
    1370                1375                1380
Gly Phe Gly Leu Leu Tyr Ala His Asn Ser Tyr Tyr Gly Tyr Met
    1385                1390                1395
Gly Tyr Pro Lys Ala Arg Trp Tyr Ser Lys Glu Cys Ala Glu Ser
    1400                1405                1410
Val Thr Ala Trp Gly Arg His Tyr Ile Glu Met Thr Ile Lys Glu
    1415                1420                1425
Ile Glu Glu Lys Phe Gly Phe Lys Val Leu Tyr Ala Asp Ser Val
    1430                1435                1440
Thr Gly Asp Thr Glu Ile Ile Val Lys Arg Asn Gly Arg Ile Glu
    1445                1450                1455
Phe Val Pro Ile Glu Lys Leu Phe Glu Arg Val Asp Tyr Arg Ile
    1460                1465                1470
```

-continued

Gly Glu Lys Glu Tyr Cys Ile Leu Glu Asp Val Glu Ala Leu Thr
1475                1480                1485

Leu Asp Asn Arg Gly Lys Leu Ile Trp Lys Lys Val Pro Tyr Val
1490                1495                1500

Met Arg His Arg Ala Lys Lys Val Tyr Arg Ile Trp Ile Thr
1505                1510                1515

Asn Ser Trp Tyr Ile Asp Val Thr Glu Asp His Ser Leu Ile Val
1520                1525                1530

Ala Glu Asp Gly Leu Lys Glu Ala Arg Pro Met Glu Ile Glu Gly
1535                1540                1545

Lys Ser Leu Ile Ala Thr Lys Asp Asp Leu Ser Gly Val Glu Tyr
1550                1555                1560

Ile Lys Pro His Ala Ile Glu Glu Ile Ser Tyr Asn Gly Tyr Val
1565                1570                1575

Tyr Asp Ile Glu Val Glu Gly Thr His Arg Phe Phe Ala Asn Gly
1580                1585                1590

Ile Leu Val His Asn Thr Asp Gly Phe Tyr Ala Thr Ile Pro Gly
1595                1600                1605

Glu Lys Pro Glu Thr Ile Lys Lys Lys Ala Lys Glu Phe Leu Lys
1610                1615                1620

Tyr Ile Asn Ser Lys Leu Pro Gly Leu Leu Glu Leu Glu Tyr Glu
1625                1630                1635

Gly Phe Tyr Leu Arg Gly Phe Phe Val Ala Lys Lys Arg Tyr Ala
1640                1645                1650

Val Ile Asp Glu Glu Gly Arg Ile Thr Thr Arg Gly Leu Glu Val
1655                1660                1665

Val Arg Arg Asp Trp Ser Glu Ile Ala Lys Glu Thr Gln Ala Lys
1670                1675                1680

Val Leu Glu Ala Ile Leu Lys Glu Asp Ser Val Glu Lys Ala Val
1685                1690                1695

Glu Ile Val Lys Asp Val Val Glu Glu Ile Ala Lys Tyr Gln Val
1700                1705                1710

Pro Leu Glu Lys Leu Val Ile His Glu Gln Ile Thr Lys Asp Leu
1715                1720                1725

Ser Glu Tyr Lys Ala Ile Gly Pro His Val Ala Ile Ala Lys Arg
1730                1735                1740

Leu Ala Ala Lys Gly Ile Lys Val Arg Pro Gly Thr Ile Ile Ser
1745                1750                1755

Tyr Ile Val Leu Arg Gly Ser Gly Lys Ile Ser Asp Arg Val Ile
1760                1765                1770

Leu Leu Ser Glu Tyr Asp Pro Lys Lys His Lys Tyr Asp Pro Asp
1775                1780                1785

Tyr Tyr Ile Glu Asn Gln Val Leu Pro Ala Val Leu Arg Ile Leu
1790                1795                1800

Glu Ala Phe Gly Tyr Arg Lys Glu Asp Leu Lys Tyr Gln Ser Ser
1805                1810                1815

Lys Gln Val Gly Leu Asp Ala Trp Leu Lys Lys
1820                1825

<210> SEQ ID NO 60
<211> LENGTH: 771
<212> TYPE: PRT
<213> ORGANISM: Pyrococcus abyssi
<220> FEATURE:
<221> NAME/KEY: MOD_RES
<222> LOCATION: (705)..(705)
<223> OTHER INFORMATION: Any amino acid

<400> SEQUENCE: 60

```
Met Ile Ile Asp Ala Asp Tyr Ile Thr Glu Asp Gly Lys Pro Ile Ile
1               5                   10                  15

Arg Ile Phe Lys Lys Glu Lys Gly Glu Phe Lys Val Glu Tyr Asp Arg
            20                  25                  30

Thr Phe Arg Pro Tyr Ile Tyr Ala Leu Leu Lys Asp Asp Ser Ala Ile
        35                  40                  45

Asp Glu Val Lys Lys Ile Thr Ala Glu Arg His Gly Lys Ile Val Arg
    50                  55                  60

Ile Thr Glu Val Glu Lys Val Gln Lys Lys Phe Leu Gly Arg Pro Ile
65                  70                  75                  80

Glu Val Trp Lys Leu Tyr Leu Glu His Pro Gln Asp Val Pro Ala Ile
                85                  90                  95

Arg Glu Lys Ile Arg Glu His Pro Ala Val Val Asp Ile Phe Glu Tyr
            100                 105                 110

Asp Ile Pro Phe Ala Lys Arg Tyr Leu Ile Asp Lys Gly Leu Thr Pro
        115                 120                 125

Met Glu Gly Asn Glu Glu Leu Thr Phe Leu Ala Val Asp Ile Glu Thr
    130                 135                 140

Leu Tyr His Glu Gly Glu Glu Phe Gly Lys Gly Pro Ile Ile Met Ile
145                 150                 155                 160

Ser Tyr Ala Asp Glu Glu Gly Ala Lys Val Ile Thr Trp Lys Ser Ile
                165                 170                 175

Asp Leu Pro Tyr Val Glu Val Val Ser Ser Glu Arg Glu Met Ile Lys
            180                 185                 190

Arg Leu Val Lys Val Ile Arg Glu Lys Asp Pro Asp Val Ile Ile Thr
        195                 200                 205

Tyr Asn Gly Asp Asn Phe Asp Phe Pro Tyr Leu Leu Lys Arg Ala Glu
    210                 215                 220

Lys Leu Gly Ile Lys Leu Pro Leu Gly Arg Asp Asn Ser Glu Pro Lys
225                 230                 235                 240

Met Gln Arg Met Gly Asp Ser Leu Ala Val Glu Ile Lys Gly Arg Ile
                245                 250                 255

His Phe Asp Leu Phe Pro Ala Ile Arg Arg Thr Ile Asn Leu Pro Thr
            260                 265                 270

Tyr Thr Leu Glu Thr Val Tyr Glu Val Ile Phe Gly Lys Ser Lys Glu
        275                 280                 285

Lys Val Tyr Ala His Glu Ile Ala Glu Ala Trp Glu Thr Gly Lys Gly
    290                 295                 300

Leu Glu Arg Val Ala Lys Tyr Ser Met Glu Asp Ala Lys Val Thr Ser
305                 310                 315                 320

Glu Leu Gly Lys Glu Phe Phe Pro Met Glu Ala Gln Leu Ala Arg Leu
                325                 330                 335

Val Gly His Pro Val Trp Asp Val Ser Arg Ser Ser Thr Gly Asn Leu
            340                 345                 350

Val Glu Trp Phe Leu Leu Thr Lys Ala Tyr Glu Arg Asn Glu Leu Ala
        355                 360                 365

Pro Asn Lys Pro Asp Glu Arg Glu Tyr Glu Arg Leu Arg Glu Ser
    370                 375                 380

Tyr Glu Gly Gly Tyr Val Asn Glu Pro Glu Lys Gly Leu Trp Glu Gly
385                 390                 395                 400
```

Ile Val Ser Leu Asp Phe Arg Ser Leu Tyr Pro Ser Ile Ile Ile Thr
                405                 410                 415

His Asn Val Ser Pro Asp Thr Leu Asn Arg Glu Asn Cys Lys Glu Tyr
            420                 425                 430

Asp Val Ala Pro Gln Val Gly His Arg Phe Cys Lys Asp Phe Pro Gly
        435                 440                 445

Phe Ile Pro Ser Leu Leu Gly Asn Leu Leu Glu Glu Arg Gln Lys Ile
    450                 455                 460

Lys Lys Arg Met Lys Glu Ser Lys Asp Pro Val Glu Lys Lys Leu Leu
465                 470                 475                 480

Asp Tyr Arg Gln Arg Ala Ile Lys Ile Leu Ala Asn Ser Tyr Tyr Gly
                485                 490                 495

Tyr Tyr Gly Tyr Ala Lys Ala Arg Trp Tyr Cys Lys Glu Cys Ala Glu
            500                 505                 510

Ser Val Thr Ala Trp Gly Arg Gln Tyr Ile Asp Leu Val Arg Arg Glu
        515                 520                 525

Leu Glu Ser Arg Gly Phe Lys Val Leu Tyr Ile Asp Thr Asp Gly Leu
    530                 535                 540

Tyr Ala Thr Ile Pro Gly Ala Lys His Glu Glu Ile Lys Glu Lys Ala
545                 550                 555                 560

Leu Lys Phe Val Glu Tyr Ile Asn Ser Lys Leu Pro Gly Leu Leu Glu
                565                 570                 575

Leu Glu Tyr Glu Gly Phe Tyr Ala Arg Gly Phe Phe Val Thr Lys Lys
            580                 585                 590

Lys Tyr Ala Leu Ile Asp Glu Glu Gly Lys Ile Val Thr Arg Gly Leu
        595                 600                 605

Glu Ile Val Arg Arg Asp Trp Ser Glu Ile Ala Lys Glu Thr Gln Ala
    610                 615                 620

Lys Val Leu Glu Ala Ile Leu Lys His Gly Asn Val Asp Glu Ala Val
625                 630                 635                 640

Lys Ile Val Lys Glu Val Thr Glu Lys Leu Ser Lys Tyr Glu Ile Pro
                645                 650                 655

Pro Glu Lys Leu Val Ile Tyr Glu Gln Ile Thr Arg Pro Leu Ser Glu
            660                 665                 670

Tyr Lys Ala Ile Gly Pro His Val Ala Val Ala Lys Arg Leu Ala Ala
        675                 680                 685

Lys Gly Val Lys Val Lys Pro Gly Met Val Ile Gly Tyr Ile Val Leu
    690                 695                 700

Xaa Gly Asp Gly Pro Ile Ser Lys Arg Ala Ile Ala Ile Glu Glu Phe
705                 710                 715                 720

Asp Pro Lys Lys His Lys Tyr Asp Ala Glu Tyr Tyr Ile Glu Asn Gln
                725                 730                 735

Val Leu Pro Ala Val Glu Arg Ile Leu Arg Ala Phe Gly Tyr Arg Lys
            740                 745                 750

Glu Asp Leu Arg Tyr Gln Lys Thr Lys Gln Val Gly Leu Gly Ala Trp
        755                 760                 765

Leu Lys Phe
    770

<210> SEQ ID NO 61
<211> LENGTH: 771
<212> TYPE: PRT
<213> ORGANISM: Pyrococcus sp.

```
<400> SEQUENCE: 61

Met Ile Ile Asp Ala Asp Tyr Ile Thr Glu Asp Gly Lys Pro Ile Ile
1               5                   10                  15

Arg Ile Phe Lys Lys Glu Lys Gly Glu Phe Lys Val Glu Tyr Asp Arg
            20                  25                  30

Thr Phe Arg Pro Tyr Ile Tyr Ala Leu Leu Lys Asp Asp Ser Ala Ile
        35                  40                  45

Asp Glu Val Lys Lys Ile Thr Ala Glu Arg His Gly Lys Ile Val Arg
    50                  55                  60

Ile Thr Glu Val Glu Lys Val Gln Lys Lys Phe Leu Gly Arg Pro Ile
65                  70                  75                  80

Glu Val Trp Lys Leu Tyr Leu Glu His Pro Gln Asp Val Pro Ala Ile
                85                  90                  95

Arg Glu Lys Ile Arg Glu His Pro Ala Val Val Asp Ile Phe Glu Tyr
            100                 105                 110

Asp Ile Pro Phe Ala Lys Arg Tyr Leu Ile Asp Lys Gly Leu Thr Pro
        115                 120                 125

Met Glu Gly Asn Glu Glu Leu Thr Phe Leu Ala Val Asp Ile Glu Thr
    130                 135                 140

Leu Tyr His Glu Gly Glu Glu Phe Gly Lys Gly Pro Ile Ile Met Ile
145                 150                 155                 160

Ser Tyr Ala Asp Glu Glu Gly Ala Lys Val Ile Thr Trp Lys Ser Ile
                165                 170                 175

Asp Leu Pro Tyr Val Glu Val Val Ser Ser Glu Arg Glu Met Ile Lys
            180                 185                 190

Arg Leu Val Lys Val Ile Arg Glu Lys Asp Pro Asp Val Ile Ile Thr
        195                 200                 205

Tyr Asn Gly Asp Asn Phe Asp Phe Pro Tyr Leu Leu Lys Arg Ala Glu
    210                 215                 220

Lys Leu Gly Ile Lys Leu Pro Leu Gly Arg Asp Asn Ser Glu Pro Lys
225                 230                 235                 240

Met Gln Arg Met Gly Asp Ser Leu Ala Val Glu Ile Lys Gly Arg Ile
                245                 250                 255

His Phe Asp Leu Phe Pro Val Ile Arg Arg Thr Ile Asn Leu Pro Thr
            260                 265                 270

Tyr Thr Leu Glu Ala Val Tyr Glu Ala Ile Phe Gly Lys Ser Lys Glu
        275                 280                 285

Lys Val Tyr Ala His Glu Ile Ala Glu Ala Trp Glu Thr Gly Lys Gly
    290                 295                 300

Leu Glu Arg Val Ala Lys Tyr Ser Met Glu Asp Ala Lys Val Thr Phe
305                 310                 315                 320

Glu Leu Gly Lys Glu Phe Phe Pro Met Glu Ala Gln Leu Ala Arg Leu
                325                 330                 335

Val Gly Gln Pro Val Trp Asp Val Ser Arg Ser Ser Thr Gly Asn Leu
            340                 345                 350

Val Glu Trp Phe Leu Leu Arg Lys Ala Tyr Glu Arg Asn Glu Leu Ala
        355                 360                 365

Pro Asn Lys Pro Asp Glu Arg Glu Tyr Glu Arg Arg Leu Arg Glu Ser
    370                 375                 380

Tyr Glu Gly Gly Tyr Val Lys Glu Pro Glu Lys Gly Leu Trp Glu Gly
385                 390                 395                 400

Ile Val Ser Leu Asp Phe Arg Ser Leu Tyr Pro Ser Ile Ile Ile Thr
                405                 410                 415
```

His Asn Val Ser Pro Asp Thr Leu Asn Arg Glu Asn Cys Lys Glu Tyr
                420                 425                 430

Asp Val Ala Pro Gln Val Gly His Arg Phe Cys Lys Asp Phe Pro Gly
                435                 440                 445

Phe Ile Pro Ser Leu Leu Gly Asn Leu Leu Glu Arg Gln Lys Ile
450                 455                 460

Lys Lys Arg Met Lys Glu Ser Lys Asp Pro Val Glu Lys Lys Leu Leu
465                 470                 475                 480

Asp Tyr Arg Gln Arg Ala Ile Lys Ile Leu Ala Asn Ser Tyr Tyr Gly
                485                 490                 495

Tyr Tyr Gly Tyr Ala Lys Ala Arg Trp Tyr Cys Lys Glu Cys Ala Glu
                500                 505                 510

Ser Val Thr Ala Trp Gly Arg Gln Tyr Ile Asp Leu Val Arg Arg Glu
                515                 520                 525

Leu Glu Ser Ser Gly Phe Lys Val Leu Tyr Ile Asp Thr Asp Gly Leu
    530                 535                 540

Tyr Ala Thr Ile Pro Gly Ala Lys Pro Asn Glu Ile Lys Glu Lys Ala
545                 550                 555                 560

Leu Lys Phe Val Glu Tyr Ile Asn Ser Lys Leu Pro Gly Leu Leu Glu
                565                 570                 575

Leu Glu Tyr Glu Gly Phe Tyr Ala Arg Gly Phe Phe Val Thr Lys Lys
                580                 585                 590

Lys Tyr Ala Leu Ile Asp Glu Glu Gly Lys Ile Val Thr Arg Gly Leu
                595                 600                 605

Glu Ile Val Arg Arg Asp Trp Ser Glu Ile Ala Lys Glu Thr Gln Ala
                610                 615                 620

Lys Val Leu Glu Ala Ile Leu Lys His Gly Asn Val Asp Glu Ala Val
625                 630                 635                 640

Lys Ile Val Lys Glu Val Thr Glu Lys Leu Ser Lys Tyr Glu Ile Pro
                645                 650                 655

Pro Glu Lys Leu Val Ile Tyr Glu Gln Ile Thr Arg Pro Leu Ser Glu
                660                 665                 670

Tyr Lys Ala Ile Gly Pro His Val Ala Val Ala Lys Arg Leu Ala Ala
                675                 680                 685

Lys Gly Val Lys Val Lys Pro Gly Met Val Ile Gly Tyr Ile Val Leu
690                 695                 700

Arg Gly Asp Gly Pro Ile Ser Lys Arg Ala Ile Ala Ile Glu Glu Phe
705                 710                 715                 720

Asp Pro Lys Lys His Lys Tyr Asp Ala Glu Tyr Tyr Ile Glu Asn Gln
                725                 730                 735

Val Leu Pro Ala Val Glu Arg Ile Leu Arg Ala Phe Gly Tyr Arg Lys
                740                 745                 750

Glu Asp Leu Arg Tyr Gln Lys Thr Lys Gln Val Gly Leu Gly Ala Trp
                755                 760                 765

Leu Lys Phe
    770

<210> SEQ ID NO 62
<211> LENGTH: 1235
<212> TYPE: PRT
<213> ORGANISM: Pyrococcus horikoshii

<400> SEQUENCE: 62

Met Ile Leu Asp Ala Asp Tyr Ile Thr Glu Asp Gly Lys Pro Ile Ile

```
1               5                   10                  15
Arg Ile Phe Lys Lys Glu Asn Gly Glu Phe Lys Val Glu Tyr Asp Arg
                20                  25                  30
Asn Phe Arg Pro Tyr Ile Tyr Ala Leu Leu Arg Asp Asp Ser Ala Ile
                35                  40                  45
Asp Glu Ile Lys Lys Ile Thr Ala Gln Arg His Gly Lys Val Val Arg
                50                  55                  60
Ile Val Glu Thr Glu Lys Ile Gln Arg Lys Phe Leu Gly Arg Pro Ile
65                  70                  75                  80
Glu Val Trp Lys Leu Tyr Leu Glu His Pro Gln Asp Val Pro Ala Ile
                85                  90                  95
Arg Asp Lys Ile Arg Glu His Pro Ala Val Val Asp Ile Phe Glu Tyr
                100                 105                 110
Asp Ile Pro Phe Ala Lys Arg Tyr Leu Ile Asp Lys Gly Leu Thr Pro
                115                 120                 125
Met Glu Gly Asn Glu Lys Leu Thr Phe Leu Ala Val Asp Ile Glu Thr
                130                 135                 140
Leu Tyr His Glu Gly Glu Glu Phe Gly Lys Gly Pro Val Ile Met Ile
145                 150                 155                 160
Ser Tyr Ala Asp Glu Glu Gly Ala Lys Val Ile Thr Trp Lys Lys Ile
                165                 170                 175
Asp Leu Pro Tyr Val Glu Val Val Ser Ser Glu Arg Glu Met Ile Lys
                180                 185                 190
Arg Leu Ile Arg Val Ile Lys Glu Lys Asp Pro Asp Val Ile Ile Thr
                195                 200                 205
Tyr Asn Gly Asp Asn Phe Asp Phe Pro Tyr Leu Leu Lys Arg Ala Glu
                210                 215                 220
Lys Leu Gly Ile Lys Leu Leu Leu Gly Arg Asp Asn Ser Glu Pro Lys
225                 230                 235                 240
Met Gln Lys Met Gly Asp Ser Leu Ala Val Glu Ile Lys Gly Arg Ile
                245                 250                 255
His Phe Asp Leu Phe Pro Val Ile Arg Arg Thr Ile Asn Leu Pro Thr
                260                 265                 270
Tyr Thr Leu Glu Ala Val Tyr Glu Ala Ile Phe Gly Lys Pro Lys Glu
                275                 280                 285
Lys Val Tyr Ala Asp Glu Ile Ala Lys Ala Trp Glu Thr Gly Glu Gly
                290                 295                 300
Leu Glu Arg Val Ala Lys Tyr Ser Met Glu Asp Ala Lys Val Thr Tyr
305                 310                 315                 320
Glu Leu Gly Arg Glu Phe Phe Pro Met Glu Ala Gln Leu Ala Arg Leu
                325                 330                 335
Val Gly Gln Pro Val Trp Asp Val Ser Arg Ser Ser Thr Gly Asn Leu
                340                 345                 350
Val Glu Trp Phe Leu Leu Arg Lys Ala Tyr Glu Arg Asn Glu Leu Ala
                355                 360                 365
Pro Asn Lys Pro Asp Glu Lys Glu Tyr Glu Arg Arg Leu Arg Glu Ser
                370                 375                 380
Tyr Glu Gly Gly Tyr Val Lys Glu Pro Glu Lys Gly Leu Trp Glu Gly
385                 390                 395                 400
Ile Val Ser Leu Asp Phe Arg Ser Leu Tyr Pro Ser Ile Ile Ile Thr
                405                 410                 415
His Asn Val Ser Pro Asp Thr Leu Asn Arg Glu Gly Cys Glu Glu Tyr
                420                 425                 430
```

```
Asp Val Ala Pro Lys Val Gly His Arg Phe Cys Lys Asp Phe Pro Gly
            435                 440                 445

Phe Ile Pro Ser Leu Leu Gly Gln Leu Leu Glu Glu Arg Gln Lys Ile
450                 455                 460

Lys Lys Arg Met Lys Glu Ser Lys Asp Pro Val Glu Lys Lys Leu Leu
465                 470                 475                 480

Asp Tyr Arg Gln Arg Ala Ile Lys Ile Leu Ala Asn Ser Ile Leu Pro
            485                 490                 495

Asp Glu Trp Leu Pro Ile Val Glu Asn Glu Lys Val Arg Phe Val Lys
            500                 505                 510

Ile Gly Asp Phe Ile Asp Arg Glu Ile Glu Glu Asn Ala Glu Arg Val
            515                 520                 525

Lys Arg Asp Gly Glu Thr Glu Ile Leu Glu Val Lys Asp Leu Lys Ala
530                 535                 540

Leu Ser Phe Asn Arg Glu Thr Lys Lys Ser Glu Leu Lys Lys Val Lys
545                 550                 555                 560

Ala Leu Ile Arg His Arg Tyr Ser Gly Lys Val Tyr Ser Ile Lys Leu
            565                 570                 575

Lys Ser Gly Arg Arg Ile Lys Ile Thr Ser Gly His Ser Leu Phe Ser
            580                 585                 590

Val Lys Asn Gly Lys Leu Val Lys Val Arg Gly Asp Glu Leu Lys Pro
            595                 600                 605

Gly Asp Leu Val Val Val Pro Gly Arg Leu Lys Leu Pro Glu Ser Lys
            610                 615                 620

Gln Val Leu Asn Leu Val Glu Leu Leu Leu Lys Leu Pro Glu Glu Glu
625                 630                 635                 640

Thr Ser Asn Ile Val Met Met Ile Pro Val Lys Gly Arg Lys Asn Phe
            645                 650                 655

Phe Lys Gly Met Leu Lys Thr Leu Tyr Trp Ile Phe Gly Glu Gly Glu
            660                 665                 670

Arg Pro Arg Thr Ala Gly Arg Tyr Leu Lys His Leu Glu Arg Leu Gly
            675                 680                 685

Tyr Val Lys Leu Lys Arg Arg Gly Cys Glu Val Leu Asp Trp Glu Ser
            690                 695                 700

Leu Lys Arg Tyr Arg Lys Leu Tyr Glu Thr Leu Ile Lys Asn Leu Lys
705                 710                 715                 720

Tyr Asn Gly Asn Ser Arg Ala Tyr Met Val Glu Phe Asn Ser Leu Arg
            725                 730                 735

Asp Val Val Ser Leu Met Pro Ile Glu Glu Leu Lys Glu Trp Ile Ile
            740                 745                 750

Gly Glu Pro Arg Gly Pro Lys Ile Gly Thr Phe Ile Asp Val Asp Asp
            755                 760                 765

Ser Phe Ala Lys Leu Leu Gly Tyr Tyr Ile Ser Ser Gly Asp Val Glu
770                 775                 780

Lys Asp Arg Val Lys Phe His Ser Lys Asp Gln Asn Val Leu Glu Asp
785                 790                 795                 800

Ile Ala Lys Leu Ala Glu Lys Leu Phe Gly Lys Val Arg Arg Gly Arg
            805                 810                 815

Gly Tyr Ile Glu Val Ser Gly Lys Ile Ser His Ala Ile Phe Arg Val
            820                 825                 830

Leu Ala Glu Gly Lys Arg Ile Pro Glu Phe Ile Phe Thr Ser Pro Met
            835                 840                 845
```

```
Asp Ile Lys Val Ala Phe Leu Lys Gly Leu Asn Gly Asn Ala Glu Glu
    850                 855                 860

Leu Thr Phe Ser Thr Lys Ser Glu Leu Leu Val Asn Gln Leu Ile Leu
865                 870                 875                 880

Leu Leu Asn Ser Ile Gly Val Ser Asp Ile Lys Ile Glu His Glu Lys
                885                 890                 895

Gly Val Tyr Arg Val Tyr Ile Asn Lys Lys Glu Ser Ser Asn Gly Asp
            900                 905                 910

Ile Val Leu Asp Ser Val Glu Ser Ile Glu Val Glu Lys Tyr Glu Gly
        915                 920                 925

Tyr Val Tyr Asp Leu Ser Val Glu Asp Asn Glu Asn Phe Leu Val Gly
    930                 935                 940

Phe Gly Leu Leu Tyr Ala His Asn Ser Tyr Tyr Gly Tyr Tyr Gly Tyr
945                 950                 955                 960

Ala Lys Ala Arg Trp Tyr Cys Lys Glu Cys Ala Glu Ser Val Thr Ala
                965                 970                 975

Trp Gly Arg Gln Tyr Ile Asp Leu Val Arg Arg Glu Leu Glu Ala Arg
            980                 985                 990

Gly Phe Lys Val Leu Tyr Ile Asp Thr Asp Gly Leu Tyr Ala Thr Ile
        995                 1000                1005

Pro Gly Val Lys Asp Trp Glu Glu Val Lys Arg Arg Ala Leu Glu
    1010                1015                1020

Phe Val Asp Tyr Ile Asn Ser Lys Leu Pro Gly Val Leu Glu Leu
    1025                1030                1035

Glu Tyr Glu Gly Phe Tyr Ala Arg Gly Phe Phe Val Thr Lys Lys
    1040                1045                1050

Lys Tyr Ala Leu Ile Asp Glu Gly Lys Ile Val Thr Arg Gly
    1055                1060                1065

Leu Glu Ile Val Arg Arg Asp Trp Ser Glu Ile Ala Lys Glu Thr
    1070                1075                1080

Gln Ala Arg Val Leu Glu Ala Ile Leu Lys His Gly Asn Val Glu
    1085                1090                1095

Glu Ala Val Lys Ile Val Lys Asp Val Thr Glu Lys Leu Thr Asn
    1100                1105                1110

Tyr Glu Val Pro Pro Glu Lys Leu Val Ile Tyr Glu Gln Ile Thr
    1115                1120                1125

Arg Pro Ile Asn Glu Tyr Lys Ala Ile Gly Pro His Val Ala Val
    1130                1135                1140

Ala Lys Arg Leu Met Ala Arg Gly Ile Lys Val Lys Pro Gly Met
    1145                1150                1155

Val Ile Gly Tyr Ile Val Leu Arg Gly Asp Gly Pro Ile Ser Lys
    1160                1165                1170

Arg Ala Ile Ser Ile Glu Glu Phe Asp Pro Arg Lys His Lys Tyr
    1175                1180                1185

Asp Ala Glu Tyr Tyr Ile Glu Asn Gln Val Leu Pro Ala Val Glu
    1190                1195                1200

Arg Ile Leu Lys Ala Phe Gly Tyr Lys Arg Glu Asp Leu Arg Trp
    1205                1210                1215

Gln Lys Thr Lys Gln Val Gly Leu Gly Ala Trp Ile Lys Val Lys
    1220                1225                1230

Lys Ser
    1235
```

<210> SEQ ID NO 63
<211> LENGTH: 759
<212> TYPE: PRT
<213> ORGANISM: Pyrococcus sp.

<400> SEQUENCE: 63

```
Met Ile Leu Asp Ala Asp Tyr Ile Thr Glu Asn Gly Lys Pro Ile Ile
1               5                   10                  15

Arg Leu Phe Lys Lys Glu Asn Gly Lys Phe Lys Val Glu Tyr Asp Arg
            20                  25                  30

Asn Phe Arg Pro Tyr Ile Tyr Ala Leu Leu Lys Asp Asp Ser Ala Ile
        35                  40                  45

Asp Asp Val Arg Lys Ile Thr Ser Glu Arg His Gly Lys Val Val Arg
    50                  55                  60

Val Ile Asp Val Glu Lys Val Ser Lys Lys Phe Leu Gly Arg Pro Ile
65                  70                  75                  80

Glu Val Trp Lys Leu Tyr Phe Glu His Pro Gln Asp Val Pro Ala Ile
                85                  90                  95

Arg Asp Lys Ile Arg Glu His Pro Ala Val Ile Asp Ile Phe Glu Tyr
            100                 105                 110

Asp Ile Pro Phe Ala Lys Arg Tyr Leu Ile Asp Lys Gly Leu Ile Pro
        115                 120                 125

Met Glu Gly Asn Glu Glu Leu Ser Phe Leu Ala Val Asp Ile Glu Thr
    130                 135                 140

Leu Tyr His Glu Gly Glu Glu Phe Gly Lys Gly Pro Ile Ile Met Ile
145                 150                 155                 160

Ser Tyr Ala Asp Glu Glu Gly Ala Lys Val Ile Thr Trp Lys Lys Ile
                165                 170                 175

Asp Leu Pro Tyr Val Glu Val Val Ala Asn Glu Arg Glu Met Ile Lys
            180                 185                 190

Arg Leu Val Arg Ile Ile Arg Glu Lys Asp Pro Asp Ile Ile Ile Thr
        195                 200                 205

Tyr Asn Gly Asp Asn Phe Asp Phe Pro Tyr Leu Leu Lys Arg Ala Glu
    210                 215                 220

Lys Leu Gly Ile Lys Leu Pro Leu Gly Arg Asp Asn Ser Glu Pro Lys
225                 230                 235                 240

Met Gln Arg Leu Gly Glu Ser Leu Ala Val Glu Ile Lys Gly Arg Ile
                245                 250                 255

His Phe Asp Leu Phe Pro Val Ile Arg Arg Thr Ile Asn Leu Pro Thr
            260                 265                 270

Tyr Thr Leu Arg Thr Val Tyr Glu Ala Ile Phe Gly Lys Pro Lys Glu
        275                 280                 285

Lys Val Tyr Pro His Glu Ile Ala Glu Ala Trp Glu Thr Gly Lys Gly
    290                 295                 300

Leu Glu Arg Val Ala Lys Tyr Ser Met Glu Asp Ala Lys Val Thr Tyr
305                 310                 315                 320

Glu Leu Gly Lys Glu Phe Phe Pro Met Glu Ala Gln Leu Ala Arg Leu
                325                 330                 335

Val Gly Gln Pro Val Trp Asp Val Ser Arg Ser Ser Thr Gly Asn Leu
            340                 345                 350

Val Glu Trp Phe Leu Leu Arg Lys Ala Tyr Glu Arg Asn Glu Leu Ala
        355                 360                 365

Pro Asn Lys Pro Asp Glu Lys Glu Leu Ala Arg Arg Arg Gly Ser Tyr
    370                 375                 380
```

Tyr Glu Gly Gly Tyr Val Lys Glu Pro Glu Lys Gly Leu Trp Glu Gly
385                 390                 395                 400

Ile Val Ser Leu Asp Phe Arg Ser Leu Tyr Pro Ser Ile Ile Ile Thr
            405                 410                 415

His Asn Val Ser Pro Asp Thr Leu Asn Arg Glu Gly Cys Gly Lys Tyr
        420                 425                 430

Asp Glu Ala Pro Glu Val Gly His Arg Phe Cys Lys Asp Phe Pro Gly
    435                 440                 445

Phe Ile Pro Ser Leu Leu Gly Asp Leu Leu Glu Glu Arg Gln Lys Ile
450                 455                 460

Lys Lys Arg Met Lys Glu Ser Lys Asp Pro Ile Glu Lys Lys Leu Leu
465                 470                 475                 480

Asp Tyr Arg Gln Arg Ala Ile Lys Ile Leu Ala Asn Ser Phe Tyr Gly
            485                 490                 495

Tyr Tyr Gly Tyr Ala Lys Ala Arg Trp Tyr Cys Lys Glu Cys Ala Glu
        500                 505                 510

Ser Val Thr Ala Trp Gly Arg Gln Tyr Ile Glu Leu Val Arg Arg Glu
    515                 520                 525

Leu Glu Glu Arg Gly Phe Lys Val Leu Tyr Ile Asp Thr Asp Gly Leu
530                 535                 540

Tyr Ala Thr Ile Pro Gly Glu Lys Asn Trp Glu Glu Ile Lys Arg Lys
545                 550                 555                 560

Ala Leu Glu Phe Val Asn Tyr Ile Asn Ser Lys Leu Pro Gly Ile Leu
            565                 570                 575

Glu Leu Glu Tyr Glu Gly Phe Tyr Thr Arg Gly Phe Phe Val Thr Lys
        580                 585                 590

Lys Lys Tyr Ala Leu Ile Asp Glu Glu Gly Lys Ile Ile Thr Arg Gly
    595                 600                 605

Leu Glu Ile Val Arg Arg Asp Trp Ser Glu Ile Ala Lys Glu Thr Gln
610                 615                 620

Ala Lys Val Leu Glu Ala Ile Leu Lys His Gly Asn Val Glu Glu Ala
625                 630                 635                 640

Val Lys Ile Val Lys Glu Val Thr Glu Lys Leu Ser Asn Tyr Glu Ile
            645                 650                 655

Pro Val Glu Lys Leu Val Ile Tyr Glu Gln Ile Thr Arg Pro Leu Asn
        660                 665                 670

Glu Tyr Lys Ala Ile Gly Pro His Val Ala Val Ala Lys Arg Leu Ala
    675                 680                 685

Ala Lys Gly Ile Lys Ile Lys Pro Gly Met Val Ile Gly Tyr Val Leu
690                 695                 700

Leu Arg Gly Asp Gly Pro Ile Ser Lys Arg Ala Ile Ala Ile Glu Glu
705                 710                 715                 720

Phe Asp Gly Lys Lys His Lys Tyr Asp Ala Glu Tyr Tyr Ile Glu Asn
            725                 730                 735

Gln Val Leu Pro Ala Val Glu Arg Ile Leu Lys Ala Phe Gly Tyr Lys
        740                 745                 750

Lys Glu Asp Leu Arg Trp Gln
            755

<210> SEQ ID NO 64
<211> LENGTH: 775
<212> TYPE: PRT
<213> ORGANISM: Pyrococcus sp.

<400> SEQUENCE: 64

```
Met Ile Leu Asp Ala Asp Tyr Ile Thr Glu Asp Gly Lys Pro Ile Ile
1               5                   10                  15

Arg Ile Phe Lys Lys Glu Asn Gly Glu Phe Lys Val Glu Tyr Asp Arg
                20                  25                  30

Asn Phe Arg Pro Tyr Ile Tyr Ala Leu Leu Lys Asp Asp Ser Gln Ile
            35                  40                  45

Asp Glu Val Arg Lys Ile Thr Ala Glu Arg His Gly Lys Ile Val Arg
        50                  55                  60

Ile Ile Asp Ala Glu Lys Val Arg Lys Lys Phe Leu Gly Arg Pro Ile
65                  70                  75                  80

Glu Val Trp Arg Leu Tyr Phe Glu His Pro Gln Asp Val Pro Ala Ile
                85                  90                  95

Arg Asp Lys Ile Arg Glu His Ser Ala Val Ile Asp Ile Phe Glu Tyr
            100                 105                 110

Asp Ile Pro Phe Ala Lys Arg Tyr Leu Ile Asp Lys Gly Leu Ile Pro
        115                 120                 125

Met Glu Gly Asp Glu Glu Leu Lys Leu Leu Ala Phe Asp Ile Glu Thr
130                 135                 140

Leu Tyr His Glu Gly Glu Glu Phe Ala Lys Gly Pro Ile Ile Met Ile
145                 150                 155                 160

Ser Tyr Ala Asp Glu Glu Glu Ala Lys Val Ile Thr Trp Lys Lys Ile
                165                 170                 175

Asp Leu Pro Tyr Val Glu Val Ser Ser Glu Arg Glu Met Ile Lys
            180                 185                 190

Arg Phe Leu Lys Val Ile Arg Glu Lys Asp Pro Asp Val Ile Ile Thr
        195                 200                 205

Tyr Asn Gly Asp Ser Phe Asp Leu Pro Tyr Leu Val Lys Arg Ala Glu
210                 215                 220

Lys Leu Gly Ile Lys Leu Pro Leu Gly Arg Asp Gly Ser Glu Pro Lys
225                 230                 235                 240

Met Gln Arg Leu Gly Asp Met Thr Ala Val Glu Ile Lys Gly Arg Ile
                245                 250                 255

His Phe Asp Leu Tyr His Val Ile Arg Arg Thr Ile Asn Leu Pro Thr
            260                 265                 270

Tyr Thr Leu Glu Ala Val Tyr Glu Ala Ile Phe Gly Lys Pro Lys Glu
        275                 280                 285

Lys Val Tyr Ala His Glu Ile Ala Glu Ala Trp Glu Thr Gly Lys Gly
290                 295                 300

Leu Glu Arg Val Ala Lys Tyr Ser Met Glu Asp Ala Lys Val Thr Tyr
305                 310                 315                 320

Glu Leu Gly Arg Glu Phe Phe Pro Met Glu Ala Gln Leu Ser Arg Leu
                325                 330                 335

Val Gly Gln Pro Leu Trp Asp Val Ser Arg Ser Ser Thr Gly Asn Leu
            340                 345                 350

Val Glu Trp Tyr Leu Leu Arg Lys Ala Tyr Glu Arg Asn Glu Leu Ala
        355                 360                 365

Pro Asn Lys Pro Asp Glu Arg Glu Tyr Glu Arg Arg Leu Arg Glu Ser
370                 375                 380

Tyr Ala Gly Gly Tyr Val Lys Glu Pro Glu Lys Gly Leu Trp Glu Gly
385                 390                 395                 400

Leu Val Ser Leu Asp Phe Arg Ser Leu Tyr Pro Ser Ile Ile Ile Thr
                405                 410                 415
```

His Asn Val Ser Pro Asp Thr Leu Asn Arg Glu Gly Cys Arg Glu Tyr
            420                 425                 430

Asp Val Ala Pro Glu Val Gly His Lys Phe Cys Lys Asp Phe Pro Gly
            435                 440                 445

Phe Ile Pro Ser Leu Leu Lys Arg Leu Leu Asp Glu Arg Gln Glu Ile
450                 455                 460

Lys Arg Lys Met Lys Ala Ser Lys Asp Pro Ile Glu Lys Lys Met Leu
465                 470                 475                 480

Asp Tyr Arg Gln Arg Ala Ile Lys Ile Leu Ala Asn Ser Tyr Tyr Gly
            485                 490                 495

Tyr Tyr Gly Tyr Ala Lys Ala Arg Trp Tyr Cys Lys Glu Cys Ala Glu
            500                 505                 510

Ser Val Thr Ala Trp Gly Arg Glu Tyr Ile Glu Phe Val Arg Lys Glu
            515                 520                 525

Leu Glu Glu Lys Phe Gly Phe Lys Val Leu Tyr Ile Asp Thr Asp Gly
            530                 535                 540

Leu Tyr Ala Thr Ile Pro Gly Ala Lys Pro Glu Glu Ile Lys Lys Lys
545                 550                 555                 560

Ala Leu Glu Phe Val Asp Tyr Ile Asn Ala Lys Leu Pro Gly Leu Leu
            565                 570                 575

Glu Leu Glu Tyr Glu Gly Phe Tyr Val Arg Gly Phe Phe Val Thr Lys
            580                 585                 590

Lys Lys Tyr Ala Leu Ile Asp Glu Glu Gly Lys Ile Ile Thr Arg Gly
            595                 600                 605

Leu Glu Ile Val Arg Arg Asp Trp Ser Glu Ile Ala Lys Glu Thr Gln
610                 615                 620

Ala Lys Val Leu Glu Ala Ile Leu Lys His Gly Asn Val Glu Glu Ala
625                 630                 635                 640

Val Lys Ile Val Lys Glu Val Thr Glu Lys Leu Ser Lys Tyr Glu Ile
            645                 650                 655

Pro Pro Glu Lys Leu Val Ile Tyr Glu Gln Ile Thr Arg Pro Leu His
            660                 665                 670

Glu Tyr Lys Ala Ile Gly Pro His Val Ala Val Ala Lys Arg Leu Ala
            675                 680                 685

Ala Arg Gly Val Lys Val Arg Pro Gly Met Val Ile Gly Tyr Ile Val
690                 695                 700

Leu Arg Gly Asp Gly Pro Ile Ser Lys Arg Ala Ile Leu Ala Glu Glu
705                 710                 715                 720

Phe Asp Leu Arg Lys His Lys Tyr Asp Ala Glu Tyr Tyr Ile Glu Asn
            725                 730                 735

Gln Val Leu Pro Ala Val Leu Arg Ile Leu Glu Ala Phe Gly Tyr Arg
            740                 745                 750

Lys Glu Asp Leu Arg Trp Gln Lys Thr Lys Gln Thr Gly Leu Thr Ala
            755                 760                 765

Trp Leu Asn Ile Lys Lys Lys
770                 775

<210> SEQ ID NO 65
<211> LENGTH: 775
<212> TYPE: PRT
<213> ORGANISM: Pyrococcus glycovorans

<400> SEQUENCE: 65

Met Ile Leu Asp Ala Asp Tyr Ile Thr Glu Asp Gly Lys Pro Ile Ile
1               5                   10                  15

-continued

```
Arg Ile Phe Lys Lys Glu Asn Gly Glu Phe Lys Val Glu Tyr Asp Arg
         20                  25                  30

Asn Phe Arg Pro Tyr Ile Tyr Ala Leu Leu Lys Asp Asp Ser Gln Ile
         35                  40                  45

Asp Glu Val Lys Lys Ile Thr Ala Glu Arg His Gly Lys Ile Val Arg
 50                  55                  60

Ile Val Asp Val Glu Lys Val Lys Lys Phe Leu Gly Arg Pro Ile
 65                  70                  75                  80

Glu Val Trp Lys Leu Tyr Phe Glu His Pro Gln Asp Val Pro Ala Ile
                 85                  90                  95

Arg Asp Lys Ile Arg Glu His Pro Ala Val Val Asp Ile Phe Glu Tyr
             100                 105                 110

Asp Ile Pro Phe Ala Lys Arg Tyr Leu Ile Asp Lys Gly Leu Ile Pro
         115                 120                 125

Met Glu Gly Asp Glu Glu Leu Lys Leu Leu Ala Phe Asp Ile Glu Thr
 130                 135                 140

Leu Tyr His Glu Gly Glu Glu Phe Ala Lys Gly Pro Ile Ile Met Ile
145                 150                 155                 160

Ser Tyr Ala Asp Glu Glu Gly Ala Lys Val Ile Thr Trp Lys Lys Val
                 165                 170                 175

Asp Leu Pro Tyr Val Glu Val Ser Ser Glu Arg Glu Met Ile Lys
             180                 185                 190

Arg Phe Leu Lys Val Ile Arg Glu Lys Asp Pro Asp Val Ile Ile Thr
         195                 200                 205

Tyr Asn Gly Asp Ser Phe Asp Leu Pro Tyr Leu Val Lys Arg Ala Glu
 210                 215                 220

Lys Leu Gly Ile Lys Leu Pro Leu Gly Arg Asp Gly Ser Glu Pro Lys
225                 230                 235                 240

Met Gln Arg Leu Gly Asp Met Thr Ala Val Glu Ile Lys Gly Arg Ile
                 245                 250                 255

His Phe Asp Leu Tyr His Val Ile Arg Arg Thr Ile Asn Leu Pro Thr
             260                 265                 270

Tyr Thr Leu Glu Ala Val Tyr Glu Ala Ile Phe Gly Lys Pro Lys Glu
         275                 280                 285

Lys Val Tyr Ala His Glu Ile Ala Glu Ala Trp Glu Thr Gly Lys Gly
 290                 295                 300

Leu Glu Arg Val Ala Lys Tyr Ser Met Glu Asp Ala Lys Val Thr Tyr
305                 310                 315                 320

Glu Leu Gly Arg Glu Phe Phe Pro Met Glu Ala Gln Leu Ser Arg Leu
                 325                 330                 335

Val Gly Gln Pro Leu Trp Asp Val Ser Arg Ser Ser Thr Gly Asn Leu
             340                 345                 350

Val Glu Trp Tyr Leu Leu Arg Lys Ala Tyr Glu Arg Asn Glu Leu Ala
         355                 360                 365

Pro Asn Lys Pro Asp Glu Arg Glu Tyr Glu Arg Arg Leu Arg Glu Ser
 370                 375                 380

Tyr Ala Gly Gly Tyr Val Lys Glu Pro Glu Lys Gly Leu Trp Glu Gly
385                 390                 395                 400

Leu Val Ser Leu Asp Phe Arg Ser Leu Tyr Pro Ser Ile Ile Ile Thr
                 405                 410                 415

His Asn Val Ser Pro Asp Thr Leu Asn Arg Glu Gly Cys Met Glu Tyr
             420                 425                 430
```

```
Asp Val Ala Pro Glu Val Lys His Lys Phe Cys Lys Asp Phe Pro Gly
            435                 440                 445

Phe Ile Pro Ser Leu Leu Lys Arg Leu Leu Asp Glu Arg Gln Glu Ile
450                 455                 460

Lys Arg Arg Met Lys Ala Ser Lys Asp Pro Ile Glu Lys Lys Met Leu
465                 470                 475                 480

Asp Tyr Arg Gln Arg Ala Ile Lys Ile Leu Ala Asn Ser Tyr Tyr Gly
            485                 490                 495

Tyr Tyr Gly Tyr Ala Lys Ala Arg Trp Tyr Cys Lys Glu Cys Ala Glu
            500                 505                 510

Ser Val Thr Ala Trp Gly Arg Glu Tyr Ile Glu Phe Val Arg Lys Glu
            515                 520                 525

Leu Glu Glu Lys Phe Gly Phe Lys Val Leu Tyr Ile Asp Thr Asp Gly
            530                 535                 540

Leu Tyr Ala Thr Ile Pro Gly Ala Lys Pro Glu Glu Ile Lys Arg Lys
545                 550                 555                 560

Ala Leu Glu Phe Val Glu Tyr Ile Asn Ala Lys Leu Pro Gly Leu Leu
            565                 570                 575

Glu Leu Glu Tyr Glu Gly Phe Tyr Val Arg Gly Phe Phe Val Thr Lys
            580                 585                 590

Lys Lys Tyr Ala Leu Ile Asp Glu Glu Gly Lys Ile Ile Thr Arg Gly
            595                 600                 605

Leu Glu Ile Val Arg Arg Asp Trp Ser Glu Ile Ala Lys Glu Thr Gln
            610                 615                 620

Ala Lys Val Leu Glu Ala Ile Leu Lys His Gly Asn Val Glu Glu Ala
625                 630                 635                 640

Val Lys Ile Val Lys Glu Val Thr Glu Lys Leu Ser Lys Tyr Glu Ile
            645                 650                 655

Pro Pro Glu Lys Leu Val Ile Tyr Glu Gln Ile Thr Arg Pro Leu His
            660                 665                 670

Glu Tyr Lys Ala Ile Gly Pro His Val Ala Val Ala Lys Arg Leu Ala
            675                 680                 685

Ala Arg Gly Val Lys Val Arg Pro Gly Met Val Ile Gly Tyr Ile Val
            690                 695                 700

Leu Arg Gly Asp Gly Pro Ile Ser Lys Arg Ala Ile Leu Ala Glu Glu
705                 710                 715                 720

Phe Asp Pro Arg Lys His Lys Tyr Asp Ala Glu Tyr Tyr Ile Glu Asn
            725                 730                 735

Gln Val Leu Pro Ala Val Leu Arg Ile Leu Glu Ala Phe Gly Tyr Arg
            740                 745                 750

Lys Glu Asp Leu Arg Trp Gln Lys Thr Lys Gln Thr Gly Leu Thr Ala
            755                 760                 765

Trp Leu Asn Val Lys Lys Lys
            770                 775

<210> SEQ ID NO 66
<211> LENGTH: 775
<212> TYPE: PRT
<213> ORGANISM: Pyrococcus furiosus

<400> SEQUENCE: 66

Met Ile Leu Asp Val Asp Tyr Ile Thr Glu Glu Gly Lys Pro Val Ile
1               5                   10                  15

Arg Leu Phe Lys Lys Glu Asn Gly Lys Phe Lys Ile Glu His Asp Arg
            20                  25                  30
```

```
Thr Phe Arg Pro Tyr Ile Tyr Ala Leu Leu Arg Asp Asp Ser Lys Ile
         35                  40                  45

Glu Glu Val Lys Lys Ile Thr Gly Glu Arg His Gly Lys Ile Val Arg
 50                  55                  60

Ile Val Asp Val Glu Lys Val Glu Lys Phe Leu Gly Lys Pro Ile
 65                  70                  75                  80

Thr Val Trp Lys Leu Tyr Leu Glu His Pro Gln Asp Val Pro Thr Ile
                 85                  90                  95

Arg Glu Lys Val Arg Glu His Pro Ala Val Val Asp Ile Phe Glu Tyr
                100                 105                 110

Asp Ile Pro Phe Ala Lys Arg Tyr Leu Ile Asp Lys Gly Leu Ile Pro
            115                 120                 125

Met Glu Gly Glu Glu Leu Lys Ile Leu Ala Phe Asp Ile Glu Thr
    130                 135                 140

Leu Tyr His Glu Gly Glu Glu Phe Gly Lys Gly Pro Ile Ile Met Ile
145                 150                 155                 160

Ser Tyr Ala Asp Glu Asn Glu Ala Lys Val Ile Thr Trp Lys Asn Ile
                165                 170                 175

Asp Leu Pro Tyr Val Glu Val Val Ser Ser Glu Arg Glu Met Ile Lys
                180                 185                 190

Arg Phe Leu Arg Ile Ile Arg Glu Lys Asp Pro Asp Ile Ile Val Thr
        195                 200                 205

Tyr Asn Gly Asp Ser Phe Asp Phe Pro Tyr Leu Ala Lys Arg Ala Glu
210                 215                 220

Lys Leu Gly Ile Lys Leu Thr Ile Gly Arg Asp Gly Ser Glu Pro Lys
225                 230                 235                 240

Met Gln Arg Ile Gly Asp Met Thr Ala Val Glu Val Lys Gly Arg Ile
                245                 250                 255

His Phe Asp Leu Tyr His Val Ile Thr Arg Thr Ile Asn Leu Pro Thr
                260                 265                 270

Tyr Thr Leu Glu Ala Val Tyr Glu Ala Ile Phe Gly Lys Pro Lys Glu
        275                 280                 285

Lys Val Tyr Ala Asp Glu Ile Ala Lys Ala Trp Glu Ser Gly Glu Asn
290                 295                 300

Leu Glu Arg Val Ala Lys Tyr Ser Met Glu Asp Ala Lys Ala Thr Tyr
305                 310                 315                 320

Glu Leu Gly Lys Glu Phe Leu Pro Met Glu Ile Gln Leu Ser Arg Leu
                325                 330                 335

Val Gly Gln Pro Leu Trp Asp Val Ser Arg Ser Ser Thr Gly Asn Leu
                340                 345                 350

Val Glu Trp Phe Leu Leu Arg Lys Ala Tyr Glu Arg Asn Glu Val Ala
        355                 360                 365

Pro Asn Lys Pro Ser Glu Glu Glu Tyr Gln Arg Arg Leu Arg Glu Ser
370                 375                 380

Tyr Thr Gly Gly Phe Val Lys Glu Pro Glu Lys Gly Leu Trp Glu Asn
385                 390                 395                 400

Ile Val Tyr Leu Asp Phe Arg Ala Leu Tyr Pro Ser Ile Ile Ile Thr
                405                 410                 415

His Asn Val Ser Pro Asp Thr Leu Asn Leu Glu Gly Cys Lys Asn Tyr
                420                 425                 430

Asp Ile Ala Pro Gln Val Gly His Lys Phe Cys Lys Asp Ile Pro Gly
        435                 440                 445
```

```
Phe Ile Pro Ser Leu Leu Gly His Leu Leu Glu Glu Arg Gln Lys Ile
    450                 455                 460
Lys Thr Lys Met Lys Glu Thr Gln Asp Pro Ile Glu Lys Ile Leu Leu
465                 470                 475                 480
Asp Tyr Arg Gln Lys Ala Ile Lys Leu Leu Ala Asn Ser Phe Tyr Gly
                485                 490                 495
Tyr Tyr Gly Tyr Ala Lys Ala Arg Trp Tyr Cys Lys Glu Cys Ala Glu
            500                 505                 510
Ser Val Thr Ala Trp Gly Arg Lys Tyr Ile Glu Leu Val Trp Lys Glu
        515                 520                 525
Leu Glu Glu Lys Phe Gly Phe Lys Val Leu Tyr Ile Asp Thr Asp Gly
530                 535                 540
Leu Tyr Ala Thr Ile Pro Gly Gly Glu Ser Glu Glu Ile Lys Lys Lys
545                 550                 555                 560
Ala Leu Glu Phe Val Lys Tyr Ile Asn Ser Lys Leu Pro Gly Leu Leu
                565                 570                 575
Glu Leu Glu Tyr Glu Gly Phe Tyr Lys Arg Gly Phe Phe Val Thr Lys
            580                 585                 590
Lys Arg Tyr Ala Val Ile Asp Glu Glu Gly Lys Val Ile Thr Arg Gly
        595                 600                 605
Leu Glu Ile Val Arg Arg Asp Trp Ser Glu Ile Ala Lys Glu Thr Gln
610                 615                 620
Ala Arg Val Leu Glu Thr Ile Leu Lys His Gly Asp Val Glu Glu Ala
625                 630                 635                 640
Val Arg Ile Val Lys Glu Val Ile Gln Lys Leu Ala Asn Tyr Glu Ile
                645                 650                 655
Pro Pro Glu Lys Leu Ala Ile Tyr Glu Gln Ile Thr Arg Pro Leu His
            660                 665                 670
Glu Tyr Lys Ala Ile Gly Pro His Val Ala Val Ala Lys Lys Leu Ala
        675                 680                 685
Ala Lys Gly Val Lys Ile Lys Pro Gly Met Val Ile Gly Tyr Ile Val
690                 695                 700
Leu Arg Gly Asp Gly Pro Ile Ser Asn Arg Ala Ile Leu Ala Glu Glu
705                 710                 715                 720
Tyr Asp Pro Lys Lys His Lys Tyr Asp Ala Glu Tyr Tyr Ile Glu Asn
                725                 730                 735
Gln Val Leu Pro Ala Val Leu Arg Ile Leu Glu Gly Phe Gly Tyr Arg
            740                 745                 750
Lys Glu Asp Leu Arg Tyr Gln Lys Thr Arg Gln Val Gly Leu Thr Ser
        755                 760                 765
Trp Leu Asn Ile Lys Lys Ser
    770                 775

<210> SEQ ID NO 67
<211> LENGTH: 775
<212> TYPE: PRT
<213> ORGANISM: Thermococcus sp.

<400> SEQUENCE: 67

Met Ile Leu Asp Thr Asp Tyr Ile Thr Glu Asn Gly Lys Pro Val Ile
1               5                   10                  15
Arg Val Phe Lys Lys Glu Asn Gly Glu Phe Lys Ile Glu Tyr Asp Arg
                20                  25                  30
Thr Phe Glu Pro Tyr Phe Tyr Ala Leu Leu Lys Asp Asp Ser Ala Ile
            35                  40                  45
```

```
Glu Asp Val Lys Lys Val Thr Ala Lys Arg His Gly Thr Val Val Lys
    50                  55                  60
Val Lys Arg Ala Glu Lys Val Gln Lys Lys Phe Leu Gly Arg Pro Ile
65                  70                  75                  80
Glu Val Trp Lys Leu Tyr Phe Asn His Pro Gln Asp Val Pro Ala Ile
                85                  90                  95
Arg Asp Arg Ile Arg Ala His Pro Ala Val Val Asp Ile Tyr Glu Tyr
                100                 105                 110
Asp Ile Pro Phe Ala Lys Arg Tyr Leu Ile Asp Lys Gly Leu Ile Pro
            115                 120                 125
Met Glu Gly Asp Glu Leu Thr Met Leu Ala Phe Asp Ile Glu Thr
    130                 135                 140
Leu Tyr His Glu Gly Glu Phe Gly Thr Gly Pro Ile Leu Met Ile
145                 150                 155                 160
Ser Tyr Ala Asp Gly Ser Glu Ala Arg Val Ile Thr Trp Lys Lys Ile
                165                 170                 175
Asp Leu Pro Tyr Val Asp Val Val Ser Thr Glu Lys Glu Met Ile Lys
            180                 185                 190
Arg Phe Leu Arg Val Val Arg Glu Lys Asp Pro Asp Val Leu Ile Thr
    195                 200                 205
Tyr Asn Gly Asp Asn Phe Asp Phe Ala Tyr Leu Lys Lys Arg Cys Glu
    210                 215                 220
Glu Leu Gly Ile Lys Phe Thr Leu Gly Arg Asp Gly Ser Glu Pro Lys
225                 230                 235                 240
Ile Gln Arg Met Gly Asp Arg Phe Ala Val Glu Val Lys Gly Arg Ile
                245                 250                 255
His Phe Asp Leu Tyr Pro Val Ile Arg Arg Thr Ile Asn Leu Pro Thr
            260                 265                 270
Tyr Thr Leu Glu Ala Val Tyr Glu Ala Val Phe Gly Lys Pro Lys Glu
    275                 280                 285
Lys Val Tyr Ala Glu Glu Ile Ala Gln Ala Trp Glu Ser Gly Glu Gly
290                 295                 300
Leu Glu Arg Val Ala Arg Tyr Ser Met Glu Asp Ala Lys Val Thr Tyr
305                 310                 315                 320
Glu Leu Gly Arg Glu Phe Phe Pro Met Glu Ala Gln Leu Ser Arg Leu
                325                 330                 335
Ile Gly Gln Ser Leu Trp Asp Val Ser Arg Ser Ser Thr Gly Asn Leu
            340                 345                 350
Val Glu Trp Phe Leu Leu Arg Lys Ala Tyr Lys Arg Asn Glu Leu Ala
    355                 360                 365
Pro Asn Lys Pro Asp Glu Arg Glu Leu Ala Arg Arg Gly Gly Tyr
    370                 375                 380
Ala Gly Gly Tyr Val Lys Glu Pro Glu Arg Gly Leu Trp Asp Asn Ile
385                 390                 395                 400
Val Tyr Leu Asp Phe Arg Ser Leu Tyr Pro Ser Ile Ile Ile Thr His
                405                 410                 415
Asn Val Ser Pro Asp Thr Leu Asn Arg Glu Gly Cys Lys Glu Tyr Asp
            420                 425                 430
Val Ala Pro Glu Val Gly His Lys Phe Cys Lys Asp Phe Pro Gly Phe
    435                 440                 445
Ile Pro Ser Leu Leu Gly Asp Leu Leu Glu Glu Arg Gln Lys Ile Lys
450                 455                 460
```

```
Arg Lys Met Lys Ala Thr Val Asp Pro Leu Glu Lys Lys Leu Leu Asp
465                 470                 475                 480

Tyr Arg Gln Arg Ala Ile Lys Ile Leu Ala Asn Ser Phe Tyr Gly Tyr
                485                 490                 495

Tyr Gly Tyr Ala Lys Ala Arg Trp Tyr Cys Lys Glu Cys Ala Glu Ser
            500                 505                 510

Val Thr Ala Trp Gly Arg Glu Tyr Ile Glu Met Val Ile Arg Glu Leu
        515                 520                 525

Glu Glu Lys Phe Gly Phe Lys Val Leu Tyr Ala Asp Thr Asp Gly Leu
    530                 535                 540

His Ala Thr Ile Pro Gly Ala Asp Ala Glu Thr Val Lys Lys Lys Ala
545                 550                 555                 560

Lys Glu Phe Leu Lys Tyr Ile Asn Pro Lys Leu Pro Gly Leu Leu Glu
                565                 570                 575

Leu Glu Tyr Glu Gly Phe Tyr Val Arg Gly Phe Phe Val Thr Lys Lys
            580                 585                 590

Lys Tyr Ala Val Ile Asp Glu Glu Gly Lys Ile Thr Thr Arg Gly Leu
        595                 600                 605

Glu Ile Val Arg Arg Asp Trp Ser Glu Ile Ala Lys Glu Thr Gln Ala
610                 615                 620

Arg Val Leu Glu Ala Ile Leu Lys His Gly Asp Val Glu Glu Ala Val
625                 630                 635                 640

Arg Ile Val Lys Glu Val Thr Glu Lys Leu Ser Lys Tyr Glu Val Pro
                645                 650                 655

Pro Glu Lys Leu Val Ile His Glu Gln Ile Thr Arg Asp Leu Arg Asp
            660                 665                 670

Tyr Lys Ala Thr Gly Pro His Val Ala Val Ala Lys Arg Leu Ala Ala
        675                 680                 685

Arg Gly Val Lys Ile Arg Pro Gly Thr Val Ile Ser Tyr Ile Val Leu
690                 695                 700

Lys Gly Ser Gly Arg Ile Gly Asp Arg Ala Ile Pro Ala Asp Glu Phe
705                 710                 715                 720

Asp Pro Thr Lys His Arg Tyr Asp Ala Glu Tyr Tyr Ile Glu Asn Gln
                725                 730                 735

Val Leu Pro Ala Val Glu Arg Ile Leu Lys Ala Phe Gly Tyr Arg Lys
            740                 745                 750

Glu Asp Leu Arg Tyr Gln Lys Thr Lys Gln Val Gly Leu Gly Ala Trp
        755                 760                 765

Leu Lys Val Lys Gly Lys
770                 775

<210> SEQ ID NO 68
<211> LENGTH: 1699
<212> TYPE: PRT
<213> ORGANISM: Thermococcus sp.

<400> SEQUENCE: 68

Met Ile Leu Asp Thr Asp Tyr Ile Thr Glu Asp Gly Lys Pro Val Ile
1               5                   10                  15

Arg Val Phe Lys Lys Glu Asn Gly Glu Phe Lys Ile Glu Tyr Asp Arg
                20                  25                  30

Asn Phe Glu Pro Tyr Phe Tyr Ala Leu Leu Lys Asp Asp Ser Ala Ile
            35                  40                  45

Glu Glu Val Lys Lys Ile Thr Ala Lys Arg His Gly Thr Val Val Lys
        50                  55                  60
```

```
Val Lys Arg Ala Glu Lys Val Lys Lys Phe Leu Gly Arg Pro Ile
 65                  70                  75                  80

Glu Val Trp Lys Leu Tyr Phe Thr His Pro Gln Asp Val Pro Ala Ile
                 85                  90                  95

Arg Asp Lys Ile Arg Glu His Pro Ala Val Ile Asp Ile Tyr Glu Tyr
                100                 105                 110

Asp Ile Pro Phe Ala Lys Arg Tyr Leu Ile Asp Lys Gly Leu Ile Pro
                115                 120                 125

Met Glu Gly Asp Glu Lys Leu Lys Met Leu Ala Phe Asp Ile Glu Thr
                130                 135                 140

Leu Tyr His Glu Gly Glu Glu Phe Ala Glu Gly Pro Ile Leu Met Ile
145                 150                 155                 160

Ser Tyr Ala Asp Glu Glu Gly Ala Arg Val Ile Thr Trp Lys Lys Val
                165                 170                 175

Asp Leu Pro Tyr Val Asp Val Val Ser Thr Glu Lys Glu Met Ile Lys
                180                 185                 190

Arg Phe Leu Arg Val Val Lys Glu Lys Asp Pro Asp Val Leu Ile Thr
                195                 200                 205

Tyr Asn Gly Asp Asn Phe Asp Phe Ala Tyr Leu Lys Arg Arg Ser Glu
210                 215                 220

Lys Leu Gly Val Lys Phe Ile Leu Gly Arg Asp Gly Ser Glu Pro Lys
225                 230                 235                 240

Ile Gln Arg Met Gly Asp Arg Phe Ala Val Glu Val Lys Gly Arg Ile
                245                 250                 255

His Phe Asp Leu Tyr Pro Val Ile Arg Arg Thr Ile Asn Leu Pro Thr
                260                 265                 270

Tyr Thr Leu Glu Ala Val Tyr Glu Ala Ile Phe Gly Lys Pro Lys Glu
                275                 280                 285

Lys Val Tyr Ala Glu Glu Ile Ala Thr Ala Trp Glu Thr Gly Glu Gly
                290                 295                 300

Leu Glu Arg Val Ala Arg Tyr Ser Met Glu Asp Ala Lys Val Thr Phe
305                 310                 315                 320

Glu Leu Gly Lys Glu Phe Phe Pro Met Glu Ala Gln Leu Ser Arg Leu
                325                 330                 335

Ile Gly Gln Ser Leu Trp Asp Val Ser Arg Ser Ser Thr Gly Asn Leu
                340                 345                 350

Val Glu Trp Phe Leu Leu Arg Lys Ala Tyr Glu Arg Asn Glu Leu Ala
                355                 360                 365

Pro Asn Lys Pro Asp Glu Arg Glu Leu Ala Arg Arg Gln Ser Tyr
                370                 375                 380

Ala Gly Gly Tyr Val Lys Glu Pro Glu Arg Gly Leu Trp Asn Asn Ile
385                 390                 395                 400

Val Tyr Leu Asp Phe Arg Ser Leu Tyr Pro Ser Ile Ile Thr His
                405                 410                 415

Asn Val Ser Pro Asp Thr Leu Asn Arg Glu Gly Cys Lys Glu Tyr Asp
                420                 425                 430

Val Ala Pro Gln Val Gly His Lys Phe Cys Lys Asp Phe Pro Gly Phe
                435                 440                 445

Ile Pro Ser Leu Leu Gly Asp Leu Leu Glu Glu Arg Gln Lys Ile Lys
                450                 455                 460

Arg Lys Met Arg Ala Thr Ile Asp Pro Val Glu Lys Lys Leu Leu Asp
465                 470                 475                 480
```

```
Tyr Arg Gln Arg Ala Ile Lys Ile Leu Ala Asn Ser Ile Leu Pro Asp
                485                 490                 495

Glu Trp Leu Pro Leu Leu Val Asn Gly Arg Leu Lys Leu Val Arg Ile
            500                 505                 510

Gly Asp Phe Val Asp Asn Thr Met Lys Lys Gly Gln Pro Leu Glu Asn
        515                 520                 525

Asp Gly Thr Glu Val Leu Glu Val Ser Gly Ile Glu Ala Ile Ser Phe
    530                 535                 540

Asn Arg Lys Thr Lys Ile Ala Glu Ile Lys Pro Val Lys Ala Leu Ile
545                 550                 555                 560

Arg His Arg Tyr Arg Gly Lys Val Tyr Asp Ile Lys Leu Ser Ser Gly
                565                 570                 575

Arg Asn Ile Lys Val Thr Glu Gly His Ser Leu Phe Ala Phe Arg Asp
            580                 585                 590

Gly Glu Leu Val Glu Val Thr Gly Gly Glu Ile Lys Pro Gly Asp Phe
        595                 600                 605

Ile Ala Val Pro Arg Arg Val Asn Leu Pro Glu Arg His Glu Arg Ile
    610                 615                 620

Asn Leu Ile Glu Ile Leu Leu Gly Leu Pro Pro Glu Glu Thr Ser Asp
625                 630                 635                 640

Ile Val Leu Thr Ile Pro Val Lys Gly Arg Lys Asn Phe Phe Lys Gly
                645                 650                 655

Met Leu Arg Thr Leu Arg Trp Ile Phe Glu Glu Glu Gln Arg Pro Arg
            660                 665                 670

Thr Ala Arg Arg Tyr Leu Glu His Leu Gln Lys Leu Gly Tyr Val Lys
        675                 680                 685

Leu Met Lys Arg Ala Tyr Glu Ile Val Asn Lys Glu Ala Leu Arg Asn
    690                 695                 700

Tyr Arg Lys Leu Tyr Glu Val Leu Ala Glu Arg Val Lys Tyr Asn Gly
705                 710                 715                 720

Asn Lys Arg Glu Tyr Leu Val His Phe Asn Asp Leu Arg Asn Glu Ile
                725                 730                 735

Lys Phe Met Pro Asp Glu Glu Leu Glu Glu Trp Lys Val Gly Thr Leu
            740                 745                 750

Asn Gly Phe Arg Met Glu Pro Phe Ile Glu Val Gly Glu Asp Phe Ala
        755                 760                 765

Lys Leu Leu Gly Tyr Tyr Val Ser Glu Gly Tyr Ala Arg Lys Gln Arg
    770                 775                 780

Asn Gln Lys Asn Gly Trp Ser Tyr Ser Val Lys Ile Tyr Asn Asn Asp
785                 790                 795                 800

Gln Arg Val Leu Asp Asp Met Glu Lys Leu Ala Ser Lys Phe Phe Gly
                805                 810                 815

Arg Val Arg Arg Gly Lys Asn Tyr Val Glu Ile Ser Arg Lys Met Ala
            820                 825                 830

Tyr Val Leu Phe Glu Ser Leu Cys Gly Thr Leu Ala Glu Asn Lys Arg
        835                 840                 845

Val Pro Glu Val Ile Phe Thr Ser Pro Glu Ser Val Arg Trp Ala Phe
    850                 855                 860

Phe Glu Gly Tyr Phe Ile Gly Asp Gly Asp Leu His Pro Ser Lys Arg
865                 870                 875                 880

Val Arg Leu Ser Thr Lys Ser Glu Glu Leu Val Asn Gly Leu Val Val
                885                 890                 895

Leu Leu Asn Ser Leu Gly Ile Ser Ala Ile Lys Ile Arg Phe Asp Ser
```

```
              900             905             910
Gly Val Tyr Arg Val Val Asn Glu Glu Leu Pro Phe Leu Gly Asn
            915             920             925

Arg Lys Arg Lys Asn Ala Tyr Ser His Val Ile Pro Lys Glu Ile
        930             935             940

Leu Glu Glu Thr Phe Gly Lys Gln Phe Gln Lys Asn Met Ser Pro Ala
945             950             955             960

Lys Leu Asn Glu Lys Val Glu Lys Gly Glu Leu Asp Ala Gly Lys Ala
            965             970             975

Arg Arg Ile Ala Trp Leu Leu Glu Gly Asp Ile Val Leu Asp Arg Val
        980             985             990

Glu Lys Val Thr Val Glu Asp Tyr Glu Gly Tyr Val Tyr Asp Leu Ser
        995             1000            1005

Val Glu Glu Asn Glu Asn Phe Leu Ala Gly Phe Gly Met Leu Tyr
    1010            1015            1020

Ala His Asn Ser Tyr Tyr Gly Tyr Tyr Gly Tyr Ala Lys Ala Arg
    1025            1030            1035

Trp Tyr Cys Arg Glu Cys Ala Glu Ser Val Thr Ala Trp Gly Arg
    1040            1045            1050

Ser Tyr Ile Glu Thr Thr Ile Arg Glu Ile Glu Glu Lys Phe Gly
    1055            1060            1065

Phe Lys Val Leu Tyr Ala Asp Ser Val Ala Gly Asn Thr Glu Val
    1070            1075            1080

Ile Ile Arg Arg Asn Gly Lys Val Glu Phe Val Pro Ile Glu Lys
    1085            1090            1095

Leu Phe Gln Arg Val Asp Tyr Arg Ile Gly Glu Lys Glu Tyr Cys
    1100            1105            1110

Ala Leu Glu Gly Val Glu Ala Leu Thr Leu Asp Asn Arg Gly Arg
    1115            1120            1125

Leu Val Trp Arg Lys Val Pro Tyr Ile Met Arg His Lys Thr Asn
    1130            1135            1140

Lys Lys Ile Tyr Arg Val Trp Phe Thr Asn Ser Trp Tyr Leu Asp
    1145            1150            1155

Val Thr Glu Asp His Ser Leu Ile Gly Tyr Leu Asn Thr Ser Lys
    1160            1165            1170

Val Lys Ser Glu Lys Pro Leu Lys Glu Arg Leu Val Glu Val Lys
    1175            1180            1185

Pro Arg Glu Leu Gly Glu Lys Val Lys Ser Leu Ile Thr Leu Asn
    1190            1195            1200

Arg Ala Ile Ala Arg Ser Ile Lys Ala Asn Pro Ile Ala Val Arg
    1205            1210            1215

Leu Trp Glu Leu Ile Gly Leu Leu Val Gly Asp Gly Asn Trp Gly
    1220            1225            1230

Gly His Ser Lys Trp Ala Lys Tyr Tyr Val Gly Leu Ser Cys Gly
    1235            1240            1245

Leu Asp Lys Ala Glu Ile Glu Glu Lys Val Leu Arg Pro Leu Lys
    1250            1255            1260

Glu Ala Gly Ile Ile Ser Asn Tyr Tyr Gly Lys Ser Lys Lys Gly
    1265            1270            1275

Asp Val Ser Ile Leu Ser Lys Trp Leu Ala Gly Phe Met Val Lys
    1280            1285            1290

Tyr Phe Lys Asp Glu Asn Gly Asn Lys Arg Ile Pro Ser Phe Met
    1295            1300            1305
```

```
Phe Asn Leu Pro Arg Glu Tyr Ile Glu Ala Phe Leu Arg Gly Leu
    1310                1315            1320

Phe Ser Ala Asp Gly Thr Val Ser Leu Arg Arg Gly Ile Pro Glu
    1325                1330            1335

Ile Arg Leu Thr Ser Val Asn Arg Glu Leu Ser Asn Glu Val Arg
    1340                1345            1350

Lys Leu Leu Trp Leu Val Gly Val Ser Asn Ser Met Phe Thr Glu
    1355                1360            1365

Thr Thr Pro Asn Lys Tyr Leu Gly Asn Glu Ser Gly Thr Arg Ser
    1370                1375            1380

Ile His Val Arg Ile Lys Asn Lys His Arg Phe Ala Lys Arg Ile
    1385                1390            1395

Gly Phe Leu Leu Asp Arg Lys Ala Thr Lys Leu Ser Asp Asn Leu
    1400                1405            1410

Arg Glu His Thr Asn Lys Lys Met Ala Tyr Arg Tyr Asp Phe Asp
    1415                1420            1425

Leu Val Tyr Pro Lys Lys Ile Glu Glu Ile Asn Tyr Asp Arg Tyr
    1430                1435            1440

Val Tyr Asp Ile Glu Val Glu Gly Thr His Arg Phe Phe Ala Asn
    1445                1450            1455

Gly Ile Leu Val His Asn Thr Asp Gly Phe Phe Ala Thr Ile Pro
    1460                1465            1470

Gly Ala Asp Ala Glu Thr Val Lys Lys Lys Ala Met Glu Phe Leu
    1475                1480            1485

Lys Tyr Ile Asn Ala Lys Leu Pro Gly Leu Leu Glu Leu Glu Tyr
    1490                1495            1500

Glu Gly Phe Tyr Val Arg Gly Phe Phe Val Thr Lys Lys Lys Tyr
    1505                1510            1515

Ala Val Ile Asp Glu Glu Gly Lys Ile Thr Thr Arg Gly Leu Glu
    1520                1525            1530

Ile Val Arg Arg Asp Trp Ser Glu Ile Ala Lys Glu Thr Gln Ala
    1535                1540            1545

Arg Val Leu Glu Ala Ile Leu Lys His Gly Asp Val Glu Glu Ala
    1550                1555            1560

Val Arg Ile Val Lys Glu Val Thr Glu Lys Leu Ser Lys Tyr Glu
    1565                1570            1575

Val Pro Pro Glu Lys Leu Val Ile His Glu Gln Ile Thr Arg Asp
    1580                1585            1590

Leu Lys Asp Tyr Lys Ala Thr Gly Pro His Val Ala Val Ala Lys
    1595                1600            1605

Arg Leu Ala Ala Arg Gly Ile Lys Ile Arg Pro Gly Thr Val Ile
    1610                1615            1620

Ser Tyr Ile Val Leu Lys Gly Ser Gly Arg Ile Gly Asp Arg Ala
    1625                1630            1635

Ile Pro Phe Asp Glu Phe Asp Pro Ala Lys His Lys Tyr Asp Ala
    1640                1645            1650

Glu Tyr Tyr Ile Glu Asn Gln Val Leu Pro Ala Val Glu Arg Ile
    1655                1660            1665

Leu Arg Ala Phe Gly Tyr Arg Lys Glu Asp Leu Arg Tyr Gln Lys
    1670                1675            1680

Thr Lys Gln Val Gly Leu Gly Ala Trp Leu Lys Val Lys Gly Lys
    1685                1690            1695
```

Lys

<210> SEQ ID NO 69
<211> LENGTH: 773
<212> TYPE: PRT
<213> ORGANISM: Thermococcus gorgonarius

<400> SEQUENCE: 69

```
Met Ile Leu Asp Thr Asp Tyr Ile Thr Glu Asp Gly Lys Pro Val Ile
1               5                   10                  15

Arg Ile Phe Lys Lys Glu Asn Gly Glu Phe Lys Ile Asp Tyr Asp Arg
            20                  25                  30

Asn Phe Glu Pro Tyr Ile Tyr Ala Leu Leu Lys Asp Asp Ser Ala Ile
        35                  40                  45

Glu Asp Val Lys Lys Ile Thr Ala Glu Arg His Gly Thr Thr Val Arg
    50                  55                  60

Val Val Arg Ala Glu Lys Val Lys Lys Lys Phe Leu Gly Arg Pro Ile
65                  70                  75                  80

Glu Val Trp Lys Leu Tyr Phe Thr His Pro Gln Asp Val Pro Ala Ile
                85                  90                  95

Arg Asp Lys Ile Lys Glu His Pro Ala Val Val Asp Ile Tyr Glu Tyr
            100                 105                 110

Asp Ile Pro Phe Ala Lys Arg Tyr Leu Ile Asp Lys Gly Leu Ile Pro
        115                 120                 125

Met Glu Gly Asp Glu Glu Leu Lys Met Leu Ala Phe Asp Ile Glu Thr
    130                 135                 140

Leu Tyr His Glu Gly Glu Glu Phe Ala Glu Gly Pro Ile Leu Met Ile
145                 150                 155                 160

Ser Tyr Ala Asp Glu Glu Gly Ala Arg Val Ile Thr Trp Lys Asn Ile
                165                 170                 175

Asp Leu Pro Tyr Val Asp Val Val Ser Thr Glu Lys Glu Met Ile Lys
            180                 185                 190

Arg Phe Leu Lys Val Val Lys Glu Lys Asp Pro Asp Val Leu Ile Thr
        195                 200                 205

Tyr Asn Gly Asp Asn Phe Asp Phe Ala Tyr Leu Lys Lys Arg Ser Glu
    210                 215                 220

Lys Leu Gly Val Lys Phe Ile Leu Gly Arg Glu Gly Ser Glu Pro Lys
225                 230                 235                 240

Ile Gln Arg Met Gly Asp Arg Phe Ala Val Glu Val Lys Gly Arg Ile
                245                 250                 255

His Phe Asp Leu Tyr Pro Val Ile Arg Arg Thr Ile Asn Leu Pro Thr
            260                 265                 270

Tyr Thr Leu Glu Ala Val Tyr Glu Ala Ile Phe Gly Gln Pro Lys Glu
        275                 280                 285

Lys Val Tyr Ala Glu Glu Ile Ala Gln Ala Trp Glu Thr Gly Glu Gly
    290                 295                 300

Leu Glu Arg Val Ala Arg Tyr Ser Met Glu Asp Ala Lys Val Thr Tyr
305                 310                 315                 320

Glu Leu Gly Lys Glu Phe Phe Pro Met Glu Ala Gln Leu Ser Arg Leu
                325                 330                 335

Val Gly Gln Ser Leu Trp Asp Val Ser Arg Ser Ser Thr Gly Asn Leu
            340                 345                 350

Val Glu Trp Phe Leu Leu Arg Lys Ala Tyr Glu Arg Asn Glu Leu Ala
        355                 360                 365
```

-continued

Pro Asn Lys Pro Asp Glu Arg Glu Leu Ala Arg Arg Arg Glu Ser Tyr
    370                 375                 380

Ala Gly Gly Tyr Val Lys Glu Pro Glu Arg Gly Leu Trp Glu Asn Ile
385                 390                 395                 400

Val Tyr Leu Asp Phe Arg Ser Leu Tyr Pro Ser Ile Ile Ile Thr His
                405                 410                 415

Asn Val Ser Pro Asp Thr Leu Asn Arg Glu Gly Cys Glu Glu Tyr Asp
            420                 425                 430

Val Ala Pro Gln Val Gly His Lys Phe Cys Lys Asp Phe Pro Gly Phe
        435                 440                 445

Ile Pro Ser Leu Leu Gly Asp Leu Leu Glu Glu Arg Gln Lys Val Lys
450                 455                 460

Lys Lys Met Lys Ala Thr Ile Asp Pro Ile Glu Lys Lys Leu Leu Asp
465                 470                 475                 480

Tyr Arg Gln Arg Ala Ile Lys Ile Leu Ala Asn Ser Phe Tyr Gly Tyr
                485                 490                 495

Tyr Gly Tyr Ala Lys Ala Arg Trp Tyr Cys Lys Glu Cys Ala Glu Ser
            500                 505                 510

Val Thr Ala Trp Gly Arg Gln Tyr Ile Glu Thr Thr Ile Arg Glu Ile
        515                 520                 525

Glu Glu Lys Phe Gly Phe Lys Val Leu Tyr Ala Asp Thr Asp Gly Phe
530                 535                 540

Phe Ala Thr Ile Pro Gly Ala Asp Ala Glu Thr Val Lys Lys Lys Ala
545                 550                 555                 560

Lys Glu Phe Leu Asp Tyr Ile Asn Ala Lys Leu Pro Gly Leu Leu Glu
                565                 570                 575

Leu Glu Tyr Glu Gly Phe Tyr Lys Arg Gly Phe Phe Val Thr Lys Lys
            580                 585                 590

Lys Tyr Ala Val Ile Asp Glu Glu Asp Lys Ile Thr Thr Arg Gly Leu
        595                 600                 605

Glu Ile Val Arg Arg Asp Trp Ser Glu Ile Ala Lys Glu Thr Gln Ala
610                 615                 620

Arg Val Leu Glu Ala Ile Leu Lys His Gly Asp Val Glu Glu Ala Val
625                 630                 635                 640

Arg Ile Val Lys Glu Val Thr Glu Lys Leu Ser Lys Tyr Glu Val Pro
                645                 650                 655

Pro Glu Lys Leu Val Ile Tyr Glu Gln Ile Thr Arg Asp Leu Lys Asp
            660                 665                 670

Tyr Lys Ala Thr Gly Pro His Val Ala Val Ala Lys Arg Leu Ala Ala
        675                 680                 685

Arg Gly Ile Lys Ile Arg Pro Gly Thr Val Ile Ser Tyr Ile Val Leu
690                 695                 700

Lys Gly Ser Gly Arg Ile Gly Asp Arg Ala Ile Pro Phe Asp Glu Phe
705                 710                 715                 720

Asp Pro Ala Lys His Lys Tyr Asp Ala Glu Tyr Tyr Ile Glu Asn Gln
                725                 730                 735

Val Leu Pro Ala Val Glu Arg Ile Leu Arg Ala Phe Gly Tyr Arg Lys
            740                 745                 750

Glu Asp Leu Arg Tyr Gln Lys Thr Arg Gln Val Gly Leu Gly Ala Trp
        755                 760                 765

Leu Lys Pro Lys Thr
770

```
<210> SEQ ID NO 70
<211> LENGTH: 1467
<212> TYPE: PRT
<213> ORGANISM: Thermococcus zilligii

<400> SEQUENCE: 70

Met Ile Leu Asp Ala Asp Tyr Ile Thr Glu Asp Gly Lys Pro Val Ile
1               5                   10                  15

Arg Val Phe Lys Lys Glu Lys Gly Glu Phe Lys Ile Asp Tyr Asp Arg
            20                  25                  30

Asp Phe Glu Pro Tyr Ile Tyr Ala Leu Leu Lys Asp Asp Ser Ala Ile
        35                  40                  45

Glu Asp Ile Lys Lys Ile Thr Ala Glu Arg His Gly Thr Thr Val Arg
    50                  55                  60

Val Thr Arg Ala Glu Arg Val Lys Lys Phe Leu Gly Arg Pro Val
65                  70                  75                  80

Glu Val Trp Lys Leu Tyr Phe Thr His Pro Gln Asp Val Pro Ala Ile
                85                  90                  95

Arg Asp Lys Ile Arg Glu His Pro Ala Val Val Asp Ile Tyr Glu Tyr
            100                 105                 110

Asp Ile Pro Phe Ala Lys Arg Tyr Leu Ile Asp Arg Gly Leu Ile Pro
        115                 120                 125

Met Glu Gly Asp Glu Glu Leu Arg Met Leu Ala Phe Asp Ile Glu Thr
    130                 135                 140

Leu Tyr His Glu Gly Glu Glu Phe Gly Glu Gly Pro Ile Leu Met Ile
145                 150                 155                 160

Ser Tyr Ala Asp Glu Glu Gly Ala Arg Val Ile Thr Trp Lys Asn Ile
                165                 170                 175

Asp Leu Pro Tyr Val Glu Ser Val Ser Thr Glu Lys Glu Met Ile Lys
            180                 185                 190

Arg Phe Leu Lys Val Ile Gln Glu Lys Asp Pro Asp Val Leu Ile Thr
        195                 200                 205

Tyr Asn Gly Asp Asn Phe Asp Phe Ala Tyr Leu Lys Lys Arg Ser Glu
    210                 215                 220

Thr Leu Gly Val Lys Phe Ile Leu Gly Arg Asp Gly Ser Glu Pro Lys
225                 230                 235                 240

Ile Gln Arg Met Gly Asp Arg Phe Ala Val Glu Val Lys Gly Arg Ile
                245                 250                 255

His Phe Asp Leu Tyr Pro Val Ile Arg Arg Thr Ile Asn Leu Pro Thr
            260                 265                 270

Tyr Thr Leu Glu Thr Val Tyr Glu Ala Ile Phe Gly Gln Pro Lys Glu
        275                 280                 285

Lys Val Tyr Ala Glu Glu Ile Ala Arg Ala Trp Glu Ser Gly Glu Gly
    290                 295                 300

Leu Glu Arg Val Ala Arg Tyr Ser Met Glu Asp Ala Lys Ala Thr Tyr
305                 310                 315                 320

Glu Leu Gly Lys Glu Phe Phe Pro Met Glu Ala Gln Leu Ser Arg Leu
                325                 330                 335

Val Gly Gln Ser Leu Trp Asp Val Ser Arg Ser Ser Thr Gly Asn Leu
            340                 345                 350

Val Glu Trp Phe Leu Leu Arg Lys Ala Tyr Glu Arg Asn Glu Leu Ala
        355                 360                 365

Pro Asn Lys Pro Asp Glu Arg Glu Leu Ala Arg Arg Ala Glu Ser Tyr
    370                 375                 380
```

```
Ala Gly Gly Tyr Val Lys Glu Pro Glu Lys Gly Leu Trp Glu Asn Ile
385                 390                 395                 400

Val Tyr Leu Asp Tyr Lys Ser Leu Tyr Pro Ser Ile Ile Ile Thr His
            405                 410                 415

Asn Val Ser Pro Asp Thr Leu Asn Arg Glu Gly Cys Arg Glu Tyr Asp
        420                 425                 430

Val Ala Pro Gln Val Gly His Arg Phe Cys Lys Asp Phe Pro Gly Phe
        435                 440                 445

Ile Pro Ser Leu Leu Gly Asp Leu Leu Glu Glu Arg Gln Lys Val Lys
    450                 455                 460

Lys Lys Met Lys Ala Thr Val Asp Pro Ile Glu Arg Lys Leu Leu Asp
465                 470                 475                 480

Tyr Arg Gln Arg Ala Ile Lys Ile Leu Ala Asn Ser Ile Leu Pro Asp
            485                 490                 495

Glu Trp Ile Pro Leu Leu Ile Asn Gly Arg Leu Lys Leu Val Arg Ile
                500                 505                 510

Gly Asp Phe Val Asp Ser Ala Met Lys Glu Leu Lys Pro Met Lys Arg
            515                 520                 525

Asp Glu Thr Glu Val Leu Glu Val Ser Gly Ile Gly Ala Ile Ser Phe
530                 535                 540

Asn Arg Lys Thr Lys Arg Ser Glu Thr Met Pro Val Arg Ala Leu Leu
545                 550                 555                 560

Arg His Arg Tyr Ser Gly Lys Val Tyr Gly Ile Lys Leu Ser Ser Gly
            565                 570                 575

Arg Lys Ile Lys Val Thr Ala Gly His Ser Leu Phe Thr Phe Arg Asp
            580                 585                 590

Gly Glu Leu Val Glu Ile Lys Gly Glu Glu Ile Lys Pro Gly Asp Phe
            595                 600                 605

Ile Ala Val Pro Gly Arg Ile Asn Leu Pro Glu Arg Gln Glu Arg Ile
    610                 615                 620

Asn Leu Val Glu Val Leu Leu Gly Leu Pro Glu Glu Glu Thr Ala Asp
625                 630                 635                 640

Ile Val Leu Thr Ile Pro Val Lys Gly Arg Arg Asn Phe Phe Lys Gly
            645                 650                 655

Met Leu Arg Thr Leu Arg Trp Ile Phe Gly Glu Glu Lys Arg Pro Gly
            660                 665                 670

Thr Ala Arg Arg Tyr Leu Glu His Leu Gln Thr Leu Gly Tyr Val Arg
        675                 680                 685

Leu Gly Lys Ile Gly Tyr Glu Ile Val Asn Glu Ala Leu Arg Asp
    690                 695                 700

Tyr Arg Gly Leu Tyr Glu Thr Leu Thr Gly Lys Val Lys Tyr Asn Gly
705                 710                 715                 720

Asn Lys Arg Glu Tyr Leu Val His Phe Asn Asp Leu Arg Asp Ile Ile
            725                 730                 735

Arg Leu Met Pro Glu Lys Glu Leu Lys Glu Trp Lys Val Gly Thr Leu
        740                 745                 750

Asn Gly Phe Arg Met Glu Thr Ser Ile Glu Val Lys Glu Asp Phe Ala
        755                 760                 765

Lys Leu Leu Ser Tyr Tyr Val Ser Glu Gly Tyr Ala Gly Lys Gln Arg
    770                 775                 780

Ser Gln Lys Asn Gly Trp Asn Tyr Ser Val Lys Leu Tyr Asn Asn Asp
785                 790                 795                 800

Gln Asn Val Leu Asp Asp Met Glu Thr Leu Ala Ser Lys Phe Phe Gly
```

-continued

```
                805                 810                 815
Lys Val Arg Arg Gly Lys Asn Tyr Val Glu Ile Pro Arg Lys Met Ala
                820                 825                 830

Tyr Val Leu Phe Glu Ser Leu Cys Gly Thr Leu Ala Glu Asn Lys Arg
                835                 840                 845

Val Pro Glu Ile Ile Phe Thr Ser Pro Glu Ser Val Arg Trp Ala Phe
        850                 855                 860

Leu Glu Gly Cys Phe Ile Gly Asp Gly Asp Leu His Pro Gly Lys Gly
865                 870                 875                 880

Val Arg Leu Ser Thr Lys Ser Glu Glu Leu Val Asn Gly Leu Val Ile
                885                 890                 895

Leu Leu Asn Ser Leu Gly Val Ser Ala Leu Arg Ile Trp Leu Asp Ser
                900                 905                 910

Gly Val Tyr Arg Val Leu Val Asn Glu Glu Leu Pro Phe Leu Asp Lys
        915                 920                 925

Gly Lys Lys Lys Thr Pro Tyr Val Thr Ser Lys Glu Ile Pro Glu Glu
        930                 935                 940

Ala Phe Gly Lys Arg Phe Gln Arg Asn Ile Ser Leu Glu Lys Leu Arg
945                 950                 955                 960

Glu Lys Val Glu Lys Gly Glu Pro Asp Ala Glu Lys Val Lys Arg Val
                965                 970                 975

Val Trp Leu Leu Glu Gly Asp Ile Val Leu Asp Arg Val Glu Glu Val
            980                 985                 990

Ala Val Asp Asp Tyr Glu Gly Tyr  Val Tyr Asp Leu Ser Val Glu Glu
                995                 1000                1005

Asn Glu  Asn Phe Leu Ala Gly  Phe Gly Met Leu Tyr  Ala His Asn
    1010                1015                1020

Ser Tyr  Tyr Gly Tyr Tyr Gly  Tyr Ala Asn Ala Arg  Trp Tyr Cys
    1025                1030                1035

Arg Glu  Cys Ala Glu Ser Val  Thr Ala Trp Gly Arg  Gln Tyr Ile
    1040                1045                1050

Glu Thr  Thr Met Arg Glu Ile  Glu Glu Lys Phe Gly  Phe Lys Val
    1055                1060                1065

Leu Tyr  Ala Asp Ser Val Thr  Gly Asp Thr Glu Val  Ile Ile Arg
    1070                1075                1080

Arg Asn  Gly Arg Ile Glu Phe  Val Pro Ile Glu Arg  Leu Phe Glu
    1085                1090                1095

His Val  Asp Tyr Arg Val Gly  Glu Lys Glu Tyr Cys  Val Leu Ser
    1100                1105                1110

Gly Val  Glu Ala Leu Thr Leu  Asp Asn Arg Gly Arg  Leu Val Trp
    1115                1120                1125

Lys Lys  Val Pro Tyr Val Met  Arg His Lys Thr Asp  Lys Arg Ile
    1130                1135                1140

Tyr Arg  Val Trp Val Thr Asn  Ser Arg Tyr Leu Asn  Val Thr Glu
    1145                1150                1155

Asp His  Ser Leu Ile Gly Tyr  Leu Asp Gly Lys Tyr  Leu Glu Ile
    1160                1165                1170

Arg Pro  Ala Asp Ile Pro Lys  Asp Pro Asp Ile Lys  Leu Ile Thr
    1175                1180                1185

Leu Ala  Ser Pro Gly Leu Gln  Glu Val Ala Leu Lys  Thr Pro Ser
    1190                1195                1200

Arg Leu  Glu Glu Ile Thr Tyr  Glu Gly Tyr Val Tyr  Asp Ile Glu
    1205                1210                1215
```

```
Val Glu Gly Thr His Arg Phe Phe Ala Asn Gly Ile Leu Val His
    1220            1225                1230

Asn Thr Asp Gly Phe Phe Ala Thr Ile Pro Gly Ala Asp Ala Glu
    1235            1240                1245

Thr Val Lys Lys Lys Ala Lys Glu Phe Leu Asn Tyr Ile Asn Pro
    1250            1255                1260

Arg Leu Pro Gly Leu Leu Glu Leu Glu Tyr Glu Gly Phe Tyr Arg
    1265            1270                1275

Arg Gly Phe Phe Val Thr Lys Lys Lys Tyr Ala Val Ile Asp Glu
    1280            1285                1290

Glu Asp Lys Ile Thr Thr Arg Gly Leu Glu Ile Val Arg Arg Asp
    1295            1300                1305

Trp Ser Glu Ile Ala Lys Glu Thr Gln Ala Arg Val Leu Glu Ala
    1310            1315                1320

Ile Leu Lys His Gly Asp Val Glu Glu Ala Val Arg Ile Val Lys
    1325            1330                1335

Glu Val Thr Glu Lys Leu Ser Arg Tyr Glu Val Pro Pro Glu Lys
    1340            1345                1350

Leu Val Ile Tyr Glu Gln Ile Thr Arg Asp Leu Arg Asp Tyr Arg
    1355            1360                1365

Ala Thr Gly Pro His Val Ala Val Ala Lys Arg Leu Ala Ala Arg
    1370            1375                1380

Gly Ile Lys Ile Arg Pro Gly Thr Val Ile Ser Tyr Ile Val Leu
    1385            1390                1395

Lys Gly Pro Gly Arg Val Gly Asp Arg Ala Ile Pro Phe Asp Glu
    1400            1405                1410

Phe Asp Pro Ala Lys His Arg Tyr Asp Ala Glu Tyr Tyr Ile Glu
    1415            1420                1425

Asn Gln Val Leu Pro Ala Val Glu Arg Ile Leu Arg Ala Phe Gly
    1430            1435                1440

Tyr Arg Lys Glu Asp Leu Arg Tyr Gln Lys Thr Lys Gln Ala Gly
    1445            1450                1455

Leu Gly Ala Trp Leu Lys Pro Lys Thr
    1460            1465

<210> SEQ ID NO 71
<211> LENGTH: 1308
<212> TYPE: PRT
<213> ORGANISM: Hermococcus sp.

<400> SEQUENCE: 71

Met Ile Leu Asp Val Asp Tyr Ile Thr Glu Asp Gly Lys Pro Val Ile
1               5                   10                  15

Arg Ile Phe Lys Lys Glu Lys Gly Glu Phe Lys Ile Glu Tyr Asp Arg
                20                  25                  30

Asp Phe Glu Pro Tyr Ile Tyr Ala Leu Leu Lys Asp Asp Ser Ala Ile
            35                  40                  45

Glu Glu Val Lys Lys Ile Thr Ala Glu Arg His Gly Lys Val Val Lys
        50                  55                  60

Val Lys Arg Ala Glu Lys Val Asn Lys Lys Phe Leu Gly Arg Pro Val
65                  70                  75                  80

Glu Val Trp Lys Leu Tyr Phe Glu His Pro Gln Asp Val Pro Ala Ile
                85                  90                  95

Arg Asp Lys Ile Arg Ala His Pro Gly Val Ile Asp Ile Tyr Glu Tyr
```

```
                100                 105                 110
Asp Ile Pro Phe Ala Lys Arg Tyr Leu Ile Asp Lys Gly Leu Val Pro
            115                 120                 125

Met Glu Gly Asp Glu Glu Leu Lys Met Leu Ala Phe Asp Ile Glu Thr
        130                 135                 140

Leu Tyr His Glu Gly Glu Glu Phe Gly Thr Gly Pro Ile Leu Met Ile
145                 150                 155                 160

Ser Tyr Ala Asp Glu Asn Glu Ala Arg Val Ile Thr Trp Lys Lys Ile
                165                 170                 175

Asp Leu Pro Tyr Val Asp Val Val Ser Thr Glu Lys Glu Met Ile Lys
            180                 185                 190

Arg Phe Leu Arg Val Val Lys Glu Lys Asp Pro Asp Val Leu Ile Thr
        195                 200                 205

Tyr Asn Gly Asp Asn Phe Asp Phe Ala Tyr Leu Lys Lys Arg Cys Glu
210                 215                 220

Lys Leu Gly Ile Ser Phe Thr Leu Gly Arg Asp Gly Ser Glu Pro Lys
225                 230                 235                 240

Ile His Arg Met Gly Asp Arg Phe Ala Val Glu Val Lys Gly Arg Ile
                245                 250                 255

His Phe Asp Leu Tyr Pro Val Ile Arg Arg Thr Ile Asn Leu Pro Thr
            260                 265                 270

Tyr Thr Leu Glu Val Val Tyr Glu Ala Val Phe Gly Lys Pro Lys Glu
        275                 280                 285

Lys Val Tyr Ala Glu Glu Ile Thr Leu Ala Trp Glu Ser Gly Glu Gly
290                 295                 300

Leu Glu Arg Val Ala Arg Tyr Ser Met Glu Asp Ala Lys Ala Thr Tyr
305                 310                 315                 320

Glu Leu Gly Arg Glu Phe Phe Pro Met Glu Ala Gln Leu Ser Arg Leu
                325                 330                 335

Ile Gly Gln Ser Leu Trp Asp Val Ser Arg Ser Ser Thr Gly Asn Leu
            340                 345                 350

Val Glu Trp Phe Leu Leu Arg Lys Ala Tyr Glu Arg Asn Glu Leu Ala
        355                 360                 365

Pro Asn Lys Pro Asp Glu Gly Glu Leu Ala Arg Arg Arg Asn Ser Tyr
370                 375                 380

Ala Gly Gly Tyr Val Lys Glu Pro Glu Arg Gly Leu Trp Asp Asn Ile
385                 390                 395                 400

Val Tyr Leu Asp Phe Arg Ser Leu Tyr Pro Ser Ile Ile Ile Thr His
                405                 410                 415

Asn Val Ser Pro Asp Thr Leu Asn Arg Glu Gly Cys Lys Glu Tyr Asp
            420                 425                 430

Val Ala Pro Gln Val Gly His Lys Phe Cys Lys Asp Phe Pro Gly Phe
        435                 440                 445

Ile Pro Ser Leu Leu Gly Asn Leu Leu Glu Glu Arg Gln Lys Ile Lys
450                 455                 460

Arg Lys Met Lys Ala Thr Ile Asp Pro Leu Glu Lys Lys Leu Leu Asp
465                 470                 475                 480

Tyr Arg Gln Arg Ala Ile Lys Ile Leu Ala Asn Ser Ile Leu Pro Asp
                485                 490                 495

Glu Trp Val Pro Leu Leu Ile Asp Gly Arg Leu Lys Leu Thr Arg Ile
            500                 505                 510

Gly Asp Phe Val Asp Asn Ala Met Asp Glu Gly Asn Pro Leu Lys Ser
        515                 520                 525
```

```
Asn Glu Thr Glu Val Leu Glu Val Leu Gly Ile Asn Ala Ile Ser Phe
    530                 535                 540

Asn Arg Lys Thr Lys Ile Ser Glu Val Arg Pro Val Arg Ala Leu Ile
545                 550                 555                 560

Arg His Arg Tyr Arg Gly Lys Val Tyr Ser Ile Lys Leu Ser Ser Gly
                565                 570                 575

Arg Lys Ile Lys Val Thr Glu Gly His Ser Leu Phe Thr Val Lys Asn
            580                 585                 590

Gly Glu Leu Val Glu Val Thr Gly Gly Lys Val Lys Pro Gly Asp Phe
                595                 600                 605

Ile Ala Val Pro Arg Arg Ile Asn Leu Pro Glu Arg His Glu Arg Ile
610                 615                 620

Asn Leu Ala Asp Val Leu Leu Asn Leu Pro Glu Glu Thr Ala Asp
625                 630                 635                 640

Val Val Leu Thr Ile Pro Thr Lys Gly Arg Lys Asn Phe Phe Arg Gly
                645                 650                 655

Met Leu Arg Thr Leu Arg Trp Ile Phe Glu Gly Glu Lys Arg Pro Arg
                660                 665                 670

Thr Ala Arg Arg Tyr Leu Glu His Leu Gln Lys Leu Gly Tyr Val Arg
                675                 680                 685

Leu Lys Lys Ile Gly Tyr Glu Val Leu Asp Glu Lys Ala Leu Arg Lys
690                 695                 700

Tyr Arg Ala Leu Tyr Glu Val Leu Ala Glu Lys Val Arg Tyr Asn Gly
705                 710                 715                 720

Asn Lys Arg Glu Tyr Leu Val Ala Phe Asn Asp Leu Arg Asp Lys Ile
                725                 730                 735

Glu Phe Met Pro Glu Glu Leu Arg Glu Trp Lys Ile Gly Thr Leu
                740                 745                 750

Asn Gly Phe Arg Met Glu Pro Phe Ile Glu Val Asn Glu Asp Leu Ala
                755                 760                 765

Lys Leu Leu Gly Tyr Tyr Val Ser Glu Gly Tyr Ala Gly Lys Gln Arg
                770                 775                 780

Asn Gln Lys Asn Gly Trp Ser Tyr Ser Val Lys Leu Tyr Asn Asn Asp
785                 790                 795                 800

Gln Lys Val Leu Asp Asp Met Glu Arg Leu Ala Ser Lys Phe Phe Gly
                805                 810                 815

Lys Val Arg Arg Gly Lys Asn Tyr Val Glu Met Pro Lys Lys Met Ala
                820                 825                 830

Tyr Val Leu Phe Lys Ser Leu Cys Gly Thr Leu Ala Glu Asn Lys Arg
                835                 840                 845

Val Pro Glu Val Ile Phe Thr Ser Pro Glu Asn Val Arg Trp Ala Phe
850                 855                 860

Leu Glu Gly Tyr Phe Ile Gly Asp Gly Asp Leu His Pro Ser Lys Arg
865                 870                 875                 880

Val Arg Leu Ser Thr Lys Ser Glu Thr Leu Val Asn Gly Leu Ile Ile
                885                 890                 895

Leu Leu Asn Ser Leu Gly Ile Ser Ala Val Lys Ile Arg Phe Glu Ser
                900                 905                 910

Gly Val Tyr Arg Val Leu Val Asn Glu Glu Leu Ser Phe Leu Gly Asn
                915                 920                 925

Ser Lys Lys Lys Asn Ala Tyr Tyr Ser His Val Ile Pro Lys Glu Ile
                930                 935                 940
```

```
Leu Glu Asp Val Phe Glu Lys Arg Phe Gln Lys Asn Val Ser Pro Lys
945                 950                 955                 960

Lys Leu Arg Glu Lys Ile Lys Arg Gly Glu Leu Asn Gln Glu Lys Ala
            965                 970                 975

Lys Arg Ile Ser Trp Leu Leu Glu Gly Asp Ile Val Leu Asp Arg Val
            980                 985                 990

Glu Glu Val Glu Val Glu Asp Tyr Asn Gly Tyr Val Tyr Asp Leu Ser
        995                 1000                1005

Val Glu Glu Asn Glu Asn Phe Leu Ala Gly Phe Gly Met Ile Tyr
    1010                1015                1020

Ala His Asn Ser Tyr Tyr Gly Tyr Tyr Gly Tyr Pro Arg Ala Arg
    1025                1030                1035

Trp Tyr Cys Lys Glu Cys Ala Glu Ser Val Thr Ala Trp Gly Arg
    1040                1045                1050

Glu Tyr Ile Glu Met Thr Ile Arg Glu Ile Glu Glu Lys Tyr Gly
    1055                1060                1065

Phe Lys Val Leu Tyr Ala Asp Thr Asp Gly Phe Tyr Ala Thr Ile
    1070                1075                1080

Pro Gly Ala Asp Ala Glu Thr Val Lys Lys Lys Ala Lys Glu Phe
    1085                1090                1095

Leu Lys Tyr Ile Asn Ala Lys Leu Pro Gly Leu Leu Glu Leu Glu
    1100                1105                1110

Tyr Glu Gly Phe Tyr Lys Arg Gly Phe Phe Val Thr Lys Lys Lys
    1115                1120                1125

Tyr Ala Val Ile Asp Glu Glu Gly Lys Ile Val Thr Arg Gly Leu
    1130                1135                1140

Glu Ile Val Arg Arg Asp Trp Ser Asp Ile Ala Lys Glu Thr Gln
    1145                1150                1155

Ala Arg Val Leu Glu Ala Leu Leu Lys Asp Gly Asn Val Glu Lys
    1160                1165                1170

Ala Val Lys Ile Val Lys Glu Ile Thr Glu Lys Leu Ser Lys Tyr
    1175                1180                1185

Glu Ile Pro Pro Glu Lys Leu Val Ile His Glu Gln Ile Thr Arg
    1190                1195                1200

Glu Leu Lys Asp Tyr Lys Ala Thr Gly Pro His Val Ala Ile Ala
    1205                1210                1215

Lys Arg Leu Ala Ala Arg Gly Ile Lys Val Arg Pro Gly Thr Ile
    1220                1225                1230

Ile Ser Tyr Ile Val Leu Lys Gly Ser Gly Arg Ile Gly Asp Arg
    1235                1240                1245

Ala Ile Pro Phe Asp Glu Phe Asp Pro Thr Lys His Lys Tyr Asp
    1250                1255                1260

Ala Asp Tyr Tyr Ile Glu Asn Gln Val Leu Pro Ala Val Met Arg
    1265                1270                1275

Ile Leu Glu Ala Phe Gly Tyr Lys Lys Glu Asp Leu Arg Tyr Gln
    1280                1285                1290

Lys Thr Arg Gln Val Gly Leu Gly Ala Trp Leu Lys Pro Lys Lys
    1295                1300                1305
```

<210> SEQ ID NO 72
<211> LENGTH: 1671
<212> TYPE: PRT
<213> ORGANISM: Pyrococcus sp.

<400> SEQUENCE: 72

-continued

```
Met Ile Leu Asp Thr Asp Tyr Ile Thr Glu Asp Gly Lys Pro Val Ile
1               5                   10                  15

Arg Ile Phe Lys Lys Glu Asn Gly Glu Phe Lys Ile Glu Tyr Asp Arg
                20                  25                  30

Thr Phe Glu Pro Tyr Phe Tyr Ala Leu Leu Lys Asp Asp Ser Ala Ile
            35                  40                  45

Glu Glu Val Lys Lys Ile Thr Ala Glu Arg His Gly Thr Val Val Thr
        50                  55                  60

Val Lys Arg Val Glu Lys Val Gln Lys Lys Phe Leu Gly Arg Pro Val
65                  70                  75                  80

Glu Val Trp Lys Leu Tyr Phe Thr His Pro Gln Asp Val Pro Ala Ile
                85                  90                  95

Arg Asp Lys Ile Arg Glu His Pro Ala Val Ile Asp Ile Tyr Glu Tyr
                100                 105                 110

Asp Ile Pro Phe Ala Lys Arg Tyr Leu Ile Asp Lys Gly Leu Val Pro
            115                 120                 125

Met Glu Gly Asp Glu Glu Leu Lys Met Leu Ala Phe Asp Ile Glu Thr
        130                 135                 140

Leu Tyr His Glu Gly Glu Glu Phe Ala Glu Gly Pro Ile Leu Met Ile
145                 150                 155                 160

Ser Tyr Ala Asp Glu Glu Gly Ala Arg Val Ile Thr Trp Lys Asn Val
                165                 170                 175

Asp Leu Pro Tyr Val Asp Val Val Ser Thr Glu Arg Glu Met Ile Lys
            180                 185                 190

Arg Phe Leu Arg Val Val Lys Glu Lys Asp Pro Asp Val Leu Ile Thr
        195                 200                 205

Tyr Asn Gly Asp Asn Phe Asp Phe Ala Tyr Leu Lys Lys Arg Cys Glu
210                 215                 220

Lys Leu Gly Ile Asn Phe Ala Leu Gly Arg Asp Gly Ser Glu Pro Lys
225                 230                 235                 240

Ile Gln Arg Met Gly Asp Arg Phe Ala Val Glu Val Lys Gly Arg Ile
                245                 250                 255

His Phe Asp Leu Tyr Pro Val Ile Arg Arg Thr Ile Asn Leu Pro Thr
            260                 265                 270

Tyr Thr Leu Glu Ala Val Tyr Glu Ala Val Phe Gly Gln Pro Lys Glu
        275                 280                 285

Lys Val Tyr Ala Glu Glu Ile Thr Thr Ala Trp Glu Thr Gly Glu Asn
        290                 295                 300

Leu Glu Arg Val Ala Arg Tyr Ser Met Glu Asp Ala Lys Val Thr Tyr
305                 310                 315                 320

Glu Leu Gly Lys Glu Phe Leu Pro Met Glu Ala Gln Leu Ser Arg Leu
                325                 330                 335

Ile Gly Gln Ser Leu Trp Asp Val Ser Arg Ser Ser Thr Gly Asn Leu
            340                 345                 350

Val Glu Trp Phe Leu Leu Arg Lys Ala Tyr Glu Arg Asn Glu Leu Ala
        355                 360                 365

Pro Asn Lys Pro Asp Glu Lys Glu Leu Ala Arg Arg Gln Ser Tyr
370                 375                 380

Glu Gly Gly Tyr Val Lys Glu Pro Glu Arg Gly Leu Trp Glu Asn Ile
385                 390                 395                 400

Val Tyr Leu Asp Phe Arg Cys His Pro Ala Asp Thr Lys Val Val Val
            405                 410                 415
```

-continued

```
Lys Gly Lys Gly Ile Ile Asn Ile Ser Glu Val Gln Glu Gly Asp Tyr
            420                 425                 430
Val Leu Gly Ile Asp Gly Trp Gln Arg Val Arg Lys Val Trp Glu Tyr
            435                 440                 445
Asp Tyr Lys Gly Glu Leu Val Asn Ile Asn Gly Leu Lys Cys Thr Pro
            450                 455                 460
Asn His Lys Leu Pro Val Val Thr Lys Asn Glu Arg Gln Thr Arg Ile
465                 470                 475                 480
Arg Asp Ser Leu Ala Lys Ser Phe Leu Thr Lys Val Lys Gly Lys
            485                 490                 495
Ile Ile Thr Thr Pro Leu Phe Tyr Glu Ile Gly Arg Ala Thr Ser Glu
            500                 505                 510
Asn Ile Pro Glu Glu Val Leu Lys Gly Glu Leu Ala Gly Ile Leu
            515                 520                 525
Leu Ala Glu Gly Thr Leu Leu Arg Lys Asp Val Glu Tyr Phe Asp Ser
            530                 535                 540
Ser Arg Lys Lys Arg Ile Ser His Gln Tyr Arg Val Glu Ile Thr
545                 550                 555                 560
Ile Gly Lys Asp Glu Glu Phe Arg Asp Arg Ile Thr Tyr Ile Phe
            565                 570                 575
Glu Arg Leu Phe Gly Ile Thr Pro Ser Ile Ser Glu Lys Lys Gly Thr
            580                 585                 590
Asn Ala Val Thr Leu Lys Val Ala Lys Lys Asn Val Tyr Leu Lys Val
            595                 600                 605
Lys Glu Ile Met Asp Asn Ile Glu Ser Leu His Ala Pro Ser Val Leu
            610                 615                 620
Arg Gly Phe Phe Glu Gly Asp Gly Ser Val Asn Arg Val Arg Arg Ser
625                 630                 635                 640
Ile Val Ala Thr Gln Gly Thr Lys Asn Glu Trp Lys Ile Lys Leu Val
            645                 650                 655
Ser Lys Leu Leu Ser Gln Leu Gly Ile Pro His Gln Thr Tyr Thr Tyr
            660                 665                 670
Gln Tyr Gln Glu Asn Gly Lys Asp Arg Ser Arg Tyr Ile Leu Glu Ile
            675                 680                 685
Thr Gly Lys Asp Gly Leu Ile Leu Phe Gln Thr Leu Ile Gly Phe Ile
            690                 695                 700
Ser Glu Arg Lys Asn Ala Leu Leu Asn Lys Ala Ile Ser Gln Arg Glu
705                 710                 715                 720
Met Asn Asn Leu Glu Asn Asn Gly Phe Tyr Arg Leu Ser Glu Phe Asn
            725                 730                 735
Val Ser Thr Glu Tyr Tyr Glu Gly Lys Val Tyr Asp Leu Thr Leu Glu
            740                 745                 750
Gly Thr Pro Tyr Tyr Phe Ala Asn Gly Ile Leu Thr His Asn Ser Leu
            755                 760                 765
Tyr Pro Ser Ile Ile Thr His Asn Val Ser Pro Asp Thr Leu Asn
            770                 775                 780
Arg Glu Gly Cys Lys Glu Tyr Asp Val Ala Pro Gln Val Gly His Arg
785                 790                 795                 800
Phe Cys Lys Asp Phe Pro Gly Phe Ile Pro Ser Leu Leu Gly Asp Leu
            805                 810                 815
Leu Glu Glu Arg Gln Lys Ile Lys Lys Met Lys Ala Thr Ile Asp
            820                 825                 830
Pro Ile Glu Arg Lys Leu Leu Asp Tyr Arg Gln Arg Ala Ile Lys Ile
```

```
                835                 840                 845
Leu Ala Asn Ser Ile Leu Pro Glu Glu Trp Leu Pro Val Leu Glu Glu
        850                 855                 860

Gly Glu Val His Phe Val Arg Ile Gly Glu Leu Ile Asp Arg Met Met
865                 870                 875                 880

Glu Glu Asn Ala Gly Lys Val Lys Arg Glu Gly Thr Glu Val Leu
                885                 890                 895

Glu Val Ser Gly Leu Glu Val Pro Ser Phe Asn Arg Arg Thr Lys Lys
        900                 905                 910

Ala Glu Leu Lys Arg Val Lys Ala Leu Ile Arg His Asp Tyr Ser Gly
        915                 920                 925

Lys Val Tyr Thr Ile Arg Leu Lys Ser Gly Arg Ile Lys Ile Thr
        930                 935                 940

Ser Gly His Ser Leu Phe Ser Val Arg Asn Gly Glu Leu Val Glu Val
945                 950                 955                 960

Thr Gly Asp Glu Leu Lys Pro Gly Asp Leu Val Ala Val Pro Arg Arg
                965                 970                 975

Leu Glu Leu Pro Glu Arg Asn His Val Leu Asn Leu Val Glu Leu Leu
                980                 985                 990

Leu Gly Thr Pro Glu Glu Glu Thr Leu Asp Ile Val Met Thr Ile Pro
        995                 1000                1005

Val Lys Gly Lys Lys Asn Phe Phe Lys Gly Met Leu Arg Thr Leu
    1010                1015                1020

Arg Trp Ile Phe Gly Glu Lys Arg Pro Arg Thr Ala Arg Arg
    1025                1030                1035

Tyr Leu Arg His Leu Glu Asp Leu Gly Tyr Val Arg Leu Lys Lys
    1040                1045                1050

Ile Gly Tyr Glu Val Leu Asp Trp Asp Ser Leu Lys Asn Tyr Arg
    1055                1060                1065

Arg Leu Tyr Glu Ala Leu Val Glu Asn Val Arg Tyr Asn Gly Asn
    1070                1075                1080

Lys Arg Glu Tyr Leu Val Glu Phe Asn Ser Ile Arg Asp Ala Val
    1085                1090                1095

Gly Ile Met Pro Leu Lys Glu Leu Lys Glu Trp Lys Ile Gly Thr
    1100                1105                1110

Leu Asn Gly Phe Arg Met Ser Pro Leu Ile Glu Val Asp Glu Ser
    1115                1120                1125

Leu Ala Lys Leu Leu Gly Tyr Tyr Val Ser Glu Gly Tyr Ala Arg
    1130                1135                1140

Lys Gln Arg Asn Pro Lys Asn Gly Trp Ser Tyr Ser Val Lys Leu
    1145                1150                1155

Tyr Asn Glu Asp Pro Glu Val Leu Asp Asp Met Glu Arg Leu Ala
    1160                1165                1170

Ser Arg Phe Phe Gly Lys Val Arg Arg Gly Arg Asn Tyr Val Glu
    1175                1180                1185

Ile Pro Lys Lys Ile Gly Tyr Leu Leu Phe Glu Asn Met Cys Gly
    1190                1195                1200

Val Leu Ala Glu Asn Lys Arg Ile Pro Glu Phe Val Phe Thr Ser
    1205                1210                1215

Pro Lys Gly Val Arg Leu Ala Phe Leu Glu Gly Tyr Phe Ile Gly
    1220                1225                1230

Asp Gly Asp Val His Pro Asn Lys Arg Leu Arg Leu Ser Thr Lys
    1235                1240                1245
```

```
Ser Glu Leu Leu Ala Asn Gln Leu Val Leu Leu Asn Ser Val
    1250            1255            1260

Gly Val Ser Ala Val Lys Leu Gly His Asp Ser Gly Val Tyr Arg
1265            1270            1275

Val Tyr Ile Asn Glu Glu Leu Pro Phe Val Lys Leu Asp Lys Lys
    1280            1285            1290

Lys Asn Ala Tyr Tyr Ser His Val Ile Pro Lys Glu Val Leu Ser
    1295            1300            1305

Glu Val Phe Gly Lys Val Phe Gln Lys Asn Val Ser Pro Gln Thr
    1310            1315            1320

Phe Arg Lys Met Val Glu Asp Gly Arg Leu Asp Pro Glu Lys Ala
    1325            1330            1335

Gln Arg Leu Ser Trp Leu Ile Glu Gly Asp Val Val Leu Asp Arg
    1340            1345            1350

Val Glu Ser Val Asp Val Glu Asp Tyr Asp Gly Tyr Val Tyr Asp
    1355            1360            1365

Leu Ser Val Glu Asp Asn Glu Asn Phe Leu Val Gly Phe Gly Leu
    1370            1375            1380

Val Tyr Ala His Asn Ser Tyr Tyr Gly Tyr Tyr Gly Tyr Ala Arg
    1385            1390            1395

Ala Arg Trp Tyr Cys Lys Glu Cys Ala Glu Ser Val Thr Ala Trp
    1400            1405            1410

Gly Arg Glu Tyr Ile Thr Met Thr Ile Lys Glu Ile Glu Glu Lys
    1415            1420            1425

Tyr Gly Phe Lys Val Ile Tyr Ser Asp Thr Asp Gly Phe Phe Ala
    1430            1435            1440

Thr Ile Pro Gly Ala Asp Ala Glu Thr Val Lys Lys Lys Ala Met
    1445            1450            1455

Glu Phe Leu Lys Tyr Ile Asn Ala Lys Leu Pro Gly Ala Leu Glu
    1460            1465            1470

Leu Glu Tyr Glu Gly Phe Tyr Lys Arg Gly Phe Phe Val Thr Lys
    1475            1480            1485

Lys Lys Tyr Ala Val Ile Asp Glu Glu Gly Lys Ile Thr Thr Arg
    1490            1495            1500

Gly Leu Glu Ile Val Arg Arg Asp Trp Ser Glu Ile Ala Lys Glu
1505            1510            1515

Thr Gln Ala Arg Val Leu Glu Ala Leu Leu Lys Asp Gly Asp Val
    1520            1525            1530

Glu Lys Ala Val Arg Ile Val Lys Glu Val Thr Glu Lys Leu Ser
    1535            1540            1545

Lys Tyr Glu Val Pro Pro Glu Lys Leu Val Ile His Glu Gln Ile
    1550            1555            1560

Thr Arg Asp Leu Lys Asp Tyr Lys Ala Thr Gly Pro His Val Ala
    1565            1570            1575

Val Ala Lys Arg Leu Ala Ala Arg Gly Val Lys Ile Arg Pro Gly
    1580            1585            1590

Thr Val Ile Ser Tyr Ile Val Leu Lys Gly Ser Gly Arg Ile Gly
    1595            1600            1605

Asp Arg Ala Ile Pro Phe Asp Glu Phe Asp Pro Thr Lys His Lys
    1610            1615            1620

Tyr Asp Ala Glu Tyr Tyr Ile Glu Asn Gln Val Leu Pro Ala Val
    1625            1630            1635
```

```
Glu Arg Ile Leu Arg Ala Phe Gly Tyr Arg Lys Glu Asp Leu Arg
    1640                1645                1650

Tyr Gln Lys Thr Arg Gln Val Gly Leu Ser Ala Trp Leu Lys Pro
    1655                1660                1665

Lys Gly Thr
    1670

<210> SEQ ID NO 73
<211> LENGTH: 774
<212> TYPE: PRT
<213> ORGANISM: Thermococcus kodakarensis

<400> SEQUENCE: 73

Met Ile Leu Asp Thr Asp Tyr Ile Thr Glu Asp Gly Lys Pro Val Ile
1               5                   10                  15

Arg Ile Phe Lys Lys Glu Asn Gly Glu Phe Lys Ile Glu Tyr Asp Arg
            20                  25                  30

Thr Phe Glu Pro Tyr Phe Tyr Ala Leu Leu Lys Asp Asp Ser Ala Ile
        35                  40                  45

Glu Glu Val Lys Lys Ile Thr Ala Glu Arg His Gly Thr Val Val Thr
    50                  55                  60

Val Lys Arg Val Glu Lys Val Gln Lys Lys Phe Leu Gly Arg Pro Val
65                  70                  75                  80

Glu Val Trp Lys Leu Tyr Phe Thr His Pro Gln Asp Val Pro Ala Ile
                85                  90                  95

Arg Asp Lys Ile Arg Glu His Pro Ala Val Ile Asp Ile Tyr Glu Tyr
            100                 105                 110

Asp Ile Pro Phe Ala Lys Arg Tyr Leu Ile Asp Lys Gly Leu Val Pro
        115                 120                 125

Met Glu Gly Asp Glu Glu Leu Lys Met Leu Ala Phe Asp Ile Glu Thr
    130                 135                 140

Leu Tyr His Glu Gly Glu Glu Phe Ala Glu Gly Pro Ile Leu Met Ile
145                 150                 155                 160

Ser Tyr Ala Asp Glu Glu Gly Ala Arg Val Ile Thr Trp Lys Asn Val
                165                 170                 175

Asp Leu Pro Tyr Val Asp Val Val Ser Thr Glu Arg Glu Met Ile Lys
            180                 185                 190

Arg Phe Leu Arg Val Val Lys Glu Lys Asp Pro Asp Val Leu Ile Thr
        195                 200                 205

Tyr Asn Gly Asp Asn Phe Asp Phe Ala Tyr Leu Lys Lys Arg Cys Glu
    210                 215                 220

Lys Leu Gly Ile Asn Phe Ala Leu Gly Arg Asp Gly Ser Glu Pro Lys
225                 230                 235                 240

Ile Gln Arg Met Gly Asp Arg Phe Ala Val Glu Val Lys Gly Arg Ile
                245                 250                 255

His Phe Asp Leu Tyr Pro Val Ile Arg Arg Thr Ile Asn Leu Pro Thr
            260                 265                 270

Tyr Thr Leu Glu Ala Val Tyr Glu Ala Val Phe Gly Gln Pro Lys Glu
        275                 280                 285

Lys Val Tyr Ala Glu Glu Ile Thr Thr Ala Trp Glu Thr Gly Glu Asn
    290                 295                 300

Leu Glu Arg Val Ala Arg Tyr Ser Met Glu Asp Ala Lys Val Thr Tyr
305                 310                 315                 320

Glu Leu Gly Lys Glu Phe Leu Pro Met Glu Ala Gln Leu Ser Arg Leu
                325                 330                 335
```

```
Ile Gly Gln Ser Leu Trp Asp Val Ser Arg Ser Thr Gly Asn Leu
            340                 345                 350

Val Glu Trp Phe Leu Leu Arg Lys Ala Tyr Glu Arg Asn Glu Leu Ala
            355                 360                 365

Pro Asn Lys Pro Asp Glu Lys Glu Leu Ala Arg Arg Gln Ser Tyr
            370                 375             380

Glu Gly Gly Tyr Val Lys Glu Pro Glu Arg Gly Leu Trp Glu Asn Ile
385                 390                 395                 400

Val Tyr Leu Asp Phe Arg Ser Leu Tyr Pro Ser Ile Ile Ile Thr His
                405                 410                 415

Asn Val Ser Pro Asp Thr Leu Asn Arg Glu Gly Cys Lys Glu Tyr Asp
            420                 425                 430

Val Ala Pro Gln Val Gly His Arg Phe Cys Lys Asp Phe Pro Gly Phe
            435                 440                 445

Ile Pro Ser Leu Leu Gly Asp Leu Leu Glu Glu Arg Gln Lys Ile Lys
            450                 455                 460

Lys Lys Met Lys Ala Thr Ile Asp Pro Ile Glu Arg Lys Leu Leu Asp
465                 470                 475                 480

Tyr Arg Gln Arg Ala Ile Lys Ile Leu Ala Asn Ser Tyr Tyr Gly Tyr
                485                 490                 495

Tyr Gly Tyr Ala Arg Ala Arg Trp Tyr Cys Lys Glu Cys Ala Glu Ser
            500                 505                 510

Val Thr Ala Trp Gly Arg Glu Tyr Ile Thr Met Thr Ile Lys Glu Ile
            515                 520                 525

Glu Glu Lys Tyr Gly Phe Lys Val Ile Tyr Ser Asp Thr Asp Gly Phe
            530                 535                 540

Phe Ala Thr Ile Pro Gly Ala Asp Ala Glu Thr Val Lys Lys Lys Ala
545                 550                 555                 560

Met Glu Phe Leu Lys Tyr Ile Asn Ala Lys Leu Pro Gly Ala Leu Glu
                565                 570                 575

Leu Glu Tyr Glu Gly Phe Tyr Lys Arg Gly Phe Phe Val Thr Lys Lys
            580                 585                 590

Lys Tyr Ala Val Ile Asp Glu Glu Gly Lys Ile Thr Thr Arg Gly Leu
            595                 600                 605

Glu Ile Val Arg Arg Asp Trp Ser Glu Ile Ala Lys Glu Thr Gln Ala
            610                 615                 620

Arg Val Leu Glu Ala Leu Leu Lys Asp Gly Asp Val Glu Lys Ala Val
625                 630                 635                 640

Arg Ile Val Lys Glu Val Thr Glu Lys Leu Ser Lys Tyr Glu Val Pro
                645                 650                 655

Pro Glu Lys Leu Val Ile His Glu Gln Ile Thr Arg Asp Leu Lys Asp
            660                 665                 670

Tyr Lys Ala Thr Gly Pro His Val Ala Val Ala Lys Arg Leu Ala Ala
            675                 680                 685

Arg Gly Val Lys Ile Arg Pro Gly Thr Val Ile Ser Tyr Ile Val Leu
            690                 695                 700

Lys Gly Ser Gly Arg Ile Gly Asp Arg Ala Ile Pro Phe Asp Glu Phe
705                 710                 715                 720

Asp Pro Thr Lys His Lys Tyr Asp Ala Glu Tyr Tyr Ile Glu Asn Gln
                725                 730                 735

Val Leu Pro Ala Val Glu Arg Ile Leu Arg Ala Phe Gly Tyr Arg Lys
            740                 745                 750
```

Glu Asp Leu Arg Tyr Gln Lys Thr Arg Gln Val Gly Leu Ser Ala Trp
            755                 760                 765
Leu Lys Pro Lys Gly Thr
    770

<210> SEQ ID NO 74
<211> LENGTH: 781
<212> TYPE: PRT
<213> ORGANISM: Sulfolobus tokodaz

<400> SEQUENCE: 74

Met Ile Asp Asn Phe Phe Ile Leu Asp Phe Ser Tyr Asp Val Val Glu
1               5                   10                  15

Asn Lys Pro Val Ile Tyr Ile Trp Ala Ile Asp Lys Glu Gly Asn Arg
            20                  25                  30

Val Val Leu Leu Glu Lys Lys Phe Arg Pro Tyr Phe Tyr Ala Leu Val
        35                  40                  45

Asp Asp Asn Tyr Asn Ile Asp Glu Ile Arg Lys Glu Ile Leu Lys Leu
    50                  55                  60

Ser Lys Pro Tyr Ser Pro Ile Thr Ser Ile Asn Val Glu Glu Lys Lys
65                  70                  75                  80

Tyr Phe Gly Ser Pro Val Arg Val Leu Lys Ile Glu Thr Val Ile Pro
                85                  90                  95

Ala Tyr Val Arg Val Tyr Arg Asp Glu Val Ala Lys Ile Lys Gly Val
            100                 105                 110

Lys Ser Val Leu Glu Ala Asp Ile Arg Phe Tyr Met Arg Tyr Ser Ile
        115                 120                 125

Asp Asn Asn Leu Lys Pro Phe Tyr Trp Ile Glu Ala Glu Val Glu Glu
    130                 135                 140

Ile Lys Glu Asn Asn Phe Arg Val Lys Lys Val Tyr Glu Leu Lys Lys
145                 150                 155                 160

Ile Asn Lys Leu Tyr Glu Asp Lys Ile Pro Glu Leu Lys Val Leu Ala
                165                 170                 175

Phe Asp Ile Glu Val Tyr Asn Lys Tyr Gly Ser Pro Asn Pro Arg Arg
            180                 185                 190

Asp Pro Val Ile Ile Gly Val Trp Thr Lys Glu Gly Gly Lys Gln
        195                 200                 205

Phe Leu Ala Asp Lys Tyr Asp Asp Leu Arg Ala Ile Arg Glu Phe Ile
    210                 215                 220

Asn Phe Val Gln Thr Tyr Asp Pro Asp Ile Ile Val Gly Tyr Asn Ile
225                 230                 235                 240

Asn Asn Phe Asp Trp Pro Tyr Leu Leu Glu Arg Ala Asn Ile Arg Gly
                245                 250                 255

Ile Arg Leu Asp Val Gly Arg Arg Val Asn Gly Glu Pro Ser Gln Gly
            260                 265                 270

Val Tyr Gly His Tyr Ser Ile Thr Gly Arg Leu Asn Val Asp Leu Tyr
        275                 280                 285

Gly Phe Ala Gln Ser Ile Gln Glu Val Lys Val Lys Thr Leu Glu Asn
    290                 295                 300

Ile Ala Asp Tyr Leu Gly Val Leu Pro Lys Glu Lys Arg Thr Ile Val
305                 310                 315                 320

Glu Trp Tyr Asp Ile Pro Lys Tyr Trp Asp Asp Glu Lys Lys Arg Asp
                325                 330                 335

Ile Leu Leu Lys Tyr Asn Leu Asp Asp Ala Lys Ser Ala Tyr Leu Leu
            340                 345                 350

```
Gly Glu Val Phe Ile Pro Phe Gly Ile Glu Leu Thr Arg Ile Ser Gly
            355                 360                 365

Leu Pro Leu Asp Gln Leu Ser Met Ala Ser Val Gly His Arg Val Glu
        370                 375                 380

Trp Leu Leu Met Arg Glu Ala Tyr Lys Tyr Asn Glu Leu Ile Pro Asn
385                 390                 395                 400

Lys Glu Glu Arg Glu Tyr Glu Ser Tyr Glu Gly Leu Val Ile Ser
                405                 410                 415

Pro Leu Pro Gly Ile His Glu Asp Val Tyr Val Leu Asp Phe Ser Ser
                420                 425                 430

Met Tyr Pro Ser Ile Met Ile Lys Tyr Asn Ile Gly Pro Asp Thr Leu
            435                 440                 445

Val Lys Gly Glu Cys Glu Asn Cys Trp Ile Ser Pro Ala Gly His Lys
        450                 455                 460

Phe Arg Lys Asp Pro Pro Gly Leu Tyr Lys Asn Val Leu Glu Lys Leu
465                 470                 475                 480

Ile Gln Glu Arg Lys Glu Val Lys Lys Leu Met Glu Lys Thr Met Asp
                485                 490                 495

Glu Tyr Asp Lys Arg Val Leu Asp Ala Arg Gln Arg Ala Leu Lys Val
                500                 505                 510

Met Ala Asn Ala Phe Tyr Gly Tyr Met Gly Trp Leu Gly Ala Arg Trp
            515                 520                 525

Tyr Ser Lys Glu Gly Ala Glu Ala Val Thr Ala Trp Gly Arg Gln Ile
        530                 535                 540

Ile Ser Glu Ser Ala Lys Ile Ala Lys Glu Lys Gly Phe Thr Val Ile
545                 550                 555                 560

Tyr Gly Asp Thr Asp Ser Ile Phe Val Lys Gly Gly Gly Asp Ile Asn
                565                 570                 575

Ser Leu Ile Thr Glu Ile Ser Ser Lys Phe Gly Leu Glu Ile Lys Ile
            580                 585                 590

Asp Lys Ile Tyr Lys Arg Val Phe Phe Thr Glu Asn Lys Lys Arg Tyr
        595                 600                 605

Ala Gly Leu Thr Glu Asp Gly Lys Ile Asp Ile Val Gly Phe Glu Ala
        610                 615                 620

Val Arg Gly Asp Trp Cys Asp Leu Ala Lys Gln Val Gln Thr Asn Val
625                 630                 635                 640

Ile Glu Leu Ile Leu Lys Ser Gly Lys Val Glu Asp Ala Ile Lys Tyr
                645                 650                 655

Val Lys Thr Val Ile Phe Asp Leu Arg Arg Tyr Asn Phe Arg Ile Glu
                660                 665                 670

Asp Leu Ile Ile Trp Lys Thr Ile Asp Lys Asn Leu Asp Glu Tyr Asp
            675                 680                 685

Val Thr Ala Pro His Val Ala Ala Lys Lys Ala Ala Lys Ala Gly
        690                 695                 700

Tyr Leu Val Ser Lys Gly Val Lys Ile Gly Tyr Val Ile Val Lys Gly
705                 710                 715                 720

Ser Gly Lys Ile Ser Asp Lys Ala Glu Pro Tyr Phe Leu Ile Lys Glu
                725                 730                 735

Lys Asn Lys Ile Asp Val Glu Tyr Tyr Ile Asp Lys Gln Ile Ile Pro
                740                 745                 750

Val Ala Met Arg Ile Leu Glu Gly Phe Gly Val Lys Glu Ser Ser Leu
            755                 760                 765
```

```
Lys Thr Gly Gly Val Asp Ile Leu Ser Phe Phe Lys Lys
        770                 775                 780
```

<210> SEQ ID NO 75
<211> LENGTH: 733
<212> TYPE: PRT
<213> ORGANISM: Desulfurococcus sp.

<400> SEQUENCE: 75

```
Met Ile Leu Asp Ala Asp Tyr Ile Thr Glu Asp Gly Lys Pro Val Ile
1               5                   10                  15

Arg Val Phe Lys Lys Glu Lys Gly Glu Phe Lys Ile Asp Tyr Asp Arg
            20                  25                  30

Asp Phe Glu Pro Tyr Ile Tyr Ala Leu Leu Lys Asp Asp Ser Ala Ile
        35                  40                  45

Glu Asp Ile Lys Lys Ile Thr Ala Glu Arg His Gly Thr Thr Val Arg
    50                  55                  60

Val Thr Arg Ala Glu Arg Val Lys Lys Phe Leu Gly Arg Pro Val
65                  70                  75                  80

Glu Val Trp Lys Leu Tyr Phe Thr His Pro Gln Asp Val Pro Ala Ile
                85                  90                  95

Arg Asp Lys Ile Arg Glu His Pro Ala Val Val Asp Ile Tyr Glu Tyr
            100                 105                 110

Asp Ile Pro Phe Ala Lys Arg Tyr Leu Ile Asp Arg Gly Leu Ile Pro
        115                 120                 125

Met Glu Gly Asp Glu Glu Leu Arg Met Leu Ala Phe Asp Ile Glu Thr
    130                 135                 140

Leu Ala His Ala Gly Ala Ala Gly Ala Gly Pro Ile Leu Met Ile
145                 150                 155                 160

Ser Tyr Ala Asp Glu Glu Gly Ala Arg Val Ile Thr Trp Lys Asn Ile
                165                 170                 175

Asp Leu Pro Tyr Val Glu Ser Val Ser Thr Glu Lys Glu Met Ile Lys
            180                 185                 190

Arg Phe Leu Lys Val Ile Gln Glu Lys Asp Pro Asp Val Leu Ile Thr
        195                 200                 205

Tyr Asn Gly Asp Asn Phe Asp Phe Ala Tyr Leu Lys Lys Arg Ser Glu
    210                 215                 220

Met Leu Gly Val Lys Phe Ile Leu Gly Arg Asp Gly Ser Glu Pro Lys
225                 230                 235                 240

Ile Gln Arg Met Gly Asp Arg Phe Ala Val Glu Val Lys Gly Arg Ile
                245                 250                 255

His Phe Asp Leu Tyr Pro Val Ile Arg Arg Thr Ile Asn Leu Pro Thr
            260                 265                 270

Tyr Thr Leu Glu Thr Val Tyr Glu Pro Val Phe Gly Gln Pro Ala Glu
        275                 280                 285

Lys Val Tyr Ala Glu Glu Ile Ala Glu Ala Trp Ala Ser Gly Glu Gly
    290                 295                 300

Leu Glu Arg Val Ala Arg Tyr Ser Met Glu Asp Ala Lys Ala Thr Tyr
305                 310                 315                 320

Glu Leu Gly Lys Glu Phe Phe Pro Met Glu Ala Gln Leu Ser Arg Leu
                325                 330                 335

Val Gly Gln Ser Leu Trp Asp Val Ser Arg Ser Ser Thr Gly Asn Leu
            340                 345                 350

Val Glu Trp Phe Leu Leu Arg Lys Ala Tyr Glu Arg Asn Asp Val Ala
        355                 360                 365
```

Pro Asn Lys Pro Asp Glu Arg Glu Leu Ala Arg Arg Thr Glu Ser Tyr
        370                 375                 380

Ala Gly Gly Tyr Val Lys Glu Pro Glu Lys Gly Leu Trp Glu Asn Ile
385                 390                 395                 400

Val Tyr Leu Asp Tyr Lys Ser Leu Tyr Pro Ser Ile Ile Ile Thr His
                405                 410                 415

Asn Val Ser Pro Asp Thr Leu Asn Arg Glu Gly Cys Arg Glu Tyr Asp
            420                 425                 430

Val Ala Pro Gln Val Gly His Arg Phe Cys Lys Asp Phe Pro Gly Phe
        435                 440                 445

Ile Pro Ser Leu Leu Gly Asp Leu Leu Glu Glu Arg Gln Lys Val Lys
450                 455                 460

Lys Lys Met Lys Ala Thr Val Asp Pro Ile Glu Arg Lys Leu Leu Asp
465                 470                 475                 480

Tyr Arg Gln Arg Ala Ile Lys Ile Leu Ala Asn Ser Tyr Tyr Gly Tyr
                485                 490                 495

Tyr Ala Tyr Ala Asn Ala Arg Trp Tyr Cys Arg Glu Cys Ala Glu Ser
            500                 505                 510

Val Thr Ala Trp Gly Arg Gln Tyr Ile Glu Thr Thr Met Arg Glu Ile
        515                 520                 525

Glu Glu Lys Phe Gly Phe Lys Val Leu Tyr Ala Asp Thr Asp Gly Phe
530                 535                 540

Phe Ala Thr Ile Pro Gly Ala Asp Ala Glu Thr Val Lys Asn Lys Ala
545                 550                 555                 560

Lys Glu Phe Leu Asn Tyr Ile Asn Pro Arg Leu Pro Gly Leu Leu Glu
                565                 570                 575

Leu Glu Tyr Glu Gly Phe Tyr Arg Arg Gly Phe Phe Val Thr Lys Lys
            580                 585                 590

Lys Tyr Ala Val Ile Asp Glu Glu Asp Lys Ile Thr Thr Arg Gly Leu
        595                 600                 605

Glu Ile Val Arg Arg Asp Trp Ser Glu Ile Ala Lys Glu Thr Gln Ala
610                 615                 620

Arg Val Leu Glu Ala Ile Leu Lys His Gly Asp Val Glu Glu Ala Val
625                 630                 635                 640

Arg Ile Val Lys Glu Val Thr Glu Lys Leu Ser Arg His Glu Val Pro
                645                 650                 655

Pro Glu Lys Leu Val Ile Tyr Glu Ala Gly Pro His Val Ala Ala Ala
            660                 665                 670

Ala Thr Val Ile Ser Tyr Ile Val Leu Lys Gly Pro Gly Arg Val Gly
        675                 680                 685

Asp Arg Ala Ile Pro Phe Asp Glu Phe Asp Pro Ala Lys His Arg Tyr
690                 695                 700

Asp Ala Glu Tyr Tyr Ile Glu Asn Gln Val Leu Pro Ala Val Glu Arg
705                 710                 715                 720

Ile Leu Arg Ala Phe Gly Tyr Arg Lys Glu Asp Leu Arg
                725                 730

<210> SEQ ID NO 76
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:

<221> NAME/KEY: MOD_RES
<222> LOCATION: (4)..(4)
<223> OTHER INFORMATION: Any amino acid

<400> SEQUENCE: 76

Asp His Ser Xaa Ile Glu Leu Arg
1               5

<210> SEQ ID NO 77
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Any amino acid

<400> SEQUENCE: 77

Asp His Xaa Ser Leu Tyr Pro Ser
1               5

<210> SEQ ID NO 78
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 78

Asp His Gly Tyr
1

<210> SEQ ID NO 79
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Any amino acid

<400> SEQUENCE: 79

Gly Lys Xaa His Asn Phe Gly Val Leu Tyr Gly
1               5                   10

<210> SEQ ID NO 80
<211> LENGTH: 2327
<212> TYPE: DNA
<213> ORGANISM: Pyrococcus furiosus

<400> SEQUENCE: 80
atgattttag atgtggatta cataactgaa gaaggaaaac ctgttattag gctattcaaa      60
aaagagaacg gaaaatttaa gatagagcat gatagaactt ttagaccata catttacgct     120
cttctcaggg atgattcaaa gattgaagaa gttaagaaaa taacggggga aaggcatgga     180
aagattgtga gaattgttga tgtagagaag gttgagaaaa gtttctcgg caagcctatt     240 accgtgtgga aactttattt ggaacatccc caagatcgtc ccactattag agaaaaagtt     300
agagaacatc cagcagttgt ggacatcttc gaatacgata ttccatttgc aaagagatac     360

| ctcatcgaca aaggcctaat accaatggag ggggaagaag agctaaagat tcttgccttc | 420 |
| gatatagaaa ccctctatca cgaaggagaa gagtttggaa aaggcccaat tataatgatt | 480 |
| agttatgcag atgaaaatga agcaaaggtg attacttgga aaaacataga tcttccatac | 540 |
| gttgaggttg tatcaagcga gagagagatg ataaagagat ttctcaggat tatcagggag | 600 |
| aaggatcctg acattatagt tacttataat ggagactcat tcgacttccc atatttagcg | 660 |
| aaaagggcag aaaaacttgg gattaaatta accattggaa gagatggaag cgagcccaag | 720 |
| atgcagagaa taggcgatat gacggctgta gaagtcaagg gaagaataca tttcgacttg | 780 |
| tatcatgtaa taacaaggac aataaatctc ccaacataca cactagaggc tgtatatgaa | 840 |
| gcaattttg aaagccaaa ggagaaggta tacgccgacg atagcaaa agcctgggaa | 900 |
| agtggagaga accttgagag agttgccaaa tactcgatgg aagatgcaaa gacaacttat | 960 |
| gaactcggga agaattcct tccaatggaa attcagcttt caagattagt tggacaacct | 1020 |
| ttatgggatg tttcaaggtc aagcacaggg aaccttgtag agtggttctt acttaggaaa | 1080 |
| gcctacgaaa gaaacgaagt agctccaaac aagccaagtg aagaggagta tcaaagaagg | 1140 |
| ctcagggaga gctacacagg tggattcgtt aaagagccag aaaagggggtt gtgggaaaac | 1200 |
| atagtatacc tagattttag agccctatat ccctcgatta taattaccca caatgtttct | 1260 |
| cccgatactc taaatcttga gggatgcaag aactatgata tcgctcctca agtaggccac | 1320 |
| aagttctgca aggacatccc tggttttata ccaagtctct tgggacattt gttagaggaa | 1380 |
| agacaaaaga ttaagacaaa atgaaggaaa ctcaagatcc tatagaaaaa atactccttg | 1440 |
| actatagacg aaaagcgata aaactcttag caaattcttt ctacggatat tatggctatg | 1500 |
| caaaagcaag atggtactgt aaggagtgtg ctgagagcgt tactgcctgg ggaagaaagt | 1560 |
| acatcgagtt agtatggaag gagctcgaag aaaagtttgg attaaagtc ctctacattg | 1620 |
| acactgatgg tctctatgca actatcccag gaggagaaag tgaggaaata agaaaaagg | 1680 |
| ctctagaatt tgtaaaatac ataaaattcaa agctccctgg actgctagag cttgaatatg | 1740 |
| aagggtttta taagagggga ttcttcgtta cgaagaagag gtatgcagta atagatgaag | 1800 |
| aaggaaaact cattactcgt ggtttagaga tagttaggag agattggagt gaaattgcaa | 1860 |
| agaaactca agctagagtt ttggagacaa tactaaaaca cggagatgtt gaagaagctg | 1920 |
| tgagaatagt aaaagaagta atacaaaagc ttgccaatta tgaaattcca ccagagaagc | 1980 |
| tcgtaatata tgagcagata acaagaccat tacatgagta taaggcgata ggtcctcacg | 2040 |
| tagctgttgc aaagaaacta gctgctaaag gagttaaaat aaagccagga atggtaattg | 2100 |
| gatacatagt acttagaggc gatggtccaa ttagcaatag ggcaattcta gctgaggaat | 2160 |
| acgatcccaa aaagcacaag tatgacgcag aatattcat tgagaaccag gttcttccag | 2220 |
| cggtacttag gatattggag ggatttggat acagaaagga agacctcaga taccaaaaga | 2280 |
| caagacaagt cggcctaact tcctggctta acattaaaaa atcctga | 2327 |

<210> SEQ ID NO 81
<211> LENGTH: 2330
<212> TYPE: DNA
<213> ORGANISM: Thermococcus sp.

<400> SEQUENCE: 81

| atgatccttg acgttgatta catcaccgag aatggaaagc ccgtcatcag ggtcttcaag | 60 |
| aaggagaacg gcgagttcag gattgaatac gaccgcgagt tcgagcccta cttctacgcg | 120 |
| ctcctcaggg acgactctgc catcgaagaa atcaaaaaga taaccgcgga gaggcacggc | 180 |

-continued

```
agggtcgtta aggttaagcg cgcggagaag gtgaagaaaa agttcctcgg caggtctgtg      240
gaggtctggg tcctctactt cacgcacccg caggacgttc cggcaatccg cgacaaaata      300
aggaagcacc ccgcggtcat cgacatctac gagtacgaca tacccttcgc caagcgctac      360
ctcatagaca agggcctaat cccgatggaa ggtgaggaag agcttaaact catgtccttc      420
gcaatcgcga cgctctacca cgagggagaa gagtttggaa ccgggccgat tctgatgata      480
agctacgccg atgaaagcga ggcgcgcgtg ataacctgga agaagatcga ccttccttac      540
gttgaggttg tctccaccga aaggagatg attaagcgct tcttgagggt cgttaaggag       600
aaggacccgg acgtgctgat aacatacaac ggcgacaact tcgacttcgc ctacctgaaa      660
aagcgctgtg agaagcttgg cgtgagcttt accctcggga gggacgggag cgagccgaag      720
atacagcgca tggggacag gtttgcggtc gaggtgaagg gcagggtaca cttcgacctt       780
tatccagtca taaggcgcac cataaacctc ccgacctaca cccttgaggc tgtatacgag      840
gcggttttcg gcaagcccaa ggagaaggtc tacgccgagg atagccacc gcctgggag       900 accggcgagg ggcttgagag ggtcgcgcgc tactcgatgg aggacgcgag ggttacctac     960
gagcttggca gggagttctt cccgatggag gcccagcttt ccaggctcat cggccaaggc    1020
ctctgggacg tttccgctc cagcaccggc aacctcgtcg agtggttcct cctaaggaag    1080
gcctacgaga ggaacgaact cgctcccaac aagcccgacg agagggagct ggcgaggaga    1140 aggggggggct acgccggtgg ctacgtcaag gagccggagc ggggactgtg ggacaatatc    1200
gtgtatctag actttcgtag tctctaccct tcaatcataa tcaccacaa cgtctcgcca      1260 gatacgctca accgcgaggg gtgtaggagc tacgacgttg cccccgaggt cggtcacaag     1320
ttctgcaagg acttccccgg cttcattccg agcctgctcg gaaacctgct ggaggaaagg     1380
cagaagataa agaggaaatg aaggcaactc tcgacccgct ggagaagaat ctcctcgatt     1440
acaggcaacg cgccatcaag attctcgcca cagctacta cggctactac ggctatgcca     1500
gggcaagatg gtactgcagg gagtgcgccg agagcgttac ggcatgggga agggagtaca    1560
tcgaaatggt catcagagag cttgaggaaa agttcggttt taaagtcctc tatgcagaca    1620
cagacggtct ccatgccacc attcctggag cggacgctga acagtcaag aaaaaggcaa     1680 tggagttctt aaactatatc aatcccaaac tgcccggcct tctcgaactc gaatacgagg     1740
gcttctacgt caggggcttc ttcgtcacga agaaaaagta cgcggtcatc gacgaggagg    1800
gcaagataac cacgcgcggg cttgagatag tcaggcgcga ctggagcgag atagcgaagg    1860
agacgcaggc gagggttttg gaggcgtac tcaggcacgg tgacgttgaa gaggccgtca    1920
gaattgtcag ggaagtcacc gaaaagctga gcaagtacga ggttccgccg agaagctgg    1980 ttatccacga gcagataacg cgcgagctca aggactacaa ggccaccggc cgcacgtag    2040 ccatagcgaa gcgtttggcc gccagaggtg ttaaaatccg gcccggaact gtgataagct    2100
acatcgttct gaagggctcc ggaaggatag gcgacagggc gattcccttc gacgagttcg    2160
acccgacgaa gcacaagtac gatgcggact actacatcga gaaccaggtt ctgccggcag    2220
ttgagagaat cctcagggcc ttcggctacc gcaaggaaga cctgcgctac cagaagacga    2280
ggcaggtcgg gcttggcgcg tggctgaagc cgaagggaa gaagaagtga                2330
```

<210> SEQ ID NO 82
<211> LENGTH: 53
<212> TYPE: PRT
<213> ORGANISM: Pyrococcus furiosus

<400> SEQUENCE: 82

Gly Phe Ile Pro Ser Leu Leu Gly His Leu Leu Glu Glu Arg Gln Lys
1               5                   10                  15

Ile Lys Thr Lys Met Lys Glu Thr Gln Asp Pro Ile Glu Lys Ile Leu
            20                  25                  30

Leu Asp Tyr Arg Gln Lys Ala Ile Lys Leu Leu Ala Asn Ser Phe Tyr
        35                  40                  45

Gly Tyr Tyr Gly Tyr
    50

<210> SEQ ID NO 83
<211> LENGTH: 72
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 83
ttgtttaact ttaagaagga gatatacata tgattttaga gtgtggattac ataactgaag     60 aaggaaaacc tg                                                          72

<210> SEQ ID NO 84
<211> LENGTH: 68
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 84
ccggatctca gtggtggtgg tggtggtgtt ttgtcttaat cttttgtctt tcctctaaca     60
aatgtccc                                                               68

<210> SEQ ID NO 85
<211> LENGTH: 66
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 85
ttgtttaact ttaagaagga gatatacata tgaaggaaac tcaagatcct atagaaaaaa     60
tactcc                                                                 66

<210> SEQ ID NO 86
<211> LENGTH: 67
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 86
ccggatctca gtggtggtgg tggtggtgtc tcttttgctt ttctaacatg tctactagtt     60
cttttgg                                                                67

<210> SEQ ID NO 87
<211> LENGTH: 64
<212> TYPE: DNA
<213> ORGANISM: Artificial Sequence

```
<220> FEATURE:
<223> OTHER INFORMATION: Description of Artificial Sequence: Synthetic
      primer

<400> SEQUENCE: 87
ttgtttaact ttaagaagga gatatacata tgatccttga cgttgattac atcaccgaga    60
atgg                                                                64

<210> SEQ ID NO 88
<211> LENGTH: 58
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 88
ggaaaggcag aagataaaga ggaaatgaag gaaactcaag atcctataga aaaaatac     58

<210> SEQ ID NO 89
<211> LENGTH: 58
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 89
gtattttttc tataggatct tgagtttcct tcatttcctc tttatcttct gcctttcc     58

<210> SEQ ID NO 90
<211> LENGTH: 53
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 90
ccggatctca gtggtggtgg tggtggtgct tcttcttccc cttcggcttc agc           53

<210> SEQ ID NO 91
<211> LENGTH: 466
<212> TYPE: PRT
<213> ORGANISM: Thermococcus sp.

<400> SEQUENCE: 91

Met Ile Leu Asp Val Asp Tyr Ile Thr Glu Asn Gly Lys Pro Val Ile
1               5                   10                  15

Arg Val Phe Lys Lys Glu Asn Gly Glu Phe Arg Ile Glu Tyr Asp Arg
            20                  25                  30

Glu Phe Glu Pro Tyr Phe Tyr Ala Leu Leu Arg Asp Asp Ser Ala Ile
        35                  40                  45

Glu Glu Ile Lys Lys Ile Thr Ala Glu Arg His Gly Arg Val Val Lys
    50                  55                  60

Val Lys Arg Ala Glu Lys Val Lys Lys Phe Leu Gly Arg Ser Val
65                  70                  75                  80

Glu Val Trp Val Leu Tyr Phe Thr His Pro Gln Asp Val Pro Ala Ile
                85                  90                  95

Arg Asp Lys Ile Arg Lys His Pro Ala Val Ile Asp Ile Tyr Glu Tyr
            100                 105                 110

Asp Ile Pro Phe Ala Lys Arg Tyr Leu Ile Asp Lys Gly Leu Ile Pro
```

```
            115                 120                 125
Met Glu Gly Glu Glu Leu Lys Leu Met Ser Phe Ala Ile Ala Thr
    130                 135                 140

Leu Tyr His Glu Gly Glu Phe Gly Thr Gly Pro Ile Leu Met Ile
145                 150                 155                 160

Ser Tyr Ala Asp Glu Ser Glu Ala Arg Val Ile Thr Trp Lys Lys Ile
                165                 170                 175

Asp Leu Pro Tyr Val Glu Val Ser Thr Lys Glu Met Ile Lys
            180                 185                 190

Arg Phe Leu Arg Val Val Lys Glu Lys Asp Pro Asp Val Leu Ile Thr
        195                 200                 205

Tyr Asn Gly Asp Asn Phe Asp Phe Ala Tyr Leu Lys Lys Arg Cys Glu
    210                 215                 220

Lys Leu Gly Val Ser Phe Thr Leu Gly Arg Asp Gly Ser Glu Pro Lys
225                 230                 235                 240

Ile Gln Arg Met Gly Asp Arg Phe Ala Val Glu Val Lys Gly Arg Val
                245                 250                 255

His Phe Asp Leu Tyr Pro Val Ile Arg Arg Thr Ile Asn Leu Pro Thr
            260                 265                 270

Tyr Thr Leu Glu Ala Val Tyr Glu Ala Val Phe Gly Lys Pro Lys Glu
        275                 280                 285

Lys Val Tyr Ala Glu Glu Ile Ala Thr Ala Trp Glu Thr Gly Glu Gly
290                 295                 300

Leu Glu Arg Val Ala Arg Tyr Ser Met Glu Asp Ala Arg Val Thr Tyr
305                 310                 315                 320

Glu Leu Gly Arg Glu Phe Phe Pro Met Glu Ala Gln Leu Ser Arg Leu
                325                 330                 335

Ile Gly Gln Gly Leu Trp Asp Val Ser Arg Ser Ser Thr Gly Asn Leu
            340                 345                 350

Val Glu Trp Phe Leu Leu Arg Lys Ala Tyr Glu Arg Asn Glu Leu Ala
        355                 360                 365

Pro Asn Lys Pro Asp Glu Arg Glu Leu Ala Arg Arg Gly Gly Tyr
370                 375                 380

Ala Gly Gly Tyr Val Lys Glu Pro Glu Arg Gly Leu Trp Asp Asn Ile
385                 390                 395                 400

Val Tyr Leu Asp Phe Arg Ser Leu Tyr Pro Ser Ile Ile Thr His
                405                 410                 415

Asn Val Ser Pro Asp Thr Leu Asn Arg Glu Gly Cys Arg Ser Tyr Asp
            420                 425                 430

Val Ala Pro Glu Val Gly His Lys Phe Cys Lys Asp Phe Pro Gly Phe
        435                 440                 445

Ile Pro Ser Leu Leu Gly Asn Leu Leu Glu Glu Arg Gln Lys Ile Lys
    450                 455                 460

Arg Lys
465

<210> SEQ ID NO 92
<211> LENGTH: 310
<212> TYPE: PRT
<213> ORGANISM: Thermococcus sp.

<400> SEQUENCE: 92

Met Lys Ala Thr Leu Asp Pro Leu Glu Lys Asn Leu Leu Asp Tyr Arg
1               5                   10                  15
```

Gln Arg Ala Ile Lys Ile Leu Ala Asn Ser Tyr Tyr Gly Tyr Gly
         20                  25                  30

Tyr Ala Arg Ala Arg Trp Tyr Cys Arg Glu Cys Ala Glu Ser Val Thr
             35                  40                  45

Ala Trp Gly Arg Glu Tyr Ile Glu Met Val Ile Arg Glu Leu Glu Glu
 50                  55                  60

Lys Phe Gly Phe Lys Val Leu Tyr Ala Asp Thr Asp Gly Leu His Ala
 65                  70                  75                  80

Thr Ile Pro Gly Ala Asp Ala Glu Thr Val Lys Lys Ala Met Glu
                 85                  90                  95

Phe Leu Asn Tyr Ile Asn Pro Lys Leu Pro Gly Leu Leu Glu Leu Glu
                100                 105                 110

Tyr Glu Gly Phe Tyr Val Arg Gly Phe Phe Val Thr Lys Lys Lys Tyr
            115                 120                 125

Ala Val Ile Asp Glu Glu Gly Lys Ile Thr Thr Arg Gly Leu Glu Ile
        130                 135                 140

Val Arg Arg Asp Trp Ser Glu Ile Ala Lys Glu Thr Gln Ala Arg Val
145                 150                 155                 160

Leu Glu Ala Ile Leu Arg His Gly Asp Val Glu Glu Ala Val Arg Ile
                165                 170                 175

Val Arg Glu Val Thr Glu Lys Leu Ser Lys Tyr Glu Val Pro Pro Glu
            180                 185                 190

Lys Leu Val Ile His Glu Gln Ile Thr Arg Glu Leu Lys Asp Tyr Lys
        195                 200                 205

Ala Thr Gly Pro His Val Ala Ile Ala Lys Arg Leu Ala Ala Arg Gly
    210                 215                 220

Val Lys Ile Arg Pro Gly Thr Val Ile Ser Tyr Ile Val Leu Lys Gly
225                 230                 235                 240

Ser Gly Arg Ile Gly Asp Arg Ala Ile Pro Phe Asp Glu Phe Asp Pro
                245                 250                 255

Thr Lys His Lys Tyr Asp Ala Asp Tyr Tyr Ile Glu Asn Gln Val Leu
            260                 265                 270

Pro Ala Val Glu Arg Ile Leu Arg Ala Phe Gly Tyr Arg Lys Glu Asp
        275                 280                 285

Leu Arg Tyr Gln Lys Thr Arg Gln Val Gly Leu Gly Ala Trp Leu Lys
    290                 295                 300

Pro Lys Gly Lys Lys Lys
305                 310

<210> SEQ ID NO 93
<211> LENGTH: 2327
<212> TYPE: DNA
<213> ORGANISM: Pyrococcus furiosus

<400> SEQUENCE: 93
atgattttag atgtggatta cataactgaa gaaggaaaac ctgttattag gctattcaaa       60
aaagagaacg gaaaatttaa gatagagcat gatagaactt ttagaccata catttacgct      120
cttctcaggg atgattcaaa gattgaagaa gttaagaaaa taacggggga aaggcatgga      180
aagattgtga gaattgttga tgtagagaag gttgagaaaa gtttctcgg caagcctatt       240 accgtgtgga aactttattt ggaacatccc caagatgttc ccactattag agaaaaagtt      300
agagaacatc cagcagttgt ggacatcttc gaatacgata ttccatttgc aaagagatac      360
ctcatcgaca aaggcctaat accaatggag ggggaagaag agctaaagat tcttgccttc      420

```
gctatagcaa ccctctatca cgaaggagaa gagtttggaa aaggcccaat tataatgatt    480
agttatgcag atgaaaatga agcaaaggtg attacttgga aaaacataga tcttccatac    540
gttgaggttg tatcaagcga gagagagatg ataaagagat ttctcaggat tatcagggag    600
aaggatcctg acattatagt tactyataat ggagactcat tcgacttccc atatttagcg    660
aaaagggcag aaaaacttgg gattaaatta accattggaa gagatggaag cgagcccaag    720
atgcagagaa taggcgatat gacggctgta gaagtcaagg gaagaataca tttcgacttg    780
tatcatgtaa taacaaggac aataaatctc ccaacataca cactagaggc tgtatatgaa    840
gcaattttg gaaagccaaa ggagaaggta tacgccgacg atagcaaa agcctgggaa      900
agtggagaga accttgagag agttgccaaa tactcgatgg aagatgcaaa ggcaacttat    960
gaactcggga agaattcct tccaatgaaa attcagcttt caagattagt tggacaacct    1020
ttatgggatg tttcaaggtc aagcacaggg aaccttgtag agtggttctt acttaggaaa    1080
gcctacgaaa gaaacgaagt agctccaaac aagccaagtg aagaggagta tcaaagaagg    1140
ctcagggaga gctacacagg tggattcgtt aaagagccag aaaaggggtt gtgggaaaac    1200
atagtatacc tagattttag agccctatat ccctcgatta taattaccca caatgtttct    1260
cccgatactc taaatcttga gggatgcaag aactatgata tcgctcctca gtaggccac    1320
aagttctgca aggacatccc tggttttata ccaagtctct tgggacattt gttagaggaa    1380
agacaaaaga ttaagacaaa atgaaggaaa ctcaagatcc tatagaaaaa atactccttg    1440
actatagacg aaaagcgata aaactcttag caaattcttt ctacggatat tatggctatg    1500
caaaagcaag atggtactgt aaggagtgtg ctgagagcgt tactgcctgg ggaagaaagt    1560
acatcgagtt agtatggaag gagctcgaag aaaagtttgg atttaaagtc ctctacattg    1620
acactgatgg tctctatgca actatcccag gaggagaaag tgaggaaata aagaaaaagg    1680
ctctagaatt tgtaaaatac ataaattcaa agctccctgg actgctagag cttgaatatg    1740
aagggtttta agaggggga ttcttcgtta cgaagaagag gtatgcagta atagatgaag    1800
aaggaaaagt cattactcgt ggtttagaga tagttaggag agattggagt gaaattgcaa    1860
aagaaactca agctagagtt ttggagacaa tactaaaaca cggagatgtt gaagaagctg    1920
tgagaatagt aaaagaagta atacaaaagc ttgccaatta tgaaattcca ccagagaagc    1980
tcgcaatata tgagcagata acaagaccat tacatgagta taaggcgata ggtcctcacg    2040
tagctgttgc aaagaaacta gctgctaaag gagttaaaat aaagccagga atggtaattg    2100
gatacatagt acttagaggc gatggtccaa ttagcaatag ggcaattcta gctgaggaat    2160
acgatcccaa aaagcacaag tatgacgcag aatattacat tgagaaccag gttcttccag    2220
cggtacttag gatattggag ggatttggat acagaaagga agacctcaga taccaaaaga    2280
caagacaagt cggcctaact tcctggctta acattaaaaa atcctag                 2327
```

<210> SEQ ID NO 94
<211> LENGTH: 467
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 94

Met Ile Leu Asp Val Asp Tyr Ile Thr Glu Glu Gly Lys Pro Val Ile
1               5                   10                  15

Arg Leu Phe Lys Lys Glu Asn Gly Lys Phe Lys Ile Glu His Asp Arg

```
            20                  25                  30
Thr Phe Arg Pro Tyr Ile Tyr Ala Leu Leu Arg Asp Asp Ser Lys Ile
            35                  40                  45
Glu Glu Val Lys Lys Ile Thr Gly Glu Arg His Gly Lys Ile Val Arg
            50                  55                  60
Ile Val Asp Val Glu Lys Val Glu Lys Lys Phe Leu Gly Lys Pro Ile
65                  70                  75                  80
Thr Val Trp Lys Leu Tyr Leu Glu His Pro Gln Asp Val Pro Thr Ile
                85                  90                  95
Arg Glu Lys Val Arg Glu His Pro Ala Val Val Asp Ile Phe Glu Tyr
                100                 105                 110
Asp Ile Pro Phe Ala Lys Arg Tyr Leu Ile Asp Lys Gly Leu Ile Pro
                115                 120                 125
Met Glu Gly Glu Glu Leu Lys Ile Leu Ala Phe Ala Ile Ala Thr
                130                 135                 140
Leu Tyr His Glu Gly Glu Glu Phe Gly Lys Gly Pro Ile Ile Met Ile
145                 150                 155                 160
Ser Tyr Ala Asp Glu Asn Glu Ala Lys Val Ile Thr Trp Lys Asn Ile
                165                 170                 175
Asp Leu Pro Tyr Val Glu Val Ser Ser Glu Arg Glu Met Ile Lys
                180                 185                 190
Arg Phe Leu Arg Ile Ile Arg Glu Lys Asp Pro Asp Ile Ile Val Thr
                195                 200                 205
Tyr Asn Gly Asp Ser Phe Asp Phe Pro Tyr Leu Ala Lys Arg Ala Glu
                210                 215                 220
Lys Leu Gly Ile Lys Leu Thr Ile Gly Arg Asp Gly Ser Glu Pro Lys
225                 230                 235                 240
Met Gln Arg Ile Gly Asp Met Thr Ala Val Glu Val Lys Gly Arg Ile
                245                 250                 255
His Phe Asp Leu Tyr His Val Ile Thr Arg Thr Ile Asn Leu Pro Thr
                260                 265                 270
Tyr Thr Leu Glu Ala Val Tyr Glu Ala Ile Phe Gly Lys Pro Lys Glu
                275                 280                 285
Lys Val Tyr Ala Asp Glu Ile Ala Lys Ala Trp Glu Ser Gly Glu Asn
                290                 295                 300
Leu Glu Arg Val Ala Lys Tyr Ser Met Glu Asp Ala Lys Ala Thr Tyr
305                 310                 315                 320
Glu Leu Gly Lys Glu Phe Leu Pro Met Glu Ile Gln Leu Ser Arg Leu
                325                 330                 335
Val Gly Gln Pro Leu Trp Asp Val Ser Arg Ser Ser Thr Gly Asn Leu
                340                 345                 350
Val Glu Trp Phe Leu Leu Arg Lys Ala Tyr Glu Arg Asn Glu Val Ala
                355                 360                 365
Pro Asn Lys Pro Ser Glu Glu Glu Tyr Gln Arg Arg Leu Arg Glu Ser
                370                 375                 380
Tyr Thr Gly Gly Phe Val Lys Glu Pro Glu Lys Gly Leu Trp Glu Asn
385                 390                 395                 400
Ile Val Tyr Leu Asp Phe Arg Ala Leu Tyr Pro Ser Ile Ile Ile Thr
                405                 410                 415
His Asn Val Ser Pro Asp Thr Leu Asn Leu Glu Gly Cys Lys Asn Tyr
                420                 425                 430
Asp Ile Ala Pro Gln Val Gly His Lys Phe Cys Lys Asp Ile Pro Gly
                435                 440                 445
```

```
Phe Ile Pro Ser Leu Leu Gly His Leu Leu Glu Glu Arg Gln Lys Ile
    450                 455                 460

Lys Thr Lys
465

<210> SEQ ID NO 95
<211> LENGTH: 308
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 95

Met Lys Glu Thr Gln Asp Pro Ile Glu Lys Ile Leu Leu Asp Tyr Arg
1               5                   10                  15

Arg Lys Ala Ile Lys Leu Leu Ala Asn Ser Phe Tyr Gly Tyr Tyr Gly
            20                  25                  30

Tyr Ala Lys Ala Arg Trp Tyr Cys Lys Glu Cys Ala Glu Ser Val Thr
        35                  40                  45

Ala Trp Gly Arg Lys Tyr Ile Glu Leu Val Trp Lys Glu Leu Glu Glu
    50                  55                  60

Lys Phe Gly Phe Lys Val Leu Tyr Ile Asp Thr Asp Gly Leu Tyr Ala
65                  70                  75                  80

Thr Ile Pro Gly Gly Glu Ser Glu Glu Ile Lys Lys Lys Ala Leu Glu
                85                  90                  95

Phe Val Lys Tyr Ile Asn Ser Lys Leu Pro Gly Leu Leu Glu Leu Glu
            100                 105                 110

Tyr Glu Gly Phe Tyr Lys Arg Gly Phe Phe Val Thr Lys Lys Arg Tyr
        115                 120                 125

Ala Val Ile Asp Glu Glu Gly Lys Val Ile Thr Arg Gly Leu Glu Ile
    130                 135                 140

Val Arg Arg Asp Trp Ser Glu Ile Ala Lys Glu Thr Gln Ala Arg Val
145                 150                 155                 160

Leu Glu Thr Ile Leu Lys His Gly Asp Val Glu Glu Ala Val Arg Ile
                165                 170                 175

Val Lys Glu Val Ile Gln Lys Leu Ala Asn Tyr Glu Ile Pro Pro Glu
            180                 185                 190

Lys Leu Ala Ile Tyr Glu Gln Ile Thr Arg Pro Leu His Glu Tyr Lys
        195                 200                 205

Ala Ile Gly Pro His Val Ala Val Ala Lys Lys Leu Ala Ala Lys Gly
    210                 215                 220

Val Lys Ile Lys Pro Gly Met Val Ile Gly Tyr Ile Val Leu Arg Gly
225                 230                 235                 240

Asp Gly Pro Ile Ser Asn Arg Ala Ile Leu Ala Glu Glu Tyr Asp Pro
                245                 250                 255

Lys Lys His Lys Tyr Asp Ala Glu Tyr Tyr Ile Glu Asn Gln Val Leu
            260                 265                 270

Pro Ala Val Leu Arg Ile Leu Glu Gly Phe Gly Tyr Arg Lys Glu Asp
        275                 280                 285

Leu Arg Tyr Gln Lys Thr Arg Gln Val Gly Leu Thr Ser Trp Leu Asn
    290                 295                 300

Ile Lys Lys Ser
305
```

<210> SEQ ID NO 96
<211> LENGTH: 2414
<212> TYPE: DNA
<213> ORGANISM: Thermococcus sp.

<400> SEQUENCE: 96

```
atgatccttg acgttgatta catcaccgag aatggaaagc ccgtcatcag ggtcttcaag      60
aaggagaacg gcgagttcag gattgaatac gaccgcgagt tcgagcccta cttctacgcg     120
ctcctcaggg acgactctgc catcgaagaa atcaaaaaga taaccgcgga gaggcacggc     180
agggtcgtta aggttaagcg cgcggagaag gtgaagaaaa agttcctcgg caggtctgtg     240
gaggtctggg tcctctactt cacgcacccg caggacgttc cggcaatccg cgacaaaata     300
aggaagcacc ccgcggtcat cgacatctac gagtacgaca tacccttcgc caagcgctac     360
ctcatagaca agggcctaat cccgatggaa ggtgaggaag agcttaaact catgtccttc     420
gccatcgcga cgctctacca cgagggagaa gagtttggaa ccgggccgat tctgatgata     480
agctacgccg atgaaagcga ggcgcgcgtg ataacctgga agaagatcga ccttccttac     540
gttgaggttg tctccaccga gaaggagatg attaagcgct tcttgagggt cgttaaggag     600
aaggacccgg acgtgctgat aacatacaac ggcgacaact tcgacttcgc ctacctgaaa     660
aagcgctgtg agaagcttgg cgtgagcttt accctcggga gggacgggag cgagccgaag     720
atacagcgca tggggacag gtttgcggtc gaggtgaagg gcagggtaca cttcgacctt     780
tatccagtca taaggcgcac cataaacctc ccgacctaca cccttgaggc tgtatacgag     840
gcggttttcg gcaagcccaa ggagaaggtc tacgccgagg atagccac cgcctgggag     900
accggcgagg ggcttgagag ggtcgcgcgc tactcgatgg aggacgcgag ggttacctac     960
gagcttggca gggagttctt cccgatggag gcccagcttt ccaggctcat cggccaaggc    1020
ctctgggacg tttcccgctc cagcaccggc aacctcgtcg agtggttcct cctaaggaag    1080
gcctacgaga ggaacgaact cgctcccaac aagcccgacg agagggagct ggcgaggaga    1140
aggggggct acgccggtgg ctacgtcaag gagccggagc ggggactgtg ggacaatatc    1200
gtgtatctag actttcgtag tcactaccct tcaatcataa tcaccacaca cgtctcgcca    1260
gatacgctca accgcgaggg gtgtaggagc tacgacgttg cccccgaggt cggtcacaag    1320
ttctgcaagg acttccccgg cttcattccg agcctgctcg gaaacctgct ggaggaaagg    1380
cagaagatag caaggaagat gaaggcagaa gatagcaagg aagatgaagg cagaagatag    1440
caaggaagat gaaggcaact ctcgacccgc tggagaagaa tctcctcgat tacaggcaac    1500
gcgccatcaa gatcttagcc aacagctact acggctacta cggctatgcc agggcaagat    1560
ggtactgcag ggagtgcgcc gagagcgtta cggcatgggg aagggagtac atcgaaatgg    1620
tcatcagaga gcttgaggaa aagttcggtt ttaaagtcct ctatgcagac acagacggtc    1680
tccatgccac cattcctgga gcggacgctg aaacagtcaa gaaaaaggca atggagttct    1740
taaactatat caatcccaaa ctgcccggcc ttctcgaact cgaatacgag ggcttctacg    1800
tcaggggctt cttcgtcacg aagaaaaagt acgcggtcat cgacgaggag ggcaagataa    1860
ccacgcgcgg gcttgagata gtcaggcgcg actggagcga gatagcgaag gagacgcagg    1920
cgagggtttt ggaggcgata ctcaggcacg gtgacgttga agaggccgtc agaattgtca    1980
gggaagtcac cgaaaagctg agcaagtacg aggttccgcc ggagaagctg gttatccacg    2040
agcagataac gcgcgagctc aaggactaca aggccaccgg cccgcacgta gccatagcga    2100
agcgtttggc cgccagaggt gttaaaatcc ggcccggaac tgtgataagc tacatcgttc    2160
```

```
tgaagggctc cggamggata ggcgacaggg cgattcccct cgacgagttc gacccgacga  2220
agcacaagta cgatgcggac tactacatcg agaaccaggt tctgccggca gttgagagaa  2280
tcctcagggc cttcggctac cgcaaggaag acctgcgcta ccagaagacg aggcaggtcg  2340
ggcttggcgc gtggctgaag ccgaagggga agaagaaggg tggcggtggc ggtcatcacc  2400
atcatcatca ctga                                                    2414
```

```
<210> SEQ ID NO 97
<211> LENGTH: 479
<212> TYPE: PRT
<213> ORGANISM: Thermococcus sp.

<400> SEQUENCE: 97
```

Met Ile Leu Asp Val Asp Tyr Ile Thr Glu Asn Gly Lys Pro Val Ile
1               5                   10                  15

Arg Val Phe Lys Lys Glu Asn Gly Glu Phe Arg Ile Glu Tyr Asp Arg
            20                  25                  30

Glu Phe Glu Pro Tyr Phe Tyr Ala Leu Leu Arg Asp Asp Ser Ala Ile
        35                  40                  45

Glu Glu Ile Lys Lys Ile Thr Ala Glu Arg His Gly Arg Val Val Lys
    50                  55                  60

Val Lys Arg Ala Glu Lys Val Lys Lys Phe Leu Gly Arg Ser Val
65                  70                  75                  80

Glu Val Trp Val Leu Tyr Phe Thr His Pro Gln Asp Val Pro Ala Ile
                85                  90                  95

Arg Asp Lys Ile Arg Lys His Pro Ala Val Ile Asp Ile Tyr Glu Tyr
            100                 105                 110

Asp Ile Pro Phe Ala Lys Arg Tyr Leu Ile Asp Lys Gly Leu Ile Pro
        115                 120                 125

Met Glu Gly Glu Glu Glu Leu Lys Leu Met Ser Phe Ala Ile Ala Thr
130                 135                 140

Leu Tyr His Glu Gly Glu Glu Phe Gly Thr Gly Pro Ile Leu Met Ile
145                 150                 155                 160

Ser Tyr Ala Asp Glu Ser Glu Ala Arg Val Ile Thr Trp Lys Lys Ile
                165                 170                 175

Asp Leu Pro Tyr Val Glu Val Ser Thr Glu Lys Glu Met Ile Lys
            180                 185                 190

Arg Phe Leu Arg Val Val Lys Glu Lys Asp Pro Asp Val Leu Ile Thr
        195                 200                 205

Tyr Asn Gly Asp Asn Phe Asp Phe Ala Tyr Leu Lys Lys Arg Cys Glu
    210                 215                 220

Lys Leu Gly Val Ser Phe Thr Leu Gly Arg Asp Gly Ser Glu Pro Lys
225                 230                 235                 240

Ile Gln Arg Met Gly Asp Arg Phe Ala Val Glu Val Lys Gly Arg Val
                245                 250                 255

His Phe Asp Leu Tyr Pro Val Ile Arg Arg Thr Ile Asn Leu Pro Thr
            260                 265                 270

Tyr Thr Leu Glu Ala Val Tyr Glu Ala Val Phe Gly Lys Pro Lys Glu
        275                 280                 285

Lys Val Tyr Ala Glu Glu Ile Ala Thr Ala Trp Glu Thr Gly Glu Gly
    290                 295                 300

Leu Glu Arg Val Ala Arg Tyr Ser Met Glu Asp Ala Arg Val Thr Tyr
305                 310                 315                 320

Glu Leu Gly Arg Glu Phe Phe Pro Met Glu Ala Gln Leu Ser Arg Leu

```
              325                 330                 335
Ile Gly Gln Gly Leu Trp Asp Val Ser Arg Ser Thr Gly Asn Leu
            340                 345                 350
Val Glu Trp Phe Leu Leu Arg Lys Ala Tyr Glu Arg Asn Glu Leu Ala
            355                 360                 365
Pro Asn Lys Pro Asp Glu Arg Glu Leu Ala Arg Arg Gly Gly Tyr
            370                 375                 380
Ala Gly Gly Tyr Val Lys Glu Pro Glu Arg Gly Leu Trp Asp Asn Ile
385                 390                 395                 400
Val Tyr Leu Asp Phe Arg Ser His Tyr Pro Ser Ile Ile Ile Thr His
                405                 410                 415
Asn Val Ser Pro Asp Thr Leu Asn Arg Glu Gly Cys Arg Ser Tyr Asp
            420                 425                 430
Val Ala Pro Glu Val Gly His Lys Phe Cys Lys Asp Phe Pro Gly Phe
            435                 440                 445
Ile Pro Ser Leu Leu Gly Asn Leu Leu Glu Glu Arg Gln Lys Ile Ala
            450                 455                 460
Arg Lys Met Lys Ala Glu Asp Ser Lys Glu Asp Glu Gly Arg Arg
465                 470                 475

<210> SEQ ID NO 98
<211> LENGTH: 310
<212> TYPE: PRT
<213> ORGANISM: Thermococcus sp.
<220> FEATURE:
<221> NAME/KEY: MOD_RES
<222> LOCATION: (243)..(243)
<223> OTHER INFORMATION: Any amino acid

<400> SEQUENCE: 98

Met Lys Ala Thr Leu Asp Pro Leu Glu Lys Asn Leu Leu Asp Tyr Arg
1               5                   10                  15
Gln Arg Ala Ile Lys Ile Leu Ala Asn Ser Tyr Tyr Gly Tyr Tyr Gly
            20                  25                  30
Tyr Ala Arg Ala Arg Trp Tyr Cys Arg Glu Cys Ala Glu Ser Val Thr
        35                  40                  45
Ala Trp Gly Arg Glu Tyr Ile Glu Met Val Ile Arg Glu Leu Glu Glu
50                  55                  60
Lys Phe Gly Phe Lys Val Leu Tyr Ala Asp Thr Asp Gly Leu His Ala
                65                  70                  75                  80
Thr Ile Pro Gly Ala Asp Ala Glu Thr Val Lys Lys Lys Ala Met Glu
            85                  90                  95
Phe Leu Asn Tyr Ile Asn Pro Lys Leu Pro Gly Leu Leu Glu Leu Glu
            100                 105                 110
Tyr Glu Gly Phe Tyr Val Arg Gly Phe Phe Val Thr Lys Lys Lys Tyr
            115                 120                 125
Ala Val Ile Asp Glu Glu Gly Lys Ile Thr Thr Arg Gly Leu Glu Ile
130                 135                 140
Val Arg Arg Asp Trp Ser Glu Ile Ala Lys Glu Thr Gln Ala Arg Val
                145                 150                 155                 160
Leu Glu Ala Ile Leu Arg His Gly Asp Val Glu Ala Val Arg Ile
            165                 170                 175
Val Arg Glu Val Thr Glu Lys Leu Ser Lys Tyr Glu Val Pro Pro Glu
            180                 185                 190
Lys Leu Val Ile His Glu Gln Ile Thr Arg Glu Leu Lys Asp Tyr Lys
            195                 200                 205
```

```
Ala Thr Gly Pro His Val Ala Ile Ala Lys Arg Leu Ala Ala Arg Gly
210                 215                 220

Val Lys Ile Arg Pro Gly Thr Val Ile Ser Tyr Ile Val Leu Lys Gly
            225                 230                 235             240

Ser Gly Xaa Ile Gly Asp Arg Ala Ile Pro Phe Asp Glu Phe Asp Pro
            245                 250                 255

Thr Lys His Lys Tyr Asp Ala Asp Tyr Tyr Ile Glu Asn Gln Val Leu
        260                 265                 270

Pro Ala Val Glu Arg Ile Leu Arg Ala Phe Gly Tyr Arg Lys Glu Asp
    275                 280                 285

Leu Arg Tyr Gln Lys Thr Arg Gln Val Gly Leu Gly Ala Trp Leu Lys
290                 295                 300

Pro Lys Gly Lys Lys Lys
                305                 310

<210> SEQ ID NO 99
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(4)
<223> OTHER INFORMATION: Any amino acid

<400> SEQUENCE: 99

Lys His Xaa Xaa Asn Ser Leu Tyr Gly
1               5

<210> SEQ ID NO 100
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 100

His His His His His His
1               5

<210> SEQ ID NO 101
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 101
atcagaaacg aacgcatcat caagt                                          25

<210> SEQ ID NO 102
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 102
gcctcgcata tcaggaagca c                                              21
```

```
<210> SEQ ID NO 103
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 103
gaggagagca ggaaaggtgg aac                                              23

<210> SEQ ID NO 104
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 104
gaggtacagg gttgaggcta gtg                                              23

<210> SEQ ID NO 105
<211> LENGTH: 53
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(5)
<223> OTHER INFORMATION: Any amino acid
<220> FEATURE:
<221> NAME/KEY: MOD_RES
<222> LOCATION: (6)..(6)
<223> OTHER INFORMATION: Met, Val, Leu or Ile
<220> FEATURE:
<221> NAME/KEY: MOD_RES
<222> LOCATION: (8)..(9)
<223> OTHER INFORMATION: Any amino acid
<220> FEATURE:
<221> NAME/KEY: MOD_RES
<222> LOCATION: (11)..(11)
<223> OTHER INFORMATION: Met, Val, Leu or Ile
<220> FEATURE:
<221> NAME/KEY: MOD_RES
<222> LOCATION: (12)..(13)
<223> OTHER INFORMATION: Any amino acid
<220> FEATURE:
<221> NAME/KEY: MOD_RES
<222> LOCATION: (15)..(15)
<223> OTHER INFORMATION: Any amino acid
<220> FEATURE:
<221> NAME/KEY: MOD_RES
<222> LOCATION: (16)..(16)
<223> OTHER INFORMATION: Met, Val, Leu or Ile
<220> FEATURE:
<221> NAME/KEY: MOD_RES
<222> LOCATION: (18)..(19)
<223> OTHER INFORMATION: Any amino acid
<220> FEATURE:
<221> NAME/KEY: MOD_RES
<222> LOCATION: (21)..(22)
<223> OTHER INFORMATION: Any amino acid
<220> FEATURE:
<221> NAME/KEY: MOD_RES
<222> LOCATION: (23)..(23)
<223> OTHER INFORMATION: Ser or Thr
<220> FEATURE:
<221> NAME/KEY: MOD_RES
<222> LOCATION: (24)..(25)
<223> OTHER INFORMATION: Any amino acid and this region may encompass 1
```

```
        or 2 residues
<220> FEATURE:
<221> NAME/KEY: MOD_RES
<222> LOCATION: (27)..(28)
<223> OTHER INFORMATION: Any amino acid
<220> FEATURE:
<221> NAME/KEY: MOD_RES
<222> LOCATION: (29)..(29)
<223> OTHER INFORMATION: Asp or Glu
<220> FEATURE:
<221> NAME/KEY: MOD_RES
<222> LOCATION: (30)..(30)
<223> OTHER INFORMATION: Gln, Lys or Arg
<220> FEATURE:
<221> NAME/KEY: MOD_RES
<222> LOCATION: (31)..(31)
<223> OTHER INFORMATION: Any amino acid
<220> FEATURE:
<221> NAME/KEY: MOD_RES
<222> LOCATION: (32)..(32)
<223> OTHER INFORMATION: Met, Val, Leu or Ile
<220> FEATURE:
<221> NAME/KEY: MOD_RES
<222> LOCATION: (35)..(35)
<223> OTHER INFORMATION: Any amino acid
<220> FEATURE:
<221> NAME/KEY: MOD_RES
<222> LOCATION: (38)..(38)
<223> OTHER INFORMATION: Gln, Lys or Arg
<220> FEATURE:
<221> NAME/KEY: MOD_RES
<222> LOCATION: (40)..(40)
<223> OTHER INFORMATION: Met, Val, Leu or Ile
<220> FEATURE:
<221> NAME/KEY: MOD_RES
<222> LOCATION: (42)..(43)
<223> OTHER INFORMATION: Met, Val, Leu or Ile
<220> FEATURE:
<221> NAME/KEY: MOD_RES
<222> LOCATION: (46)..(46)
<223> OTHER INFORMATION: Any amino acid
<220> FEATURE:
<221> NAME/KEY: MOD_RES
<222> LOCATION: (47)..(47)
<223> OTHER INFORMATION: Phe or Tyr
<220> FEATURE:
<221> NAME/KEY: MOD_RES
<222> LOCATION: (51)..(53)
<223> OTHER INFORMATION: Any amino acid

<400> SEQUENCE: 105

Gly Xaa Xaa Xaa Xaa Leu Xaa Xaa Leu Xaa Xaa Xaa Arg Xaa Xaa
 1               5                  10                  15

Lys Xaa Xaa Met Xaa Xaa Xaa Xaa Asp Xaa Xaa Xaa Xaa Xaa
                20                  25                  30

Leu Asp Xaa Arg Gln Xaa Ala Xaa Lys Xaa Xaa Ala Asn Xaa Xaa Tyr
        35                  40                  45

Gly Tyr Xaa Xaa Xaa
        50

<210> SEQ ID NO 106
<211> LENGTH: 50
<212> TYPE: PRT
<213> ORGANISM: Glycine max

<400> SEQUENCE: 106

Gly Ile Leu Pro Glu Ile Leu Glu Glu Leu Leu Thr Ala Arg Lys Arg
 1               5                  10                  15

Ala Lys Ala Asp Leu Lys Glu Ala Lys Asp Pro Leu Glu Lys Ala Val
                20                  25                  30

Leu Asp Gly Arg Gln Leu Ala Leu Lys Ile Ser Ala Asn Ser Val Tyr
```

```
                35                  40                  45

Gly Phe
    50

<210> SEQ ID NO 107
<211> LENGTH: 50
<212> TYPE: PRT
<213> ORGANISM: Arabidopsis thaliana

<400> SEQUENCE: 107

Gly Ile Leu Pro Glu Ile Leu Glu Glu Leu Thr Ala Arg Lys Arg
1               5                   10                  15

Ala Lys Ala Asp Leu Lys Glu Ala Lys Asp Pro Leu Glu Lys Ala Val
                20                  25                  30

Leu Asp Gly Arg Gln Leu Ala Leu Lys Ile Ser Ala Asn Ser Val Tyr
            35                  40                  45

Gly Phe
    50

<210> SEQ ID NO 108
<211> LENGTH: 50
<212> TYPE: PRT
<213> ORGANISM: Homo sapiens

<400> SEQUENCE: 108

Gly Leu Leu Pro Gln Ile Leu Glu Asn Leu Leu Ser Ala Arg Lys Arg
1               5                   10                  15

Ala Lys Ala Glu Leu Ala Lys Glu Thr Asp Pro Leu Arg Arg Gln Val
                20                  25                  30

Leu Asp Gly Arg Gln Leu Ala Leu Lys Val Ser Ala Asn Ser Val Tyr
            35                  40                  45

Gly Phe
    50

<210> SEQ ID NO 109
<211> LENGTH: 50
<212> TYPE: PRT
<213> ORGANISM: Homo sapiens

<400> SEQUENCE: 109

Gly Leu Leu Pro Gln Ile Leu Glu Asn Leu Leu Ser Ala Arg Lys Arg
1               5                   10                  15

Ala Lys Ala Glu Leu Ala Lys Glu Thr Asp Pro Leu Arg Arg Gln Val
                20                  25                  30

Leu Asp Gly Arg Gln Leu Gly Leu Lys Val Ser Ala Asn Ser Val Tyr
            35                  40                  45

Gly Phe
    50

<210> SEQ ID NO 110
<211> LENGTH: 50
<212> TYPE: PRT
<213> ORGANISM: Mus sp.

<400> SEQUENCE: 110

Gly Leu Leu Pro Gln Ile Leu Glu Asn Leu Leu Ser Ala Arg Lys Arg
1               5                   10                  15

Ala Lys Ala Glu Leu Ala Gln Glu Thr Asp Pro Leu Arg Arg Gln Val
                20                  25                  30
```

```
Leu Asp Gly Arg Gln Leu Ala Leu Lys Val Ser Ala Asn Ser Val Tyr
         35                  40                  45

Gly Phe
    50

<210> SEQ ID NO 111
<211> LENGTH: 50
<212> TYPE: PRT
<213> ORGANISM: Danio sp.

<400> SEQUENCE: 111

Gly Leu Leu Pro Glu Ile Leu Glu Asn Leu Leu Ser Ala Arg Lys Arg
1               5                   10                  15

Ala Lys Ala Glu Leu Lys Lys Glu Thr Asp Pro Phe Lys Lys Gln Val
            20                  25                  30

Leu Asp Gly Arg Gln Leu Ala Leu Lys Ile Ser Ala Asn Ser Val Tyr
         35                  40                  45

Gly Phe
    50

<210> SEQ ID NO 112
<211> LENGTH: 50
<212> TYPE: PRT
<213> ORGANISM: Dictyostelium discoideum

<400> SEQUENCE: 112

Gly Leu Leu Pro Arg Ile Leu Glu Glu Leu Leu Ser Ala Arg Lys Lys
1               5                   10                  15

Ala Lys Asp Glu Leu Lys Asn Glu Lys Asp Pro Phe Lys Arg Ala Val
            20                  25                  30

Leu Asp Gly Arg Gln Leu Ala Leu Lys Ile Ser Ala Asn Ser Val Tyr
         35                  40                  45

Gly Phe
    50

<210> SEQ ID NO 113
<211> LENGTH: 50
<212> TYPE: PRT
<213> ORGANISM: Tribolium castaneum

<400> SEQUENCE: 113

Gly Leu Leu Pro His Ile Leu Gln His Leu Leu Ala Ala Arg Lys Lys
1               5                   10                  15

Thr Lys Ala Glu Leu Lys Glu Ala Thr Asp Pro Val Leu Arg Ala Val
            20                  25                  30

Leu Asp Gly Arg Gln Leu Ala Tyr Lys Ile Ser Ala Asn Ser Val Tyr
         35                  40                  45

Gly Phe
    50

<210> SEQ ID NO 114
<211> LENGTH: 51
<212> TYPE: PRT
<213> ORGANISM: Methanothermobacter thermautotrophicus

<400> SEQUENCE: 114

Gly Phe Val Pro Ser Val Ile Gly Glu Ile Leu Ser Glu Arg Val Arg
1               5                   10                  15

Ile Lys Glu Glu Met Lys Gly Ser Asp Pro Met Glu Arg Lys Ile
            20                  25                  30
```

```
Leu Asn Val Gln Gln Glu Ala Leu Lys Arg Leu Ala Asn Thr Met Tyr
        35                  40                  45

Gly Val Tyr
    50

<210> SEQ ID NO 115
<211> LENGTH: 51
<212> TYPE: PRT
<213> ORGANISM: Methanosphaera sp.

<400> SEQUENCE: 115

Gly Phe Ile Pro Ser Ile Ile Gly Tyr Ile Leu Asp Glu Arg Gln Arg
1               5                   10                  15

Ile Lys Lys Leu Met Tyr Glu Glu Thr Val Pro Glu Gln Lys Lys Ala
            20                  25                  30

Tyr Asp Phe Glu Gln Gln Gly Leu Lys Arg Leu Ala Asn Ser Met Phe
        35                  40                  45

Gly Ala Tyr
    50

<210> SEQ ID NO 116
<211> LENGTH: 46
<212> TYPE: PRT
<213> ORGANISM: Pyrococcus sp.

<400> SEQUENCE: 116

Gly Phe Ile Pro Ser Leu Leu Lys Arg Leu Leu Asp Glu Arg Gln Glu
1               5                   10                  15

Ile Lys Arg Lys Met Lys Ala Ser Lys Asp Pro Ile Glu Lys Lys Met
            20                  25                  30

Leu Asp Tyr Arg Gln Arg Ala Ile Lys Ile Leu Ala Asn Ser
        35                  40                  45

<210> SEQ ID NO 117
<211> LENGTH: 46
<212> TYPE: PRT
<213> ORGANISM: Pyrococcus glycovorans

<400> SEQUENCE: 117

Gly Phe Ile Pro Ser Leu Leu Lys Arg Leu Leu Asp Glu Arg Gln Glu
1               5                   10                  15

Ile Lys Arg Lys Met Lys Ala Ser Lys Asp Pro Ile Glu Lys Lys Met
            20                  25                  30

Leu Asp Tyr Arg Gln Arg Ala Ile Lys Ile Leu Ala Asn Ser
        35                  40                  45

<210> SEQ ID NO 118
<211> LENGTH: 46
<212> TYPE: PRT
<213> ORGANISM: Pyrococcus glycovorans

<400> SEQUENCE: 118

Gly Phe Ile Pro Ser Leu Leu Lys Arg Leu Leu Asp Glu Arg Gln Glu
1               5                   10                  15

Ile Lys Arg Arg Met Lys Ala Ser Lys Asp Pro Ile Glu Lys Lys Met
            20                  25                  30

Leu Asp Tyr Arg Gln Arg Ala Ile Lys Ile Leu Ala Asn Ser
        35                  40                  45
```

```
<210> SEQ ID NO 119
<211> LENGTH: 37
<212> TYPE: PRT
<213> ORGANISM: Pyrococcus sp.

<400> SEQUENCE: 119

Gln Glu Ile Lys Arg Lys Met Lys Ala Ser Lys Asp Pro Ile Glu Lys
1               5                   10                  15

Lys Lys Leu Asp Tyr Arg Gln Arg Ala Ile Lys Ile Leu Ala Asn Ser
            20                  25                  30

Tyr Tyr Gly Tyr Tyr
        35

<210> SEQ ID NO 120
<211> LENGTH: 51
<212> TYPE: PRT
<213> ORGANISM: Pyrococcus furiosus

<400> SEQUENCE: 120

Gly Phe Ile Pro Ser Leu Leu Gly His Leu Leu Glu Glu Arg Gln Lys
1               5                   10                  15

Ile Lys Thr Lys Met Lys Glu Thr Gln Asp Pro Ile Glu Lys Ile Leu
            20                  25                  30

Leu Asp Tyr Arg Gln Lys Ala Ile Lys Leu Leu Ala Asn Ser Phe Tyr
        35                  40                  45

Gly Tyr Tyr
    50

<210> SEQ ID NO 121
<211> LENGTH: 46
<212> TYPE: PRT
<213> ORGANISM: Thermococcus litoralis

<400> SEQUENCE: 121

Gly Phe Ile Pro Ser Leu Leu Gly His Leu Leu Glu Glu Arg Gln Lys
1               5                   10                  15

Ile Lys Thr Lys Met Lys Glu Gln Gln Asp Pro Ile Glu Lys Ile Leu
            20                  25                  30

Leu Asp Tyr Arg Gln Lys Ala Ile Lys Leu Leu Ala Asn Ser
        35                  40                  45

<210> SEQ ID NO 122
<211> LENGTH: 46
<212> TYPE: PRT
<213> ORGANISM: Thermococcus sp.

<400> SEQUENCE: 122

Gly Phe Ile Pro Ser Leu Leu Gly Asn Leu Leu Glu Glu Arg Gln Lys
1               5                   10                  15

Ile Lys Arg Lys Met Lys Ala Thr Ile Asp Pro Leu Glu Lys Lys Leu
            20                  25                  30

Leu Asp Tyr Arg Gln Arg Ala Ile Lys Ile Leu Ala Asn Ser
        35                  40                  45

<210> SEQ ID NO 123
<211> LENGTH: 46
<212> TYPE: PRT
<213> ORGANISM: Thermococcus sp.

<400> SEQUENCE: 123

Gly Phe Ile Pro Ser Leu Leu Gly Asp Leu Leu Glu Glu Arg Gln Lys
```

```
                1               5                  10                  15
Ile Lys Arg Lys Met Arg Ala Thr Ile Asp Pro Val Glu Lys Lys Leu
                20                  25                  30

Leu Asp Tyr Arg Gln Arg Ala Ile Lys Ile Leu Ala Asn Ser
            35                  40                  45
```

<210> SEQ ID NO 124
<211> LENGTH: 51
<212> TYPE: PRT
<213> ORGANISM: Thermococcus sp.

<400> SEQUENCE: 124

```
Gly Phe Ile Pro Ser Leu Leu Gly Asp Leu Leu Glu Glu Arg Gln Lys
1               5                   10                  15

Ile Lys Arg Lys Met Lys Ala Thr Val Asp Pro Leu Glu Lys Lys Leu
                20                  25                  30

Leu Asp Tyr Arg Gln Arg Ala Ile Lys Ile Leu Ala Asn Ser Phe Tyr
            35                  40                  45

Gly Tyr Tyr
    50
```

<210> SEQ ID NO 125
<211> LENGTH: 46
<212> TYPE: PRT
<213> ORGANISM: Thermococcus zilligii

<400> SEQUENCE: 125

```
Gly Phe Ile Pro Ser Leu Leu Gly Asp Leu Leu Glu Glu Arg Gln Lys
1               5                   10                  15

Val Lys Lys Lys Met Lys Ala Thr Val Asp Pro Ile Glu Arg Lys Leu
                20                  25                  30

Leu Asp Tyr Arg Gln Arg Ala Ile Lys Ile Leu Ala Asn Ser
            35                  40                  45
```

<210> SEQ ID NO 126
<211> LENGTH: 46
<212> TYPE: PRT
<213> ORGANISM: Desulfurococcus sp.

<400> SEQUENCE: 126

```
Gly Phe Ile Pro Ser Leu Leu Gly Asp Leu Leu Glu Glu Arg Gln Lys
1               5                   10                  15

Val Lys Lys Lys Met Lys Ala Thr Val Asp Pro Ile Glu Arg Lys Leu
                20                  25                  30

Leu Asp Tyr Arg Gln Arg Ala Ile Lys Ile Leu Ala Asn Ser
            35                  40                  45
```

<210> SEQ ID NO 127
<211> LENGTH: 51
<212> TYPE: PRT
<213> ORGANISM: Thermococcus fumicolans

<400> SEQUENCE: 127

```
Gly Phe Ile Pro Ser Leu Leu Gly Asp Leu Leu Asp Glu Arg Gln Lys
1               5                   10                  15

Val Lys Lys His Met Lys Ala Thr Val Asp Pro Ile Glu Lys Lys Leu
                20                  25                  30

Leu Asp Tyr Arg Gln Arg Ala Ile Lys Ile Leu Ala Asn Ser Phe Tyr
            35                  40                  45
```

-continued

Gly Tyr Tyr
    50

<210> SEQ ID NO 128
<211> LENGTH: 50
<212> TYPE: PRT
<213> ORGANISM: Thermococcus gorgonarius

<400> SEQUENCE: 128

Gly Ile Pro Ser Leu Leu Gly Asp Leu Leu Glu Glu Arg Gln Lys Val
1               5                   10                  15

Lys Lys Lys Met Lys Ala Thr Ile Asp Pro Ile Glu Lys Lys Leu Leu
            20                  25                  30

Asp Tyr Arg Gln Arg Ala Ile Lys Ile Leu Ala Asn Ser Phe Tyr Gly
        35                  40                  45

Tyr Tyr
    50

<210> SEQ ID NO 129
<211> LENGTH: 46
<212> TYPE: PRT
<213> ORGANISM: Thermococcus kodakarensis

<400> SEQUENCE: 129

Gly Phe Ile Pro Ser Leu Leu Gly Asp Leu Leu Glu Glu Arg Gln Lys
1               5                   10                  15

Ile Lys Lys Lys Met Lys Ala Thr Ile Asp Pro Ile Glu Arg Lys Leu
            20                  25                  30

Leu Asp Tyr Arg Gln Arg Ala Ile Lys Ile Leu Ala Asn Ser
        35                  40                  45

<210> SEQ ID NO 130
<211> LENGTH: 46
<212> TYPE: PRT
<213> ORGANISM: Pyrococcus horikoshii

<400> SEQUENCE: 130

Gly Phe Ile Pro Ser Leu Leu Gly Gln Leu Leu Glu Glu Arg Gln Lys
1               5                   10                  15

Ile Lys Lys Arg Met Lys Glu Ser Lys Asp Pro Val Glu Lys Lys Leu
            20                  25                  30

Leu Asp Tyr Arg Gln Arg Ala Ile Lys Ile Leu Ala Asn Ser
        35                  40                  45

<210> SEQ ID NO 131
<211> LENGTH: 46
<212> TYPE: PRT
<213> ORGANISM: Pyrococcus abyssi

<400> SEQUENCE: 131

Gly Phe Ile Pro Ser Leu Leu Gly Asn Leu Leu Glu Glu Arg Gln Lys
1               5                   10                  15

Ile Lys Lys Arg Met Lys Glu Ser Lys Asp Pro Val Glu Lys Lys Leu
            20                  25                  30

Leu Asp Tyr Arg Gln Arg Ala Ile Lys Ile Leu Ala Asn Ser
        35                  40                  45

<210> SEQ ID NO 132
<211> LENGTH: 51
<212> TYPE: PRT
<213> ORGANISM: Pyrococcus sp.

<400> SEQUENCE: 132

Gly Phe Ile Pro Ser Leu Leu Gly Asp Leu Leu Glu Glu Arg Gln Lys
1               5                   10                  15

Ile Lys Lys Arg Met Lys Glu Ser Lys Asp Pro Ile Glu Lys Lys Leu
            20                  25                  30

Leu Asp Tyr Arg Gln Arg Ala Ile Lys Ile Leu Ala Asn Ser Phe Tyr
        35                  40                  45

Gly Tyr Tyr
        50

<210> SEQ ID NO 133
<211> LENGTH: 47
<212> TYPE: PRT
<213> ORGANISM: Thermococcus sp.

<400> SEQUENCE: 133

Gly Phe Ile Pro Ser Leu Leu Gly Ala Leu Leu Asp Glu Arg Gln Lys
1               5                   10                  15

Ile Lys Lys Arg Met Lys Ala Ser Ile Asp Pro Leu Glu Lys Lys Leu
            20                  25                  30

Leu Asp Tyr Arg Gln Lys Ala Ile Lys Ile Leu Ala Asn Ser Leu
        35                  40                  45

<210> SEQ ID NO 134
<211> LENGTH: 47
<212> TYPE: PRT
<213> ORGANISM: Thermococcus hydrothermalis

<400> SEQUENCE: 134

Gly Phe Ile Pro Ser Leu Leu Gly Ala Leu Leu Asp Glu Arg Gln Lys
1               5                   10                  15

Ile Lys Lys Arg Met Lys Ala Ser Ile Asp Pro Leu Glu Lys Lys Leu
            20                  25                  30

Leu Asp Tyr Arg Gln Lys Ala Ile Lys Ile Leu Ala Asn Ser Leu
        35                  40                  45

<210> SEQ ID NO 135
<211> LENGTH: 46
<212> TYPE: PRT
<213> ORGANISM: Thermococcus aggregans

<400> SEQUENCE: 135

Gly Phe Ile Pro Ser Ile Leu Gly Glu Leu Ile Thr Met Arg Gln Glu
1               5                   10                  15

Ile Lys Lys Lys Met Lys Ala Thr Ile Asp Pro Ile Glu Lys Lys Met
            20                  25                  30

Leu Asp Tyr Arg Gln Arg Ala Val Lys Leu Leu Ala Asn Ser
        35                  40                  45

<210> SEQ ID NO 136
<211> LENGTH: 50
<212> TYPE: PRT
<213> ORGANISM: Methanosarcina acetivorans

<400> SEQUENCE: 136

Gly Ile Val Pro Ser Ile Leu Glu Asp Leu Leu Asn Lys Arg Gly Asp
1               5                   10                  15

Thr Lys Lys Arg Met Lys Arg Thr Ser Asp Glu Asn Glu His Arg Val
            20                  25                  30

```
Leu Asp Ala Thr Gln Leu Ala Ile Lys Ile Leu Leu Asn Ser Phe Tyr
            35                  40                  45

Gly Tyr
    50

<210> SEQ ID NO 137
<211> LENGTH: 50
<212> TYPE: PRT
<213> ORGANISM: Methanococcoides burtonii

<400> SEQUENCE: 137

Gly Ile Val Pro Ser Val Leu Glu Ser Leu Asp Lys Arg Ile Glu
1               5                   10                  15

Thr Lys Lys Leu Met Lys Gln Ala Ser Asp Glu Gly Glu Tyr Gln Val
            20                  25                  30

Leu Asp Ala Thr Gln Leu Ala Leu Lys Ile Leu Leu Asn Ser Phe Tyr
            35                  40                  45

Gly Tyr
    50

<210> SEQ ID NO 138
<211> LENGTH: 50
<212> TYPE: PRT
<213> ORGANISM: Sulfolobus tokodaii

<400> SEQUENCE: 138

Gly Leu Tyr Lys Asn Val Leu Glu Lys Leu Ile Gln Glu Arg Lys Glu
1               5                   10                  15

Val Lys Lys Leu Met Glu Lys Thr Met Asp Glu Tyr Asp Lys Arg Val
            20                  25                  30

Leu Asp Ala Arg Gln Arg Ala Leu Lys Val Met Ala Asn Ala Phe Tyr
            35                  40                  45

Gly Tyr
    50

<210> SEQ ID NO 139
<211> LENGTH: 50
<212> TYPE: PRT
<213> ORGANISM: Sulfurisphaera ohwakuensis

<400> SEQUENCE: 139

Gly Leu Tyr Lys Asn Val Leu Glu Lys Leu Ile Gln Glu Arg Lys Glu
1               5                   10                  15

Val Lys Lys Leu Met Glu Lys Thr Ile Asp Glu Tyr Asp Lys Arg Val
            20                  25                  30

Leu Asp Ala Arg Gln Arg Ala Leu Lys Val Met Ala Asn Ala Phe Tyr
            35                  40                  45

Gly Tyr
    50

<210> SEQ ID NO 140
<211> LENGTH: 51
<212> TYPE: PRT
<213> ORGANISM: Aeropyrum pernix

<400> SEQUENCE: 140

Gly Phe Phe Lys Lys Ile Leu Glu Arg Phe Leu Ser Trp Arg Arg Gln
1               5                   10                  15

Ile Arg Ser Glu Met Lys Lys His Pro Pro Asp Ser Pro Glu Tyr Lys
```

Leu Leu Asp Glu Arg Gln Lys Ala Ile Lys Leu Leu Ala Asn Ala Ser
            35                  40                  45

Tyr Gly Tyr
    50

<210> SEQ ID NO 141
<211> LENGTH: 51
<212> TYPE: PRT
<213> ORGANISM: Pyrodictium occultum

<400> SEQUENCE: 141

Gly Phe Phe Lys Thr Val Leu Glu Asn Leu Leu Lys Leu Arg Arg Gln
1               5                   10                  15

Val Lys Glu Lys Met Lys Glu Phe Pro Pro Asp Ser Pro Glu Tyr Arg
            20                  25                  30

Leu Tyr Asp Glu Arg Gln Lys Ala Leu Lys Val Leu Ala Asn Ala Ser
            35                  40                  45

Tyr Gly Tyr
    50

<210> SEQ ID NO 142
<211> LENGTH: 51
<212> TYPE: PRT
<213> ORGANISM: Pyrobaculum sp.

<400> SEQUENCE: 142

Gly Phe Ile Pro Leu Val Leu Arg Gln Leu Ile Glu Leu Arg Lys Arg
1               5                   10                  15

Val Arg Glu Glu Leu Lys Lys Tyr Pro Pro Asp Ser Pro Glu Tyr Arg
            20                  25                  30

Val Leu Asp Glu Arg Gln Arg Ala Leu Lys Ile Met Ala Asn Ala Met
            35                  40                  45

Tyr Gly Tyr
    50

<210> SEQ ID NO 143
<211> LENGTH: 49
<212> TYPE: PRT
<213> ORGANISM: Thermoplasma volcanium

<400> SEQUENCE: 143

Gly Leu Ile Pro Arg Ile Leu Gln Glu Leu Met Ala Asp Arg Asp Asp
1               5                   10                  15

Val Lys Lys Arg Met Lys Glu Ala Lys Ser Glu Asp Glu Arg Leu Phe
            20                  25                  30

Tyr Asp Gly Ile Gln Asn Ala Ile Lys Val Leu Met Asn Thr Phe Tyr
            35                  40                  45

Gly

<210> SEQ ID NO 144
<211> LENGTH: 49
<212> TYPE: PRT
<213> ORGANISM: Saccharomyces cerevisiae

<400> SEQUENCE: 144

Gly Val Leu Pro Arg Leu Leu Ala Asn Leu Val Asp Arg Arg Arg Glu
1               5                   10                  15

Val Lys Lys Val Met Lys Thr Glu Thr Asp Pro His Lys Arg Val Gln

```
                20                  25                  30

Cys Asp Ile Arg Gln Gln Ala Leu Lys Leu Thr Ala Asn Ser Met Tyr
        35                  40                  45

Gly

<210> SEQ ID NO 145
<211> LENGTH: 51
<212> TYPE: PRT
<213> ORGANISM: Crocidura russula cytomegalovirus 1

<400> SEQUENCE: 145

Pro Ser Ile Leu Ala Glu Leu Leu Thr Arg Trp Leu Ala Gln Arg Lys
1               5                   10                  15

Ala Val Arg Glu Ser Met Lys Arg Cys Glu Asp Pro Met Arg Arg Leu
            20                  25                  30

Leu Leu Asp Lys Glu Gln Leu Ala Leu Lys Val Thr Cys Asn Ser Phe
        35                  40                  45

Tyr Gly Phe
    50

<210> SEQ ID NO 146
<211> LENGTH: 48
<212> TYPE: PRT
<213> ORGANISM: Human herpesvirus 5

<400> SEQUENCE: 146

Leu Ser Glu Leu Leu Asn Lys Trp Val Ser Gln Arg Arg Ala Val Arg
1               5                   10                  15

Glu Cys Met Arg Glu Cys Gln Asp Pro Val Arg Arg Met Leu Leu Asp
            20                  25                  30

Lys Glu Gln Met Ala Leu Lys Val Thr Cys Asn Ala Phe Tyr Gly Phe
        35                  40                  45

<210> SEQ ID NO 147
<211> LENGTH: 8
<212> TYPE: PRT
<213> ORGANISM: Pyrococcus furiosus

<400> SEQUENCE: 147

Glu Arg Gln Lys Ile Lys Thr Lys
1               5

<210> SEQ ID NO 148
<211> LENGTH: 6
<212> TYPE: PRT
<213> ORGANISM: Pyrococcus furiosus

<400> SEQUENCE: 148

Met Lys Glu Thr Gln Asp
1               5

<210> SEQ ID NO 149
<211> LENGTH: 7
<212> TYPE: PRT
<213> ORGANISM: Pyrococcus furiosus

<400> SEQUENCE: 149

Glu Arg Gln Lys Ile Lys Thr
1               5

<210> SEQ ID NO 150
```

```
<211> LENGTH: 8
<212> TYPE: PRT
<213> ORGANISM: Pyrococcus furiosus

<400> SEQUENCE: 150

Met Lys Met Lys Glu Thr Gln Asp
1               5

<210> SEQ ID NO 151
<211> LENGTH: 8
<212> TYPE: PRT
<213> ORGANISM: Pyrococcus furiosus

<400> SEQUENCE: 151

Met Lys Lys Lys Glu Thr Gln Asp
1               5

<210> SEQ ID NO 152
<211> LENGTH: 10
<212> TYPE: PRT
<213> ORGANISM: Pyrococcus furiosus

<400> SEQUENCE: 152

Val Leu Tyr Ile Asp Thr Asp Gly Leu Tyr
1               5                   10

<210> SEQ ID NO 153
<211> LENGTH: 7
<212> TYPE: PRT
<213> ORGANISM: Pyrococcus furiosus

<400> SEQUENCE: 153

Met Ala Thr Ile Pro Gly Gly
1               5

<210> SEQ ID NO 154
<211> LENGTH: 51
<212> TYPE: DNA
<213> ORGANISM: Thermococcus sp.

<400> SEQUENCE: 154
aggcagaaga taaagaggaa atgaaggcaa ctctcgaccc gctggagaag a         51

<210> SEQ ID NO 155
<211> LENGTH: 17
<212> TYPE: PRT
<213> ORGANISM: Thermococcus sp.

<400> SEQUENCE: 155

Ala Glu Asp Lys Glu Glu Met Lys Ala Thr Leu Asp Pro Leu Glu Lys
1               5                   10                  15

Asn

<210> SEQ ID NO 156
<211> LENGTH: 7
<212> TYPE: PRT
<213> ORGANISM: Thermococcus sp.

<400> SEQUENCE: 156

Arg Gln Lys Ile Lys Arg Lys
1               5

<210> SEQ ID NO 157
<211> LENGTH: 9
```

```
<212> TYPE: PRT
<213> ORGANISM: Thermococcus sp.

<400> SEQUENCE: 157

Arg Gln Leu Ser Thr Arg Trp Arg Arg
1               5

<210> SEQ ID NO 158
<211> LENGTH: 51
<212> TYPE: DNA
<213> ORGANISM: Thermococcus sp.

<400> SEQUENCE: 158
ggcagaagat agcaaggaag atgaaggcaa ctctcgaccc gctggagaag a          51

<210> SEQ ID NO 159
<211> LENGTH: 17
<212> TYPE: PRT
<213> ORGANISM: Thermococcus sp.

<400> SEQUENCE: 159

Gln Lys Ile Ala Arg Lys Met Lys Ala Thr Leu Asp Pro Leu Glu Lys
1               5                   10                  15

Asn

<210> SEQ ID NO 160
<211> LENGTH: 9
<212> TYPE: PRT
<213> ORGANISM: Thermococcus sp.

<400> SEQUENCE: 160

Arg Gln Leu Ser Thr Arg Trp Arg Arg
1               5

<210> SEQ ID NO 161
<211> LENGTH: 467
<212> TYPE: PRT
<213> ORGANISM: Pyrococcus furiosus

<400> SEQUENCE: 161

Met Ile Leu Asp Val Asp Tyr Ile Thr Glu Glu Gly Lys Pro Val Ile
1               5                   10                  15

Arg Leu Phe Lys Lys Glu Asn Gly Lys Phe Lys Ile Glu His Asp Arg
                20                  25                  30

Thr Phe Arg Pro Tyr Ile Tyr Ala Leu Leu Arg Asp Asp Ser Lys Ile
            35                  40                  45

Glu Glu Val Lys Lys Ile Thr Gly Glu Arg His Gly Lys Ile Val Arg
        50                  55                  60

Ile Val Asp Val Glu Lys Val Glu Lys Lys Phe Leu Gly Lys Pro Ile
65                  70                  75                  80

Thr Val Trp Lys Leu Tyr Leu Glu His Pro Gln Asp Val Pro Thr Ile
                85                  90                  95

Arg Glu Lys Val Arg Glu His Pro Ala Val Val Asp Ile Phe Glu Tyr
            100                 105                 110

Asp Ile Pro Phe Ala Lys Arg Tyr Leu Ile Asp Lys Gly Leu Ile Pro
        115                 120                 125

Met Glu Gly Glu Glu Glu Leu Lys Ile Leu Ala Phe Ala Ile Ala Thr
    130                 135                 140

Leu Tyr His Glu Gly Glu Glu Phe Gly Lys Gly Pro Ile Ile Met Ile
145                 150                 155                 160
```

Ser Tyr Ala Asp Glu Asn Glu Ala Lys Val Ile Thr Trp Lys Asn Ile
                165                 170                 175

Asp Leu Pro Tyr Val Glu Val Val Ser Ser Arg Glu Met Ile Lys
            180                 185                 190

Arg Phe Leu Arg Ile Ile Arg Glu Lys Asp Pro Asp Ile Ile Val Thr
        195                 200                 205

Tyr Asn Gly Asp Ser Phe Asp Phe Pro Tyr Leu Ala Lys Arg Ala Glu
    210                 215                 220

Lys Leu Gly Ile Lys Leu Thr Ile Gly Arg Asp Gly Ser Glu Pro Lys
225                 230                 235                 240

Met Gln Arg Ile Gly Asp Met Thr Ala Val Glu Val Lys Gly Arg Ile
                245                 250                 255

His Phe Asp Leu Tyr His Val Ile Thr Arg Thr Ile Asn Leu Pro Thr
            260                 265                 270

Tyr Thr Leu Glu Ala Val Tyr Glu Ala Ile Phe Gly Lys Pro Lys Glu
        275                 280                 285

Lys Val Tyr Ala Asp Glu Ile Ala Lys Ala Trp Glu Ser Gly Glu Asn
    290                 295                 300

Leu Glu Arg Val Ala Lys Tyr Ser Met Glu Asp Ala Lys Ala Thr Tyr
305                 310                 315                 320

Glu Leu Gly Lys Glu Phe Leu Pro Met Glu Ile Gln Leu Ser Arg Leu
                325                 330                 335

Val Gly Gln Pro Leu Trp Asp Val Ser Arg Ser Ser Thr Gly Asn Leu
            340                 345                 350

Val Glu Trp Phe Leu Leu Arg Lys Ala Tyr Glu Arg Asn Glu Val Ala
        355                 360                 365

Pro Asn Lys Pro Ser Glu Glu Glu Tyr Gln Arg Arg Leu Arg Glu Ser
    370                 375                 380

Tyr Thr Gly Gly Phe Val Lys Glu Pro Glu Lys Gly Leu Trp Glu Asn
385                 390                 395                 400

Ile Val Tyr Leu Asp Phe Arg Ala Leu Tyr Pro Ser Ile Ile Ile Thr
                405                 410                 415

His Asn Val Ser Pro Asp Thr Leu Asn Leu Glu Gly Cys Lys Asn Tyr
            420                 425                 430

Asp Ile Ala Pro Gln Val Gly His Lys Phe Cys Lys Asp Ile Pro Gly
        435                 440                 445

Phe Ile Pro Ser Leu Leu Gly His Leu Leu Glu Glu Arg Gln Lys Ile
    450                 455                 460

Lys Thr Lys
465

<210> SEQ ID NO 162
<211> LENGTH: 308
<212> TYPE: PRT
<213> ORGANISM: Pyrococcus furiosus

<400> SEQUENCE: 162

Met Lys Glu Thr Gln Asp Pro Ile Glu Lys Ile Leu Leu Asp Tyr Arg
1               5                   10                  15

Gln Lys Ala Ile Lys Leu Leu Ala Asn Ser Phe Tyr Gly Tyr Tyr Gly
            20                  25                  30

Tyr Ala Lys Ala Arg Trp Tyr Cys Lys Glu Cys Ala Glu Ser Val Thr
        35                  40                  45

Ala Trp Gly Arg Lys Tyr Ile Glu Leu Val Trp Lys Glu Leu Glu Glu

```
                    50                  55                  60
Lys Phe Gly Phe Lys Val Leu Tyr Ile Asp Thr Asp Gly Leu Tyr Ala
 65                  70                  75                  80

Thr Ile Pro Gly Gly Glu Ser Glu Ile Lys Lys Ala Leu Glu
                 85                  90                  95

Phe Val Lys Tyr Ile Asn Ser Lys Leu Pro Gly Leu Leu Glu Leu Glu
                100                 105                 110

Tyr Glu Gly Phe Tyr Lys Arg Gly Phe Phe Val Thr Lys Lys Arg Tyr
                115                 120                 125

Ala Val Ile Asp Glu Glu Gly Lys Val Ile Thr Arg Gly Leu Glu Ile
130                 135                 140

Val Arg Arg Asp Trp Ser Glu Ile Ala Lys Glu Thr Gln Ala Arg Val
145                 150                 155                 160

Leu Glu Thr Ile Leu Lys His Gly Asp Val Glu Glu Ala Val Arg Ile
                165                 170                 175

Val Lys Glu Val Ile Gln Lys Leu Ala Asn Tyr Glu Ile Pro Pro Glu
                180                 185                 190

Lys Leu Ala Ile Tyr Glu Gln Ile Thr Arg Pro Leu His Glu Tyr Lys
                195                 200                 205

Ala Ile Gly Pro His Val Ala Val Ala Lys Lys Leu Ala Ala Lys Gly
    210                 215                 220

Val Lys Ile Lys Pro Gly Met Val Ile Gly Tyr Ile Val Leu Arg Gly
225                 230                 235                 240

Asp Gly Pro Ile Ser Asn Arg Ala Ile Leu Ala Glu Glu Tyr Asp Pro
                245                 250                 255

Lys Lys His Lys Tyr Asp Ala Glu Tyr Tyr Ile Glu Asn Gln Val Leu
                260                 265                 270

Pro Ala Val Leu Arg Ile Leu Glu Gly Phe Gly Tyr Arg Lys Glu Asp
                275                 280                 285

Leu Arg Tyr Gln Lys Thr Arg Gln Val Gly Leu Thr Ser Trp Leu Asn
                290                 295                 300

Ile Lys Lys Ser
305

<210> SEQ ID NO 163
<211> LENGTH: 51
<212> TYPE: DNA
<213> ORGANISM: Pyrococcus furiosus

<400> SEQUENCE: 163
gaaagacaaa agattaagac aaaatgaagg aaactcaaga tcctatagaa a          51

<210> SEQ ID NO 164
<211> LENGTH: 4
<212> TYPE: PRT
<213> ORGANISM: Pyrococcus furiosus

<400> SEQUENCE: 164

Lys Thr Lys Asp
1

<210> SEQ ID NO 165
<211> LENGTH: 12
<212> TYPE: PRT
<213> ORGANISM: Pyrococcus furiosus

<400> SEQUENCE: 165
```

```
Asp Lys Met Lys Glu Thr Gln Asp Pro Ile Glu Lys
1               5                   10

<210> SEQ ID NO 166
<211> LENGTH: 8
<212> TYPE: PRT
<213> ORGANISM: Pyrococcus furiosus

<400> SEQUENCE: 166

Glu Arg Gln Lys Ile Lys Thr Lys
1               5

<210> SEQ ID NO 167
<211> LENGTH: 6
<212> TYPE: PRT
<213> ORGANISM: Pyrococcus furiosus

<400> SEQUENCE: 167

Arg Lys Leu Lys Ile Leu
1               5
```

COMPOSITIONS AND METHODS USING SPLIT POLYMERASES

CROSS-REFERENCE TO RELATED APPLICATIONS

This application relies on the disclosure of and claims the benefit of the filing dates of U.S. provisional patent application No. 60/878,020, filed on 29 Dec. 2006, and U.S. provisional patent application No. 60/881,694, filed on 19 Jan. 2007, the entire disclosures of both of which are hereby incorporated herein by reference.

BACKGROUND OF THE INVENTION

1. Field of the Invention

The present invention relates to compositions and methods utilizing split polymerases composed of at least two discrete polypeptides that stably associate to form a single polymerase. The invention further relates to nucleic acid constructs for expressing the split polymerases of the invention, and methods for making the split polymerases of the invention. The enzymes of the invention are useful in many applications calling for DNA synthesis.

2. Description of Related Art

Detectable labeling of nucleic acids is required for many applications in molecular biology, including applications for research as well as clinical diagnostic techniques. A commonly used method of labeling nucleic acids uses one or more unconventional nucleotides and a polymerase enzyme that catalyzes the template-dependent incorporation of the unconventional nucleotide(s) into the newly synthesized complementary strand.

The ability of a DNA polymerase to incorporate the correct deoxynucleotide is the basis for high fidelity DNA replication in vivo. Amino acids within the active site of polymerases form a specific binding pocket that favors the placement of the correct complementary nucleotide opposite the template nucleotide. If a mismatched nucleotide, ribonucleotide, or nucleotide analog fills that position, the precise alignment of the amino acids contacting the incoming nucleotide may be distorted into a position unfavorable for DNA polymerization. Because of this, the unconventional nucleotides or nucleotide analogs used to label DNA tend to be incorporated into the elongated strand less efficiently than do the standard deoxynucleotide triphosphates (dNTPs; the so-called "standard" dNTPs include deoxyadenosine triphosphate (dATP), deoxycytosine triphosphate (dCTP), deoxyguanosine triphosphate (dGTP), and thymidine triphosphate (dTTP, also called TTP)).

The reduced efficiency with which unconventional nucleotides are incorporated by the polymerase increases the amount of the unconventional nucleotide necessary for DNA labeling. The reduced efficiency of incorporation of a particular nucleotide can also adversely affect the performance of techniques or assays, such as DNA sequencing, which depend upon unbiased incorporation of unconventional nucleotides for homogeneous signal strength.

The identity and exact arrangement of the amino acids of a DNA polymerase that contact an incoming nucleotide triphosphate determine the nature of the nucleotides, both conventional and unconventional, that may be incorporated by that polymerase enzyme. Changes in the exact placement of the amino acids that contact the incoming nucleotide triphosphate at any stage of binding or chain elongation can dramatically alter the polymerase's capacity for utilization of unusual or unconventional nucleotides. Sometimes changes in distant amino acids can influence the incorporation of nucleotide analogs due to indirect global or structural effects. Polymerases with increased capacity to incorporate nucleotide analogs are useful for labeling DNA or RNA strands with nucleotides modified with signal moieties such as dyes, reactive groups or unstable isotopes.

In addition to labeled nucleotides, an extremely important class of modified nucleotides is the dideoxynucleotides. The so-called "Sanger" or "dideoxy" DNA sequencing method (Sanger et al., 1977, *Proc. Natl. Acad. Sci. USA* 74: 5463, which is incorporated herein by reference) relies upon the template-directed incorporation of nucleotides onto an annealed primer by a DNA polymerase from a mixture containing deoxy- and dideoxynucleotides. The incorporation of a dideoxynucleotide results in chain termination, the inability of the enzyme to catalyze further extension of that strand. Electrophoretic separation of reaction products results in a "ladder" of extension products wherein each extension product ends in a particular dideoxynucleotide complementary to the nucleotide opposite it in the template. The distance of the dideoxynucleotide analog from the primer is indicated by the length of the extension product. When four reactions, each containing one of the four dideoxynucleotide analogs ddA, ddC, ddG, or ddT (ddNTPs) are separated on the same gel, the sequence of the template may be read directly from the ladder patterns. Extension products may be detected in several ways, including for example, the inclusion of isotopically- or fluorescently-labeled primers, deoxynucleotide triphosphates or dideoxynucleotide triphosphates in the reaction.

Fluorescent labeling has the advantages of faster data collection, since detection may be performed while the gel is running, and longer reads of sequence data from a single reaction and gel are possible. Further, fluorescent sequence detection has allowed sequencing to be performed in a single reaction tube containing four differentially-labeled fluorescent dye terminators (the so-called dye-terminator method, Lee et al., 1992, *Nucleic Acids Res.* 20: 2471, incorporated herein by reference).

A desirable quality of a polymerase useful for DNA sequencing is improved incorporation of dideoxynucleotides. Improved incorporation of dideoxynucleotides can make processes such as DNA sequencing more cost effective by reducing the requirement for expensive radioactive or fluorescent dye-labeled dideoxynucleotides. Moreover, unbiased dideoxynucleotide incorporation provides improved signal uniformity, leading to increased accuracy of base determination. The even signal output further allows subtle sequence differences caused by factors like allelic variation to be detected. Allelic variation, which produces two different half strength signals at the position of relevance, can easily be concealed by the varied signal strengths caused by polymerases with non-uniform ddNTP utilization.

Dual-labeled nucleotide analogs (see, e.g., US Patent Publication 20040014096) are nucleotide analogs that have both fluorescent and quenching groups attached, resulting in a molecule that is non-fluorescent before it is incorporated, whereby the fluorescent group is cleaved off of the nucleotide. Dual-labeled nucleotide analogs containing both a fluorescent moiety and a quencher moiety can be used as chain terminators in place of dideoxynucleotide chain terminators commonly used in the art. A chain terminating dual-labeled nucleotide analog has a sugar moiety which is, or is equivalent to a 2',3'-dideoxypyrofuranose molecule. The dual-labeled nucleotide analogs have the advantage of reduced background fluorescence compared with more traditionally labeled chain terminating nucleotide analogs. Since the dual-labeled nucleotide analogs do not emit a fluorescent signal unless they are incorporated into a polynucleotide chain, background fluorescence resulting from unincorporated analogs is significantly reduced. Dual-labeled nucleotide analogs are also useful for monitoring progress of real time amplification in quantitative PCR (QPCR) methods.

The use of such dual-labeled analogs is limited by the low utilization of such analogs by polymerases. In order to promote incorporation of the analogs into the growing strand, relatively high concentrations of the analogs must be used. The analogs are expensive and decrease the rate of extension, potentially decreasing processivity of the polymerase. High concentrations of the dual-labeled analogs can also result in increased background signal and inter-molecular quenching. A polymerase with reduced discrimination towards dual-labeled nucleotide analogs could result in decreased cost by decreasing the amount of analog required per reaction, while increasing fluorescent signal and sensitivity in both QPCR and sequencing reactions.

Incorporation of ribonucleotides by the native form of DNA polymerase is a rare event. Mutants that incorporate higher levels of ribonucleotides can be used for applications such as sequencing by partial ribosubstitution. In this system, a mixture of ribonucleotides and deoxynucleotides corresponding to the same base are incorporated by the mutant polymerase (Barnes, 1978 *J. Mol. Biol.* 119:83-99). When the ribosequencing reactions are exposed to alkaline conditions and heat, fragmentation of the extended strand occurs. If the reactions for all four bases are separated on a denaturing acrylamide gel, they produce a sequencing ladder. The applicants of the present patent application have realized that there is a need in the art for polymerase mutants with higher utilization of ribonucleotides for this alternative method of sequencing.

Alternatively, the incorporation of ribonucleotides followed by alkaline hydrolysis can be utilized in a system that requires random cleavage of DNA molecules such as DNA shuffling ((Stemmer, 1994, *Nature*, 370: 389-391), which has also been called molecular breeding, sexual PCR, and directed evolution.

Another desirable quality in a DNA labeling enzyme is thermal stability. DNA polymerases exhibiting thermal stability have revolutionized many aspects of molecular biology and clinical diagnostics since the development of the polymerase chain reaction (PCR), which uses cycles of thermal denaturation, primer annealing, and enzymatic primer extension to amplify DNA templates. The prototype thermostable DNA polymerase is Taq polymerase, originally isolated from the thermophilic eubacterium *Thermus aquaticus*. So-called "cycle sequencing" reactions using thermostable DNA polymerases have the advantage of requiring smaller amounts of starting template relative to conventional (i.e., non-cycle) sequencing reactions.

There are three major families of DNA polymerases, termed families A, B, and C. The classification of a polymerase into one of these three families is based on structural similarity of a given polymerase to *E. coli* DNA polymerase I (Family A), II (Family B) or III (Family C). As examples, Family A DNA polymerases include, but are not limited to Klenow DNA polymerase, *Thermus aquaticus* DNA polymerase I (Taq polymerase) and bacteriophage T7 DNA polymerase; Family B DNA polymerases, formerly known as α-family polymerases (Braithwaite and Ito, 1991, *Nuc. Acids Res.* 19:4045), include, but are not limited to human α, δ and ε DNA polymerases, T4, RB69, and Φ29 bacteriophage DNA polymerases, and *Pyrococcus furiosus* DNA polymerase (Pfu polymerase); and family C DNA polymerases include, but are not limited to *Bacillus subtilis* DNA polymerase III, and *E. coli* DNA polymerase III α and ε subunits (listed as products of the dnaE and dnaQ genes, respectively, by Braithwaite and Ito, 1993, *Nucleic Acids Res.* 21: 787). An alignment of DNA polymerase protein sequences of each family across a broad spectrum of archaeal, bacterial, viral, and eukaryotic organisms is presented in Braithwaite and Ito (1993, supra), which is incorporated herein by reference.

As shown in Braithwaite and Ito (1993, supra), within regions I, II, and III, a set of highly conserved residues form three chemically distinct clusters consisting of exposed, aromatic residues (RB69 numbering, Y416, Y567, and Y391), negatively charged residues (D621, D623, D411, D684, and E686), and a positively charged cluster (K560, R481, and K486). Comparison with a Taq polymerase-DNA complex suggests that these three clusters encompass the region in which the primer terminus and the incoming dNTP would be expected to bind. Modeling of the dNTP and primer template complex in RB69 was carried out using the atomic coordinates of the reverse transcriptase c-DNA co-crystal. The model predicts the RB69 Y416 packs under the deoxyribose portion of the dNTP. Tyrosine at this position has been implicated in ribose selectivity, contributing to polymerase discrimination between ribonucleotides and deoxyribonucleotides in mammalian reverse transcriptases (Y115) (Gao et al., 1997, *Proc. Natl. Acad. Sci. USA* 94:407; Joyce, 1994, *Proc. Natl. Acad. Sci. USA* 94:1619).

Region III of the Family B polymerases (also referred to as motif B) has also been demonstrated to play a role in nucleotide recognition. This region, which corresponds to AA 487 to 495 of JDF-3 Family B DNA polymerase, has a consensus sequence $KX_3$ NSXYG (SEQ ID NO:1) (Jung et al., 1990, supra; Blasco et al., 1992, supra; Dong et al., 1993, *J. Biol. Chem.* 268:21163; Zhu et al., 1994, *Biochem. Biophys. Acta* 1219:260; Dong and Wang, 1995, *J. Biol. Chem.* 270:21563), and is functionally, but not structurally (Wang et al., 1997, supra), analogous to $KX_3$ (F/Y)$GX_2$ YG (SEQ ID NO: 2) in helix O of the Family A DNA polymerases. In Family A DNA polymerases, such as the fragment and Taq DNA polymerases, the O helix contains amino acids that play a major role in dNTP binding (Astatke al., 1998, *J. Mol. Biol.* 278: 147; Astatke et al., 1995, *J. Biol. Chem.* 270:1945; Polesky et al., 1992, 1. *Biol. Chem.* 267:8417; Polesky et al., 1990, *J. Biol. Chem.* 265:14579; Pandey et al., 1994, *J. Biol. Chem.* 269:13259; Kaushik et al., 1996, *Biochem.* 35:7256). Specifically, helix O contains the F (F763 in the fragment; F667 in Taq) which confers ddNTP discrimination in Family A DNA polymerases ($KX_3$(F/Y)$GX_2$YG; SEQ ID NO: 2) (Tabor and Richardson, 1995, supra).

The term used to describe the tendency of DNA polymerases to not incorporate unnatural nucleotides into the nascent DNA polymer is "discrimination". In Family A DNA polymerases, the effective discrimination against incorporation of dideoxynucleotide analogs is largely associated with a single amino acid residue. The majority of enzymes from the Family A DNA polymerases have a phenylalanine (phe or F) residue at the position equivalent to F762 in *E. coli* fragment of DNA polymerase and demonstrate a strong discrimination against dideoxynucleotides. A few polymerases (e.g. T7 DNA polymerase) have a tyrosine (tyr or Y) residue at the corresponding position and exhibit relatively weak discrimination against dideoxynucleotides. Family A polymerases with tyrosine at this position readily incorporate dideoxynucleotides at levels equal to or only slightly different from the levels at which they incorporate deoxynucleotides. Conversion of the tyrosine or phenylalanine residues in the site responsible for discrimination reverses the dideoxynucleotide discrimination profile of the Family A enzymes (Tabor and Richardson, 1995, *Proc. Natl. Acad. Sci. USA* 92:6449).

Among the thermostable DNA polymerases, a mutant form of the Family A DNA polymerase from *Thermus aquaticus*, known as AmpliTaq FS® (Perkin Elmer), contains a F667Y mutation at the position equivalent to F762 of DNA polymerase and exhibits increased dideoxynucleotide uptake (i.e., reduced discrimination against ddNTPs) relative to the wild-type enzyme. The reduced discrimination for dideoxynucleotide uptake makes it more useful for fluorescent and labeled dideoxynucleotide sequencing than the wild-type enzyme.

The F667Y mutant of Taq DNA polymerase is not suited for use with fluorescein-labeled dideoxynucleotides, necessitating the use of rhodamine dye terminators. Rhodamine dye terminators that are currently utilized with Taq sequencing reactions stabilize DNA secondary structure, causing compression of signal. Efforts to eliminate compression problems have resulted in systems that use high amounts of the nucleotide analog deoxyinosine triphosphate (dITP) in place of deoxyguanosine triphosphate. While incorporation of (dITP) reduces the compression of the signal, the presence of dITP in the reaction produces additional complications including lowered reaction temperatures and increased reaction times. Additionally, the use of rhodamine dyes in sequencing requires undesirable post-reaction purification (Brandis, 1999 *Nuc. Acid Res.* 27:1912). In the Family A *E. coli* DNA polymerase I fragment, modification of a conserved glutamate residue (E7 10) reduces discrimination against ribonucleotides (Astatke et al., 1998, *Proc. Natl. Acad. Sci. USA* 96:3402).

In Family A DNA polymerases, such as the Klenow fragment and Taq DNA polymerases, the O helix contains amino acids that play a major role in dNTP binding (Astatke et al., 1998, *J. Mol. Biol.* 278:147; Astatke et al., 1995, 1 *Biol. Chem.* 270:1945; Polesky et al., 1992, *J. Biol. Chem.* 267:84 17; Polesky et al., 1990, *J. Biol. Chem.* 265:14579; Pandey et al., 1994, *J. Biol. Chem.* 269:13259; Kaushik et al., 1996, *Biochem.* 35:7256). Specifically, helix O contains the F (F763 in the Klenow fragment; F667 in Taq) which confers ddNTP discrimination in Family A DNA polymerases ($KX_3(F/Y)GX_2YG$; SEQ ID NO: 2) (Tabor and Richardson, 1995, supra).

With the exception of the position of acidic residues involved in catalysis in the so-called palm domain, Family B DNA polymerases exhibit substantially different structure compared to Family A DNA polymerases (Wang et al., 1997, *Cell* 89:1087; Hopfner et al., 1999, *Proc. Natl. Acad. Sci. USA* 96:3600). The unique structure of Family B DNA polymerases may permit a completely different spectrum of interactions with nucleotide analogs, perhaps allowing utilization of analogs that are unsuitable for use with Family A DNA polymerases due to structural constraints. Thermostable Family B DNA polymerases have been identified in hyperthermophilic archaea. These organisms grow at temperatures higher than 91° C. and their enzymes demonstrate greater thermostability (Mathur et al., 1992, *Stratagies* 5:11) than the thermophilic eubacterial Family A DNA polymerases. Alignments of a number of Family B DNA polymerases can be seen in FIGS. 2 and 6.

Structural analysis of A family polymerases, Pol β, HIV reverse transcriptase, and the B family polymerase gp43 demonstrate that all share a functional polymerase structure which resembles a right hand built by the palm, fingers, and thumb domains (see Brautigman and Steitz, 1998, *Curr Opin Struc Biol* 8:54 for review, incorporated herein by reference). The palm domains show a similar topology among all families, except Pol β. The fingers and thumb domain are highly diverse among the different families, and although the thumb domains are mainly alpha-helical, the detailed structures of the domains are not related. Perhaps surprisingly, the fingers and thumb domains in all four families have arisen from different ancestors.

As polymerases are used for many laboratory applications, a number of polymerases have been developed to have properties that are desirable for a variety of laboratory applications. For example, mutations at sites corresponding to amino acids E141 and D143 in *Pyrococcus furiosus* (Pfu) (SEQ ID NO: 3) are known to eliminate 3 'to 5' exonuclease activity. Mutations at sites corresponding to amino acids L409, Y410, P411, R461, K465, Q472, A486, R488, L490, A491, N492, Y495, and Y497 are known to reduce nucleotide discrimination in polymerases (see, e.g., U.S. Pat. No. 6,946,273, U.S. Pat. No. 6,333,183, U.S. Pat. No. 5,882,904, U.S. Pat. No. 5,827,716, Yang et al. 1999 *Biochemistry* 38:8094, Gardner and Jack, 1999 *Nucleic Acids Research* 27:2545, incorporated herein by reference). A mutation at amino acid V93, specifically V93R, (Pfu numbering) is known to disrupt uracil detection. A non-sequence-specific DNA binding domain, such as the DNA binding domain of Sso7d, can be incorporated into a polymerase to increase the processivity of the polymerase. Moreover, sites corresponding to the amino acids provided in Pfu DNA polymerase can be easily mapped onto other Family B polymerase sequences using published sequence alignments (e.g., Braithwaite and Ito, 1993, supra; Brautigman and Steitz, 1998, supra; and Hopfner et al., 1999, supra; Biles and Connolly, 2004, supra; Gardner and Jack, 1999, supra; Edgell et al., 1997. *J. Bacteriol.* 179:2632) or any of a number of sequence alignment programs such as BLAST).

Introducing splits into enzymes as a strategy to broaden substrate utilization is very different from currently used approaches, which are based on amino acid replacements. There are four examples of natural splits in the polymerase family. The T4-phage family includes five members that contain splits within the fingers domain (Petrov et al (2006) *J Mol Biol.* 361:46-68). These splits occur naturally and it is unknown whether the split enzymes exhibit unique characteristics such as broader substrate utilization compared to non-split T4-like phage DNA polymerases. The second natural split is the one reported in the archaeal *Methanobacterium thermoautotrophicum* DNA polymerase (Kelman et al (99) JBC 274:28751-61). This split also occurs naturally and is found downstream (outside) of the fingers domain. This split has also not been characterized in terms of whether it exhibits broader substrate utilization compared to non-split archaeal DNA polymerases. In the two examples of natural splits, the polymerase fragments are encoded by distinct genes that are separated by anywhere from 2 bp to 3 kb (T4-like phage) to 85 Kbp (Mth) in the genome. The third example of a natural split is in the archaeal DNA polymerase gene. However, this split occurs within a mini-intein of *N. equitans* DNA polymerase, where the polymerase is expressed as two separate polypeptides, which are then spliced together (trans-splicing) to create a full length polymerase. The split is located outside of the fingers domain and has additional sequence (inteins) to stabilize the protein until the splicing event is complete (Choi et al. (06) *J. Mol. Biol.* 356:1093-1106) The fourth example of a natural split is found in the archael *Sulfolobus solfataricus* DNA polymerase B1 (Savino et al. (2004) *Structure.* 12:2001-2008). In this case, the polymerase is proteolytically cleaved to produce two active fragments, a 50 kD fragment with DNA polymerase activity and a 40 kD fragment with exonuclease activity. However, the authors do not state whether these activities are reduced relative to wild type nor have the proteolytic fragments been tested for alternative or improved activities. The split in this example is also found outside the fingers domain.

Polymerases having reduced discrimination are useful for applications that require incorporation of non-conventional nucleic acids. Such applications include the labeling of nucleic acid arrays, often referred to as nucleic acid or DNA "chips", in the simultaneous analyses of multiple different nucleic acid sequences. Many of these applications, such as those described in U.S. Pat. No. 5,882,904 (Riedl et al.), will benefit from DNA polymerases exhibiting reduced discrimination against the incorporation of non-conventional nucleotides, particularly fluorescently-labeled non-conventional nucleotides. Applications being addressed in the chip format include DNA sequencing and mutation detection, among others. Examples include the "mini-sequencing" methods (e.g., Pastinen et al., 1997, *Genome Res.* 7: 606; Syvanen, 1999, *Human Mutation* 13: 1-10) and the arrayed primer extension (APEX) mutation detection method (Shumaker et al., 1996, *Hum. Mutat.* 7: 346).

The present applicants have recognized that there is a need in the art for a non-discriminating DNA polymerase for use in chip or gel based mini-sequencing systems. Such a system would advantageously permit detection of multiplexed single nucleotide polymorphisms (SNPs) and allow for quantitative genotyping. Identification of sequence variation permits the diagnosis and treatment of genetic disorders, predisposition to multifactorial diseases, and sensitivity to new or existing pharmaceutical products.

Additionally, the applicants have recognized that there is a need in the art for DNA polymerases with reduced discrimination against unconventional nucleotides. They have realized that there is particularly a need in the art for thermostable DNA polymerases exhibiting reduced discrimination against dideoxynucleotides, and further, for DNA polymerases exhibiting reduced discrimination against fluorescently labeled dideoxynucleotides. They have also recognized that there is a particular need for thermostable DNA polymerases exhibiting reduced discrimination against nucleotide analogs containing modifications in the polyphosphate portion of a nucleotide, especially dual-labeled oligonucleotides.

SUMMARY OF THE INVENTION

The present invention relates to enzymes into which one or more non-naturally occurring splits have been introduced to broaden substrate utilization of the enzyme. The invention can be applied to many different types of enzymes. Without limiting the invention, such a non-natural split is expected to increase flexibility between sub-domains and reduce constraints on substrate interactions. In the class of enzymes called polymerases, a split in the polymerase has been found to modify activity of the polymerase. Specifically, enzymes of this class have reduced discrimination, especially for dual-labeled nucleotide analogs, which makes them useful for applications such as QPCR and nucleic acid sequencing.

In one aspect, the present invention provides non-natural polymerases containing at least one split, and compositions comprising such polymerases. These include, but are not limited to, reverse transcriptase, RNA polymerase, DNA polymerase, and DNA primase. In one embodiment, the present invention provides split polymerases from the A Family polymerases, such as the Family A polymerase from *Thermus aquaticus*. In another embodiment, the present invention includes split polymerases from the archaeal B Family polymerases, such as *Thermococcus litoralis* (Vent) DNA polymerase, *Pyrococcus furiosus* (Pfu) DNA polymerase, *Thermococcus* JDF-3 DNA polymerase, *Pyrococcus horikoshii* (Pho) DNA polymerase, *Thermococcus gorgonarius* (Tgo) DNA polymerase, *Pyrococcus* sp. GBD (Deep Vent) DNA polymerase, *Sulfolobus solfataricus* DNA polymerase, and archaeal polymerase I. In still another embodiment, the split polymerase is a chimeric polymerase, a combination of an N-terminal fragment from a first polymerase, and a C-terminal fragment of a second polymerase. In a preferred embodiment, the fragments are from the same family of polymerases (e.g., both Family B polymerases).

The split polymerases may be comprised of other modifications or mutations in the coding sequence, either at the region of the split and/or at regions distant from where the split occurs to further improve non-natural substrate utilization, to improve stability of the split polymerase, to remove 3'-5' exonuclease activity, to eliminate uracil detection, to increase processivity, etc. Other additions to the coding sequence may allow insertion of proteolytic cleavage sites to make a post-translational split of the polymerase, insertion of "slippery sequences" that viruses use to cause frameshifts that can result in a translational start and stop (process is called programmed ribosomal frameshifting; Hansen et al., 2007, *PNAS* 104 (14):5830-5835), or may allow other ways of making a split polymerase. The polymerases can be provided as isolated or purified substances, or as part of compositions that include one or more additional substances (e.g., water or an aqueous solution). As used herein, the terms "isolated" and "purified" are used interchangeably to indicate that the subject protein, nucleic acid, etc. has been removed from its natural environment and preferably has been removed from the presence of one, some, substantially all, or all of the substances that are found to be present in the natural environment of the protein, nucleic acid, etc.

In another aspect, the invention relates to nucleic acids encoding split polymerases of the invention. A split polymerase is understood to be a polymerase expressed as at least two discrete polypeptides (e.g., an N-terminal fragment and a C-terminal fragment) that associate non-covalently to form a single, functional polymerase molecule. In a preferred embodiment, the split polymerases of the invention are encoded by a polycistronic operon in which expression of each portion or cistron of the split polymerase is translationally coupled to translation of at least one other portion of the split polymerase. In one embodiment, the polycistronic coding sequence contains at least one ribosomal reinitiation signal proximal to a frameshift termination codon. In an alternative embodiment, the split polymerases of the invention are encoded by two coding sequences that are present on two separate plasmids in the same host cell, or in two separate host cells. The nucleic acids can be provided as purified or isolated substances, alone or in compositions comprising at least one other substance (e.g., water or an aqueous solution).

In an additional aspect, the invention provides methods of making a split polymerase of the invention. In general, the method comprises introducing into a host cell a nucleic acid encoding a split polymerase wherein the coding region is operably linked to a promoter, and culturing the cell under conditions that permit production of the split polymerase. In a preferred embodiment, the split polymerase is encoded by a polycistronic operon in which expression of each portion or cistron of the split polymerase is translationally coupled to translation of at least one other portion of the split polymerase. Stated another way, the method comprises using a polycistronic coding sequence operably linked to a promoter sequence functional in a host cell into which the coding sequence is inserted. In an alternative embodiment, the split polymerase of the invention is encoded by two coding sequences that are present on two separate plasmids in the same host cell, or in two separate host cells. In both embodiments, each segment of the split polymerase is translated and the segments then assemble together, either in vivo or in vitro, to form the complete split polymerase.

In yet a further aspect, the invention provides methods of using the split polymerase of the invention. A split polymerase of the invention can be used for nucleic acid amplification, nucleic acid sequencing, quantitative PCR (QPCR), nucleic acid labeling, for synthesis with modified primers or templates, or in any reaction that requires a polymerase. In general, these embodiments are particularly suited for the use of non-conventional nucleotides and nucleotide analogs such as dual-labeled nucleotide analogs.

In embodiments, the methods of the invention are used to increase utilization (e.g., binding and/or incorporation into a growing nucleic acid chain) of non-natural nucleotides. This can be accomplished by splitting a polymerase in such a way that the polymerase shows increased activity for non-natural nucleotides. Higher nucleotide analog uptake can also be increased by combining the split with other mutations in the amino acid sequence compared to using the split or the amino acid replacement alone.

In another aspect, the present invention provides compositions and kits comprising at least one split polymerase of the invention. Compositions may comprise at least one molecule of split polymerase of the invention along with one or more substances, which are typically substances which aid in the methods of the invention. In general, a kit according to the invention contains a sufficient amount of split polymerase to allow at least one method of using the split polymerase to occur and is comprised of at least one container. Kits generally comprise a polymerase or nucleic acid of the invention and optionally one or more other components useful for practicing a method of the invention, where the components of the kits are contained in one or more containers packaged in combination for ease of storage and use. Multiple containers are often present to allow for practice of methods of the invention multiple times.

BRIEF DESCRIPTION OF THE DRAWINGS

The accompanying drawings, which constitute a part of this specification, illustrate several embodiments of the invention and, together with the written description, serve to explain various principles of the invention. It is to be understood that the drawings are not to be construed as a limitation on the scope or content of the invention.

FIG. 1 shows a CLUSTAL W multiple sequence alignment of a series of finger domains from DNA Family B polymerases (SEQ ID NOS 106-146, respectively, in order of appearance).

FIGS. 2A-2B show an alignment of the amino acid sequences of a number of family B DNA polymerases. A. from *Pyrococcus furiosus* (Pfu) (SEQ ID NO: 3); Deep Vent *Pyrococcus* sp (SEQ ID NO: 7); *Pyrococcus horikoshii* (Pho) (SEQ ID NO: 8); *Thermococcus gorgonarius* (Tgo) (SEQ ID NO: 9); *Thermococcus kodakarensis* (Archaeal) (SEQ ID NO: 10) (known as Archaeal DNA polymerase I); JDF-3 *Thermococcus* sp. (SEQ ID NO: 11); 9° N *Thermococcus* sp. (SEQ ID NO: 12); and Vent *Thermococcus litoralis* (SEQ ID NO: 13). B. The consensus amino acids of the fingers motif SEQ ID NOS: 5, and 6 are indicated. Figure also discloses residues 449-492 of SEQ ID NO: 7, residues 449-492 of SEQ ID NO: 8, residues 449-492 of SEQ ID NO: 3, residues 448-491 of SEQ ID NO: 9, residues 448-491 of SEQ ID NO: 10, residues 448-491 of SEQ ID NO: 11, residues 448-491 of SEQ ID NO: 12, residues 451-494 of SEQ ID NO: 13.

FIGS. 3C-3E show three splits after amino acid 466 with a methionine residue inserted after the split to promote translation reinitiation (SEQ ID NOS 149-150, 149, 151-153, respectively, in order of appearance). In FIG. 3D, a methionine was mutated to provide a single reinitiation site.

FIG. 5 shows the amino acid coding sequence for JdF-3 Z2, a mutant with a split after amino acid 469 that results in a 10 amino acid insertion at the C-terminus of the N-terminal fragment. Panel A depicts the amino fragment of the split (SEQ ID NO: 97), Panel B shows the shift from the translational reading frame of 1 to 3 when the ribosome encounters the stop codon (TAG) and reinitiates on the ATG codon (SEQ ID NOS 158-160, respectively, in order of appearance), and Panel C depicts the carboxy fragment of the split (SEQ ID NO: 98).

FIG. 6 shows an alignment of amino acid sequences a number of family B DNA polymerases from *Pyrococcus horikoshii* (Pho) (SEQ ID NO:62) (Accession: NP_143776.1 GI:14591688); DNA polymerase 1 *Pyrococcus abyssi* (Pab polymerase) (SEQ ID NO: 60) (Accession: P77916 GI:6648073); DNA-dependent DNA polymerase; endonuclease [*Pyrococcus* sp.] (SEQ ID NO: 61) (Accession: CAA90887.1 GI:1495770); Vent *Thermococcus litoralis* (SEQ ID NO: 57) (Accession: P303 17 GI:232020); Deep Vent *Pyrococcus* sp (SEQ ID NO: 64) (Accession: Q51334 GI:2494186); 9° N *Thermococcus* sp. (90N-7) (SEQ ID NO: 67) (Accession: 1QHTA GI:8569297); *Thermococcus gorgonarius* (Tgo) (SEQ ID NO: 69) (Accession: 1TGO_A GI:4699806); *Thermococcus aggregans* (Tfu) (SEQ ID NO: 59) (Accession: 033845 GI:3913524); *Pyrococcus* sp. ST700 (ST700) (SEQ ID NO: 63) (Accession No. CAC 12847.1 GI:10799869); *Pyrococcus furiosus* (Pfu) (SEQ ID NO: 66) (Accession: AAL8 0336.1 01:18892147); DNA polymerase and endonucleases *Thermococcus* sp. GE8 (SEQ ID NO: 68) (Accession: CAC12850.1 GI:10799895); *Thermococcus litoralis* DNA dependent DNA polymerase (TLI) (SEQ ID NO: 58) (Accession: AAA72101.1 GI:348689); DNA-dependent polymerase precursor *Thermococcus* sp. NA1 (TSPNA1) (SEQ ID NO: 71) (Accession No: ABC1 1972.1 GI:83338486); DNA-directed DNA polymerase (EC 2.7.7.7) KOD, intein containing precursor *Pyrococcus* sp. (strain KOD1) (TSPKOD) (SEQ ID NO: 72) (Accession: ABC1 1972.1 GI:83338486); PolA precursor *Thermococcus zilligii* (TZI) (SEQ ID NO: 70) (Accession: ABD 14868.1 GI:86753389); *Thermococcus kodakarensis* (THY) (SEQ ID NO: 73) (Accession: 1WN7_A GI:73535447); *Pyrococcus glycovorans* (PGL) (SEQ ID NO: 65) (Accession: CAC 12849.1 GI:10799899); DNA polymerase II *Sulfolobus tokodai* str. 7 (SULFOTO) (SEQ ID NO: 74) (Accession: NP378066.1 GI: 15922397); and *Desulfurococcus* sp. Tok (TOK) (SEQ ID NO: 75) (Accession: 1D5AA GI:7546394).

FIG. 7 shows an amino acid alignment of the finger domain of a number of family B DNA polymerases from JDF-3 *Thermococcus* sp. (SEQ ID NO: 33); *Pyrococcus horikoshii* (Pho) (SEQ ID NO:34) (Accession: NP_143776.1 GI: 14591688); DNA polymerase 1 *Pyrococcus abyssi* (Pab polymerase) (SEQ ID NO: 35) (Accession: P779 16 01:6648073); DNA-dependent DNA polymerase; endonuclease [*Pyrococcus* sp. } (SEQ ID NO: 36) (Accession: CAA90887.1 GI: 1495770); Vent *Thermococcus litoralis* (SEQ ID NO: 37) (Accession: P303 17 GI:232020); Deep Vent *Pyrococcus* sp (SEQ ID NO: 38) (Accession: Q51334 GI:2494186); 9° N *Thermococcus* sp. (9ON-7) (SEQ ID NO: 39) (Accession: 1QHTA GI:8569297); *Thermococcus gorgonarius* (Tgo) (SEQ ID NO: 40) (Accession: 1TGO_A GI:4699806); *Thermococcus aggregans* (Tfu) (SEQ ID NO: 41) (Accession: 033845 GI:39 13524); *Pyrococcus* sp. ST700 (ST700) (SEQ ID NO: 42) (Accession No. CAC12847.1 01:10799869); *Pyrococcus furiosus* (Pfu) (SEQ ID NO: 43) (Accession: AAL80336.1 01:18892 147); DNA polymerase and endonucleases *Thermococcus* sp. GE8 (SEQ ID NO: 44) (Accession: CAC12850.1 01:10799895); *Thermococcus litoralis* DNA dependent DNA polymerase (TLI) (SEQ ID NO: 45) (Accession: AAA72 101.1 GI:348689); DNA-dependent polymerase precursor *hermococcus* sp. NA1 (TSPNA1) (SEQ ID NO: 46) (Accession No: ABCI 1972.1 01:83338486); DNA-directed DNA polymerase (EC 2.7.7.7) KOD, intein containing precursor—*Pyrococcus* sp. (strain KOD1) (TSPKOD) (SEQ ID NO: 47) (Accession: ABC1 1972.1 01:83338486); PolA precursor *Thermococcus zilligii* (TZI) (SEQ ID NO: 48) (Accession: ABD14868.1 GI:86753389); *Thermococcus kodakarensis* (THY) (SEQ ID NO: 49) (Accession: 1WN7_A GI:73535447); *Pyrococcus glycovorans* (PGL) (SEQ ID NO: 50) (Accession: CAC12849.1 01:10799899); DNA polymerase II *Sulfolobus tokodaz* str. 7 (SULFOTO) (SEQ ID NO: 51) (Accession: NP 378066.1 GI:15922397); and *Desulfurococcus* sp. Tok (TOK) (SEQ ID NO: 52) (Accession: 1D5AA GI:7546394). The consensus amino acids of the fingers motif SEQ ID NOS: 53 and 54 including DNA polymerase II *Sulfolobus tokodai* str. 7, and SEQ ID NOS: 55 and 56 excluding DNA polymerase II *Sulfolobus tokodai* str. 7 are indicated. In SEQ ID NOs: 54 and 56, B is M, V, L, or I; J is S or T; 0 is D or E; U is F or Y; Z is Q, K, or R; and X is any amino acid.

FIG. 8 depicts PCR amplification activity of several of the JdF-3 variants of the invention.

FIG. 9 shows the amino acid sequence of the amino fragment (Panel A) (SEQ ID NO: 161) and the carboxyl fragment (Panel B) (SEQ ID NO: 162) of the 4C11 DNA polymerase with an additional Q484R mutation.

FIG. 13 shows the amino acid sequence of the amino fragment (Panel A; Fragment I) (SEQ ID NO: 94), the shift from the translational reading frame of 1 to 3 when the ribosome encounters the stop codon (TGA) and reinitiates on the ATG codon (Panel B) (SEQ ID NOS 163-167, respectively, in order of appearance), and the carboxyl fragment (Panel C; Fragment II) (SEQ ID NO: 95) of clone SQ, a seamless split Pfu polymerase with an additional Q484R mutation.

DETAILED DESCRIPTION OF VARIOUS EMBODIMENTS OF THE INVENTION

Figures 2, 2A, 3, 4:
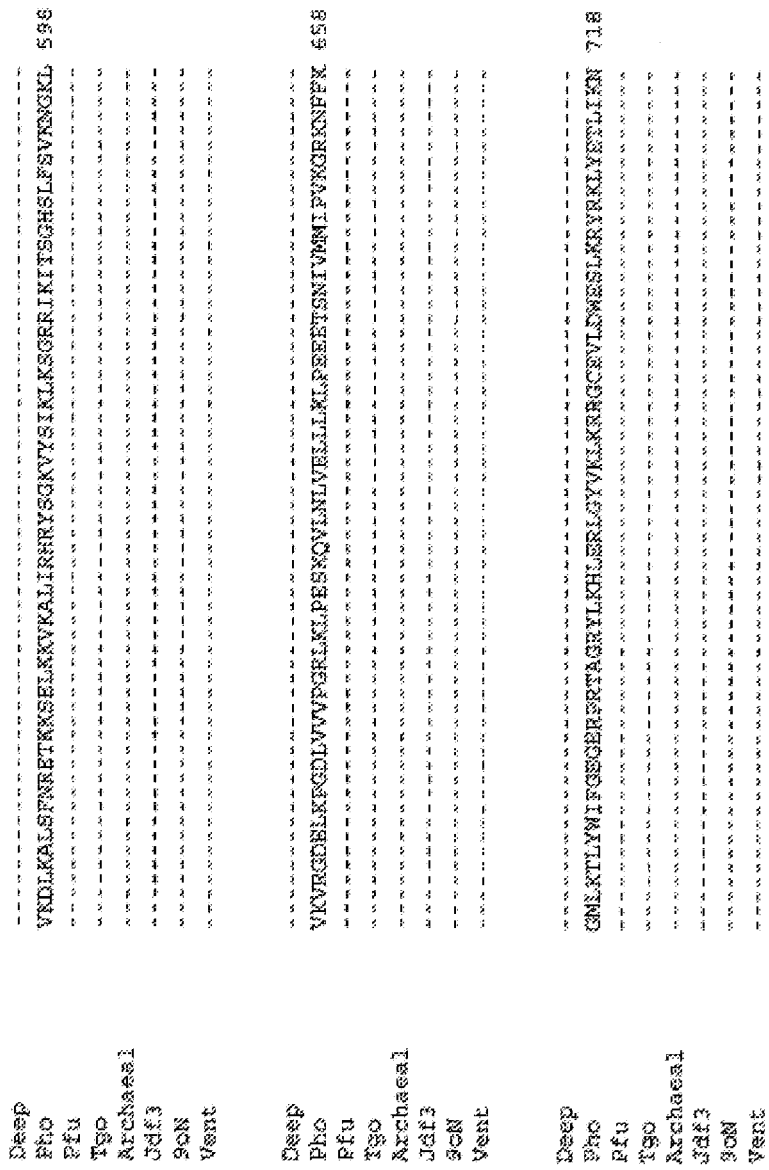

The ability to make mutations that alter protein structure has been a fundamental tool for elucidating protein function and harnessing proteins to complete reactions that they were previously unsuited for (Arnold, 1993, *FASEB J.* 7:744). Changes to alter enzyme characteristics such as rate, thermostability, pH optimum, substrate and end products in reactions are widely used in research and industry. These changes involve changing, adding, or deleting the amino acids of the targeted enzyme. A typically undesirable mutation in these schemes is a frameshift mutation in which the addition or deletion within the nucleotide sequence causes the ribosomal translation complex to read the triplet DNA codons out of register, leading to incorrect amino acid incorporation and early truncation. In most cases, early termination of translation leads to a non-functional or poorly functioning enzyme. As reported herein, the ability to strategically cause breaks in the DNA polymerase enzyme (through start and stop codons) not only maintained polymerase function but also gave the surprising ability to accept a greater range of substrates, perhaps through increased flexibility or repositioning of critical domains The present invention relates to introducing non-natural splits into enzymes to broaden substrate utilization. By "non-natural", it is meant that the split is introduced into a site where an enzyme is not known to split naturally. It thus does not address known, naturally split polymerases, for example, but does encompass such enzymes with additional or alternative split sites. The invention can be applied to many different types of enzymes. Without limiting the invention, such a non-natural split is expected to increase flexibility between sub-domains and reduce constraints on substrate interactions. One can envision that insertions at the split site (and a corresponding removal of the split) can have a similar effect to the split, by, for example, increasing flexibility between sub-domains. One can also envision that instead of making a non-natural split polymerase, a non-natural non-split polymerase may be formed. In this embodiment, a stop codon can be removed from between a pair of tandemly encoded heterodimeric enzymes to make a monomeric enzyme. For example, the Family D Pfu DNA polymerase naturally has the configuration of two tandemly encoded heterodimeric enzymes.

When the invention is used to split DNA polymerases, improved incorporation of non-natural substrates, such as dual label nucleotides (e.g., analogs as described in U.S. Patent Publication 20040014096), is seen. Splits can be introduced into the fingers domain, the 3' primer binding/editing site, duplex DNA binding site, single-stranded DNA template binding domain, etc. to improve utilization of modified primed-templates or to modify other activities of a polymerase. Also, splits near the domains involved in accessory protein binding could alter interaction with these factors, leading to differences in the assembly of replication complexes and altered activity. Accessory factors for polymerases include, but not limited to, clamp (PCNA), single stranded binding proteins (RPA) and helicases.

The invention comprises introducing splits in regions of the polymerase that interact with the incoming nucleotide, the 3' end of the primer, and/or the DNA template, or any other region that will improve some aspect of DNA polymerization, such as utilization of non-natural substrates.

One of the split polymerases of the invention, Pfu 4C11, is comprised of several mutations (1-467 V93R/A318T)/(468-775 Q484R/V604L/A662V-Sso7d7m). The nucleotide sequence that encodes Pfu 4C11 (see FIG. 3B, FIG. 9) contains a frameshift deletion that results in premature termination of translation, as compared to the wild-type sequence, and the re-initiation of translation after a one nucleotide upstream ribosomal shift without any amino acid loss or change. This process is known as translational coupling and is found in some polycistronic operons that link the translation of a second or even third gene to the regulation and transcription of the first (Aksoy et al., 1984, *J. Bacteriol* 157:363). Experimentation in *E. coli* has demonstrated that if translation is prematurely terminated, a methionine codon (AUG) within seven codons downstream can reinitiate translation without ribosome recycling factor or a Shine-Dalgarno consensus (Karamyshev, 2004, *Biochimie*. 12:933). The optimal translational coupling positions of the initiating and terminating codons have been documented as AUGA with the AUG start occurring before the UGA termination codon (Hopfner, 1999, supra). In the Pfu sequence, deletion of any single dA from nucleotides 1398 to 1402 results in the same frameshift/coupled translation end product. The truncated polypeptide (fragment I) corresponds to amino acids 1-467, while the new polypeptide corresponds to the former carboxy end of Pfu, beginning at Met 468 and encompassing amino acids 468-755 (fragment II).

Expression of the Pfu 1-467 and 468-775 fragments (produced by the frameshift), separately and together, has demonstrated that the carboxy protein domain beginning at amino acid 468 and encompassing amino acids 468-755 of SEQ ID NO: 3 is extremely insoluble when expressed apart from the amino fragment. When expressed together through coupled translation, the two peptides co-purify in equimolar amounts indicating that the fragments fold together in a stable complex. When the gene fragments encoding the two peptides are expressed in isolation from each other, the amino protein can be purified, although it does not appear to be as stable or soluble as the full-length native protein.

Figure 10:
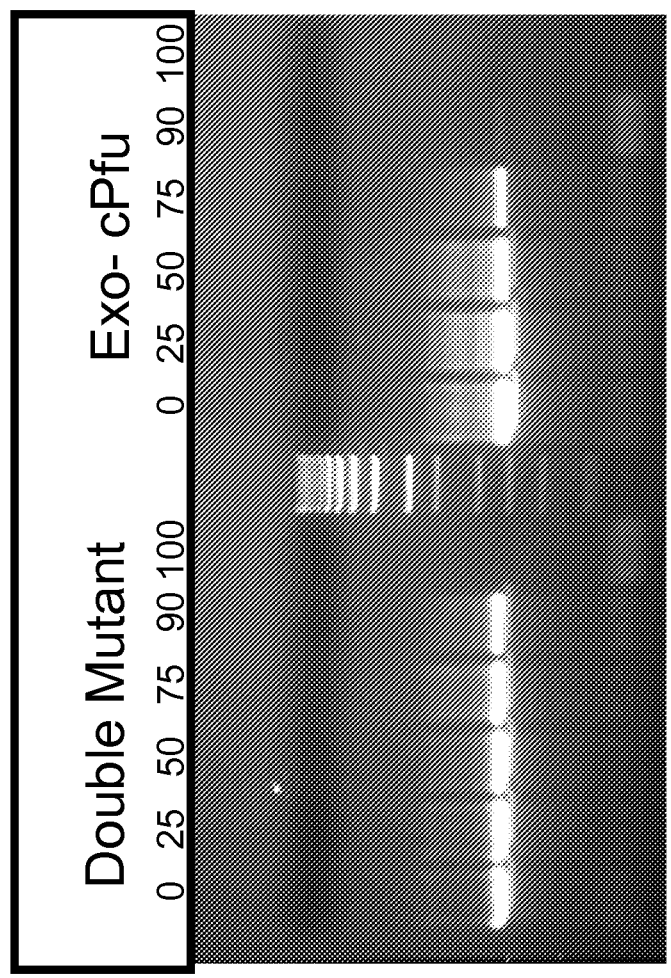
FIG. 10 shows PCR amplification activity of the frameshift (split) mutant with an additional Q484R mutation (double mutant) in the presence of a dCTP analog labeled with dabcyl at the gamma phosphate.

When the Q484R mutation is added to the split, there is a synergistic effect on nucleotide analog incorporation. The two mutations are in close proximity on opposite alpha helices near the tip of the finger. In Pfu, the split-inducing frameshift and Q484R mutations separately improve FAM-dCTP-Dabcyl uptake, while the combination of these two mutations produces even greater analog incorporation. The double mutant configuration particularly improves the uptake of dabcyl-dCTP modified at the gamma phosphate (FIG. 10). While not wishing to be bound by mechanism, it is proposed that incorporation of the bulky nucleotide analog is improved by loosening the nucleotide binding pocket when the finger folds over the incoming nucleotide.

The 4C11 split Pfu and Q484R double mutant are robust in PCR reactions and demonstrate no observable defect in activity. This is somewhat surprising in view of the fact that even small changes (especially in such a highly conserved domain) can be expected to be deleterious to activity.

Figure 11:
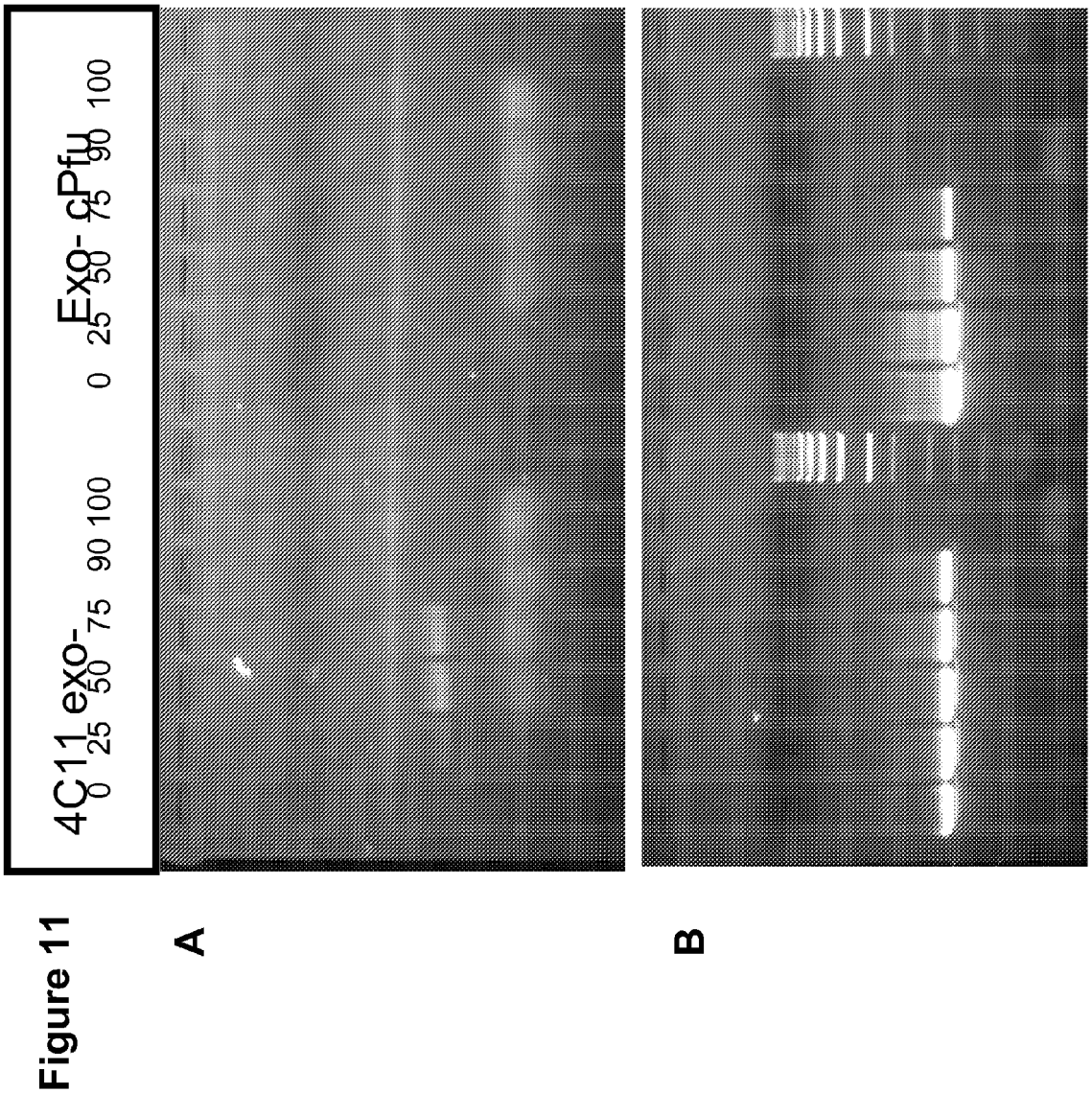
FIG. 11 depicts PCR amplification activity of the 4C11 mutant with the exo minus mutations in the presence of dCTP labeled with the nucleotide analog FCD. In panel A, the gel is unstained and the PCR products are revealed by the fluorescent label in the nucleotide. In panel B the gel is stained with ethidium bromide to show total DNA. The micromolar concentration of analog is shown above the well.

Splits were inserted into a wild-type and a mutant Q484R Pfu polymerase background, and were tested for the ability to incorporate the bulky nucleotide analog 5-aminoallyl-(5-FAM)-2'-deoxycytidine-5'-gamma-triphospho-$N^6$-(6-aminohexyl)-dabcyl (FCD) in an end point PCR assay. The reaction was run with a standard concentration of dATP, dGTP, and dTTP. The dCTP pool was a combination of dCTP and FCD, with the percentage of FCD in the dCTP pool varying from zero (100% dCTP:0% FCD) to one hundred percent (0% dCTP: 100% FCD). Electrophoresis of the PCR products on an agarose or acrylamide gel in the absence of ethidium bromide allowed the resultant FAM-labeled DNA products to be visualized with ultraviolet excitation and a green filter (FIG. 11). The gel was subsequently stained with ethidum bromide and visualized with an orange filter to reveal all DNA molecules. The wild type exo-minus Pfu was unable to incorporate the FCD analog, while the split Pfu Q484R double mutant showed an optimal uptake of FAM-dCMP at 50-75% FCD (under these conditions). In the present invention, "exo-minus" is defined as a polymerase comprising a D141A/E143A mutation (see, e.g., U.S. Pat. No. 5,489,523).

The split polymerases further containing a Q484R mutation were also tested in an exo-plus or exo-minus (not comprised of the D141A/E143A mutation and comprised of the D141A/E143A mutation, respectively) version of Pfu DNA polymerase. Because labeled analogs can be excised by an active 3' to 5' exonuclease, amplicons generated with exo-plus enzyme are less fluorescent than amplicons generated with exo-minus split Pfu Q484R, and free FAM-dCMP released by proofreading activity is readily visible on the gel. Therefore, split polymerases lacking 3' to 5' exo activity are preferred for use for incorporation of non-conventional nucleotides in an endpoint reaction. In other applications, use of polymerases with exo activity might be preferred.

Coding sequence for a mutant Sso7d protein domain (<90% identity; see U.S. Patent Publication 20050048530) was incorporated at the C-terminal end of the Pfu 468-775 (Q484R) fragment to increase the processivity of the polymerase. The polymerase was expressed from a bicistronic DNA polymerase with either the exo-plus or exo-minus version of Pfu with a split after amino acid 466. Incorporation of the DNA binding domain did not alter the discrimination properties of the polymerase as compared to a polymerase lacking a DNA binding domain.

Figures 2, 2A, 3, 4, 5:
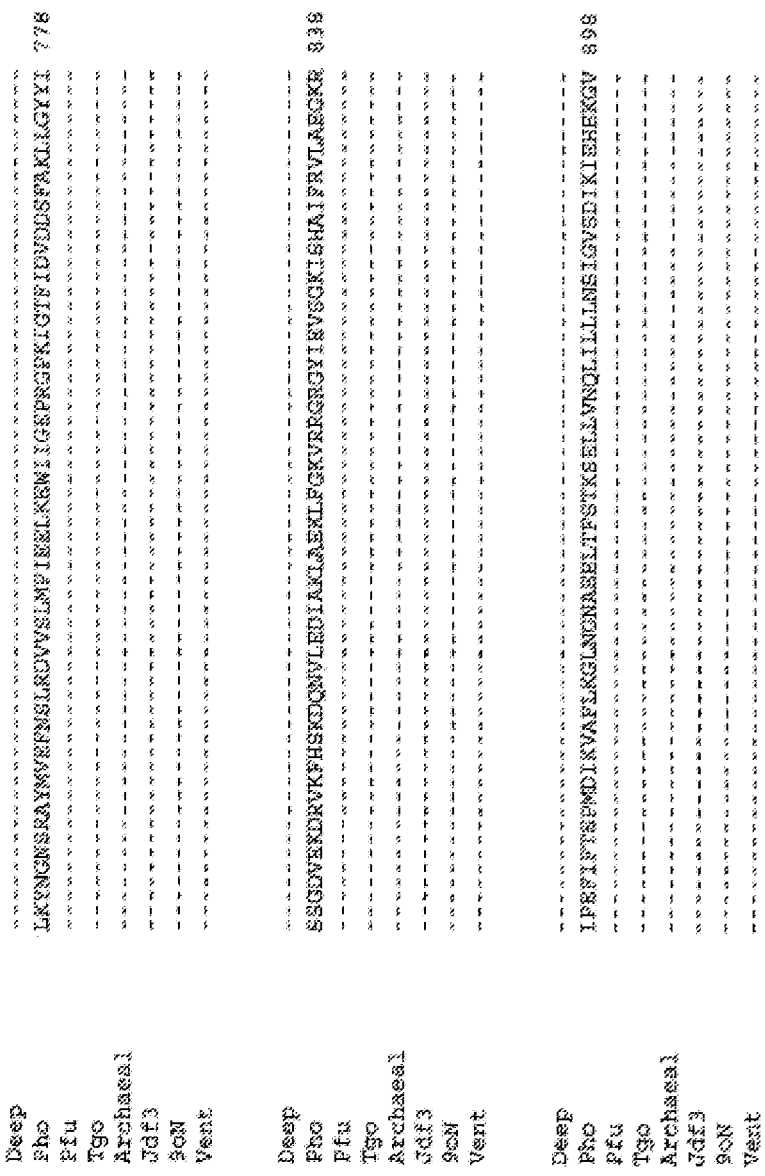
Figure 3:
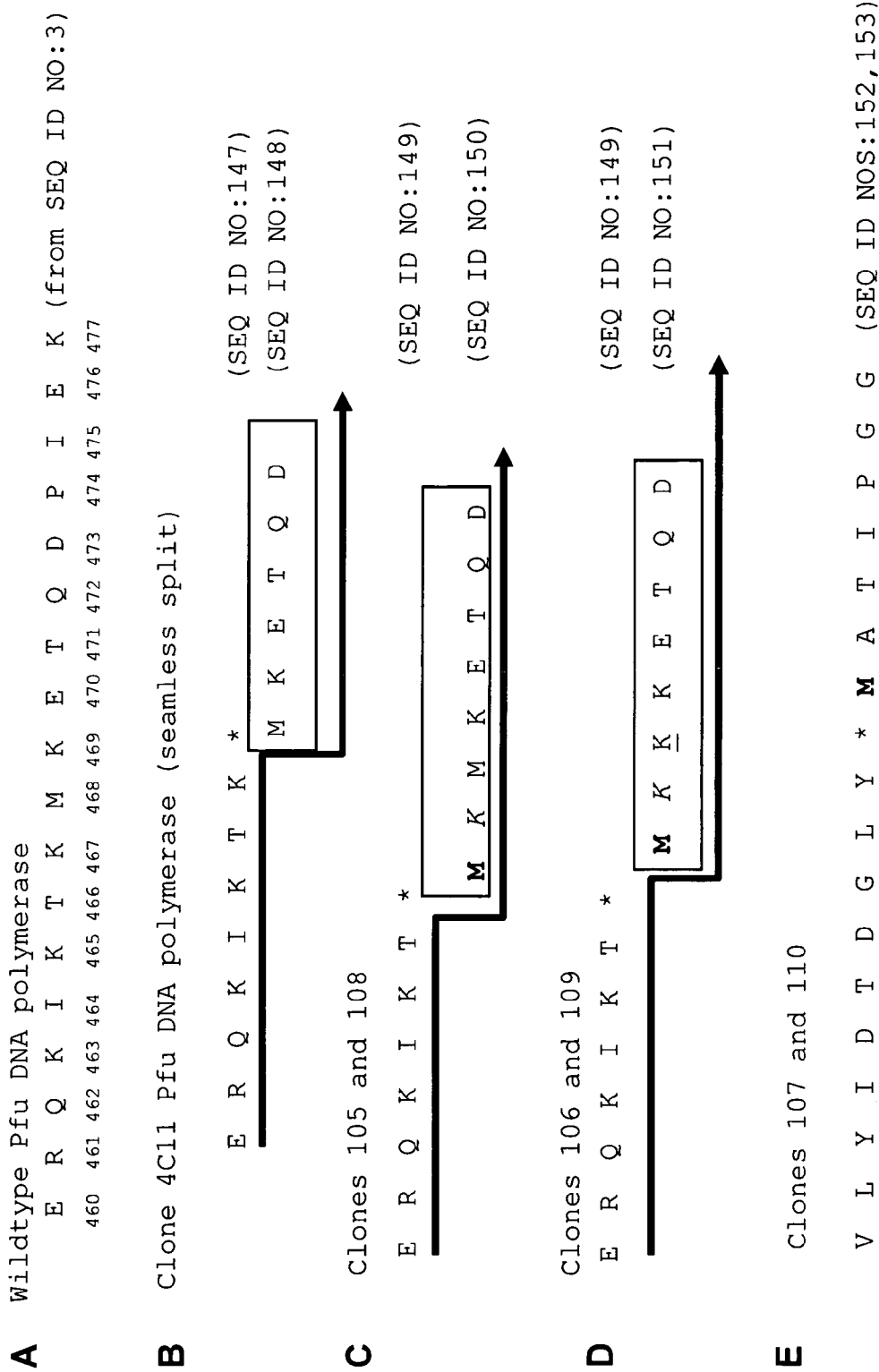
FIG. 3A-3E show the nucleic acid coding sequence and the corresponding translation product for A. Native Pfu (Residues 460-477 of SEQ ID NO: 3) and B. Pfu with a seamless split after amino acid K467 (SEQ ID NOS 147-148, respectively, in order of appearance). The ribosomal reinitiation and frameshift termination codons are noted.
Figure 4:
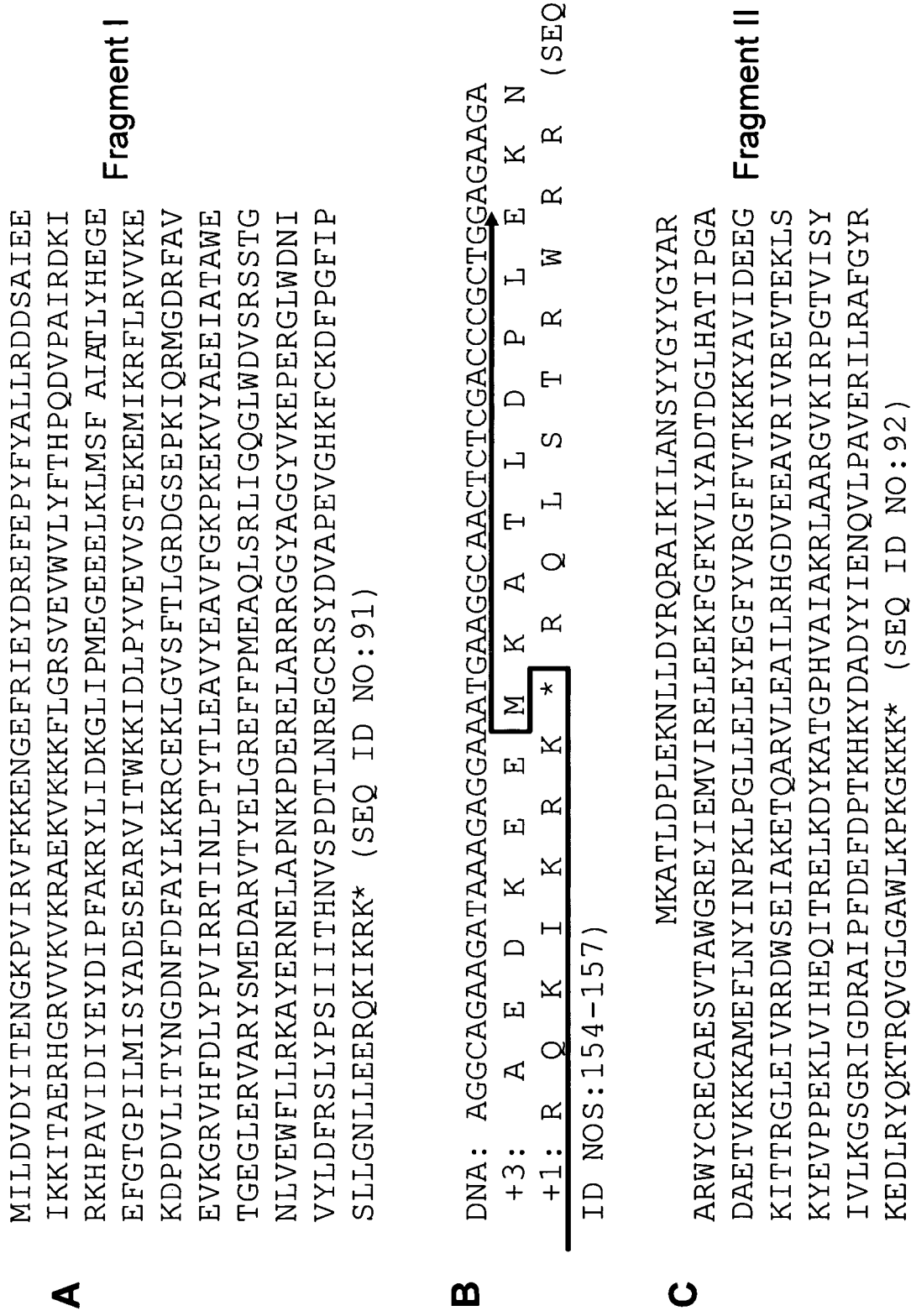
FIG. 4 shows the amino acid coding sequence for the split JdF-3 DNA polymerase, JdF-3 202. Panel A depicts the amino fragment of the split (Fragment I) (SEQ ID NO: 91), Panel B shows the shift from the translational reading frame of 1 to 3 when the ribosome encounters the stop codon (TGA) and reinitiates on the ATG codon (SEQ ID NOS 154-157, respectively, in order of appearance), and Panel C depicts the carboxy fragment of the split (Fragment II) (SEQ ID NO: 92).

To determine if increased utilization of dual labeled nucleotide analogs by insertion of a split into a polymerase was unique to Pfu, a JDF-3 split polymerase bicistronic coding sequence was made. The resulting polymerase is shown in FIG. 5 (JdF-3 Z2). In addition to the split after amino acid 469, 10 amino acids were added on to the C-terminus of the N-terminal JdF-3 fragment. This is different from the Pfu 4C11 mutation, where no amino acids were added to the wild-type sequence. The JdF-3 mutant Z2 shows an insertion in the finger near the tip of the finger domain and was found to result in increased incorporation of non-conventional nucleotides in extension reactions.

As mentioned above, the present invention provides enzymes with non-natural splits that broaden substrate utilization. The invention can be applied to many different types of enzymes. For example, the non-natural split can be in any region that modifies polymerase activity, such as in the fingers region. Preferably, the non-natural split in the polymerase results in split polymerases that have improved incorporation of a non-natural nucleotide or reduced discrimination, especially for dual-labeled nucleotide analogs. The split polymerase may be further modified to further improve incorporation of a non-natural nucleotide, to reduce 3'-5' exonuclease activity, to reduce 5'-3' exonuclease activity, to reduce uracil detection activity, to increase stability as compared to the non-split polymerase, or modified to incorporate a DNA binding domain. In preferred embodiments, the thermostable polymerases used to create the split polymerases are chosen from the Family A and Family B DNA polymerases. This includes, but is not limited to archaeal, mammalian, or bacteriophage polymerases. In one embodiment, the split polymerase is a thermostable archaeal polymerase which is comprised of one or more splits. In one embodiment, the split polymerase is a polymerase that has been split in the fingers domain.

A split polymerase is understood to be a polymerase expressed as at least two discrete polypeptides (e.g., an N-terminal fragment and a C-terminal fragment) that associate to form a single, functional polymerase molecule. In general, the association is non-covalent, although covalent bridges, such as sulfur-sulfur bridges, may form to connect the polypeptides. While not required, expression of the fragments of a split polymerase is preferably translationally coupled to promote proper folding. A split polymerase includes at least one split, preferably in the fingers domain of the protein with one split being preferred. A split is understood as a break in the amino acid sequence of the polymerase such that at least two polypeptides compose the split polymerase. The split can further result in the insertion, deletion, and/or mutation of amino acids at the site of the split. That is, if the polypeptides were joined, there would be a gap, insertion, and/or mutation as compared to the wild-type sequence at the site of the split. In preferred embodiments, up to about 5 amino acids can be deleted at the site of the split. Alternatively, in other preferred embodiments, up to about 40 amino acids can be added to either or both of the new C-terminus and/or the N-terminus created at the split. Frequently, if a methionine is not present in the wild-type coding sequence for the C-terminal fragment of the polymerase, one is added to the N-terminus of the coding sequence for the creation of a translational start site. The coding sequence for a methionine is inserted to promote ribosome reinitiation of translation in polycistronic mRNAs, or to allow initiation of translation of the C-terminal fragment from a second promoter, typically in a separate vector or expression construct. Alternatively, other initiation codons like GTG can also work in translational coupling.

Region III of various polymerases encompasses the "fingers domain," which consists of two long anti-parallel alpha helices, separated by a short loop (finger tip). An alignment of finger domains is shown in FIGS. 1 and 7. The alpha helices comprising the fingers domain of archaeal DNA polymerases correspond to helices N/O in Pfu (Biles and Connolly, 2004, supra), R—R'/S in Sso (Savino et al., 2004, Structure 12:2001) and OTP in Tgo DNA polymerase (Hopfner, Ct al., 1999 Proc. Natl. Acad. Sci. USA, 96: 3600). The structures of several archaeal DNA polymerases have been determined, and the characteristics of the fingers domain have been discussed in several publications (Hopfner, et al 1999, supra; Zhao et al, 1999. Structure 7:1189; Rodriguez et al 2000, J. Mol. Biol. 299:447; Hashimoto et al, 2001, J. Mol. Biol. 306:469; Savino et al, 2004, supra). Comparison to the bacteriophage Rb69 DNA pol-primer/template-dNTP crystal structure, implicates the conserved amino acids in the fingers domain in dNTP binding and fidelity. However, the fingers domain of T4 and T4-like phages has an extended finger tip domain that is not found in the Archeal Family B polymerases. The fingers domain is highly conserved across archaea, suggesting that all DNA polymerases have a similar helix-loop-helix motif, and therefore use the same mechanisms for dNTP recognition. Furthermore, the amino acid sequences of many polymerases are known, allowing for extrapolation of split sites and mutations from one polymerase to another. Folding of the helix-loop-helix leads to the proximal location of a number of highly conserved amino acids derived from both alpha helices.

The fingers subdomain is formed primarily by two long antiparallel α helicies, which includes conserved regions III and IV. The length of the fingers domain varies substantially within the Family B polymerases. For example, some gp43 proteins from T4 and T4-like viruses RB69, RB49, RB43, and Aeh1 include a structurally disordered 50 to 75 amino acid residue sequence at the tip of the finger that diverges widely among the gp43 proteins (Petrov et al., 2006, J. Mol. Biol. 361:46). Also, interestingly, the Family B polymerases of some archaea resemble RB69 gp43 in global structure, but lack this finger tip feature entirely in their fingers domain. However, amino acids in the short intervening sequence between the helicies, especially amino acids 472 and 473 (Pfu numbering), have been shown to be involved in polymerase fidelity (Biles and Connolly, 2004. Nucleic Acids Res. 32:e 176). In other gp43 proteins, the coding sequence is interrupted at the fingertip sequence, thus splitting the gene into two separate ORFs (open reading frames) or cistrons, 43A and 43B. A natural split polymerase has also been identified in archaea; however, the split is located outside of the fingers domain (Kelman et al., 1999. J. Biol. Chem. 274:28751).

As used herein, "Family A DNA polymerase" or "A Family DNA polymerase" or variation thereof refers to any DNA polymerase that is classified as a member of the Family A polymerases wherein the Family A classification is based on structural similarity to E. coli DNA polymerase I. Family A polymerases include, but are not limited to bacterial DNA polymerases such as E. coli DNA polymerase I, Streptococcus pneumoniae DNA polymerase I, Thermus aquaticus DNA polymerase I, Thermus flavus DNA polymerase I, Thermotoga maritima DNA polymerase I; bacteriophage DNA Polymerases T5 DNA polymerase, T7 DNA polymerase, Spo1 DNA polymerase, Spo2 DNA polymerase; yeast mitochondrial DNA polymerase II; and thermostable DNA polymerase from Thermus aquaticus (Taq).

As used herein, "Family B DNA polymerase" or "B Family DNA polymerase" or variation thereof refers to any DNA polymerase that is classified as a member of the Family B DNA polymerases, where the Family B classification is based on structural similarity to E. coli DNA polymerase II. Family B DNA polymerases, formerly known as α-family polymerases (Braithwaite and Ito, 1991, supra), include, but are not limited to human α, δ and ε DNA polymerases, T4, RB69 and Φ29 bacteriophage DNA polymerases, and Pyrococcus furiosus DNA polymerase (Pfu polymerase) (see, e.g., Table I).

Sequence comparison of the Family B DNA polymerases indicate six conserved regions I-VI, numbered in descending order of similarity (see, e.g., Braithwaite and Ito, 1993, supra, Edgell et al, 1997). Most of the conserved residues in the Family B polymerases are located within a radius of 10 Å from the polymerase catalytic center as marked by the three most conserved carboxylates (Wang et al., 1997, Cell 89:1087). The three most highly conserved regions (designated I, II, and III) converge at the center of the active site from the palm (I), the fingers (II), and base of the thumb (III) to produce a contiguous conserved surface. An alignment of the fingers domain from a wide variety of Family B polymerases shows that this region is highly conserved (FIG. 1).

Family B DNA polymerases can also be characterized by having a motif in the fingers domain having the sequence: FIPSXLXXLXXXRQXXKXXMKXXXDPX-EKXXLDYRQXAIKXLAN (SEQ ID NO: 5), wherein X is any amino acid. The sequence may be at least about 70%, 75%, 80%, 85%, 90%, 95%, or 100% identical to the motif.

The cloned Family B DNA polymerases include, but are not limited to, Vent *Thermococcus litoralis, Thermococcus* sp. (Stra11"T TY), Pab *Pyrococcus abyssi*, PYRHO *Pyrococcus horikoshii*, PYRSE *Pyrococcus* sp. (Strain GE23), Deep Vent *Pyrococcus* sp., Pfu *Pyrococcus furiosus*, JdF-3 *Thermococcus* sp., 9 deg N *Thermococcus* sp. (Strain 90N-7), KOD *Pyrococcus* sp., Tgo *Thermococcus gorgonarius*, THEFM *Thermococcus fumicolans*, METTH *Methanobacterium thermoautotrophicum*, Metj a *Methanococcus jannaschii*, POC *Pyrodictium occultum*, ApeI *Aeropyrum pernix*, ARCFU *Archaeoglobus fulgidus, Desulfurococcus* sp. Tok, and *Thermococcus kodakarensis*.

An alignment of DNA polymerase protein sequences of each family, A, B, and C, across a broad spectrum of archaeal, bacterial, viral and eukaryotic organisms is presented in Braithwaite and Ito (1993), which is incorporated herein by reference. Recently, Family D (found in Euryarchaeota subdomain of Archaea), Family X (containing, for e.g., the well-known eukaryotic polymerase Pol β), and Family Y (comprised of translesion synthesis polymerases) have been described. Conserved motifs in DNA polymerase Family A, Family B, and reverse transcriptases include Motif A (Family A consensus sequence of DhSxIELR (SEQ ID NO: 76), Family B consensus of DhxSLYPS (SEQ ID NO: 77), reverse transcriptase consensus of Dh-GY (SEQ ID NO: 78)) and Motif B (Family A consensus of GKxhNFGVLYG (SEQ ID NO: 79), Family B consensus of KhxxN-SLYG (SEQ ID NO: 99)) (Gardner and Jack, 1999, *Nucleic Acids Research*, 27:12, 2545-2553). The B-motif found in Family A and Family B DNA polymerases is also a conserved motif found in a broad range of DNA polymerases (Evans et al., 2000, *Nucleic Acids Research* 28:1059-1066). Amino acids important for primer-template interactions have also been identified in Family A and Family B polymerases (Hogg et al., 2004, *EMBO*, 23:1483-1493). Therefore, the split polymerases of the invention could be polymerases that are split in a conserved motif, other than the finger motif, of the Family A and Family B polymerases or any other polymerases that show the conserved motif.

The split polymerases of the invention can increase incorporation of non-natural nucleotides and/or increase utilization of modified primer templates relative to the non-split polymerase. They are particularly suited for reduced discrimination of non-natural nucleotides, such as dual labeled nucleotide analogs. The non-natural nucleotide may be modified at the polyphosphate and/or at the base. The modification may comprise a fluorophore or a quencher. The labels include, but are not limited to, a fluorescent label, quencher, isotope, chemiluminescent label, quantum dot label, antigen, affinity moiety, or any other structure that allows detection of the nucleotide analog. In preferred embodiments, a quencher label is attached to the polyphosphate group and a fluorescent moiety is attached to the nucleobase or sugar of the nucleotide analog.

The nucleobase moiety is preferably selected from the group consisting of adenine, cytosine, guanine, thymine, uracil and hypoxanthine, although modified forms and functional analogs of these are specifically contemplated. For example, non-conventional nucleotides, meaning a nucleotide structure that is not one of the four conventional deoxynucleotides dATP, dCTP, dGTP, and dTTP recognized by and incorporated by a DNA polymerase, are also envisioned to be applicable to the present invention. These include synthetic nucleotides, modified conventional nucleotides, ribonucleotides, and the like. Any one of the above non-conventional nucleotides may be a "conjugated nucleotide", which as used herein refers to nucleotides bearing a detectable label, including but not limited to a fluorescent label, quencher, isotope, chemiluminescent label, quantum dot label, antigen, or affinity moiety. Further, a dual-labeled nucleotide analog according to the invention may act as a chain terminator for the template-directed polymerization of a polynucleotide by a nucleic acid polymerase.

The split polymerase may be a chimeric polymerase, a combination of an N-terminal fragment from a first polymerase, and a C-terminal fragment of a second polymerase, preferably wherein the fragments are from the same family of polymerases (e.g., both Family B polymerases). Any combination of polymerases may be used in the invention, as long as the combination includes at least two discrete polypeptides that associate to form a single, functional polymerase molecule.

In the present invention, insertion of a split into the coding sequence may include the mutation of the coding sequence in at least one amino acid at the split site, typically to introduce an initiator methionine for reinitiation of translation of the C-terminal fragment of the split polymerase. Mutations may be introduced into coding sequences adjacent to the split site, especially downstream of the split site, to remove coding sequences for methionines, especially those in alternate reading frames. ATG methionine sequences in the two non-coding frames, which could compete for ribosome reinitiation, can often be removed by changing the wobble base of the codon in the correct reading frame. Methods for introducing mutations into a coding sequence without introducing mutations into the final amino acid sequence are well known to those skilled in the art.

In another embodiment of the invention, the split results in the modification of coding sequence that results in the addition of coding sequence for at least one additional amino acid as compared to the wild-type sequence at the split site. The modification may result in the insertion of coding sequence for additional amino acids, or a modification to promote backsliding of the ribosome to a reinitiation codon upstream of the termination codon. The number of amino acids added in the final polymerase as compared to the wild type polymerase may be inserted is at least 1, 2, 3, 4, 5, 6, 7, 8, 9, 10, 11, 12, 13, 14, 15, 20, 25, 30, 35, or 40-aminoacids.

In another embodiment of the invention, the split results in the deletion of coding sequence for at least one amino acid as compared to the wild-type sequence at the split site. The modification may result in the deletion of coding sequence for a number of amino acids, or a modification to promote sliding of the ribosome to a reinitiation codon downstream of the termination codon. The number of amino acids that may be deleted is at least 1, 2, 3, 4, or 5 amino acids.

In an embodiment of the invention, the split polymerase further comprises one or more mutations, as compared to the wild-type coding sequence, in addition to any mutations caused by the split. Multiple mutations can be introduced to confer a single new property to the split polymerase, or multiple mutations can be introduced to confer multiple new properties on the polymerase. The mutations can be introduced in the finger region, close to or at where the split occurs, or can be added to regions farther away from the split.

Mutations in the split polymerase can result in one or more changes in the enzyme. For example, mutations can increase the stability of the split polymerase as compared to a split polymerase not containing the mutation. In another example, the mutation can substantially reduce 3' to 5' exonuclease activity of the polymerase as compared to a polymerase not containing the mutation. In yet another example, the mutation further reduces the discrimination of the polymerase as compared to a polymerase not containing the mutation. This can result in reduced uracil detection and/or increased tendency to incorporate non-conventional nucleotides or nucleosides. In another embodiment, the polymerase includes a non-sequence specific double stranded DNA binding domain attached to the polymerase, preferably at the C-terminus of the C-terminal fragment of the split polymerase, to increase the processivity of the polymerase as compared to a polymerase not having the domain.

In an embodiment of the invention, the split polymerase is characterized by having a motif comprising RXXXK(X)$_n$-QXXXKXXXNSXGX (SEQ ID NO: 4), wherein X is any amino acid, and n=15-80. In a further embodiment, the split lies within the motif of SEQ ID NO.: 4.

In an embodiment of the invention, the split polymerase of the invention is characterized by having a motif comprising FIPSXLXXLXXXRQXXKXXMKXXXDPX-EKXXLDYRQXAIKXLAN (SEQ ID NO:5), wherein X is any amino acid. In a further embodiment, the split lies within the motif of SEQ ID NO.: 5. In an embodiment, the split lies within the region of amino acids 5 to 40 of SEQ ID NO: 5. In an embodiment, the split lies within the region of amino acids 5 to 30 of SEQ ID NO: 5. In an embodiment, the split lies within the region of amino acids 10 to 25 of SEQ ID NO: 5. In an embodiment, the split lies within the region of amino acids 15 to 25 of SEQ ID NO: 5.

In an embodiment of the invention, the polymerase is characterized by having a motif comprising FIPSBLXXL-BXXXRXXBKXZMKXJXDPBEKXBLDYRQZAIKBLAN (SEQ ID NO:6), wherein B is M, V, L, or I; J is S or T; U is F or Y; Z is Q, K, or R; and X is any amino acid. In a further embodiment, the split lies within the motif of SEQ ID NO.: 6. In an embodiment, the split lies within the region of amino acids 5 to 40 of SEQ ID NO:6. In an embodiment, the split lies within the region of amino acids 5 to 30 of SEQ ID NO: 6. In an embodiment, the split lies within the region of amino acids 10 to 25 of SEQ ID NO: 6. In an embodiment, the split lies within the region of amino acids 15 to 25 of SEQ ID NO: 6.

In an embodiment of the invention, the split polymerase is characterized by having a motif comprising GXXXXXLXX-LXXXRXXXKXXMXXXDXXXXXX-LDXRQXAXKXXANXXYGYXXX (SEQ ID NO: 53), wherein X is any amino acid, and n=15-40 wherein X is any amino acid. In a further embodiment, the split lies within the motif of SEQ ID NO.: 53. In a further embodiment, the split lies within the motif of SEQ ID NO.: 53. In an embodiment, the split lies within the region of amino acids 5 to 40 of SEQ ID NO: 53. In an embodiment, the split lies within the region of amino acids 5 to 30 of SEQ ID NO: 53. In an embodiment, the split lies within the region of amino acids 10 to 25 of SEQ ID NO: 53. In an embodiment, the split lies within the region of amino acids 15 to 25 of SEQ ID NO: 53.

In an embodiment of the invention, the split polymerase of the invention is characterized by having a motif comprising GXXXXBLXXLBXXRXXBKXXMXXJXDXX-OZXBLDXRQZABKBBANXUYGYXXX (SEQ ID NO: 54), wherein X is any amino acid. In a further embodiment, the split lies within the motif of SEQ ID NO.: 54. In an embodiment, the split lies within the region of amino acids 5 to 40 of SEQ ID NO: 54. In an embodiment, the split lies within the region of amino acids 5 to 30 of SEQ ID NO: 54. In an embodiment, the split lies within the region of amino acids 10 to 25 of SEQ ID NO: 54. In an embodiment, the split lies within the region of amino acids 15 to 25 of SEQ ID NO: 54.

In an embodiment of the invention, the spilt polymerase is characterized by having a motif comprising GFIPSXLXX-LXXXRQXXKXXMZXXXDPXXXXX-LDYRQXAIKXLANSUYGYXXY (SEQ ID NO: 55), wherein X is any amino acid, and n=15-40 wherein X is any amino acid. In a further embodiment, the split lies within the motif of SEQ ID NO.: 55. In a further embodiment, the split lies within the motif of SEQ ID NO.: 55. In an embodiment, the split lies within the region of amino acids 5 to 40 of SEQ ID NO: 55. In an embodiment, the split lies within the region of amino acids 5 to 30 of SEQ ID NO: 55. In an embodiment, the split lies within the region of amino acids 10 to 25 of SEQ ID NO: 55. In an embodiment, the split lies within the region of amino acids 15 to 25 of SEQ ID NO: 55.

In an embodiment of the invention, the split polymerase of the invention is characterized by having a motif comprising GFIPSBLXXLBXXRXXBKXXMZXJXDP-BEZBBLDYRQZAIKBLANSUYGYXXY (SEQ ID NO: 56), wherein X is any amino acid. In a further embodiment, the split lies within the motif of SEQ ID NO.: 56. In an embodiment, the split lies within the region of amino acids 5 to 40 of SEQ ID NO: 56. In an embodiment, the split lies within the region of amino acids 5 to 30 of SEQ ID NO: 56. In an embodiment, the split lies within the region of amino acids 10 to 25 of SEQ ID NO: 56. In an embodiment, the split lies within the region of amino acids 15 to 25 of SEQ ID NO: 56. In an embodiment, there is an additional Q484R mutation in SEQ ID NO:56.

In an embodiment of the invention, the polymerase is characterized by having a sequence that is at least 70% identical to SEQ ID NO: 4, 5, 6, 53, 54, 55, or 56, such as at least 75% identical, 80% identical, 85% identical, 90% identical, or 95% identical. In a further embodiment, the split lies within a sequence that is at least 70% identical to the motif of SEQ ID NO.: 4, 5, 6, 53, 54, 55, or 56, such as at least 75% identical, at least 80% identical, at least 85% identical, at least 90% identical, or at least 95% identical. In an embodiment, the split lies within the region of amino acids 5 to 40 within a sequence that is at least 70% identical to the motif of SEQ ID NO: 5, 6, 53, 54, 55, or 56, such as at least 75% identical, at least 80% identical, at least 85% identical, at least 90% identical, or at least 95% identical. In an embodiment, the split lies within the region of amino acids 5 to 30 within a sequence that is at least 70% identical to the motif of SEQ ID NO: 5 or 6, such as at least 75% identical, at least 80% identical, at least 85% identical, at least 90% identical, or at least 95% identical. In an embodiment, the split lies within the region of amino acids 10 to 25 within a sequence that is at least 70% identical to the motif of SEQ ID NO: 5 or 6, such as at least 75% identical, at least 80% identical, at least 85% identical, at least 90% identical, or at least 95% identical. In an embodiment, the split lies within the region of amino acids 15 to 25 within a sequence that is at least 70% identical to the motif of SEQ ID NO: 5, 6, 53, 54, 55, or 56, such as at least 75% identical, at least 80% identical, at least 85% identical, at least 90% identical, or at least 95% identical. Of course the identity of any of these embodiments can fall within the range disclosed without having been particularly stated, such as 84% identical or 92% identical, etc. That is, the invention contemplates any particular value or range of values within the cited ranges, and each particular value need not be specifically recited herein for one of skill in the art to understand the collection of values and ranges so contemplated.

In a further embodiment of the invention, the split is at a site within a region of Pfu DNA polymerase. Preferably, the split is introduced in the fingers domain of the polymerase. As examples, the split can be found to occur somewhere in the region of amino acids 448 to 500 (GFIPSLLGHLLEER-QKIKTKMKETQDPIEKILLDYRQKAIKL-LANSFYGYYGY) (Residues 448-500 of SEQ ID NO: 3), amino acids 460 to 480, amino acids 465 to 475, or amino acids 466 to 470 of Pfu DNA polymerase. In one embodiment, the split polymerase is located in the fingers domain and has at least 50% identity to amino acids 448 to 500 of the Pfu polymerase, such as at least 55% identity, at least 60% identity, at least 70% identity, at least 80% identity, or at least 90% identity.

To summarize, in one embodiment of the invention, a purified thermostable polymerase is provided, wherein the polymerase is a split polymerase wherein the split is within the fingers domain within a region characterized by a motif comprising: FIPSBLXXLBXXRXXBKXZMKXJXDP-BEKBLDYRQZAIKBLAN (SEQ ID NO: 6), wherein B is M, V, L, or I; J is S or T; U is F or Y; Z is Q, K, or R; and X is any amino acid. In an embodiment, the polymerase is selected from the group consisting of *Thermococcus litoralis* (Vent) DNA polymerase, *Pyrococcus furiosus* (Pfu) DNA polymerase, *Thermococcus* JdF-3 DNA polymerase, *Pyrococcus horikoshii* (Pho) DNA polymerase, *Thermococcus gorgonarius* (Tgo) DNA polymerase, *Pyrococcus* sp. GBD (Deep Vent) DNA polymerase, and archaeal polymerase I. The polymerase can be a DNA polymerase selected from the group consisting of *Pyrococcus* and *Thermococcus*. In an embodiment, the polymerase comprises a finger domain which has an amino acid sequence at least 70%, at least 80%, or at least 90% identical to SEQ ID NO: 4, 5, or 6.

In an embodiment, the invention provides an isolated nucleic acid polymerase wherein the polymerase is a split *Pyrococcus furiosus* (Pfu) DNA polymerase comprising a fingers domain, and the split is within the fingers domain. The polymerase may be comprised of a split between amino acids 448 and 500 or amino acids 467 and 468.

In an embodiment, a split polymerase of the invention further comprises a mutation in the amino acid sequence as compared to the non-split polymerase. The mutation may be at an amino acid selected from the group consisting of L409, Y410, P411, R461, K465, Q472, Q484, A486, R488, L490, A491, N492, Y495, and Y497 to reduce discrimination of the polymerase as compared to the polymerase without the mutation. The reduced discrimination may comprise reduced uracil detection or increased tendency to incorporate non-conventional nucleotides or nucleosides. The mutation is selected from the group consisting of L409H, Y410V, P411L, R461A/N, K465A/N, Q472H, Q484R/K, A486T, R488A, L490Y, A491Y, N492A, Y495S, Y497A1L. The polymerase may further comprise a mutation at an amino acid corresponding to a site in Pfu DNA polymerase selected from the group consisting of D141A/E143A double mutation, and V93R, to reduce 3' to 5' exonuclease activity as compared to the polymerase without the mutation. The polymerase may further comprise a mutation at an amino acid corresponding to a site in Pfu DNA polymerase selected from the group consisting of A318, V604, and A662, to increase stability of the split polymerase as compared to the polymerase without the mutation. In another embodiment, the mutation increases the stability of the split polymerase to a level comparable to a non-split polymerase. The mutation may be selected from the group consisting of A318T, V604L, A662V, and any combination thereof. As an example, the polymerase may comprise a mutation at an amino acid site corresponding to amino acid Q484 in Pfu DNA polymerase. A preferred mutation according to the invention is Q484R. The polymerase may further comprise an amino acid site corresponding to a site in Pfu DNA polymerase selected from the group consisting of A318T, V604L, A662V, D141A, E143A, and V93R.

In an embodiment, the polymerase further comprises a double stranded sequence-non-specific nucleic acid binding domain attached to the polymerase. The sequence-non-specific nucleic acid binding domain may be an Sso7 derivative with less than 90% identity to wild type Sso7.

In another embodiment of the invention, the invention provides a purified thermostable polymerase wherein the polymerase is a split polymerase, wherein the split is within a region characterized by a motif comprising: GXXXXBLXX-LBXXRXXBKXXMXXJXDXXOZX-BLDXRQZABKBBANXUYGYXXX (SEQ ID NO: 54), wherein B is M, V, L, or I; J is S or T; O is D or E; U is F or Y; Z is Q, K, or R; and X is any amino acid. The polymerase may be selected from the group consisting of JdF-3 *Thermococcus* sp. DNA polymerase; *Pyrococcus horikoshii* (Pho) DNA polymerase; DNA polymerase 1 *Pyrococcus abyssi* (Pab polymerase); DNA-dependent DNA polymerase; endonuclease *Pyrococcus* sp.; Vent *Thermococcus litoralis* DNA polymerase; Deep Vent *Pyrococcus* sp DNA polymerase; 9° N *Thermococcus* sp. (9° N-7) DNA polymerase; *Thermococcus gorgonarius* (Tgo) DNA polymerase; *Thermococcus aggregans* (Tfu) DNA polymerase; *Pyrococcus* sp. ST700 (ST700) DNA polymerase; *Pyrococcus furiosus* (Pfu) DNA polymerase; DNA polymerase and endonucleases *Thermococcus* sp. GE8; *Thermococcus litoralis* DNA dependent DNA polymerase (TLI); DNA-dependent polymerase precursor *Thermococcus* sp. NAI (TSPNA1); DNA-directed DNA polymerase (EC 2.7.7.7) KOD, intein containing precursor—*Pyrococcus* sp. (strain KOD1) (TSPKOD); PolA precursor *Thermococcus zilligii* (TZI); *Thermococcus kodakarensis* (THY) DNA polymerase; *Pyrococcus glycovorans* (PGL) DNA polymerase; DNA polymerase II *Sulfolobus tokodai* str. 7 (SULFOTO) DNA polymerase; and *Desulfurococcus* sp. Tok (TOK) DNA polymerase. In one embodiment, the polymerase is an archaeal DNA polymerase selected from the group consisting of *Pyrococcus* and *Thermococcus*. The polymerase may comprise a finger domain which has an amino acid sequence at least 70% identical, at least 80% identical, or at least 90% identical to SEQ ID NO. 53, 54, 55, or 56. The polymerase may further comprise a mutation at an amino acid corresponding to a site in Pfu DNA polymerase selected from the group consisting of L409, Y410, P411, R461, K465, Q472, Q484, A486, R488, L490, A491, N492, Y495, and Y497, to reduce discrimination of the polymerase as compared to the polymerase without the mutation. The polymerase may have reduced discrimination which may comprise reduced uracil detection or increased tendency to incorporate a non-conventional nucleotides or nucleosides. The polymerase may have a mutation selected from the group consisting of L409H, Y410V, P411L, R461AIN, K465A/N, Q472H, Q484R/K, A486T, R488A, L490Y, A491Y, N492A, Y495S, Y497A/L, and any combination thereof. The polymerase may have a mutation at an amino acid corresponding to a site in Pfu DNA polymerase selected from the group consisting of D141A/EI43A double mutation, and V93R further comprising at least one mutation to reduce 3' to 5' exonuclease activity as compared to the polymerase without the mutation. The polymerase may comprise a mutation at an amino acid corresponding to a site in Pfu DNA polymerase selected from the group consisting of A318, V604, and A662, to increase stability of the split polymerase as compared to the polymerase without the mutation. The mutation may increase the stability of the split polymerase to a level comparable to a non-split polymerase. The mutation may be selected from the group consisting of A318T, V604L, A662V, and any combination thereof. The polymerase may comprise a mutation at an amino acid site corresponding to amino acid Q484 in Pfu DNA polymerase, such as Q484R or Q484K. The polymerase may comprise a mutation at an amino acid site corresponding to a site in Pfu DNA polymerase selected from the group consisting of A318T, V604L, A662V, D141A, E143A, V93R, and a combination thereof. The polymerase may further comprise a double stranded sequence-non-specific nucleic acid binding domain attached to the polymerase. The sequence-non-specific nucleic acid binding domain may be an Sso7 derivative with less than 90% identity to wild type Sso7.

In summary, an amino acid sequence of a split polymerase of the invention can be comprised of a mutation in at least one amino acid corresponding to a site in Pfu DNA polymerase selected from the group consisting of L409, Y410, P411, R461, K465, Q472, Q484, A486, R488, L490, A 491, N492, Y495, and Y497. An amino acid sequence of the split polymerase may further be comprised of a mutation corresponding to a site in Pfu DNA polymerase that is selected from the group consisting of L409H, Y410V, P411L, R461A/N, K465A/N, Q472H, Q484R/K, A486T, R488A, L490Y, A491Y, N492A, Y495S, Y497A/L, and any combination thereof. In another embodiment, the amino acid sequence of a split polymerase of the invention is comprised of the double mutation D141A/E143A, single mutation V93R, or both, corresponding to a site in Pfu DNA polymerase, to reduce 3' to 5' exonuclease activity as compared to the polymerase without the mutation. In an embodiment, the amino acid sequence of the polymerase further comprises a mutation at an amino acid corresponding to a site in Pfu DNA polymerase selected from the group consisting of A318, V604, A662, and any combination thereof, to increase stability of the split polymerase as compared to the polymerase without the mutation. The amino acid sequence of the split polymerase may further be comprised of a C-terminal fusion with a DNA binding protein.

In one exemplary example, the split polymerase is the SQ split polymerase. This mutant is comprised of a seamless split after amino acid 467 to create a fragment encompassing amino acids 1-467 and a fragment encompassing amino acids 468-775 with the additional mutation Q484R. SQ may be further modified to eliminate exonuclease activity by adding D141A/E143A mutations (FIG. 13). SQ is not comprised of the additional mutations found in mutant 4C11 (1-467 V93R/A318T)/(468-775 V604L/A662V-SsO7d7m). The nucleic acid sequence of the exo-mutant SQ is also disclosed (SEQ ID NO:93). The exo-SQ mutant was found to work as well in non-conventional nucleotide incorporation assays as the 4C11 mutant. Because the exo-SQ mutant is only comprised of the seamless split, Q484R, and the exo-minus (D141A/E143A) mutations, in one embodiment, the present invention provides this set of mutations as a way of increasing non-conventional nucleotide incorporation. Herein, "exo-" or "exo-minus" refers to a mutant that does not have exonuclease activity.

In another general aspect, the present invention provides nucleic acids encoding split polymerases of the invention. Because split polymerases are only a part or portion of a complete polymerase sequence, the nucleic acids of the invention only encode for a part or portion of a polymerase in any one reading frame. Split polymerases are preferably expressed from a polycistronic, preferably bicistronic, operon in which the expression of the N-terminal polypeptide portion (fragment I) and the C-terminal polypeptide portion (fragment II) of the polymerase are translationally coupled. In another embodiment, the split polymerase is encoded by two or more coding sequences that are present on two or more separate plasmids in the same host cell, or in two separate host cells.

A coding sequence or mRNA is said to be polycistronic when it contains the genetic information to translate more than one polypeptide from a single promoter typically without disengagement of the ribosome from the mRNA. A polycistronic mRNA is composed of at least two cistrons. As used herein, a cistron is a segment of DNA that specifies a single polypeptide unit. The polypeptides expressed from a polycistronic mRNA may or may not form a complex after translation. Most of the mRNA found in prokaryotes is polycistronic.

Translationally coupled is understood to mean that translation of multiple portions of the split polymerase are translated in a coordinated manner that may allow association of the subunits at the time of translation. In other words, "translationally coupled" is understood to mean that the ribosome encounters a stop codon, terminates translation but does not disengage from the RNA, and scans for, finds, and initiates translation again at a nearby ATG. Coding sequences from each of the subunits may be under the control of the same inducible promoter to allow for coordinated expression. Alternatively, the fragments may be coded for by a single, polycistronic mRNA.

In one embodiment of the invention the split is a seamless split wherein no new amino acids are introduced or deleted at the split site as compared to the wild-type coding sequence. For example, the split in the 4C11 mutant (shown in FIG. 3B) deleted an "A" from the reading frame (AAAATGA). Fortuitously, the "A" from the downstream ATG maintained the previous codon (AAA) allowing conservation of the polymerase amino acid sequence. The second codon in the frameshift was recognized as TGA which terminates translation. Translational reinitiation at the ATG, one base upstream from the TGA, corrected the frameshift, producing a second protein fragment, which in complementation with the first fragment preserved the amino acid of the polymerase. In this way, through careful design using methods well known to those skilled in the art, a seamless split can be introduced so that there is no alteration of the polypeptide sequence. However, the invention provides for nucleic acids that are different from the wild-type nucleic acid sequence. For example, nucleotide substitutions can be made that change the nucleic acid sequence, but do not change the polypeptide sequence.

Other designs are also envisioned in the present invention, such as splits that are not seamless. In this embodiment, a frameshift creates a termination codon (TAA, TAG or TGA) in addition to shifting the protein-coding region out of frame, such that additional amino acids are introduced. The termination codon terminates translation of the first fragment, but translation can begin again if the ribosome can find a reinitiation codon within seven (upstream or downstream) codons or as far away as 46 nucleotides upstream or downstream (Karamyshev, 2004, supra). Positioning initiating codons further away is possible, but less preferred due to a likely decrease in efficiency of translation of fragment II. The reinitiating codon is usually an ATG, but can be ACG (Thr), CTG (Leu) and GTG (Val). Even if the initiation codon encodes another amino acid, methionine is inserted into the first position of the peptide chain. Of course, in these designs, the invention provides for nucleic acid sequences that are comprised of additions or deletions as compared to the wild-type nucleic acid sequence. While not critical to practice of the invention, it is often desirable to express the fragments making up the split polymerase in a manner that not only provides similar molar amounts of each fragment, but also results in production of each fragment in a temporally proximate manner. While not being limited to any one mechanism of action, it is thought that these considerations allow for proper production and folding of the various fragments to create a functional end product.

Some designs may require one or more amino acid replacements to introduce an initiating methionine. It is preferred that out of frame ATG triplets other than the one for the desired reinitiating methionine be altered to prevent incorrect reinitiation of translation. Methods of altering nucleotide sequence without altering amino acid sequence are well known to those skilled in the art. It may also be beneficial to mutate non-initiator methionines in the coding frame to introduce conservative mutations into the amino acid sequence. The relative advantages and disadvantages of altering methionines encoded in frame are well within the ability of those skilled in the art.

Splits that are not seamless will result in split polymerases that contain mutations. Therefore, the present invention provides mutant split polymerases that comprise mutations in one or more amino acids. These mutations may be added to the coding sequence to generate functional segments of the split polymerase. Mutations may also be added to allow better and/or different activity of the split polymerase and may be found in a region different from the split site. Mutations may be added to the wild type sequence of a polymerase to increase the stability of the split polymerase, to reduce 3' to 5' exonuclease activity, to reduce discrimination of the polymerase, and/or any other characteristic that may be beneficial for the use of the split polymerase. The mutations can be chosen depending on which characteristics are desired for the split polymerase and any combination of mutations can be found in one split polymerase.

In a preferred embodiment, the split polymerases of the invention are encoded by a polycistronic operon in which expression of each portion or cistron of the split polymerase is translationally coupled to translation of at least one other portion of the split polymerase. In one embodiment, the polycistronic coding sequence contains at least one ribosomal reinitiation signal proximal to a frameshift termination codon.

In an alternative embodiment, the split polymerases of the invention are encoded by two coding sequences that are present on two separate plasmids in the same host cell, or in two separate host cells. If the two plasmids are contained within a single host cell, the same inducible promoter (e.g., tetracycline or IPTG inducible) can be used to promote coordinated expression of the fragments of the split polymerase. However, it may be beneficial to use two different inducible promoters. For example, there may be cases where one fragment of the split polymerase is less stable than another and, therefore, requires a stronger promoter so that more of the less stable fragment is produced. It may also be beneficial in some cases to use a constitutive promoter, depending on the conditions for expression of the split polymerase.

In summary, the present invention provides a nucleic acid encoding for a part or all of a split polymerase. In one embodiment, the split may be in the fingers domain. In one embodiment, the nucleic acid may be further comprised of at least one mutation that improves incorporation of a non-natural nucleotide, reduces 3'-5' exonuclease activity, reduces 5'-3' exonuclease activity, reduces uracil detection activity, or increases stability when expressed as a split polymerase as compared to the non-split polymerase. In another embodiment, the nucleic acid is comprised of at least one mutation such that the split polymerase expressed from the nucleic acid comprises a mutation in at least one amino acid corresponding to a site in Pfu DNA polymerase selected from the group consisting of L409, Y410, P411, R461, K465, Q472, Q484, A486, R488, L490, A491, N492, Y495, Y497, D141, E143, V93, A318, V604, and A662.

In a further general aspect, the present invention provides methods of making a split polymerase of the invention. In general, the methods comprise providing at least two polymerase coding regions which are operably linked to at least one promoter, introducing the coding regions into a system in which the regions can be expressed, such as in at least one host cell or in an in vitro expression system, and incubating the system under conditions allowing the formation of a functional split polymerase. Stated another way, in embodiments, the methods comprise introducing at least two coding sequences encoding part of a polymerase into at least one host cell, and incubating the host cell under conditions allowing the translation of the coding regions and assembly of the translated products into a functional split polymerase in vivo. Optionally, the assembled split polymerase can be purified and/or tested for activity. Alternatively, the method may comprise assembly of the translated products into a functional split polymerase after purification of the split polymerase polypeptides from the host cells. In this case, assembly would take place outside of the host cell or in vitro.

In a preferred embodiment, the method comprises providing a polycistronic coding region sequence encoding a split polymerase, introducing the coding regions into a host cell, and culturing the cell under conditions which permit production of the split polymerase. Optionally, the split polymerase may be purified before or after assembly. Also optionally, the split polymerase produced by the methods of the invention can be tested for polymerase activity and/or can be tested for non-conventional nucleotide incorporation. In view of this aspect of the invention, it should be apparent that the invention encompasses recombinant cells comprising nucleotides encoding split polymerases, and recombinant cells comprising non-naturally occurring split polymerases.

The methods may comprise introducing into a host cell a nucleic acid comprising a polycistronic coding region sequence encoding a polymerase wherein the coding region is operably linked to a promoter, and culturing the cell under conditions that permit production of the polymerase. The host cell may be an *E. coli* or of the genus *Thermococcus* or *Pyrococcus*. In one embodiment, the method is a method of decreasing discrimination of a polymerase by introducing a split into a region of the polymerase characterized by a motif comprising: FIPSBLXXLBXXRXXBKXZMKXJXDP-BEKXBLDYRQZAIKBLAN (SEQ ID NO: 6), wherein B is M, V, L, or I; J is S or T; U is F or Y; Z is Q, K, or R; and X is any amino acid. The polymerase may be selected from the group consisting of *Thermococcus litoralis* (Vent) DNA polymerase, *Pyrococcus furiosus* (Pfu) DNA polymerase, *Thermococcus* JdF-3 DNA polymerase, *Pyrococcus horikoshii* (Pho) DNA polymerase, *Thermococcus gorgonarius* (Tgo) DNA polymerase, *Pyrococcus* sp. GBD (Deep Vent) DNA polymerase, and archaeal polymerase I. In one embodiment, the DNA polymerase is selected from the group consisting of *Pyrococcus* and *Thermococcus*, such as *Thermococcus litoralis* (Vent) DNA polymerase, *Pyrococcus furiosus* (Pfu) DNA polymerase, *Thermococcus* JdF-3 DNA polymerase, *Pyrococcus horikoshii* (Pho) DNA polymerase, *Thermococcus gorgonarius* (Tgo) DNA polymerase, *Pyrococcus* sp. GBD (Deep Vent) DNA polymerase, and archaeal polymerase I. In one embodiment, the polymerase is a split *Pyrococcus furiosus* (Pfu) DNA polymerase. The split may be between amino acids 448 and 500, or 467 and 468.

The methods may include a polymerase that has a mutation at an amino acid corresponding to a site in Pfu DNA polymerase selected from the group consisting of L409, Y410, P411, R461, K465, Q472, Q484, A486, R488, L490, A491, N492, Y495, and Y497 to reduce discrimination of the polymerase as compared to the polymerase without the mutation. The reduced discrimination may comprise reduced uracil detection or increased tendency to incorporate a non-conventional nucleotide. The mutation may be selected from the group consisting of L409H, Y410V, P41 1L, R46IA/N, K465A/N, Q472H, Q484R/K, A486T, R488A, L490Y, A491Y, N492A, Y495S, and Y497A/L. In another embodiment, the polymerase may further comprise a mutation at an amino acid corresponding to a site in Pfu DNA polymerase selected from the group consisting of D141A/E143A double mutation, and V93R, to reduce 3' to 5' exonuclease activity as compared to the polymerase without the mutation. In another embodiment, the polymerase may comprise a mutation at an amino acid corresponding to a site in Pfu DNA polymerase selected from the group consisting of A318, V604 and A662 to increase stability of the split polymerase as compared to the polymerase without the mutation. In one embodiment, the mutation increases the stability of the split polymerase to a level comparable to a non-split polymerase. Also, the mutation may be selected from the group consisting of A318T, V604L, and A662V. In preferred embodiment, the polymerase further comprises a mutation at an amino acid site corresponding to amino acid Q484 in Phi DNA polymerase, such as Q484R. The methods may further comprise a polymerase with at least one mutation at an amino acid site corresponding to a site in Pfu DNA polymerase selected from the group consisting of A318T, V604L, A662V, D141A, E143A, and V93R. In one embodiment, the methods comprise a polymerase with a double stranded sequence-non-specific nucleic acid binding domain attached to the polymerase. The sequence-non-specific nucleic acid binding domain may be an Sso7 derivative with less than 90% identity to wild type Sso7. The methods of making a split polymerase of the invention are envisioned to comprise no additional mutations (other than any formed from making the split), one mutation, or more than one mutation. The split polymerase may be one wherein the polymerase is further modified to further improve incorporation of a non-natural nucleotide, to reduce 3'-5' exonuclease activity, to reduce 5'-3' exonuclease activity, to reduce uracil detection activity, to increase stability as compared to the non-split polymerase, or modified to incorporate a DNA binding domain.

In a further aspect, the invention provides methods of using the split polymerase of the invention. A split polymerase of the invention can be used for nucleic acid amplification, nucleic acid sequencing, quantitative PCR (QPCR), nucleic acid labeling, for synthesis with modified primers or templates, or in any reaction that requires a polymerase. The invention is particularly suited for methods that involve non-conventional nucleotides and nucleotide analogs, such as dual-labeled nucleotide analogs. In another embodiment, the invention can be used to develop complementation systems where a polymerase signal is generated when two polymerase fragments that are expressed separately assemble together. In this case, one polymerase fragment could be used as a bait to screen a library fused to the other polymerase fragment.

The methods may comprise: (a) providing a DNA polymerase of the invention and (b) contacting the polymerase with a nucleic acid template, wherein the polymerase permits DNA synthesis. In another embodiment, the methods include a method for DNA synthesis with reduced discrimination as compared to synthesis with a wild type DNA polymerase comprising: (a) providing a DNA polymerase of the invention and (b) contacting the polymerase with a nucleic acid template and non-conventional nucleotides, wherein the polymerase permits DNA synthesis. The method may be a method for cloning of a DNA synthesis product comprising: (a) providing DNA polymerase of the invention and (b) contacting the DNA polymerase with a nucleic acid template, wherein the archaeal DNA polymerase permits DNA synthesis to generate a synthesized DNA product and (c) inserting said synthesized DNA product into a cloning vector. In another embodiment, the methods comprise: (a) providing a DNA polymerase of the invention; (b) generating chain terminated fragments from the DNA template to be sequenced with the DNA polymerase in the presence of at least one chain terminating agent and one or more nucleotide triphosphates, and (c) determining the sequence of the DNA from the sizes of the fragments. The method may be a method of DNA synthesis with increased incorporation of dual-labeled nucleotides as compared to synthesis with a wild type DNA polymerase comprising: (a) providing a DNA polymerase of the invention and (b) contacting the polymerase with a nucleic acid template and dual-labeled nucleotides, wherein the polymerase permits DNA synthesis. The method may be a method of quantitative PCR (QPCR) with increased incorporation of dual-labeled nucleotides as compared to QPCR with a wild type DNA polymerase comprising (a) providing a DNA polymerase of the invention; and (b) contacting the polymerase with a nucleic acid template and dual-labeled nucleotides, wherein the polymerase permits DNA synthesis. In some embodiments, the methods are performed in the absence of a reducing agent, such as dithiothreitol (DTT) or β-mercaptoethanol, to improve stability of the split polymerase.

In another embodiment, the methods of the invention are used to increase uptake of non-natural nucleotides. This can be accomplished by splitting a polymerase in such a way that the polymerase shows increased activity for non-natural nucleotides. Higher nucleotide analog uptake can also be increased by combining the split with other mutations in the amino acid sequence compared to using the split or the amino acid replacement alone.

The invention provides for a method for DNA synthesis comprising providing a non-natural split DNA polymerase, and contacting the polymerase with a nucleic acid template, wherein the polymerase permits DNA synthesis. In one embodiment, the method of DNA synthesis is a method that comprises a split polymerase with increased ability to incorporate non-natural nucleotides or increased ability to utilize modified primer templates relative to the non-split polymerase. The method may be a method of DNA synthesis such as DNA sequencing, quantitative PCR (QPCR), DNA labeling, or a combination thereof. Practice of methods of the invention gives rise to numerous compositions comprising proteins and/or nucleic acids of the invention.

In an additional general aspect, the present invention provides compositions and kits comprising at least one split polymerase of the invention. Compositions comprise at least one molecule of split polymerase or a nucleic acid of the invention. The amount of split polymerase or nucleic acid in the composition can vary widely, but generally the amount is sufficient to perform at least one method or assay of the invention, such as one that uses the split polymerase. The method or assay may involve nucleic acid sequencing, amplification, QPCR, or any other method that involves the use of a nucleic acid polymerase. In a preferred embodiment, the composition excludes reducing agents, such as DTT or β-mercaptoethanol, to better stabilize the split polymerase enzyme of the invention.

In general, a kit according to the invention contains some or all of the components, reagents, supplies, etc. to practice a method according to the invention. In kits comprising a split polymerase according to the invention, the kit typically comprises a sufficient amount of split polymerase to allow at least one reaction involving the split polymerase to occur under appropriate conditions. In one embodiment, a kit contains at least one container (e.g., vial, tube, ampoule) containing a non-natural split polymerase. In embodiments, the kit further comprises at least one other substance used in a nucleic acid polymerase reaction (e.g., amplification, sequencing). Typically, the split polymerase will be supplied in one or more container, each container containing a sufficient amount of split polymerase to allow at least one reaction involving the split polymerase to occur. Kits may also comprise one or more other substances, which are typically substances that aid in the methods of the invention. These may include sterilized water, buffers, dNTPs, control DNA, primers, etc.

EXAMPLES

The invention will be further explained by the following Examples, which are intended to be purely exemplary of the invention, and should not be considered as limiting the invention in any way.

Example 1

Preparation of Split Pfu Polymerases by Site-Directed Mutagenesis and Affinity-Tag Purification Splits were introduced into Pfu DNA polymerase by site specific mutagenesis using the QuikChange® Multi Site-Directed Mutagenesis Kit from Stratagene according to the Manufacturer's instructions. The primers used are shown in Table I.

TABLE I

| Mut. | Primer | SEQ ID NO |
|---|---|---|
| 105 | GTTAGAGGAAAGACAAAAGATTAAGACATGAAAATGAAG GAAACTCAAGATCCTATAG | 14 |
| 106 | GTTAGAGGAAAGACAAAAGATTAAGACATGAAAAAGAAG GAAACTCAAGATCCTATAG | 15 |
| 107 | CCTCTACATTGACACTGATGGTCTCTATTGAGGAGGCAC ACAAATGGCAACTATCCCAGGAGGAGAAAGTGAGG | 16 |

To make clones 105, 106 and 107, the primers above were used with a plasmid template encoding Pfu D141A/E143A (exo-) DNA polymerase with a C-terminal 6× histidine affinity tag (SEQ ID NO: 100). The 108, 109 and 110 clones were made using a similar DNA template that further contained a Q484R mutation in the Pfu DNA polymerase sequence. The split site in clone 105 was moved one residue up, so that fragment I of clone 105 corresponds to Pfu DNA polymerase residues 1-466 as compared to fragment I of 4C11 which encompasses residues 1-467. In clone 105, what was formerly lysine 467 of fragment I (in 4C11) is now found as the second residue of fragment II. Since the new split site could not be engineered without adding a methionine for reinitiation, an additional methionine is also present in clone 105. So by reference to the wild-type Pfu amino acid sequence, the resulting Split Pfu 105 mutant can be notated as: I (1-466)/II (M-467-775). Clone 106 was designed to use the same split and added methionine as clone 105, but additionally has a M3K mutation in fragment II. Therefore, the Split Pfu 106 mutant can be described as: I (1-466)/II (K467M-M468K-(469-775) by reference to wild type Pfu. Fragment I of clone 107 is terminated at the equivalent of Pfu Tyr 546. Sequence was reinitiated with a non-native methionine and enhanced with an upstream ribosomal binding domain. Thus, Split Pfu 107 can be notated as: I (1-546)/II (M-547-775). All three splits were planned individually and in combination with the Q484R mutation that further enhances FCD uptake in 4C11 (numbering relative to Pfu DNA polymerase sequence). Those clones were named: 108 (105+Q484R), 109 (106+Q484R) and 110 (107+Q484R). FIG. 3 depicts the relevant amino acid sequence of wild type Pfu DNA polymerase (Panel A), clone 4C11 (Panel B), clones 105 and 108 (Panel C), clones 106 and 109 (Panel D) and clones 107 and 110 (Panel E).

The reaction was composed of:

| 2.5 µl | of 10x QuikChange Multi reaction buffer |
|---|---|
| 18.5 µl | H$_2$O |
| 1 µl | plasmid template |
| 1 µl | dNTP mix |
| 1 µl | QuikChange Multi enzyme blend |
| 1 µl | plasmid template |

Cycling parameters were:

| 1 cycle | |
|---|---|
| 95° C. | 1 min |
| 30 cycles | |
| 95° C. | 1 min |
| 50° C. | 1 min |
| 65° C. | 17 min |

The reaction was treated with the restriction enzyme Dpn I at 37° C. for one hour to remove the parental plasmid. Two microliters of the reaction was transformed into XL10 Gold competent cells and plated on LBamp50 plates for 20 hours at 30° C. Colonies were picked and used to start 5 ml overnight cultures in LBamp50 media at 30° C. overnight. Plasmid DNA was isolated from the cells using the Strataprep® Plasmid Miniprep Kit. The prepared plasmid was sequenced to confirm the incorporation of the desired mutations. Positives were transformed into BL21-codonPlus® (DE3)-RIPL Competent Cells (Stratagene) cells and plated on LBamp50 plates overnight at 30° C. for 16 hours. Colonies were picked and grown overnight at 30° C. in LBamp50 media. After 16 hours, one ml of media was used to start a culture in 50 ml of LBamp50. The cells were grown at 30° C. until the OD=$_{600}$ reached a value of 0.8 to 1.0, and then induced with a final concentration of 1 mM IPTG. The induced cells were shaken at 30° C. for 2-4 hours before being collected by centrifugation and frozen at −20° C.

Purification of His-tagged split Pfu polymerases was performed using Ni-NTA slurry from Qiagen and following the instructions for *E. coli* cells in the QiaExpressionist Manual protocols 9 and 12 (Qiagen June 2003). Seventy-five µl of the eluted DNA polymerase was run through a Micro Bio-Spin 6 (BioRad) desalting column and into a buffer consisting of (final) 50 mM Tris-Cl pH 8.2, 0.1 mM EDTA, 100 mM KCl.

Example 2

Purification of Split Pfu

Exo-minus Pfu 4C11 (1-467 V93R/D141A/E143A/A318T)/(468-775 Q484R/V604L/A662V-Ss07d7m)/DNA polymerase was expressed in *E. coli* from a pET 11 vector. Induced cells were pelleted and resuspended in 40 mM Tris-Cl, 1 mM EDTA, pH 7.5. Protease inhibitors, lysozyme (~0.25 mg/ml), and 2-mercaptoethanol (10 mM) were added.

Cells were lysed by sonication. The extract was heat treated (85° C., 15 min.) to denature heat-labile proteins. NaCl was added to 1M, and polyethyleneimine to 0.175% to precipitate primarily contaminating nucleic acids. Precipitated material was removed by centrifugation. The supernatant was brought to 65% saturation with ammonium sulfate. Precipitated proteins were collected by centrifugation, washed once with 65% saturated ammonium sulfate, then dissolved in Buffer A-1 (40 mM Tris-Cl, 1 mM EDTA, 10 mM 2-mercaptoethanol, pH 7.5). This was dialyzed overnight against Buffer A-1 and then loaded on Q-Sepharose FF that had been equilibrated with Buffer A-1. Flow-thru fractions containing exo-4C II were collected and loaded directly on a SP-Sepharose HP column also equilibrated with Buffer A-1. After washing with Buffer A-1, exo-Pfu 4C11 was eluted as the major peak with a 30 column-volume gradient to 500 mM KCl. The peak was pooled and dialyzed overnight back into Buffer A-1. This was loaded on a Heparin Sepharose HP column equilibrated in Buffer A-1. After washing with Buffer A-1, exo-4C11 was again eluted as the major peak with a 20 column-volume gradient to 750 mM KCl. The peak was pooled, concentrated, and dialyzed into final dialysis buffer (50 mM Tris-Cl, 0.1 mM EDTA, 1 mM DTT, 100 mM KCl, 50% glycerol, pH 8.2), and stored at −20° C.

Example 3

Cloning, Expression, and Purification of Separate Pfu Fragments

Vector Preparation

The pET21b vector was prepared by amplifying the supercoiled plasmid vector with inverse primers that produced a linear molecule similar to one cut with EcoRI.

Nine 50 μl reactions were set up using the following parameters:

| | |
|---|---|
| 5 μl | 10x PfuUltra ™ II Fusion HS DNA Polymerase (Stratagene) |
| 0.5 μl | 100 mM dNTPs (25 mM each, Stratagene) |
| 1.25 μl | forward primer (100 μM) |
| 1.25 μl | reverse primer (100 μM) |
| 0.2 μl | plasmid DNA (~0.2 ng) |
| 1 μl | PfuUltra ™ II Fusion HS DNA Polymerase (Stratagene) |
| 40.8 μl | H₂O |

Cycling parameters were:

| 1 cycle | |
|---|---|
| 95° C. | 1 min |
| 30 cycles | |
| 95° C. | 45 sec |
| 50° C. | 45 sec |
| 72° C. | 2 min |
| 1 cycle | |
| 72° C. | 5 min |

After amplification, the nine replicates were combined and treated with 5 μl of Dpn I restriction enzyme (Stratagene 4 u/μl) for one hour at 37° C. to destroy the plasmid template. The DNA was purified with StrataPrep PCR kit (Stratagene) according to the manufacturer's recommended protocol.

1 μg of the purified linear vector DNA (in a total volume of 50 μl) was combined with 5.5 μl Xi-Clone Buffer and 2 μl of Xi-Clone enzyme (Genlantis) for 30 minutes at room temperature. The reaction was purified and concentrated with a DNA Cleanup Spin Column (Genlantis) and stored at 20° C.

Insert Preparation

The two Pfu DNA polymerase fragments, fragment I (Pfu 1-467, D141A, E143A, A318T) and fragment II (Pfu 468-775 Q484R, V604L/A662V), were expressed separately by cloning into pET21b. Forward and reverse primers used are shown in Table II below.

TABLE II (SEQ ID NOS 83-86, respectively, in order of appearance)

| | |
|---|---|
| Pfu Frag 1 For | TTGTTTAACTTTAAGAAGGAGATATACATATGATT TTA GAT GTG GAT TAC ATA ACT GAA GAA GGA AAA C |
| Pfu Frag 1 Rev | CCGGATCTCAGTGGTGGTGGTGGTGTTT TGT CTT AAT CTT TTG TCT TTC CTC TAA CAA ATG TCC C |
| Pfu Frag 2 For | TTGTTTAACTTTAAGAAGGAGATATACATATGAAG GAA ACT CAA GAT CCT ATA GAA AAA ATA CTC C |
| Pfu Frag 2 Rev | CCGGATCTCAGTGGTGGTGGTGGTG TCT CTT TTG CTT TTC TAA CAT GTC TAC TAG TTC TTT TGG |

The products were amplified from the 4C11 plasmid with the following primers and method.

| | |
|---|---|
| 5 μl | 10x PfuUltra ™ II Fusion HS DNA Polymerase (Stratagene) |
| 0.5 μl | 100 mM dNTPs (25 mM each, Stratagene) |
| 2 μl | forward primer (50 ng/μl) |
| 2 μl | reverse primer (50 ng/μl) |
| 1 μl | plasmid DNA (~0.2 ng) |
| 1 μl | PfuUltra ™ II Fusion HS DNA Polymerase (Stratagene) |
| 38.5 μl | H₂O |

Two 50 μl reactions were amplified for each fragment as follows:

| 1 cycle | |
|---|---|
| 95° C. | 1 min |
| 30 cycles | |
| 95° C. | 45 sec |
| 50° C. | 45 sec |
| 72° C. | 30 sec |
| 1 cycle | |
| 72° C. | 5 min |

After amplification, 4 units of the restriction enzyme Dpn I (Stratagene, 4u/μl) was added to each PCR amplification reaction to digest the plasmid template. The DNA was purified with StrataPrep PCR (Stratagene).

2 μl of the prepared pET21 b vector was added to 10 μl of purified insert and then transformed into 50 μl of XL10-Gold® Ultracompetent Cells (Stratagene). The transformed cells were plated on LB ampicillin (50 μg/ml) and incubated at 30° C. for 18 hours. Colonies were screened for the presence of insert by PCR amplification, and the insertions were verified by DNA sequencing.

Purification of the Pfu fragments was attempted using the procedure described in Example 2. When purified using the same method, fragment I exhibited a different elution profile compared to intact Pfu DNA polymerase, consistent with the differences in isoelectric point. Fragment II was extremely insoluble and was not loaded onto any columns.

Example 4

Assaying Nucleotide Analog Incorporation by Endpoint PCR

To test the ability of split Pfu enzymes to perform in PCR with and without nucleotide analogs, a simple plasmid template was used (plasmid 2-20). This plasmid contained a 800 bp insert which was amplified out of the pET vector by primers on either side of the vector insertion site.

PCR reaction mixtures designed to test FCD utilization consisted of the following:

| | |
|---|---|
| 1.2 µl | 10x cloned Pfu buffer (Stratagene) |
| 0.24 µl | 10 mM dATP, dGTP, TTP |
| 0.29 µl | Petrev primer (10 µM) |
| 0.29 µl | Petfor primer (10 µM) |
| 0.5 µl | diluted plasmid 2-20 |
| 1.0 µl | of polymerase |
| 1.0 µl | of 600 µM (total) dCTP/FCD mix (50% dCTP, 50% FCD) |
| 7.48 µl | H20 |

The enzyme was tested in the above PCR at several dilutions to find the optimal volume to use in a PCR reaction. The optimal value determined was used in comparison with wild-type exo-Pfu and other mutants.

The PCR reactions were amplified with the following parameters:

| 1 cycle | |
|---|---|
| 95° C. | 1 min |

| 30 cycles | |
|---|---|
| 95° C. | 45 sec |
| 58° C. | 45 sec |
| 72° C. | 1 min |

| 1 cycle | |
|---|---|
| 72° C. | 5 min |

When FCD is incorporated by a DNA polymerase, FAM-dCMP is added to the growing chain concomitant with the release of Dabcyl-pyrophosphate (PP). In solution or homogeneous assays (e.g., QPCR), fluorescence increases in direct proportion to the number of FAM-dCMP molecules incorporated, or the number of unquenched FAM moieties. Incorporation of analog was demonstrated for some of the split polymerases by this method.

Incorporation of analog was assessed by performing endpoint PCR, followed by gel electrophoresis and detection of fluorescent amplicon. The entire PCR reaction mixtures were run on a 1% agarose, 1×TBE gel (Wide Mini ReadyAgarose Gel, 1×TBE, 1%, 20 well, 15×10 cm, Bio-Rad Laboratories) and the FAM label was detected with ultraviolet light and a green filter. A visible band at the appropriate size results in the scoring of "yes" in Table III under analog incorporation. After recording the image, the gel was stained with ethidium bromide to visualize all DNA products.

To determine if the split polymerase was functional for incorporation of conventional nucleotides, a PCR reaction was run essentially under the conditions above with equal amounts of all four dNTPs and no nucleotide analogs. Detection limit of the gel was about 1 ng of nucleic acid per band.

A visible band at the appropriate size results in the scoring of "yes" in Table VI under conventional nucleotide incorporation.

Example 5

Preparation of Split Chimeric JdF-3/Pfu Polymerases

Chimera polymerases were constructed from JdF-3 DNA polymerase and Pfu DNA polymerase. The split was homologous to the split of 4C11 in Pfu DNA polymerase. Fragment I was encoded from the JdF-3 DNA polymerase gene while fragment II was encoded by Pfu DNA polymerase gene. The construct was engineered by making two PCR products corresponding to the first fragment and the second fragment, purifying the products and then fusing the products by splice overlap. Fragment I ended at the same amino acid as the split JdF-3 Fragment I shown in FIG. 4 (Panel B) and Fragment II started at M468 of Pfu DNA polymerase (seen in FIG. 3).

In addition to JdF-3 sequence specific nucleotides, the forward primer for the first product had extra sequence on the 5' end that would allow insertion by recombination into a pET21b vector (Table IV). The reverse primer for the first fragment contained extra sequence on the 5' end that was complimentary to the sequence at the beginning of fragment 2.

The forward primer for fragment 2 had additional 5' sequence corresponding to the end sequence of fragment 1, as well as containing the same sequence encoding the beginning of fragment 2. In addition to Pfu DNA polymerase sequence, the reverse primer of fragment 2 also contained sequence homologous to the 6× His (SEQ ID NO: 100) region of the pET2I b vector which allows for homologous recombination into the vector.

TABLE IV (SEQ ID NOS 87-90, respectively, in order of appearance)

| | |
|---|---|
| JdF3 xiF | TTGTTTAACTTTAAGAAGGAGATATACATATGATCCTTG ACGTTGATTACATCACCGAGAATGG |
| J-PchimIntF | GGA AAG GCA GAA GAT AAA GAG GAA ATG A AG GAA ACT CAA GAT CCT ATA GAA AAA ATA C |
| J-PchimIntR | GTA TTT TTT CTA TAG GAT CTT GAG TTT CCT TCA TTT CCT CTT TAT CTT CTG CCT TTC C |
| JDF3xi Rhis | CCGGATCTCAGTGGTGGTGGTGGTGGTGCTTCTTCTTCC CCTTCGGCTTCAGC |

Amplification reactions were assembled as follows:

| Fragment I PCR setup | |
|---|---|
| 10 µl | 5x Herculase II buffer (Stratagene) |
| 0.4 µl | 100 mM dNTP mix (25 mM each) |
| 1.2 µl | JdF3XiF primer 125µ1M |
| 1.2 µl | JPchimR primer 125µpM |

-continued

| Fragment I PCR setup | |
|---|---|
| 0.5 µl | exo-JdF-3 DNA polymerase plasmid clone (~50 ng/µl) |
| 1.0 µl | Herculase II Fusion DNA polymerase (Stratagene) |
| 35.7 µl | H₂0 |

| Fragment 2 PCR setup | |
|---|---|
| 10 µl | 5x Herculase II buffer (Stratagene) |
| 0.4 µl | 100 mM dNTP mix (25 mM each) |
| 1.2 µl | JPchimF primer 125µ1M |
| 1.2 µl | PfuXiR primer 125µ1M |
| 0.5 µl | exo-Pfu DNA polymerase plasmid clone (50 ng/µl) |
| 1.0 µl | Herculase II Fusion DNA polymerase (Stratagene) |
| 35.7 µl | H₂O |

Amplification conditions:

| 1 cycle | |
|---|---|
| 95° C. 30 cycles | 1 min |
| 95° C. | 45 sec |
| 50° C. | 45 sec |
| 1 cycle | |
| 72° C. | 1 min |

After amplification, Dpn I restriction enzyme was added to the reactions to destroy the parental plasmid DNA template. The products were purified with the StrataPrep PCR kit per manufacturer's instructions.

| Splice Overlap setup | |
|---|---|
| 5 µl | 10x cPfu Buffer |
| 0.4 µl | 100 mM dNTP (25 mM each) |
| 5 µl | pure fragment 1 |
| 5 µl | pure fragment 2 |
| 1 µl | Pfu Turbo DNA polymerase (Stratagene) |
| 33.6 µl | H₂O |

Amplification conditions:

| 1 cycle | |
|---|---|
| 95° C. 15 cycles | 1 min |
| 95° C. | 45 sec |
| 50° C. | 45 sec |
| 72° C. | 1 min, 50 sec |

One microliter of the splice overlap reaction was used as template in the reaction below:

| | |
|---|---|
| 5 µl | 10 cPfu Buffer |
| 0.4 µl | 100 mM dNTP (25 mM each) |
| 1.2 µl | JdF3XiF primer 125 µl M |
| 1.2 µl | PfUXiR primer 125 µl M |
| 1 µl | overlap reaction |
| 1 µl | Pfu Turbo DNA polymerase (Stratagene) |
| 40.2 µl | H₂O |

Amplification conditions:

| 1 cycle | |
|---|---|
| 95° C. 30 cycles | 1 min |
| 95° C. | 45 sec |
| 50° C. | 45 sec |
| 72° C. | 3 min |

The PCR products were gel purified and cloned into a pET21 vector which had been prepared using the Xi-Clone High Speed Cloning Kit (Genlantis) per manufacturer's instructions (as described under Vector Preparation in Example 3). The clones were transformed into XL10-Gold ultracompetent cells (Stratagene) and incubated at 30° C. for approximately 20 hours. Colonies were screened by PCR for an insert of the correct size. Positive colonies were cultured and DNA purification was performed. The plasmid insert was sequenced to confirm the split region and the 5' and 3' insertion sites.

Verified plasmids were transformed into BL21-CodonPlus (DE3)-RIL (or RILP) competent cells per manufacturer's instructions (Stratagene) and expressed and purified as described in other sections.

Example 6

Other Split Polymerases Comprising Mutations

The 4C11 Pfu split polymerase and the JdF-3 Z2 polymerase provide two substantially different types of splits. The 4C11 split is a "seamless split" in which no amino acids are introduced into or removed at the split site, and the sequence of amino acids near the split remains unchanged as compared to the wild type Pfu. The JdF-3 Z2 split polymerase includes a 10 amino acid insertion on the end of fragment I, the N-terminal fragment, including a duplication of the tripeptide of amino acids 467-469. This demonstrates a tolerance for insertions at the split site.

A number of additional amino acid mutations were investigated in the context of the 4C11 mutant. The amino acid mutations were remote from the split site, which was after amino acid 467. The Q484R mutation increased utilization of dual labeled nucleotide analogs as compared to the 4C11 mutant without the mutation. A number of other point mutations are known to increase incorporation of non-conventional nucleotide analogs such as positions corresponding to Pfu L409, Y410, P411, R461, K465, Q472, Q484, A486, R488, L490, A491, N492, Y495, and Y497. Such mutations may be useful in increasing the incorporation of non-conventional nucleotides by split polymerases in extension reactions. The three additional mutations, A318T, V604L, and A662V may contribute to the stability of the split polymerase. Other mutations that were subsequently added to 4C11, at D141A/E143A to reduce 3' to 5' exonuclease activity, and addition of an Sso-like DNA binding domain at the C-terminus of the C-terminal fragment, did not disrupt the increased dual labeled nucleotide analog incorporation observed in the initial 4C11 mutant. This demonstrates that mutations made at sites remote to the split site can have their expected activity without altering the increased dual label nucleotide analog incorporation observed with the split polymerase without further mutations.

Further split polymerases were designed in Pfu and JdF-3 using some of the primers shown in Table V. Some of the split polymerases have been expressed, purified, and tested for polymerase activity and improved non-conventional nucleotide incorporation (Table VI). Sites of splits and amino acid changes are indicated by the sites in the native polypeptide. For example, the same split found in the Pfu split polymerase 4C11, was also made in an identical site in the JdF-3 polymerase (mutants JdF-3 201 and JdF-3 202 (shown in FIG. 4)).

TABLE V

| Mut. | Primer | SEQ ID NO |
|---|---|---|
| 107.2f | CTGATGGTCTCTATGCAACTATCCCAGGATAATGGAAAGTGAGGAAATAAAG | 17 |
| 107.2r | CTTTATTTCCTCACTTTCCATTATCCTGGGATAGTTGCATAGAGACCATCAG | 18 |
| 210f | CAAAAGATTAATACAAAAATGAAGGAATGAATGCCTATAGAAAAATAC | 19 |
| 210r | GTATTTTTCTTATAGGCATTCATTCCTTCATTTTTGTCTTATCTTTTG | 20 |
| 211f | GATTAAGACAAAAATGAAGGAATGATAGAAAAATACTCCTTGACTATAGAC | 21 |
| 211r | GTCTATAGTCAAGGAGTATTTTTTCTATCATTCCTTCATTTTTGTCTTAATC | 22 |

TABLE V-continued

| Mut. | Primer | SEQ ID NO |
|---|---|---|
| 212f | CAAAAGATTAAGACAAAAATGAAGTAAATGGAAACTCAAGATCCTATAGAAAAAATA | 23 |
| 212r | GTATTTTTTCTATAGGATCTTGCATTCATTCCTTCATTTTTGTCTTAATCTTTTG | 24 |
| 213f | CAAAAGATTAAGACAAAAATGAAGTAAATGGAAACTCAAGATCCTATAGAAAAAATA | 25 |
| 213r | TATTTTTTCTATAGATCTTGAGTTTCCATTTACTTCATTTTTGTCTTAATCTTTTG | 26 |
| 214f | CATCCCTGGTTTTATACCAAGTCTCTGAATGGGACATTGTTAGAGGAAAG | 27 |
| 214r | CTTTCCTCTAACAAATGTCCCATTCAGAACTTGGTATAAAACCAGGGATG | 28 |
| 215f | GTAGGCCACAAGTTCTGCAAGGACTGATGCCCTGGTTTTATACCAAGTCTCTTGG | 29 |
| 215r | CCAAGAGACTTCCTATAAAACCAGGCATCAGTCCTTGCAGAACTTGTGGCCTAC | 30 |
| 216f | GCTATGCAAAAGCAAGATGGTACTGATGAAGGAGTGTGCTGAGAGCGTTACTGCC | 31 |
| 216r | GGCAGTAACGCTCTCAGCACACTCCTTCATCAGTACCATCTTGCTTTTGCATAGC | 32 |

TABLE VI

| Mutant Name | Enzyme | Split site | AA added (deleted) | Additional mutations | Conv. nt incorporation | Analog incorporation |
|---|---|---|---|---|---|---|
| 4C11 | Pfu | 467 | None | Q484R A318, V604L, A662V | Yes | Yes |
| SQ | Pfu | 467 | None | Q484R | Yes | Yes |
| 105 | Pfu | 466 | M before 467 | | Yes | Yes |
| 106 | Pfu | 466 | M before 467 | | | |
| 107 | Pfu | 546 | M before 547 | | No | No |
| 107.2 | Pfu | 551 | M before 552 | | No | No |
| 108 | Pfu | 466 | M before 467 | Q484R | | |
| 109 | Pfu | 466 | M before 467 | E470K, Q484R | Yes | Yes |
| 110 | Pfu | 546 | M before 547 | Q484R | | |
| 210 | Pfu | 470 | | | Yes | Yes |
| 211 | Pfu | 470 | | | | |
| 212 | Pfu | 470 | | | | |
| 213 | Pfu | 469 | M before 470 | | Yes | Yes |
| 214 | Pfu | 453 | | L454M | | |
| 215 | Pfu | 445 | | | No | No |
| 216 | Pfu | 506 | C507M | | No | No |
| JdF3fPfu-1 | JdF-3/Pfu | 1-466/ 468-end | | | Yes | |

TABLE VI-continued

| Mutant Name | Enzyme | Split site | AA added (deleted) | Additional mutations | Conv. nt incorporation | Analog incorporation |
|---|---|---|---|---|---|---|
| JdF3/Pfu-2 | JdF-3/Pfu | 1-466/ 468-end | | Q484R | | |
| JdF3/Pfu-3 | JdF-3/Pfu | 1-466/ 468-end | | S345P | | |
| JdF3/Pfu-4 | JdF-3/Pfu | 1-466/ 468-end | | Q484R, S345P | | |
| JdF-3-201 | JdF-3 | 466 | | K464A | Yes | |
| JdF-3 202 | JdF-3 | 466 | | | | |
| JdF-3 Z2 | JdF-3 | 469 | 10 AA added after M | | Yes | Yes |
| Taq-1 | Taq | 645 | | | | |
| Taq-2 | Taq | 672 | | | | |
| Taq-3 | Taq | 657 | | | | |
| Taq-4 | Taq | | | | | |

All mutants in Table VI are exo-minus and include mutations at amino acids D141A and E143A.

Test for activity in standard PCR for conventional nucleotide incorporation or for analog incorporation was performed using the method in Example 4. Conventional nucleotide incorporation is scored as a "yes" if a product of the expected size is detectable by ethidium bromide staining of an agarose gel (at least about 1 ng of nucleic acid). Analog incorporation is scored as a "yes" if a product of the expected size is detected prior to ethidium bromide staining of a comparable agarose gel under the appropriate wavelength for detection of the analog. The amount of nucleic acid detected depends on the percent analog used in the reaction, and the amount of product produced. QPCR methods can also be used to detect analog incorporation.

It is notable that the splits at amino acid 547, roughly analogous to the natural split Mth archaeal polymerase, inhibit function of Pfu DNA polymerase.

FIG. 8 shows non-conventional nucleotide incorporation assays for some of the other mutants tested. For each variant, the enzyme was purified from a 1 L culture after expression from a pET vector in *E. coli* strain BL21-DE3-CodonPlus (RIL). Purification included the following steps: heat-treatment of the cell lysate at 85° C. for 15 minutes; treatment of the heated lysate with 0.15% PEI (polyethyleneimine) and 1 M NaCl to remove nucleic acids; clarification by centrifugation; then column chromatography on Q-Sepharose FF followed by Heparin-Sepharose HP. Enzyme was found in the flow-through fraction for Q-Sepharose and was eluted with a KCl gradient from Heparin-Sepharose. The purified enzymes were analyzed by SDS-PAGE. Variant JDF-3 Z2 was comprised of predominantly two peptide fragments, as expected. Other, non-split variants were comprised of single fragments.

PCR activity was measured for JDF-3 variants using a 962 bp Lambda DNA target. The reaction was carried out in 1× Taq PCR reaction Buffer in a 25 µl reaction containing 5 ng Lambda DNA, 0.4 µM each primer (Forward: 5'-ATCAGAAACGAACGCATCATCAAGT (SEQ ID NO: 101), Reverse: 5'-GCCTCGCATATCAGGAAGCAC (SEQ ID NO: 102)), 200 µM each dGTP, dATP, TTP, and the indicated amounts of dCTP, FCD, and/or RCD (5-aminoallyl-(5-ROX)-2'-deoxycytidine-5'-triphoso-N$^6$-(6-aminohexyl)-dabcyl). Cycling conditions were: 93° C., 1 min; 30 cycles of 93° C., 1 min, 58° C., 50 sec, 72° C., 1 min; then 72° C., 10 min. Samples (5 µl or 75 ng of each reaction were run on a 1% agarose gel. The gel was photographed first in the absence of ethidium bromide with a Green filter (A) to visualize incorporated fluorescein (FCD) or with an ethidium bromide filter (B) to visualize incorporated ROX (RCD). Then, the gel was stained with ethidium bromide and photographed again with the ethidium bromide filter (C). Samples with the "a" designation comprised 25 µM FCD+25 µM dCTP in the reaction mix and samples with a "b" designation comprised 5 µM RCD+45 µM dCTP. The samples loaded were exo-minus JdF-3 (samples designated as "1"), exo-minus JdF-3, L408H, A490Y ("2"), exo-minus JdF-3 Z2 ("3"), exo-minus Pfu 4C11 ("4"), and exo-minus Pfu, L409H, A491Y ("5"). As stated previously, the exo-minus notation means that additional mutations D141A and E143A are present in the polymerase.

Both FAM (FAM-dCTP-Dabcyl uptake) incorporation (Panel A) and ROX incorporation (Panel B) were increased with the JdF-3 Z2 (lane 3 of each gel in FIG. 8), JdF-3 L408H and A490Y (lane 2), and Pfu L409H and A491Y (lane 5) mutants as compared to wild type JdF-3 (lane 1).

FIG. 9 shows the amino acid sequence of the 4C11 DNA polymerase with the Q484R mutation, comprising both the amino fragment (Panel A) and the carboxyl fragment (Panel B). The sequence has the D141A/E143A mutations (exo minus). The changed amino acids are shown slightly above the rest of the sequence. The corresponding nucleic acid sequence (SEQ ID NO: 80) is shown in the sequence listing below.

FIG. 10 depicts the results from a PCR amplification assay using the Pfu double mutant. This is a split Pfu mutant with the exo-minus mutations and with an additional Q484R mutation (different from the exo-minus Pfu 4C11 mutant described in Example 2). Amplification was performed with a dCTP analog labeled with dabcyl at the gamma phosphate. The nucleotide pool used was 200 µM dATP, dGTP and TTP. The total pool of dCTP was 50 µM and the percentage of dabcyl-dCTP in that pool varied from zero to 100 percent as indicated on the figure. The double mutant was compared to Exo-minus cPfu, a non-split polymerase that was exonuclease minus (comprised mutations D141A and E143A). As can be seen from FIG. 10, the activity of the double mutant and the non-split enzyme are substantially the same at lower concentrations of the dCTP analog (up to 75 µM). However, at higher ratios dCTP analog (at 75 and 90 µM), the non-split polymerase loses activity, but the double mutant configuration particularly improves the uptake of dabcyl dCTP modified at the gamma phosphate. Without being limited to any mechanism, this perhaps is a result of a loosening of the nucleotide binding pocket when the finger folds over the incoming nucleotide.

FIG. 11 depicts the results from PCR amplification of a plasmid template with dCTP labeled with the nucleotide analog FCD. End point PCR (plasmid template in 1× cPfu buffer; Stratagene) using 200 µM each dATP, dGTP and TTP, and a total dCTP (dCTP+FCD) pool of 50 µM was used in the reactions. The percentage of FCD in the dCTP pool varied from zero (100% dCTP:0% FCD) to one hundred percent (0% dCTP:100% FCD) as indicated in FIG. 11. The 4C11 mutant with the exo minus mutations (D141A and E143A) was compared to the non-split Pfu enzyme with the exo minus mutations (D141A and E143A). Electrophoresis of the PCR products on an agarose or acrylamide gel in the absence of ethidium bromide allowed the resultant FAM-labeled DNA products to be visualized with ultraviolet excitation and a green filter (Panel A). The gel was subsequently stained with ethidium bromide and visualized with an orange filter to reveal all DNA molecules (Panel B). As shown in the figure, the wild type (non-split) exo minus Pfu enzyme was unable to incorporate the FCD analog, while the split Pfu Q484R double mutant showed an optimal uptake of FAM-dCMP at 50-75% FCD. This experiment shows that the split polymerases of the present invention are not limited by the kind of nucleotide analog that can be used, but that the invention works for different types of modified nucleotides.

Example 7

Refolding of 4C11 Split Polymerase after Separate Expression of Each Fragment

Figure 12:
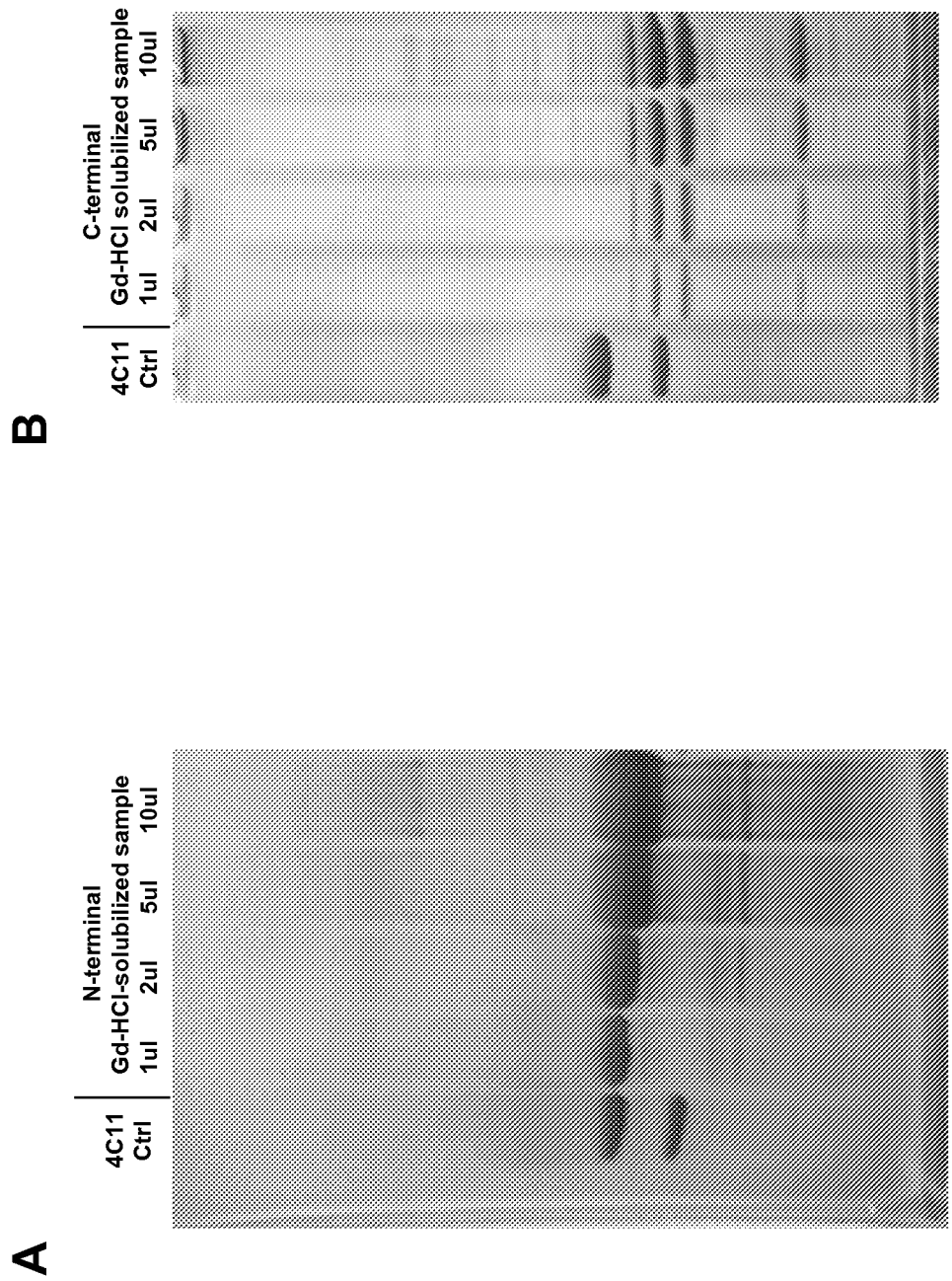
FIG. 12 shows SDS-PAGE analysis of solubilized, separately expressed 4C11 split polymerase fragments after partial purification from inclusion bodies (Panel A and B), SDS-PAGE analysis of refolded 4C11 split polymerase (Panel C), PCR assays of the refolded protein (Panel D) and SDS-PAGE analysis of the refolded protein after further purification by column chromatography (Panel E).
Figure 12:
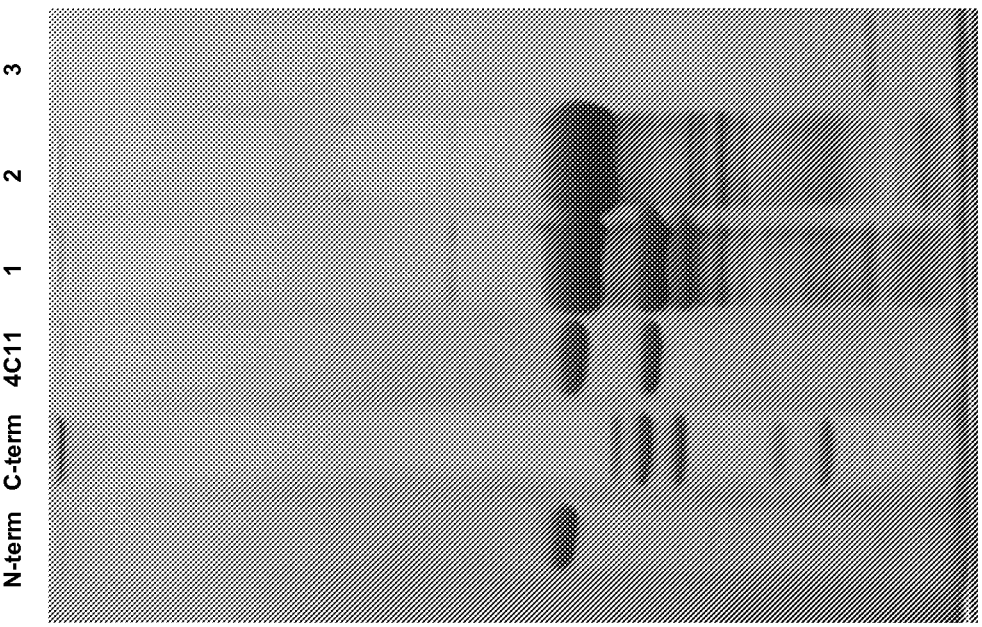
Figure 12:
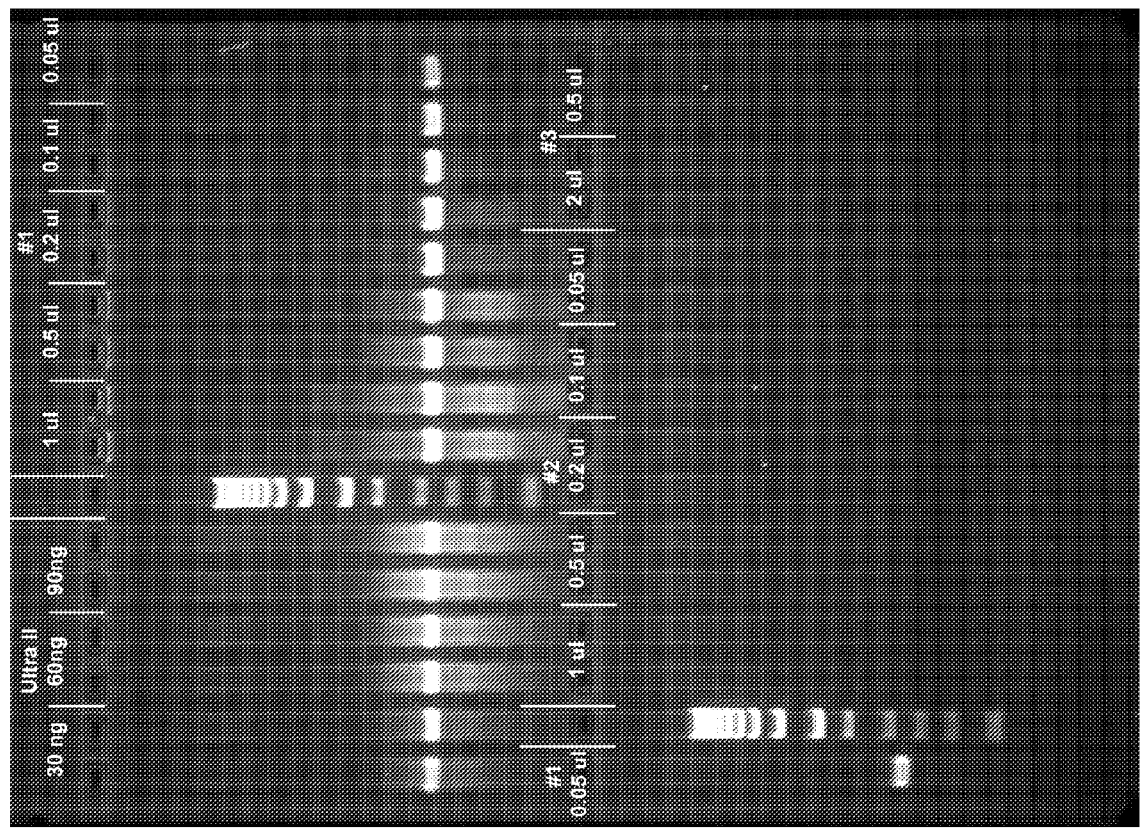
Figure 12:
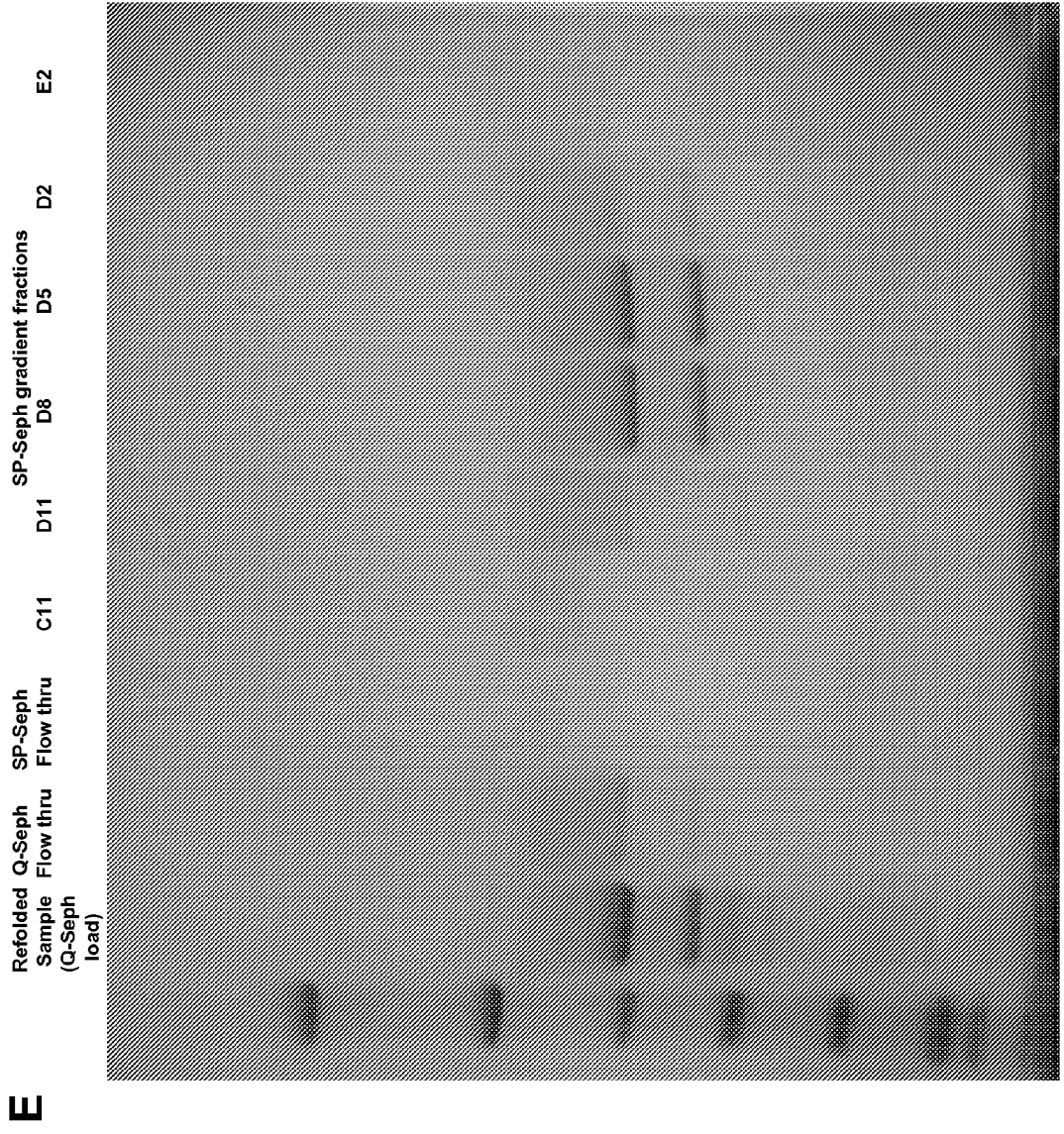

In this Example, the N-terminal and C-terminal fragments of the 4C11 split polymerase were expressed and purified separately as in Example 3. However, in this case, the fragments were also solubilized and refolded (FIG. 12). Each was expressed from a pET vector in *E. coli* strain BL21-DE3-CodonPlus RIL in a 2 L culture. The insoluble pellets (i.e. the inclusion bodies) after cell breakage were washed in turn with buffer containing 0.15% sodium deoxycholate, 1% Triton X-100, and then with buffer alone (40 mM Tris pH 7.5, 10 mM 2-mercaptoethanol). The N-terminal and C-terminal fragment pellets were solubilized with 4M or 5M guanidine HCl, respectively. SDS-PAGE samples were prepared from the guanidine HCl-containing preparations by TCA precipitation.

The partially-purified fragments were visualized by SDS-PAGE (Panels A and B). Results showed that both the N-terminal fragment (Panel A) and the C-terminal fragment (Panel B) were expressed, although in different amounts. The N-terminal fragment was approximately 50% soluble and made in large amounts. The C-terminal fragment, however, was much less abundant, and completely insoluble when expressed on its own. Based on the band intensity of the fragments compared to the intensity of staining for the 4C11 control, it was estimated that the N-terminal fragment preparation was approximately 5-fold more concentrated than the C-terminal fragment. The C-terminal fragment preparation was also less pure than the N-terminal fragment, possibly due to the initially lower yield of expressed C-terminal fragment.

For refolding experiments, the insoluble fraction of each sample was purified. Refolding experiments were performed by simply mixing the two solubilized fragments in an approximately 1:1 stoichiometric ratio (i.e. 5:1 volume of C-terminal: N-terminal). Controls included reactions with each fragment alone. Refolding was achieved by simply dialyzing the mixture against 200 volumes of buffer (40 mM Tris, pH 7.5, 1 mM EDTA, 100 mM KCl, 10% glycerol) containing no guanidine HCL and no 2-mercaptoethanol. The dialysis buffer was changed twice over a ~24 hr period. A multi-step dialysis was also tried where the guanidine HCl concentration was reduced in steps (2M, 1M, 0 M), but produced nearly identical results as the single step method. After recovery of the samples from dialysis, insoluble material was removed by centrifugation. Protein in the samples was quantitated by Bradford assay.

Refolded samples were analyzed by SDS-PAGE (Panel C). The samples loaded were solubilized N-terminal fragment (N-term), solubilized C-terminal fragment (C-term), purified 4C11 control (4C11), complete refolding reaction comprising N-terminal and C-terminal fragments (1), control refolding reaction comprising N-terminal fragment only (2), and control refolding reaction comprising C-terminal fragment only (3). The Bradford protein assays showed recovered soluble protein of 1.0 mg/ml for sample 1, 1.1 mg/ml for sample 2, and ≤0.1 mg/ml for sample 3. Interestingly, the N-terminal fragment largely refolded to a soluble state on its own. It showed slightly more recovered soluble protein than for the reaction with both fragments, possibly indicating that the very insoluble C-terminal fragment co-precipitated with a portion of the N-terminal fragment during refolding.

Refolded proteins were also analyzed by PCR assays to demonstrate successful refolding (Panel D). The samples loaded were Pfu Ultra II polymerase as a control (Ultra II), refolding reaction comprising N-terminal and C-terminal fragments (#1), refolding reaction comprising N-terminal fragment only (#2), and refolding reaction comprising C-terminal fragment only (#3). The indicated volumes of each refolding reaction (and ng amounts of Pfu Ultra II polymerase for the controls) were assayed by PCR (0.9 kb human alpha-1-antitrypsin target) in 50 µl reactions consisting of 1× Pfu Ultra II reaction buffer, 100 ng human genomic DNA, 100 ng each primer (Forward: 5'-GAGGAGAGCAGGAAAGGTG-GAAC (SEQ ID NO: 103); Reverse: 5'GAGGTACAGGGT-TGAGGCTAGTG (SEQ ID NO: 104)), and 250 µM each dGTP, dATP, dCTP, TTP. Cycling conditions: 1 cycle of 95° C., 2 min; 30 cycles of 95° C., 30 sec, 58° C., 30 sec, 72° C., 15 sec, then 1 cycle of 72° C., 10 min. 10 µl of each PCR reaction was analyzed on a 1% agarose gel. All reactions were run in duplicate. Results clearly show that PCR assays were only successful when both the N-terminal and C-terminal fragments were present. PCR amplification products were only seen in lanes containing sample #1 and the size of the products correlated to the size of the products seen in the control lanes (Ultra II).

A refolded sample was also subjected to chromatographic purification (Panel E) to demonstrate its integrity and to demonstrate that it behaved similarly to the enzyme purified from a bicistronic expression vector. A refolded sample acquired as described above using both N-terminal and C-terminal fragments was further purified using a standard method for Pfu polymerases. This included Q-Sepharose column chromatography where Pfu polymerase passes through the column without binding, followed by SP-Sepharose chromatography where Pfu polymerase binds and is subsequently eluted with a KCl gradient. The purified samples were analyzed by SDS-PAGE. The samples loaded were the initial refolded sample (which was the Q-Sepharose load), the Q-Sepharose flow thru, the SP-Sepharose flow thru, and SP-Sepharose gradient fractions (C11, D11, D8, D5, and D2). Results indicated that the refolded polymerase was successfully bound by SP-Sepharose and eluted in a purified form by the gradient. If the split polymerase is expressed from a bicistronic expression vector, the polypeptide fragments do not form inclusion bodies and therefore, do not need to be solubilized and refolded. Therefore, a preferred embodiment of the methods of the invention comprises production of a split polymerase of the invention using a polycistronic expression system to avoid the steps of solubilization from inclusion bodies and refolding of the fragments into a functional split polymerase. Expression of a split polymerase from a polycistronic expression system has advantages of ease of production, cost-effectiveness, time savings, etc.

It will be apparent to those skilled in the art that various modifications and variations can be made in the practice of the present invention without departing from the scope or spirit of the invention. Other embodiments of the invention will be apparent to those skilled in the art from consideration of the specification and practice of the invention. It is intended that the specification and examples be considered as exemplary only, with a true scope and spirit of the invention being indicated by the following claims.

For example, in some cases the fingertip region may be comprised of an additional amino acid. In such cases, the consensus sequence for the split site will more closely resemble:

GXXXXBLXXLBXXRX-BKXXMXXJX$_{(1-2)}$DXXOZXBLDXRQZABKBBAN

XUYGYXXX (SEQ ID NO: 105)

in which the lettering has the same meaning as described elsewhere, except that X$_{(1-2)}$ means that either one or two amino acids can be in that region.

The invention claimed is:

1. A split Family B DNA polymerase wherein the split is at a non-natural split site within the fingers domain of the DNA polymerase and the split polymerase exhibits increased incorporation of non-natural nucleotides or increased utilization of modified primer templates relative to the non-split polymerase.

2. The split polymerase of claim 1, wherein the Family B DNA polymerase is from a *Pyrococcus* or *Thermococcus* species.

3. The split polymerase of claim 2, which comprises SEQ ID NO:91 and SEQ ID NO:92, with or without a K464A mutation, or comprises SEQ ID NO:97 and SEQ ID NO:98.

4. The split polymerase of claim 2, which comprises SEQ ID NO:94 and SEQ ID NO:95.

5. The split polymerase of claim 1, wherein the polymerase comprises a motif having the sequence RXXXK(X)nQXXXXKXXXNSXGX (SEQ ID NO:4), where n is any number of amino acids between and including 15 and 80, and wherein the split occurs within this sequence.

6. The split polymerase of claim 1, wherein the split polymerase has at least 70% identity to amino acids 448 to 500 of SEQ ID NO:3.

7. The split polymerase of claim 1, wherein the split polymerase comprises one or more mutations that improve incorporation of a non-natural nucleotide into a nucleic acid polymerized by the split polymerase, that reduce 3'-5' exonuclease activity, that reduce 5'-3' exonuclease activity, that reduce uracil detection activity, that increase stability of the split polymerase as compared to a corresponding non-split polymerase, or that incorporate a DNA binding domain.

8. The split polymerase of claim 1, wherein the amino acid sequence of the polymerase comprises a mutation at an amino acid corresponding to one or more of the following amino acids in Pfu DNA polymerase (SEQ ID NO:3): L409, Y410, P411, R461, K465, Q472, Q484, A486, R488, L490, A491, N492, Y495, Y497, D141, E143, V93, A318, V604, and A662.

9. The split polymerase of claim 8, wherein the amino acid mutation corresponds to one or more of the following Pfu mutations: L409H, Y410V, P411L, R461A/N, K465A/N, Q472H, Q484R/K, A486T, R488A, L490Y, A491Y, N492A, Y495S, Y497A/L.

10. The split polymerase of claim 1, wherein the amino acid sequence of the polymerase comprises, with respect to a corresponding Pfu DNA polymerase sequence (SEQ ID NO:3), a double mutation D141A/E143A, a single mutation V93R, or both, which reduce 3' to 5' exonuclease activity or reduce sensitivity to uracil as compared to the same polymerase without the mutations.

11. The split polymerase of claim 1, wherein the amino acid sequence of the polymerase comprises a mutation at an amino acid corresponding to one or more of the following amino acids in Pfu DNA polymerase (SEQ ID NO:3): A318, V604, A662, wherein the mutations increase stability of the split polymerase as compared to the polymerase without the mutations.

12. The split polymerase of claim 1 which further comprises a C-terminal fusion with a DNA binding protein.

13. A composition comprising the split polymerase of claim 1 and at least one other substance required for a nucleic acid polymerization reaction.

14. A method for DNA synthesis comprising: combining the split DNA polymerase of claim 1 with a nucleic acid template and providing conditions that permit DNA synthesis.

15. The method of claim 14, wherein the method of DNA synthesis is a method of DNA sequencing, quantitative PCR (QPCR), DNA labeling, or a combination thereof.

16. The method of claim 14, wherein the split polymerase comprises SEQ ID NO:91 and SEQ ID NO:92, with or without a K464A mutation, or SEQ ID NO:94 and SEQ ID NO:95, or SEQ ID NO:97 and SEQ ID NO:98.

17. A kit comprising the split polymerase of claim 1 and at least one other substance used in a nucleic acid polymerase reaction.

* * * * *

UNITED STATES PATENT AND TRADEMARK OFFICE
CERTIFICATE OF CORRECTION

PATENT NO.      : 9,085,762 B2
APPLICATION NO. : 11/968152
DATED           : July 21, 2015
INVENTOR(S)     : Holly Hogrefe et al.

It is certified that error appears in the above-identified patent and that said Letters Patent is hereby corrected as shown below:

In the specification

In column 4, line 12, delete "D41 1," and insert -- D411, --, therefor.

In column 6, line 60, delete "1106)" and insert -- 1106.) --, therefor.

In column 6, line 61, delete "archael" and insert -- archaeal --, therefor.

In column 11, line 8, delete "sp. }" and insert -- sp.} --, therefor.

In column 11, line 25, delete "hermococcus" and insert -- Thermococcus --, therefor.

In column 11, line 35, delete "tokodaz" and insert -- tokodai --, therefor.

In column 12, line 34, delete "domains" and insert -- domains. --, therefor.

In column 14, line 11, delete "ethidum" and insert -- ethidium --, therefor.

In column 16, line 4, delete "helicies," and insert -- helices --, therefor.

In column 16, line 15, delete "helicies," and insert -- helices --, therefor.

In column 17, line 6, delete "9 deg N" and insert -- 9degN --, therefor.

In column 17, line 66, delete "as" and insert -- is --, therefor.

In column 18, line 41, delete "40-aminoacids." and insert -- 40 amino acids. --, therefor.

In column 21, line 42, delete "P41 1L," and insert -- P411L, --, therefor.

In column 22, line 47, delete "P41 1L," and insert -- P411L, --, therefor.

In column 27, line 2, delete "P41 1L," and insert -- P411L, --, therefor.

Signed and Sealed this
First Day of December, 2015

Michelle K. Lee
*Director of the United States Patent and Trademark Office*

CERTIFICATE OF CORRECTION (continued)
U.S. Pat. No. 9,085,762 B2

In the specification

In column 30, line 56, delete "KC1." and insert -- KCl. --, therefor.

In column 31, line 12, delete "exo-4C II" and insert -- exo-4C11. --, therefor.

In column 32, line 36, delete "H$_2$0" and insert -- H$_2$O --, therefor.

In column 33, lines 11-12, delete "800 bp" and insert -- ~800 bp --, therefor.

In column 33, line 24, delete "H20" and insert -- H$_2$O --, therefor.

In column 34, line 36, delete "pET2I" and insert -- pET21 --, therefor.

In column 35, line 6, delete "H$_2$0" and insert -- H$_2$O --, therefor.

In column 35, line 65, delete "H$_2$0" and insert -- H$_2$O --, therefor.

In column 42, line 6, delete "0 M)," and insert -- 0M), --, therefor.

In the claims

In column 271, lines 41-42, in claim 5, delete "(X)n" and insert -- (X)$_n$ --, therefor.